US012790392B2

(12) United States Patent
Pashine et al.

(10) Patent No.: US 12,790,392 B2
(45) Date of Patent: Nov. 10, 2026

(54) ANTIBODIES AGAINST HUMAN TREM-1 AND USES THEREOF

(71) Applicant: BRISTOL-MYERS SQUIBB COMPANY, Princeton, NJ (US)

(72) Inventors: Achal M. Pashine, Mahwah, NJ (US); Joseph Toth, Belmont, MA (US); Ginger C. Rakestraw, Somerville, MA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 1334 days.

(21) Appl. No.: 17/627,085

(22) PCT Filed: Jul. 15, 2020

(86) PCT No.: PCT/US2020/042172

§ 371 (c)(1),
(2) Date: Jan. 13, 2022

(87) PCT Pub. No.: WO2021/011681

PCT Pub. Date: Jan. 21, 2021

(65) Prior Publication Data

US 2022/0332817 A1 Oct. 20, 2022

Related U.S. Application Data

(60) Provisional application No. 62/874,316, filed on Jul. 15, 2019.

(51) Int. Cl.

| | |
|---|---|
| ***C07K 16/28*** | (2006.01) |
| ***A61K 39/00*** | (2006.01) |
| ***A61P 29/00*** | (2006.01) |
| ***A61P 37/00*** | (2006.01) |
| ***C12N 15/63*** | (2006.01) |

(52) U.S. Cl.

CPC .......... *C07K 16/2803* (2013.01); *A61P 29/00* (2018.01); *A61P 37/00* (2018.01); *C12N 15/63* (2013.01); *A61K 2039/505* (2013.01); *C07K 2317/34* (2013.01); *C07K 2317/52* (2013.01); *C07K 2317/56* (2013.01); *C07K 2317/565* (2013.01); *C07K 2317/76* (2013.01)

(58) Field of Classification Search

CPC ............ C07K 16/2803; C07K 2317/34; C07K 2317/52; C07K 2317/56; C07K 2317/565; C07K 2317/76; A61P 29/00; A61P 37/00; C12N 15/63; A61K 2039/505

See application file for complete search history.

(56) References Cited

U.S. PATENT DOCUMENTS

| | | | |
|---|---|---|---|
| 4,444,887 | A | 4/1984 | Hoffmann |
| 4,676,980 | A | 6/1987 | Segal et al. |
| 4,683,195 | A | 7/1987 | Mullis et al. |
| 4,683,202 | A | 7/1987 | Mullis |
| 4,716,111 | A | 12/1987 | Osband et al. |
| 4,736,866 | A | 4/1988 | Leder et al. |
| 4,741,900 | A | 5/1988 | Alvarez et al. |
| 4,816,397 | A | 3/1989 | Boss et al. |
| 4,816,567 | A | 3/1989 | Cabilly et al. |
| 4,870,009 | A | 9/1989 | Evans et al. |
| 4,873,191 | A | 10/1989 | Wagner et al. |
| 4,873,316 | A | 10/1989 | Meade et al. |
| 4,980,286 | A | 12/1990 | Morgan et al. |
| 4,987,071 | A | 1/1991 | Cech et al. |
| 5,116,742 | A | 5/1992 | Cech et al. |
| 5,223,409 | A | 6/1993 | Ladner et al. |
| 5,225,539 | A | 7/1993 | Winter |
| 5,272,057 | A | 12/1993 | Smulson et al. |
| 5,272,071 | A | 12/1993 | Chappel |
| 5,283,317 | A | 2/1994 | Saifer et al. |
| 5,328,470 | A | 7/1994 | Nabel et al. |
| 5,403,484 | A | 4/1995 | Ladner et al. |
| 5,413,923 | A | 5/1995 | Kucherlapati et al. |
| 5,420,526 | A | 5/1995 | Fensch |
| 5,424,286 | A | 6/1995 | Eng |
| 5,427,908 | A | 6/1995 | Dower et al. |
| 5,436,146 | A | 7/1995 | Shenk et al. |
| 5,459,039 | A | 10/1995 | Modrich et al. |
| 5,474,981 | A | 12/1995 | Leder et al. |
| 5,498,531 | A | 3/1996 | Jarrell |
| 5,516,637 | A | 5/1996 | Huang et al. |
| 5,530,101 | A | 6/1996 | Queen et al. |
| 5,545,806 | A | 8/1996 | Lonberg et al. |

(Continued)

FOREIGN PATENT DOCUMENTS

| | | | |
|---|---|---|---|
| CN | 101687916 | A | 3/2010 |
| EP | 0264166 | A1 | 4/1988 |

(Continued)

OTHER PUBLICATIONS

U.S. Appl. No. 17/627,070. ANTI-TREM-1 Antibodies and Uses Thereof, filed and published 2022. (Year: 2022).*
U.S. Appl. No. 19/376,434. ANTI-TREM-1 Antibodies and Uses Thereof, filed 2025. Unpublished. (Year: 2025).*
International Search Report and Written Opinion for International Patent Application No. PCT/US2020/042172, mailed Sep. 18, 2020, 11 pages.
Abcam., Anti-PGRPS antibody [188C424] (ab13903), accessed at http://www.abcam.com/PGRPS-antibody-188C424-ab13903.html accessed on Jun. 12, 2014.

(Continued)

*Primary Examiner* — Julie Wu
*Assistant Examiner* — Elizabeth A Shupe
(74) *Attorney, Agent, or Firm* — Morgan, Lewis & Bockius LLP

(57) ABSTRACT

Provided herein are antibodies, or antigen-binding portions thereof, that specifically bind and inhibit TREM-1 signaling. Also provided are uses of such antibodies, or antigen-binding portions thereof, in therapeutic applications, such as treatment of autoimmune diseases.

15 Claims, 6 Drawing Sheets

Figure 3:
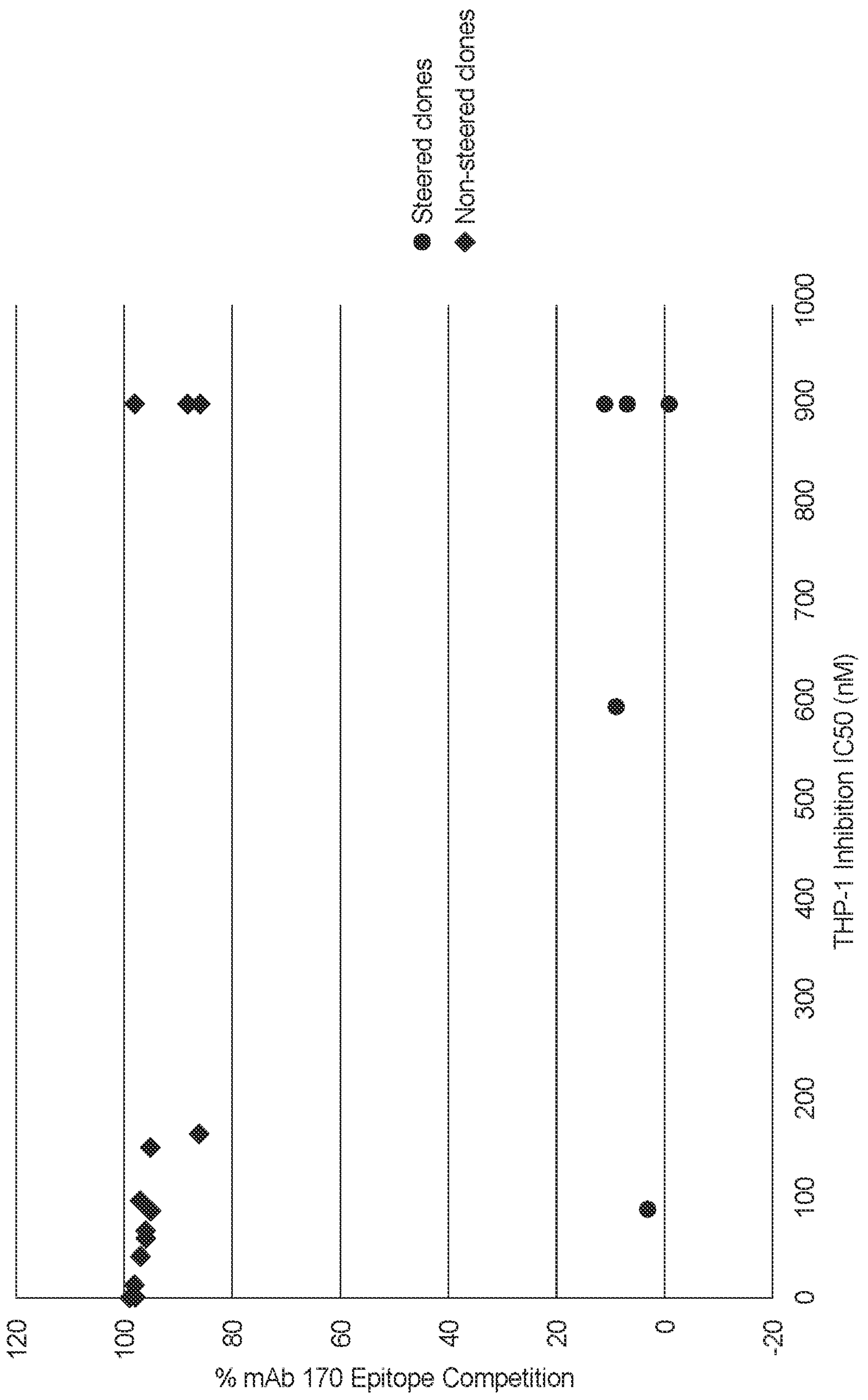

Specification includes a Sequence Listing.

(56) References Cited

U.S. PATENT DOCUMENTS

| | | | |
|---|---|---|---|
| 5,565,332 | A | 10/1996 | Hoogenboom et al. |
| 5,569,825 | A | 10/1996 | Lonberg et al. |
| 5,571,698 | A | 11/1996 | Ladner et al. |
| 5,580,717 | A | 12/1996 | Dower et al. |
| 5,585,089 | A | 12/1996 | Queen et al. |
| 5,625,126 | A | 4/1997 | Lonberg et al. |
| 5,633,425 | A | 5/1997 | Lonberg et al. |
| 5,658,727 | A | 8/1997 | Barbas et al. |
| 5,661,016 | A | 8/1997 | Lonberg et al. |
| 5,698,426 | A | 12/1997 | Huse |
| 5,733,743 | A | 3/1998 | Johnson et al. |
| 5,750,753 | A | 5/1998 | Kimae et al. |
| 5,780,225 | A | 7/1998 | Wigler et al. |
| 5,807,715 | A | 9/1998 | Morrison et al. |
| 5,814,318 | A | 9/1998 | Lonberg et al. |
| 5,821,047 | A | 10/1998 | Garrard et al. |
| 5,885,793 | A | 3/1999 | Griffiths et al. |
| 5,916,771 | A | 6/1999 | Hori et al. |
| 5,939,598 | A | 8/1999 | Kucherlapati et al. |
| 5,969,108 | A | 10/1999 | McCafferty et al. |
| 6,420,526 | B1 | 7/2002 | Ruben et al. |
| 6,504,010 | B1 | 1/2003 | Wang et al. |
| 6,509,448 | B2 | 1/2003 | Wang et al. |
| 6,638,768 | B1 | 10/2003 | Mouellic et al. |
| 6,858,204 | B2 | 2/2005 | Henderson et al. |
| 6,878,687 | B1 | 4/2005 | Ruben et al. |
| 8,013,116 | B2 | 9/2011 | Faure et al. |
| 8,231,878 | B2 | 7/2012 | Colonna et al. |
| 8,981,061 | B2 | 3/2015 | Colonna et al. |
| 9,000,127 | B2 | 4/2015 | Stennicke et al. |
| 2002/0128444 | A1 | 9/2002 | Gingras et al. |
| 2002/0172952 | A1 | 11/2002 | Henderson et al. |
| 2002/0197669 | A1 | 12/2002 | Bangur et al. |
| 2003/0049618 | A1 | 3/2003 | Ruben et al. |
| 2003/0054363 | A1 | 3/2003 | Henderson et al. |
| 2003/0077282 | A1 | 4/2003 | Bigler et al. |
| 2003/0134283 | A1 | 7/2003 | Peterson et al. |
| 2003/0165875 | A1 | 9/2003 | Colonna et al. |
| 2003/0166068 | A1 | 9/2003 | Ashida et al. |
| 2003/0170255 | A1 | 9/2003 | Watanabe et al. |
| 2003/0175858 | A1 | 9/2003 | Ruben et al. |
| 2003/0211510 | A1 | 11/2003 | Henderson et al. |
| 2004/0236092 | A1 | 11/2004 | Dziarski et al. |
| 2005/0255114 | A1 | 11/2005 | Labat et al. |
| 2006/0183125 | A1 | 8/2006 | Mariani et al. |
| 2009/0092582 | A1 | 4/2009 | Bogin et al. |
| 2010/0310560 | A1 | 12/2010 | Colonna et al. |
| 2016/0251434 | A1 | 9/2016 | Colonna et al. |
| 2017/0183406 | A1 | 6/2017 | Gurney et al. |
| 2017/0190775 | A1 | 7/2017 | Stennicke et al. |
| 2017/0320946 | A1 | 11/2017 | Colonna et al. |

FOREIGN PATENT DOCUMENTS

| | | | |
|---|---|---|---|
| EP | 0439095 | A2 | 7/1991 |
| EP | 0439098 | A2 | 7/1991 |
| EP | 0592106 | A1 | 4/1994 |
| EP | 0239400 | B1 | 8/1994 |
| EP | 1022286 | A1 | 7/2000 |
| EP | 0592106 | B1 | 11/2004 |
| EP | 1498424 | A2 | 1/2005 |
| EP | 0519596 | B1 | 2/2005 |
| EP | 2975056 | A1 | 1/2016 |
| JP | 2013216635 | A | 10/2013 |
| JP | 2015508762 | A | 3/2015 |
| JP | 2017522325 | A | 8/2017 |
| JP | 2019514347 | A | 6/2019 |
| TW | 201431878 | A | 8/2014 |
| WO | WO-8809810 | A1 | 12/1988 |
| WO | WO-8910134 | A1 | 11/1989 |
| WO | WO-9002809 | A1 | 3/1990 |
| WO | WO-9011354 | A1 | 10/1990 |
| WO | WO-9109967 | A1 | 7/1991 |
| WO | WO-9110737 | A1 | 7/1991 |
| WO | WO-9110741 | A1 | 7/1991 |
| WO | WO-9200968 | A1 | 1/1992 |
| WO | WO-9201047 | A1 | 1/1992 |
| WO | WO-9206180 | A1 | 4/1992 |
| WO | WO-9218619 | A1 | 10/1992 |
| WO | WO-9220316 | A2 | 11/1992 |
| WO | WO-9222324 | A1 | 12/1992 |
| WO | WO-9222635 | A1 | 12/1992 |
| WO | WO-9304169 | A1 | 3/1993 |
| WO | WO-9311236 | A1 | 6/1993 |
| WO | WO-9314188 | A1 | 7/1993 |
| WO | WO-9320221 | A1 | 10/1993 |
| WO | WO-9321232 | A1 | 10/1993 |
| WO | WO-9408598 | A1 | 4/1994 |
| WO | WO-9410300 | A1 | 5/1994 |
| WO | WO-9412649 | A2 | 6/1994 |
| WO | WO-9416101 | A2 | 7/1994 |
| WO | WO-9515982 | A2 | 6/1995 |
| WO | WO-9520401 | A1 | 8/1995 |
| WO | WO-9633735 | A1 | 10/1996 |
| WO | WO-9634096 | A1 | 10/1996 |
| WO | WO-9707668 | A1 | 3/1997 |
| WO | WO-9707669 | A1 | 3/1997 |
| WO | WO-9808871 | A1 | 3/1998 |
| WO | WO-9816654 | A1 | 4/1998 |
| WO | WO-9839446 | A2 | 9/1998 |
| WO | WO-9839448 | A2 | 9/1998 |
| WO | WO-9846645 | A2 | 10/1998 |
| WO | WO-9850433 | A2 | 11/1998 |
| WO | WO-9902686 | A1 | 1/1999 |
| WO | WO-0000610 | A2 | 1/2000 |
| WO | WO-0153312 | A1 | 7/2001 |
| WO | WO-0190304 | A1 | 11/2001 |
| WO | WO-03025138 | A2 | 3/2003 |
| WO | WO-03029401 | A2 | 4/2003 |
| WO | WO-03030835 | A2 | 4/2003 |
| WO | WO-03037267 | A2 | 5/2003 |
| WO | WO-03060071 | A2 | 7/2003 |
| WO | WO-03061712 | A1 | 7/2003 |
| WO | WO-03080667 | A2 | 10/2003 |
| WO | WO-2004020591 | A2 | 3/2004 |
| WO | WO-2004081233 | A1 | 9/2004 |
| WO | WO-2005005601 | A2 | 1/2005 |
| WO | WO-2005048823 | A2 | 6/2005 |
| WO | WO-2005071408 | A1 | 8/2005 |
| WO | WO-2005091944 | A2 | 10/2005 |
| WO | WO-2005113606 | A2 | 12/2005 |
| WO | WO-2006028595 | A2 | 3/2006 |
| WO | WO-2006028714 | A2 | 3/2006 |
| WO | WO-2006056492 | A1 | 6/2006 |
| WO | WO-2006065582 | A2 | 6/2006 |
| WO | WO-2006078463 | A2 | 7/2006 |
| WO | WO-2006097537 | A2 | 9/2006 |
| WO | WO-2006135886 | A2 | 12/2006 |
| WO | WO-2006138275 | A2 | 12/2006 |
| WO | WO-2007146968 | A2 | 12/2007 |
| WO | WO-2008049113 | A2 | 4/2008 |
| WO | WO-2008088849 | A2 | 7/2008 |
| WO | WO-2008121563 | A2 | 10/2008 |
| WO | WO-2009018386 | A1 | 2/2009 |
| WO | WO-2009020802 | A2 | 2/2009 |
| WO | WO-2009030771 | A1 | 3/2009 |
| WO | WO-2009117033 | A2 | 9/2009 |
| WO | WO-2009126380 | A2 | 10/2009 |
| WO | WO-2009141359 | A1 | 11/2009 |
| WO | WO-2010006060 | A2 | 1/2010 |
| WO | WO-2010042747 | A2 | 4/2010 |
| WO | WO-2010044952 | A2 | 4/2010 |
| WO | WO-2010065439 | A1 | 6/2010 |
| WO | WO-2010084169 | A2 | 7/2010 |
| WO | WO-2010132370 | A2 | 11/2010 |
| WO | WO-2010141469 | A2 | 12/2010 |
| WO | WO-2010142665 | A1 | 12/2010 |
| WO | WO-2011005481 | A1 | 1/2011 |
| WO | WO-2011028952 | A1 | 3/2011 |
| WO | WO-2011047097 | A2 | 4/2011 |
| WO | WO-2011055968 | A2 | 5/2011 |
| WO | WO-2011069104 | A2 | 6/2011 |
| WO | WO-2011091078 | A2 | 7/2011 |
| WO | WO-2011137362 | A1 | 11/2011 |

(56) References Cited

FOREIGN PATENT DOCUMENTS

| | | | | |
|---|---|---|---|---|
| WO | WO-2012064733 A2 | 5/2012 | | |
| WO | WO-2012088290 A2 | 6/2012 | | |
| WO | WO-2012088302 A2 | 6/2012 | | |
| WO | WO-2012109624 A2 | 8/2012 | | |
| WO | 2013120553 A1 | 8/2013 | | |
| WO | WO-2014072876 A1 | 5/2014 | | |
| WO | WO-2017152102 A2 * | 9/2017 | ......... | C07K 16/2803 |
| WO | WO-2018217976 | 11/2018 | | |
| WO | WO-2018217988 | 11/2018 | | |
| WO | WO-2018218056 | 11/2018 | | |
| WO | 2019032624 A1 | 2/2019 | | |

OTHER PUBLICATIONS

Abcam., Atlas Antibodies, PGRP Antibodies, United States Biological, List of Anti-PGRP Abs, accessed at http://www.antibodyresource.com/search/Antibodies/ffb4623f-177 d-13a0-16e2-1105223fb311/PG RP accessed on Jan. 8, 2014.

Abcam., Atlas Antibodies, United States Biological Peptidoglycan recognition protein short Antibodies, List of Anti-PGRP Abs accessed on http://www.antibodyresource.com/search/Antibodies/3a8d5b63-12d8-12d6-1 b99-11fb615758f5/Peptidoglycan- recognition-protein-short accessed on Jan. 8, 2014.

Abcam., Atlas Antibodies, United States Biological, 075594 Antibodies, List of Anti-PGRP Abs, accessed at http://www.antibodyresource. com/search/ Anti bodies/125bfebf-0922-1605-3416-8213e4 73b271/07 5594 accessed on Jan. 8, 2014.

Abcam., Atlas Antibodies, United States Biological, Cytokine tag7 Antibodies, List of Anti-PGRP Abs, accessed at http://www.antibodyresource .com/search/ Antibodies/17 a31750-abb9-1 c85-b872-c3a2e 796189c/Cytokine-tag 7 accessed on Jan. 8, 2014.

Abcam., Atlas Antibodies, United States Biological, Peptidoglycan recognition protein 1 Antibodies, List of Anti-PGRP Abs, accessed at http://www.antibodyresource. com/search/a ntibod ies/ede383a0-138e-c073-1710-f9db 1294bc02/Peptidoglycan- recognition-protein-1 accessed on Jan. 8, 2014.

Abcam., Atlas Antibodies, United States Biological, Peptidoglycan recognition protein 1 Antibodies, List of Anti-PGRP Abs, accessed at http://www.antibodyresource.com/search/Antibodies/1208015d-1757 -26ad-1 f04-6c9171376236/Peptidoglycan- recognition-protein-1 accessed on Jan. 8, 2014.

Abcam., Atlas Antibodies, United States Biological, Tag7 Antibodies, List of Anti-PGRP Abs accessed at http://www.antibodyresource.com/search/ Anti bodies/04 1 07168-8402-51 df-bb36-4dd2bf8e 16d 1/Tag accessed on Jan. 8, 2014.

Abcam., Atlas Antibodies, United States Biological, TNFSF3L Antibodies, List of Anti-PGRP Abs accessed at http://www.antibodyresource.com/search/Antibodies/f33a5126-45cd-5220-878c- -Ofd9aa63ba35/TNFSF3L accessed on Jan. 8, 2014.

Abravaya, K., et al., "Detection of Point Mutations with a Modified Ligase Chain Reaction (Gap-LCR)," Nucleic Acids Research 23(4):675-682, Oxford University Press, England (Feb. 1995).

Adams, P.D., et al., "PHENIX: A Comprehensive Python-based System for Macromolecular Structure Solution," Acta Crystallographica. Section D, Biological Crystallography 66(Pt 2):213-221, Wiley-Blackwell, United States (2010).

Aderem, A. and Ulevitch, R.J., "Toll-like Receptors in the Induction of the Innate Immune Response," Nature 406(6797):782-787, Nature Publishing Group, England (Aug. 2000).

Adrie, C., et al., "Postresuscitation Disease After Cardiac Arrest: A Sepsis-like Syndrome?," Current Opinion in Critical Care 10(3):208-212, Lippincott Williams & Wilkins, United States (Jun. 2004).

Alexander, H.R., et al., "A Recombinant Human Receptor Antagonist to Interleukin 1 Improves Survival After Lethal Endotoxemia in Mice," The Journal of Experimental Medicine 173(4):1029-1032, Rockefeller University Press, United States (Apr. 1991).

Allahham, A., et al., "Flow and Injection Characteristics of Pharmaceutical Parenteral Formulations Using a Micro-capillary Rheometer," International Journal of Pharmaceutics 270(1-2):139-148, Elsevier/North-Holland Biomedical Press, Netherlands (2004).

Amann, E., et al., "Tightly Regulated Tac Promoter Vectors Useful for the Expression of Unfused and Fused Proteins in *Escherichia coli*," Gene 69(2):301-315, Elsevier/North-Holland, Netherlands (1988).

Amatngalim, G.D., et al., "Cathelicidin Peptide LL-37 Modulates TREM-1 Expression and Inflammatory Responses to Microbial Compounds," Inflammation 34(5):412-425, Kluwer Academic/Plenum Publishers, United States (Oct. 2011).

Ames, R.S., et al., "Conversion of Murine Fabs Isolated From a Combinatorial Phage Display Library to Full Length Immunoglobulins," Journal of Immunological Methods 184(2):177-186, Elsevier, Netherlands (1995).

Andersen, M.D. and Faber, J.H., "Structural Characterization of Both the Non-proteolytic and Proteolytic Activation Pathways of Coagulation Factor XIII Studied by Hydrogen-deuterium Exchange Mass Spectrometry," International Journal of Mass Spectrometry 302(1-3):139-148, (2011).

Angal, S., et al., "A Single Amino Acid Substitution Abolishes the Heterogeneity of Chimeric Mouse/Human (IgG4) Antibody," Molecular Immunology 30(1):105-108, Pergamon Press, England (Jan. 1993).

Anti-TREM1 antibody produced in rabbit | Sigma-Aldrich HPA005563 product information, accessed at , https://www.laborne.com/product/Sigma-Aldrich/HPA005563.html, last accessed on Jun. 12, 2018, 3 pages.

Appelmelk, B.J., et al., "Use of Mucin and Hemoglobin in Experimental Murine Gram-negative Bacteremia Enhances the Immunoprotective Action of Antibodies Reactive With the Lipopolysaccharide Core Region," Antonie van Leeuwenhoek 52(6):537-542, Springer, Netherlands (1986).

Arnon, et al., "Monoclonal Antibodies for Immunotargeting of Drugs in Cancer Therapy," in Monoclonal Antibodies and Cancer Therapy, Reisfeld et al., eds., Alan R. Liss, Inc., (1985), pp. 243-256.

Arts, R.J., et al., "TREM-1 Interaction with the LPS/TLR4 Receptor Complex," European Cytokine Network 22(1):11-14, John Libbey Eurotext Ltd, France (2011).

Attwood, T.K., "Genomics. The Babel of Bioinformatics," Science 290(5491):471-473, American Association for the Advancement of Science, United States (Oct. 2000).

Ausubel, et al., Current Protocols in Molecular Biology, John Wiley & Sons (1992).

Bakker, A.B., et al., "DAP12-deficient Mice Fail to Develop Autoimmunity Due to Impaired Antigen Priming," Immunity 13(3):345-353, Cell Press, United States (Sep. 2000).

Bakker, A.B., et al., "Myeloid DAP12-associating Lectin (MDL)-1 is a Cell Surface Receptor Involved in the Activation of Myeloid Cells," Proceedings of the National Academy of Sciences 96(17):9792-9796, National Academy of Sciences, United States (Aug. 1999).

Bakker, A.B., et al., "NK Cell Activation: Distinct Stimulatory Pathways Counterbalancing Inhibitory Signals," Human Immunology 61(1):18-27, Elsevier/North-Holland, United States (Jan. 2000).

Baldari, C., et al., "A Novel Leader Peptide Which Allows Efficient Secretion of a Fragment of Human Interleukin 1 Beta in *Saccharomyces cerevisiae*," The EMBO Journal 6(1):229-234, Wiley Blackwell, England (Jan. 1987).

Baldwin, et al., "Analysis Results, and Future Prospective of the Therapeutic Use of the Radiolabeled Antibody in Cancer Therapy," In Monoclonal Antibodies for Cancer Detection and Therapy, eds. Adacemic Press, pp. 303-316 (1985).

Banerji, J., et al., "A Lymphocyte-specific Cellular Enhancer Is Located Downstream of the Joining Region in Immunoglobulin Heavy Chain Genes," Cell 33(3):729-740, Cell Press, United States (Jul. 1983).

Barany, F., "Genetic Disease Detection and Dna Amplification Using Cloned Thermostable Ligase," Proceedings of the National Academy of Sciences 88(1):189-193, National Academy of Sciences, United States (Jan. 1991).

(56) References Cited

OTHER PUBLICATIONS

Bartel, D.P. and Szostak, J.W., "Isolation of New Ribozymes From a Large Pool of Random Sequences," Science 261(5127):1411-1418, American Association for the Advancement of Science, United States (Sep. 1993).
Bartel, P. "Elimination of false positives that arise in using the two-hybrid system," Biotechniques 14(6):920-924, (1993).
Bauer, S., et al., "Activation of NK Cells and T Cells by NKG2D, a Receptor for Stress-inducible MICA," Science 285(5428):727-729, American Association for the Advancement of Science, United States (Jul. 1999).
Begum, N.A., et al., "Mycobacterium bovis Bcg Cell Wall-specific Differentially Expressed Genes Identified by Differential Display and cDNA Subtraction in Human Macrophages," Infection and Immunity 72(2):937-948, American Society for Microbiology, United States (Feb. 2004).
Benda, P., et al., "Differentiated Rat Glial Cell Strain in Tissue Culture," Science 161(3839):370-371, American Association for the Advancement of Science, United States (Jul. 1968).
Bethea, Deidra, et al., "Mechanisms of self-association of a human monoclonal antibody CNTO607", Protein Engineering, Design & Selection, 2012, vol. 25, No. 10, pp. 531-537.
Better, M., et al., "*Escherichia coli* Secretion of an Active Chimeric Antibody Fragment," Science 240(4855):1041-1043, Association for the Advancement of Science, United States (May 1988).
Beutler, B., "Endotoxin, Toll-like Receptor 4, and the Afferent Limb of Innate Immunity," Current opinion in microbiology 3(1):23-28, Current Biology, England (Feb. 2000).
Beutler, B., et al., "Passive Immunization Against Cachectin/tumor Necrosis Factor Protects Mice From Lethal Effect of Endotoxin," Science 229(4716):869-871, American Association for the Advancement of Science, United States (Aug. 1985).
Bird, R.E., et al., "Single-chain Antigen-binding Proteins," Science 242(4877):423-426, Association for the Advancement of Science, United States (Oct. 1988).
Bleharski, J.R., et al., "A Role for Triggering Receptor Expressed on Myeloid Cells-1 in Host Defense During the Early-induced and Adaptive Phases of the Immune Response," Journal of Immunology 170(7):3812-3818, American Association of Immunologists, United States (Apr. 2003).
Boesen, J.J., et al., "Circumvention of Chemotherapy-induced Myelosuppression by Transfer of the mdr1 Gene," Biotherapy 6(4):291-302, Kluwer Academic Publishers, Netherlands (1993).
Bolin, S.R., et al., "Survey of Cell Lines in the American Type Culture Collection for Bovine Viral Diarrhea Virus," Journal of Virological Methods 48(2-3):211-221, Elsevier/North-Holland Biomedical Press, Netherlands (Jul. 1994).
Bone, R.C., "The Pathogenesis of Sepsis," Annals of Internal Medicine 115(6):457-469, American College of Physicians, United States (Sep. 1991).
Bone, R.C., et al., "Definitions for Sepsis and Organ Failure and Guidelines for the Use of Innovative Therapies in Sepsis. The ACCP/SCCM Consensus Conference Committee. American College of Chest Physicians/Society of Critical Care Medicine," Chest 101(6):1644-1655, Elsevier, United States (Jun. 1992).
Bordelon-Riser, M.E., "Necessity for Two Human Chromosomes for Human Chorionic Gonadotropin Production in Human-mouse Hybrids," Somatic Cell Genetics 5(5):597-613, Plenum, United States (Sep. 1979).
Bork, P. and Bairoch, A., "Go Hunting in Sequence Databases but Watch out for the Traps," Trends in Genetics 12(10):425-427, Elsevier Trends Journals, England (Oct. 1996).
Bork, P., "Powers and Pitfalls in Sequence Analysis: The 70% Hurdle," Genome Research 10(4):398-400, Cold Spring Harbor Laboratory Press, United States (Apr. 2000).
Bostanci, N., et al., "Involvement of the TREM-1/DAP12 Pathway in the Innate Immune Responses to Porphyromonas Gingivalis," Molecular Immunology 49(1-2):387-394, Pergamon Press, England (Oct. 2011).
Bout, A., et al., "Lung Gene Therapy: In Vivo Adenovirus-mediated Gene Transfer to *Rhesus* Monkey Airway Epithelium," Human Gene Therapy 5(1):3-10, Liebert, United States (Jan. 1994).
Bradley, "Teratocarcinomas and Embryonic Stem Cells: A Practical Approach," Robertson, ed., IRL, Oxford, pp. 113-152 (1987).
Bradley, A., "Modifying the Mammalian Genome by Gene Targeting," Current Opinion in Biotechnology 2(6):823-829, Elsevier, England (Dec. 1991).
Brenner, S.E., "Errors in Genome Annotation," Trends in Genetics 15(4):132-133, Elsevier Trends Journals, England (Apr. 1999).
Brinkmann, U., et al., "Phage Display of Disulfide-stabilized Fv Fragments," Journal of Immunological Methods 182(1):41-50, Elsevier, Netherlands (1995).
Brown, M., et al., "Tolerance to Single, but not Multiple, Amino Acid Replacements in Antibody VH CDR2: A Means of Minimizing B Cell Wastage from Somatic Hypermutation?," Journal of Immunology 156(9):3285-3291, American Association of Immunologists, United States (May 1996).
Burton, D.R. and Barbas, C.F. 3rd., "Human Antibodies From Combinatorial Libraries," Advances in Immunology 57:191-280, Academic Press, United States (1994).
Byrne, G.W. and Ruddle, F.H., "Multiplex Gene Regulation: a Two-tiered Approach to Transgene Regulation in Transgenic Mice," Proceedings of the National Academy of Sciences USA 86(14):5473-5477 (Jul. 1989).
Calame, K., et al., "Transcriptional Controlling Elements in the Immunoglobulin and T Cell Receptor Loci," Advances in Immunology 43:235-275 (1988).
Calandra, T., et al., "Protection From Septic Shock by Neutralization of Macrophage Migration Inhibitory Factor," Nature Medicine 6(2):164-170, Nature Publishing Company, United States (2000).
Camper, S.A. and Tilghman, S.M., "Postnatal Repression of the Alpha-fetoprotein Gene Is Enhancer Independent," Genes & Development 3:537-546 (1989).
Cantoni, C., et al., "Nkp44, a Triggering Receptor Involved in Tumor Cell Lysis by Activated Human Natural Killer Cells, Is a Novel Member of the Immunoglobulin Superfamily," Journal of Experimental Medicine 189(5):787-796, Rockefeller University Press, United States (Mar. 1999 ).
Carrell., et al., "A Novel Procedure for the Synthesis of Libraries Containing Small Organic Molecules," Angewandte Chemie International Edition in English 33:2059-2061, (1994).
Cella, M., et al., "A Novel Inhibitory Receptor (ILT3) Expressed on Monocytes, Macrophages, and Dendritic Cells Involved in Antigen Processing," Journal of Experimental Medicine 185(10):1743-1751, Rockefeller University Press, United States (May 1997 ).
Chaudhri, Anuj, et al., "The Role of Amino Acid Sequence in the Self-Association of Therapeutic Monoclonal Antibodies: Insights from Coarse-Grained Modeling", The Journal of Physical Chemistry, 2013, vol. 117, pp. 1269-1279.
Chen, S.H., et al., "Gene Therapy for Brain Tumors: Regression of Experimental Gliomas by Adenovirus-mediated Gene Transfer in Vivo," Proceedings of the National Academy of Sciences 91(8):3054-3057, National Academy of Sciences, United States (Apr. 1994 ).
Cho, C.Y., et al., "An unnatural biopolymer," Science 261(5126):1303-1305, American Association for the Advancement of Science, United States (1993).
Chomel, B.B., et al., "Bartonella Henselae Prevalence in Domestic Cats in California: Risk Factors and Association Between Bacteremia and Antibody Titers," Journal of Clinical Microbiology 33(9):2445-2450, American Society for Microbiology, United States (Sep. 1995).
Chothia, C. and Lesk, A.M., "Canonical Structures for the Hypervariable Regions of Immunoglobulins," Journal of Molecular Biology 196(4):901-917, Elsevier Science, United States (Aug. 1987).
Clowes, M.M., et al., "Long-term Biological Response of Injured Rat Carotid Artery Seeded With Smooth Muscle Cells Expressing Retrovirally Introduced Human Genes," The Journal of Clinical Investigation 93(2):644-651, American Society for Clinical Investigation, United States (Feb. 1994).

(56) References Cited

OTHER PUBLICATIONS

Cohen, A.S., et al., "Emerging Technologies for Sequencing Antisense Oligonucleotides: Capillary Electrophoresis and Mass Spectrometry," Advances in Chromatography 36:127-162, CRC Press, United States (1996).
Cohen, J., "The Immunopathogenesis of Sepsis," Nature 420(6917):885-891, Nature Publishing Group, England (Dec. 2002).
Cohen, J., "TREM-1 in Sepsis," Lancet 358(9284):776-778, Elsevier, England (Sep. 2001).
Colbere-Garapin, F., et al., "A New Dominant Hybrid Selective Marker for Higher Eukaryotic Cells," Journal of Molecular Biology 150(1):1-14, Elsevier, England (Jul. 1981).
Collart, M.A., et al., "Regulation of Tumor Necrosis Factor Alpha Transcription in Macrophages: Involvement of Four Kappa B-like Motifs and of Constitutive and Inducible Forms of NF-kappa B," Molecular and Cellular Biology 10(4):1498-1506, American Society for Microbiology, United States (Apr. 1990).
Colonna, M. and Facchetti, F., "TREM-1 (Triggering Receptor Expressed on Myeloid Cells): A New Player in Acute Inflammatory Responses," The Journal of Infectious Diseases 187(2):5397-5401, Oxford University Press, United States (Jun. 2003).
Colonna, M., "Trems in the Immune System and Beyond," Nature Reviews. Immunology 3(6):445-453, Nature Pub. Group, England (Jun. 2003).
Connolly, B.D., et al., "Weak Interactions Govern the Viscosity of Concentrated Antibody Solutions: High-throughput Analysis Using the Diffusion Interaction Parameter," Biophysical Journal 103(1):69-78, Cell Press, United States (2012).
Coskun, T., et al., "Fibroblast Growth Factor 21 Corrects Obesity in Mice," Endocrinology 149(12):6018-6027, Oxford University Press, United States (Dec. 2008).
Cotten, M., et al., "Receptor-mediated Transport of DNA Into Eukaryotic Cells," Methods in Enzymology 217:618-644, Academic Press, United States (1993).
Cotton, R.G., "Current Methods of Mutation Detection," Mutation Research 285(1):125-144, Elsevier, Netherlands (Jan. 1993).
Cotton, R.G., et al., "Reactivity of Cytosine and Thymine in Single-base-pair Mismatches With Hydroxylamine and Osmium Tetroxide and Its Application to the Study of Mutations," Proceedings of the National Academy of Sciences 85(12):4397-4401, National Academy of Sciences, United States (Jun. 1988).
Cox, G., et al., "IL-10 Enhances Resolution of Pulmonary Inflammation in Vivo by Promoting Apoptosis of Neutrophils," The American Journal of Physiology 271(4 Pt 1):L566-L571, American Physiological Society, United States (Oct. 1996).
Cronin, M.T., et al., "Cystic Fibrosis Mutation Detection by Hybridization to Light-generated DNA Probe Arrays," Human Mutation 7(3):244-255, Wiley-Liss, United States (1996).
Cruickshank, D.W., "Remarks About Protein Structure Precision," Acta Crystallographica. Section D, Biological Crystallography 55(Pt 3):583-601, Wiley-Blackwell, United States (1999).
Cruikshank, W.W., et al., "A Lipidated Anti-Tat Antibody Enters Living Cells and Blocks HIV-1 Viral Replication," Journal of Acquired Immune Deficiency Syndromes and Human Retrovirology 14(3):193-203, Lippincott Williams & Wilkins, United States (Mar. 1997).
Cull, M.G., et al., "Screening for Receptor Ligands Using Large Libraries of Peptides Linked to the C Terminus of the Lac Repressor," Proceedings of the National Academy of Sciences 89(5):1865-1869, National Academy of Sciences, United States (Mar. 1992).
Cwirla, S.E., et al., "Peptides on phage: a vast library of peptides for identifying ligands," Proceedings of the National Academy of Sciences 87(16):6378-6382, National Academy of Sciences, United States, (1990).
Database EMBL, Sequence from Patent WO200283856-A2, Sep. 17, 2003 "Human G-protein Coupled Receptor Phosphorylation Site Peptide SEQ ID 131," retrieved from EBI Database accession No. ABJ38803.
Database EMBL, Sequence Information from JP2000116377-A, Oct. 10, 2000 "N-terminus of Porcine Trypsin," retrieved from EBI Database accession No. AAB03087.
Davenport, C.M., et al., "Inhibition of Pro-inflammatory Cytokine Generation by CTLA4-Ig in the Skin and Colon of Mice Adoptively Transplanted with CD45RBhi CD4+ T Cells Correlates with Suppression of Psoriasis and Colitis," International Immunopharmacology 2(5):653-672, Elsevier Science, Netherlands (2002).
Daws, M.R., et al., "Cloning and Characterization of a Novel Mouse Myeloid DAP12-associated Receptor Family," European Journal of Immunology 31(3):783-791, Wiley-VCH, Germany (Mar. 2001).
Devlin, J.J., et al., "Random peptide libraries: a source of specific protein binding molecules," Science 249(4967):404-406, American Association for the Advancement of Science, United States (1990).
Dewitt, S.H., et al., "Diversomers: an approach to nonpeptide, nonoligomeric chemical diversity," Proceedings of the National Academy of Sciences 90(15):6909-6913, National Academy of Sciences, United States (1993).
Dietrich, J., et al., "Cutting Edge: Signal-regulatory Protein Beta 1 is a DAP12-associated Activating Receptor Expressed in Myeloid Cells," Journal of Immunology 164(1):9-12, American Association of Immunologists, United States (Jan. 2000).
Dinarello, C.A., "Proinflammatory and Anti-inflammatory Cytokines as Mediators in the Pathogenesis of Septic Shock," Chest 112(6):3215-3295, Elsevier, United States (Dec. 1997).
Doerks T., et al., "Protein Annotation: Detective Work for Function Prediction," Trends in Genetics 14(6):248-250, Elsevier Trends Journals, England (Jun. 1998).
Downey, G.P., et al., "Intracellular Signaling in Neutrophil Priming and Activation," Seminars in Cell Biology 6(6):345-356, Academic Press, England (Dec. 1995).
Dziarski, R., "Peptidoglycan Recognition Proteins (PGRPS)," Molecular Immunology 40(12):877-886, Pergamon Press, England (Feb. 2004).
Dziarski, R., et al., "Peptidoglycan Recognition in Innate Immunity," Endotoxin Research 11(5):304-310, Sage Publications, United States (2005).
Dziarski, R., et al., "Review: Mammalian Peptidoglycan Recognition Proteins (PGRPs) in Innate Immunity," Innate Immunity 16(3):168-174, Sage Publications, United States (Jun. 2010).
Dziarski, R., Gupta, D., "The Peptidoglycan Recognition Proteins (PGRPs)," Genome Biology 7(8):232.1-232.13, BioMed Central Ltd, England (2006).
Echtenacher, B., et al., "Critical Protective Role of Mast Cells in a Model of Acute Septic Peritonitis," Nature 381(6577):75-77, Nature Publishing Group, England (May 1996).
Echtenacher, B., et al., "Requirement of Endogenous Tumor Necrosis Factor/cachectin for Recovery From Experimental Peritonitis," Journal of Immunology 145(11):3762-3766, American Association of Immunologists, United States (Dec. 1990).
Echtenacher, B., et al., "Tumor Necrosis Factor-dependent Adhesions as a Major Protective Mechanism Early in Septic Peritonitis in Mice," Infection and Immunity 69(6):3550-3555, American Society for Microbiology, United States (Jun. 2001).
Edlund, T., et al., "Cell-specific Expression of the Rat Insulin Gene: Evidence for Role of Two Distinct 5' Flanking Elements," Science 230(4728):912-916, American Association for the Advancement of Science, United States (Nov. 1985).
Emsley, P., et al., "Features and Development of Coot," Acta Crystallographica. Section D, Biological Crystallography 66(Pt 4):486-501, Wiley-Blackwell, United States (2010).
Engh, R.A. and Huber, R., "Accurate Bond and Angle Parameters for X-ray Protein Structure Refinement," Acta Crystallographica Section A 47(4):392-400, (1991).
Erb, E., et al., "Recursive deconvolution of combinatorial chemical libraries," Proceedings of the National Academy of Sciences 91(24):11422-11426, National Academy of Sciences, United States (1994).
Erickson, S.K., "Nonalcoholic Fatty Liver Disease," Journal of Lipid Research 50:S412-S416, American Society for Biochemistry and Molecular Biology, United States (Apr. 2009).
Eskandari, M.K., et al., "Anti-tumor Necrosis Factor Antibody Therapy Fails to Prevent Lethality After Cecal Ligation and Punc-

(56) References Cited

OTHER PUBLICATIONS ture or Endotoxemia," Journal of Immunology 148(9):2724-2730, American Association of Immunologists, United States (May 1992).
European Search Report for EP Application No. 14177547.8, European Patent Office, Munich, Germany, dated Feb. 2, 2015, 10 pages.
European Search Report for EP Application No. 14194893.5, European Patent Office, Munich, Germany, dated Jan. 14, 2016, 12 pages.
Facchetti, F., et al., "Suppurative Granulomatous Lymphadenitis. Immunohistochemical Evidence for a B-cell-associated Granuloma," The American Journal of Surgical Pathology 16(10):955-961, Wolters Kluwer Health, Inc., United States (Oct. 1992).
Felici, F., et al., "Selection of Antibody Ligands from a Large Library of Oligopeptides Expressed on a Multivalent Exposition Vector," Journal of Molecular Biology 222(2):301-310, Elsevier Science, United States (Nov. 1991).
Fell, H.P., et al., "Genetic Construction and Characterization of a Fusion Protein Consisting of a Chimeric F(ab') With Specificity for Carcinomas and Human IL-2," Journal of Immunology 146(7):2446-2452, American Association of Immunologists, United States (Apr. 1991).
Fiering, S., et al., "Single Cell Assay of a Transcription Factor Reveals a Threshold in Transcription Activated by Signals Emanating From the T-cell Antigen Receptor," Genes & Development 4(10):1823-1834, Cold Spring Harbor Laboratory Press, United States (1990).
Finn, P.J., et al. , "Synthesis and Properties of DNA-PNA Chimeric Oligomers," Nucleic Acids Research 24(17):3357-3363, Oxford University Press, England (Sep. 1996).
Fisher, C.J., et al., "Treatment of Septic Shock with the Tumor Necrosis Factor Receptor: Fc Fusion Protein the Soluble TNF Receptor Sepsis Study Group," The New England Journal of Medicine 334(26):1697-1702, Massachusetts Medical Society, United States (Jun. 1996).
Fodor, S.P., et al., "Multiplexed biochemical assays with biological chips," Nature 364(6437):555-556, Nature Publishing Group, United States (1993).
Forster, R., et al., "CCR7 Coordinates the Primary Immune Response by Establishing Functional Microenvironments in Secondary Lymphoid Organs," Cell 99(1):23-33, Cell Press, United States (Oct. 1999).
Gallop, M.A., et al., "Applications of combinatorial technologies to drug discovery. 1. Background and peptide combinatorial libraries," Journal of Medicinal Chemistry 37(9):1233-1251, (1994).
Garcia, R.A., et al., "Hydrogen/deuterium Exchange Mass Spectrometry for Investigating Protein-ligand Interactions," Assay and Drug Development Technologies 2(1):81-91, Mary Ann Liebert, Inc., United States (2004).
Gasparini, P., et al., "Restriction Site Generating-polymerase Chain Reaction (RG-PCR) for the Probeless Detection of Hidden Genetic Variation: Application to the Study of Some Common Cystic Fibrosis Mutations," Molecular and Cellular Probes 6(1):1-7, Academic Press, England (Feb. 1992).
Gautier, C., et al., "alpha-DNA Iv: alpha-anomeric and beta-anomeric Tetrathymidylates Covalently Linked to Intercalating Oxazolopyridocarbazole Synthesis, Physicochemical Properties and Poly," Nucleic Acids Research 15(16):6625-6641, Oxford University Press, England (Aug. 1987).
GenBank, "AL681036 XGC-gastrula Xenopus tropicalis cDNA clone TGas068103 5—, mRNA sequence," Accession No. AL681036.2, accessed at https://www.ncbi.nlm.nih.gov/nucest/AI681036, Nov. 10, 2003.
GenBank, "AL962750 XGC-gastrula Xenopus tropicalis cDNA clone TGas109m03 5—, mRNA sequence," Accession No. AL962750.2, accessed at https://www.ncbi.nlm.nih.gov/nucest/AI962750, Dec. 5, 2003.
GenBank, "AL968134 XGC-gastrula Xenopus tropicalis cDNA clone TGas113h24 5—, mRNA sequence," Accession No. AL968134.2, accessed at https://www.ncbi.nlm.nih.gov/nucest/AI968134, Dec. 5, 2003.
GenBank, "Cloning Vector pIRES1hyg, Complete Plasmid Sequence," Accession No. U89672.1, accessed at https://www.ncbi.nlm.nih.gov/nuccore/U89672, Mar. 21, 1997.
GenBank, "CM0-TT0011-251099-080f05 TT0011 Homo sapiens cDNA, mRNA sequence," Accession No. AW394041.1, accessed at https://www.ncbi.nlm.nih.gov/nucest/AW394041, Feb. 4, 2000.
GenBank, "*Homo sapiens* triggering receptor expressed on monocytes 1 mRNA, complete cds," Accession No. AF196329.1, accessed at https://www.ncbi.nlm.nih.gov/nuccore/AF196329, May 24, 2000.
GenBank, "*Homo sapiens* triggering receptor expressed on myeloid cells 2 mRNA, complete cds," Accession No. AF213457.1, accessed at https://www.ncbi.nlm.nih.gov/nuccore/AF213457, May 23, 2000.
GenBank, "HUM517F10B Human placenta polyA+ (TFujiwara) *Homo sapiens* cDNA clone Gen-517F10 5—, mRNA sequence," Accession No. D78812.1, accessed at https://www.ncbi.nlm.nih.gov/nucest/D78812, Jul. 20, 2006.
GenBank, "ne55f09.s1 NCI_CGAP_Co3 *Homo sapiens* cDNA clone Image:901289 3—, mRNA sequence," Accession No. AA494171.1, accessed at https://www.ncbi.nlm.nih.gov/nucest/AA494171, Jan. 6, 2011.
GenBank, "T3 end of clone 024CH09 of library SmBAC1 from strain Puerto-Rican of Schistosoma mansoni, genomic survey sequence," Accession No. AL621023.1, accessed at https://www.ncbi.nlm.nih.gov/nucgss/AI621023, Oct. 11, 2001.
GenBank, "T3 end of clone AR0AA015A03 of library AR0AA from strain CBS 732 of Zygosaccharomyces rouxii, genomic survey sequence," Accession No. AL394092.1, accessed at https://www.ncbi.nlm.nih.gov/nucgss/AI394092, Feb. 16, 2014.
GenBank, "tb95h04.x1 NCI_CGAP_Co16 *Homo sapiens* cDNA clone Image:2062135 3—, mRNA sequence," Accession No. Al337247.1, accessed at https://www.ncbi.nlm.nih.gov/nucest/A1337247, Jan. 8, 2011.
GenBank, "Tetraodon nigroviridis genome survey sequence T7 end of clone 245F13 of library G from Tetraodon nigroviridis, genomic survey sequence," Accession No. AL186456, accessed at https://www.ncbi.nlm.nih.gov/nucgss/AI186456, May 19, 2010.
GenBank, "Triggering Receptor Expressed on Myeloid Cells 1 Isoform 1 Precursor [Mus musculus]," Accession No. NP_067381.1, accessed at https://www.ncbi.nlm.nih.gov/protein/NP_067381, Jun. 3, 2017.
GenBank, "Triggering Receptor Expressed on Myeloid Cells," Accession No. Q9NP99, accessed at http://www.uniprot.org/uniprot/Q9NP99, Jun. 7, 2017.
GenBank, "UI-H-BI1-acf-g-10-0-UI.s1 NCI_CGAP_Sub3 *Homo sapiens* cDNA clone Image:2714299 3—, mRNA sequence," Accession No. AW135801.1, accessed at https://www.ncbi.nlm.nih.gov/nucest/AW135801, Jan. 6, 2011.
GenBank, "UI-H-BI1-ada-h-08-0-UI.s1 NCI_CGAP_Sub3 *Homo sapiens* cDNA clone Image:2716286 3—, mRNA sequence," Accession No. AW139363.1, accessed at https://www.ncbi.nlm.nih.gov/nucest/AW139363, Jan. 7, 2011.
GenBank, "UI-H-BI1-aea-d-11-0-UI.s1 NCI_CGAP_Sub3 *Homo sapiens* cDNA clone Image:2718764 3—, mRNA sequence," Accession No. AW139572.1, accessed at https://www.ncbi.nlm.nih.gov/nucest/AW139572, Jan. 7, 2011.
GenBank, "UI-H-BI1-aea-d-12-0-Ul.s1 NCI_CGAP_Sub3 *Homo sapiens* cDNA clone Image:2718766 3—, mRNA sequence," Accession No. AW139573.1, accessed at https://www.ncbi.nlm.nih.gov/nucest/AW139573, Oct. 30, 1999.
GenBank, "xm62e07.x1 NCI_CGAP_GC6 *Homo sapiens* cDNA clone Image:2688804 3—, mRNA sequence," Accession No. AW274906.1, accessed at https://www.ncbi.nlm.nih.gov/nucest/AW274906, Jan. 3, 2000.
GenBank, "yw70g03.r1 Soares_placenta_8to9weeks_2NbHP8to9W *Homo sapiens* cDNA clone Image:257620 5—, mRNA sequence," Accession No. N41388.1, accessed at https://www.ncbi.nlm.nih.gov/nucest/N41388, Jan. 24, 1996.
GenBank, "zk87c02.r1 Soares_pregnant_uterus_NbHPU *Homo sapiens* cDNA clone Image:489794 5—, mRNA sequence," Accession No. AA099288.1, accessed at https://www.ncbi.nlm.nih.gov/nucest/AA099288, Jan. 28, 2011.

(56) References Cited

OTHER PUBLICATIONS

GenBank, "zk87c02.s1 Soares_pregnant_uterus_NbHPU *Homo sapiens* cDNA clone Image:489794 3—, mRNA sequence," Accession No. AA101983.1, accessed at https://www.ncbi.nlm.nih.gov/nucest/AA101983, Jan. 28, 2011.
Gencic, S. and Hudson, L.D., "Conservative Amino Acid Substitution in the Myelin Proteolipid Protein of Jimpymsd Mice," The Journal of Neuroscience 10(1):117-124, Society for Neuroscience, United States (Jan. 1990).
Gentz, R., et al., "Bioassay for Trans-activation using Purified Human Immunodeficiency Virus Tat-encoded Protein: Trans-activation Requires mRNA Synthesis," Proceedings of the National Academy of Sciences USA 86(3):821-824, National Academy of Sciences, United States (Feb. 1989).
Ghosh, A., et al., "A Novel Antimicrobial Peptidoglycan Recognition Protein in the Cornea," Investigative Ophthalmology & Visual Science 50(9):4185-4191, Association for Research in Vision and Ophthalmology, United States (Sep. 2009).
Gibbs, R.A., et al., "Detection of Single DNA Base Differences by Competitive Oligonucleotide Priming," Nucleic Acids Research 17(7):2437-2448, Oxford University Press, England (Apr. 1989).
Gibot, S., et al., "A Soluble Form of the Triggering Receptor Expressed on Myeloid Cells-1 Modulates the Inflammatory Response in Murine Sepsis," The Journal of Experimental Medicine 200(11):1419-1426, Rockefeller University Press, United States (Dec. 2004).
Gibot, S., et al., "Modulation of the Triggering Receptor Expressed on the Myeloid Cell Type 1 Pathway in Murine Septic Shock," Infection and immunity 74(5):2823-2830, American Society for Microbiology, United States (May 2006).
Gibot, S., et al., "Plasma Level of a Triggering Receptor Expressed on Myeloid Cells-1: its Diagnostic Accuracy in Patients with Suspected Sepsis," Annals of Internal Medicine 141(1):9-15, American College of Physicians—American Society of Internal Medicine, United States (Jul. 2004).
Gibot, S., et al., "Soluble Triggering Receptor Expressed on Myeloid Cells and the Diagnosis of Pneumonia," The New England Journal of Medicine 350(5):451-458, Massachusetts Medical Society, United States (Jan. 2004).
Gillies, S.D., et al., "Antibody-targeted Interleukin 2 Stimulates T-cell Killing of Autologous Tumor Cells," Proceedings of the National Academy of Sciences of the United States of America 89(4):1428-1432, National Academy of Sciences, United States (1992).
Gillies, S.D., et al., "High-level Expression of Chimeric Antibodies Using Adapted cDNA Variable Region Cassettes," Journal of Immunological Methods 125(1-2):191-202, Elsevier, Netherlands (1989).
Gingras, M.C., et al., "TREM-1, MDL-1, and DAP12 Expression is Associated with a Mature Stage of Myeloid Development," Molecular Immunology 38(11):817-824, Pergamon Press, England (Mar. 2002).
Glauser, M.P., et al., "Septic Shock: Pathogenesis," Lancet 338(8769):732-736, Elsevier, England (Sep. 1991).
Goldspiel, B.R., et al., "Human Gene Therapy," Clinical Pharmacy 12(7):488-505, American Society of Hospital Pharmacists, United States (1993).
Gon, S., et al., "Involvement of Two Types of TNF Receptor in TNF-alpha Induced Neutrophil Apoptosis," Microbiology and Immunology 40(6):463-465, Wiley-Blackwell, Australia (1996).
Griffin, H.G. and Griffin, A.M., "DNA Sequencing. Recent Innovations and Future Trends," Applied Biochemistry and Biotechnology 38(1-2):147-159, Humana Press, United States (Jan.-Feb. 1993).
Griffin, M.P., et al., "Abnormal Heart Rate Characteristics Preceding Neonatal Sepsis and Sepsis-like Illness," Pediatric Research 53(6):920-926, Nature Publishing Group, United States (Jun. 2003).
Grossman, M. and Wilson, J.M., "Retroviruses: Delivery Vehicle to the Liver," Current Opinion in Genetics & Development 3(1):110-114, Elsevier, England (Feb. 1993).
Grundy, S.M., et al., "Definition of Metabolic Syndrome: Report of the National Heart, Lung, and Blood Institute/American Heart Association Conference on Scientific Issues Related to Definition," Circulation 109(3):433-438, Lippincott Williams & Wilkins, United States (Jan. 2004).
Guan, R., et al., "Crystal Structure of Human Peptidoglycan Recognition Protein S (PGRP-S) at 1.70 A Resolution," Molecular Biology 347(4):683-691, Elsevier, England (Apr. 2005).
Guatelli, J.C., et al., "Isothermal, in Vitro Amplification of Nucleic Acids by a Multienzyme Reaction Modeled After Retroviral Replication," Proceedings of the National Academy of Sciences 87(5):1874-1878, National Academy of Sciences, United States (Mar. 1990).
Haapala, D.K., et al., "Isolation From Cats of an Endogenous Type C Virus With a Novel Envelope Glycoprotein," Journal of Virology 53(3):827-833, American Society for Microbiology, United States (Mar. 1985).
Hammerling, G.J., et al., "Monoclonal Antibodies and T-Cell Hybridomas," pp. 563-681, Elsevier, Newyork (1981).
Harlow, E. and Lane, D., Antibodies: A Laboratory Manual, 2nd Edition, Cold Spring Harbor Press (1988).
Haselmayer, P., et al., "TREM-1 Ligand Expression on Platelets Enhances Neutrophil Activation," Blood 110(3):1029-1035, American Society of Hematology, United States (Aug. 2007).
Haseloff, J., et al., "Simple RNA Enzymes with New and Highly Specific Endoribonuclease Activities," Nature 334(6183): 585-591, Nature Publishing Group, England (Aug. 1988).
Hayashi, K., "PCR-SSCP: A Method for Detection of Mutations," Genetic Analysis, Techniques and Applications 9(3):73-79, Elsevier, Netherlands (Jun. 1992).
He, F., et al., "High-throughput Dynamic Light Scattering Method for Measuring Viscosity of Concentrated Protein Solutions," Analytical Biochemistry 399(1):141-143, Elsevier, United States (2010).
He, X.M., et al., "Expression of 06-methylguanine-DNA Methyltransferase in Six Human Medulloblastoma Cell Lines," Cancer Research 52(5):1144-1148, American Association for Cancer Research, United States (Mar. 1992).
Hebert, M.J., et al., "Sequential Morphologic Events During Apoptosis of Human Neutrophils. Modulation by Lipoxygenase-derived Eicosanoids," Journal of Immunology 157(7):3105-3115, American Association of Immunologists, United States (Oct. 1996).
Helene, C., "The Anti-gene Strategy: Control of Gene Expression by Triplex-forming-oligonucleotides," Anti-cancer Drug Design 6(6):569-584, Oxford University Press, United States (1991).
Helene, C., et al., "Control of Gene Expression by Triple Helix-forming Oligonucleotides. The Antigene Strategy," Annals of the New York Academy of Sciences 660:27-36, Blackwell, United States (Oct. 1992).
Hellstrom, et al., "Antibodies for Drug Delivery" in Controlled Drug Delivery, 2nd edition, Robinson et al., eds., Marcel Dekker, Inc., (1987), pp. 623-653.
Hiscott, J., et al., "Characterization of a Functional NF-kappa B Site in the Human Interleukin 1 Beta Promoter: Evidence for a Positive Autoregulatory Loop," Molecular and Cellular Biology 13(10):6231-6240, American Society for Microbiology, United States (Oct. 1993).
Hoffmann, J.A., et al., "Phylogenetic Perspectives in Innate Immunity," Science 284(5418):1313-1318, American Association for the Advancement of Science, United States (May 1999).
Holliger, P, and Hudson, P.J., "Engineered Antibody Fragments and the Rise of Single Domains," Nature Biotechnology 23(9):1126-1136, Nature America Publishing, United States (2005).
Hotchkiss, R.S. and Karl, I.E., "The Pathophysiology and Treatment of Sepsis," The New England Journal of Medicine 348(2):138-150, Massachusetts Medical Society, United States (Jan. 2003).
Houghten, R.A., et al., "The Use of Synthetic Peptide Combinatorial Libraries for the Identification of Bioactive Peptides," Biotechniques 13(3):412-421, Informa Healthcare USA, England (Sep. 1992).
Hsu, I.C., et al., "Detection of DNA Point Mutations with DNA Mismatch Repair Enzymes," Carcinogenesis 15(8):1657-1662, Irl Press, England (Aug. 1994).
Huston, J.S., et al., "Protein Engineering of Antibody Binding Sites: Recovery of Specific Activity in an Anti-digoxin Single-chain Fv Analogue Produced in *Escherichia coli*," Proceedings of the National Academy of Sciences USA 85(16):5879-5883, National Academy of Sciences, United States (Aug. 1988).

(56) References Cited

OTHER PUBLICATIONS

Huston, J.S., et al., "Protein Engineering of Single-chain Fv Analogs and Fusion Proteins," Methods in Enzymology 203:46-88, Academic Press, United States (1991).
Hybridization with Radioactive Probes, Current Protocols in Molecular Biology, John Wiley & Sons, N. Y. 6.3.1-6.3.6 (1989).
Hyrup, B. and Nielsen, P.E., "Peptide Nucleic Acids (PNA): Synthesis, Properties and Potential Applications," Bioorganic & Medicinal Chemistry 4(1):5-23, Elsevier Science, England (Jan. 1996).
Ill, C.R., et al., "Design and Construction of a Hybrid Immunoglobulin Domain With Properties of Both Heavy and Light Chain Variable Regions," Protein Engineering 10(8):949-957, IRL Press, England (1997).
Inoue, H., et al., "Sequence-dependent Hydrolysis of RNA using Modified Oligonucleotide Splints and RNase H," FEBS letters 215(2):327-330, Elsevier Science B.V, Netherlands (May 1987).
Inoue, H., et al., "Synthesis and Hybridization Studies on Two Complementary Nona(2'-O-Methyl) Ribonucleotides," Nucleic Acids Research 15(15):6131-6148, Oxford University Press, England (Aug. 1987).
International Search Report for International Application No. PCT/EP2012/074092, European Patent Office, Rijswijk, dated Jun. 20, 2013, 5 pages.
International Search Report for International Application No. PCT/EP2015/066501, European Patent Office, Rijswijk, dated Oct. 12, 2015, 6 pages.
Iwabuchi, K., et al., "Use of the two-hybrid system to identify the domain of p53 involved in oligomerization," Oncogene 8(6):1693-1696, (1993).
Jespers, L.S., et al., "Guiding the Selection of Human Antibodies from Phage Display Repertoires to a Single Epitope of an Antigen," Bio/technology 12(9):899-903, Wiley-Blackwell, United States (1994).
Jezek, Jan, et al., "Viscosity of concentrated therapeutic protein compositions", Advanced Drug Delivery Reviews, 2011, vol. 63, pp. 1107-1117.
Jobling, M.G. and Holmes, R.K., "Analysis of Structure and Function of the B Subunit of Cholera Toxin by the Use of Site-directed Mutagenesis," Molecular Microbiology 5(7):1755-1767, Blackwell Scientific Publications, England (Jul. 1991).
Kabat, E.A., et al., "Sequences of Proteins of Immunological Interest," 5th Edition, U.S. Department of Public Health and Human Services, Public Health Service, National Institutes of Health, Bethesda (1991).
Kabsch, W., "Integration, Scaling, Space-group Assignment and Post-refinement," Acta Crystallographica. Section D, Biological Crystallography 66(Pt 2):133-144, Wiley-Blackwell, United States (2010).
Kamerzell, Tim J., et al., "Protein-excipient interactions: Mechanisms and biophysical characterization applied to protein formulation development", Advanced Drug Delivery Reviews, 2011, vol. 63, pp. 1118-1159.
Kanai, S., et al., "Reversible Self-association of a Concentrated Monoclonal Antibody Solution Mediated by Fab-fab Interaction That Impacts Solution Viscosity," Journal of Pharmaceutical Sciences 97(10):4219-4227, Elsevier, United States (2008).
Kang, D., et al., "A Peptidoglycan Recognition Protein in Innate Immunity Conserved From Insects to Humans," Proceedings of the National Academy of Sciences of the United States of America 95(17):10078-10082, National Academy of Sciences, United States (Aug. 1998).
Karttunen, J. and Shastri, N., "Measurement of Ligand-induced Activation in Single Viable T Cells Using the lacZ Reporter Gene," Proceedings of the National Academy of Sciences of the United States of America 88(9):3972-3976, National Academy of Sciences, United States (1991).
Katsuura, M., et al., "CD48 Expression on Leukocytes in Infectious Diseases: Flow Cytometric Analysis of Surface Antigen," Acta Paediatrica Japonica 40(6):580-585, Blackwell Scientific, Australia (Dec. 1998).
Kaufman, R.J., et al., "Translational Efficiency of Polycistronic mRNAs and Their Utilization to Express Heterologous Genes in Mammalian Cells," The EMBO Journal 6(1):187-195, Wiley Blackwell, England (Jan. 1987).
Keane, J., et al., "Tuberculosis Associated With Infliximab, a Tumor Necrosis Factor Alpha-neutralizing Agent," The New England Journal of Medicine 345(15):1098-1104, Massachusetts Medical Society, United States (Oct. 2001).
Keen, J., et al., "Rapid Detection of Single Base Mismatches as Heteroduplexes on Hydrolink Gels," Trends in Genetics 7(1):5, Elsevier Trends Journals, England (Jan. 1991).
Kelker, M.S., et al., "Crystal Structure of Human Triggering Receptor Expressed on Myeloid Cells 1 (TREM-1) at 1.47 A," Journal of Molecular Biology 342(4): 1237-1248, Elsevier, England (2004).
Kessel, M. and Gruss, P., "Murine Developmental Control Genes," Science 249(4967):374-379, American Association for the Advancement of Science, United States (Jul. 1990).
Ketchem, Randal R., et al., "Mitigation of monoclonal antibody viscosity by modification of protein surface charge", American Chemical Society, 2012, vol. 243, p. 1.
Kettleborough, C.A., et al., "Isolation of Tumor Cell-specific Single-chain Fv From Immunized Mice Using Phage-antibody Libraries and the Re-construction of Whole Antibodies From These Antibody Fragments," European Journal of Immunology 24(4):952-958, Wiley-VCH, Germany (1994).
Kharitonenkov, A., et al., "FGF-21 as a Novel Metabolic Regulator," The Journal of Clinical Investigation 115(6):1627-1635, American Society for Clinical Investigation, United States (Jun. 2005).
Kharitonenkov, A., et al., "The Metabolic State of Diabetic Monkeys Is Regulated by Fibroblast Growth Factor-21," Endocrinology 148(2):774-781, Oxford University Press, United States (Feb. 2007).
Kiem, H.P., et al., "Retrovirus-mediated Gene Transduction Into Canine Peripheral Blood Repopulating Cells," Blood 83(6):1467-1473, American Society of Hematology, United States (Mar. 1994).
Knappik, A. and Pluckthun, A., "An Improved Affinity Tag Based on the Flag Peptide for the Detection and Purification of Recombinant Antibody Fragments," Biotechniques 17(4):754-761, Informa Healthcare USA, England (Oct. 1994).
Knudsen, L.B., "Glucagon-like Peptide-1: The Basis of a New Class of Treatment for Type 2 Diabetes," Journal of Medicinal Chemistry 47(17):4128-4134, American Chemical Society, United States (Aug. 2004).
Kohler, G., "Immunoglobulin Chain Loss in Hybridoma Lines," Proceedings of the National Academy of Sciences USA 77(4):2197-2199, National Academy of Sciences, United States (Apr. 1980).
Koller, B.H. And Smithies, O., "Inactivating the beta 2-Microglobulin Locus in Mouse Embryonic Stem Cells by Homologous Recombination," Proceedings of the National Academy of Sciences USA 86(22):8932-8935, National Academy of Sciences, United States (Nov. 1989).
Kozal, M.J., et al., "Extensive Polymorphisms Observed in HIV-1 Clade B Protease Gene Using High-density Oligonucleotide Arrays," Nature Medicine 2(7):753-759, Nature Publishing Company, United States (Jul. 1996).
Kozarsky, K.F. and Wilson, J.M., "Gene Therapy: Adenovirus Vectors," Current Opinion in Genetics & Development 3(3):499-503, Elsevier, England (Jun. 1993).
Kruse, C.A., et al., "Characterization of a Continuous Human Glioma Cell Line DBTRG-05MG: Growth Kinetics, Karyotype, Receptor Expression, and Tumor Suppressor Gene Analyses," In Vitro Cellular & Developmental Biology 28A(9-10):609-614, Tissue Culture Association, United States (Sep.-Oct. 1992).
Kubagawa, H., et al., "Biochemical Nature and Cellular Distribution of the Paired Immunoglobulin-like Receptors, PIR-A and PIR-B," The Journal of Experimental Medicine 189(2):309-318, Rockefeller University Press, United States (Jan. 1999).
Kunkel, T.A., et al., "Rapid and Efficient Site-specific Mutagenesis Without Phenotypic Selection," Methods in Enzymology 154:367-382, Academic Press, United States (1987).
Kurjan, J. and Herskowitz, I., "Structure of a Yeast Pheromone Gene (MF Alpha): A Putative Alpha-factor Precursor Contains Four Tandem Copies of Mature Alpha-factor," Cell 30(3):933-943, Cell Press, United States (Oct. 1982).

(56) References Cited

OTHER PUBLICATIONS

Kwoh, D.Y., et al., "Transcription-Based Amplification System and Detection of Amplified Human Immunodeficiency Virus Type 1 with a Bead-Based Sandwich Hybridization Format," Proceedings of the National Academy of Sciences of the United States of America 86(4):11731177, National Academy of Sciences, United States (1989).
Lakso, M., et al., "Targeted Oncogene Activation by Site-specific Recombination in Transgenic Mice," Proceedings of the National Academy of Sciences 89(14):6232-6236, National Academy of Sciences, United States (Jul. 1992).
Lam, K.S., "Application of Combinatorial Library Methods in Cancer Research and Drug Discovery," Anticancer Drug Design 12(3):145-67, (1997).
Lam, K.S., et al., "A New Type of Synthetic Peptide Library for Identifying Ligand-Binding Activity," Nature 354:82-84, Nature Publishing Group, United States (1991).
Landegren, U., et al., "A Ligase-mediated Gene Detection Technique," Science 241(4869):1077-1080, American Association for the Advancement of Science, United States (Aug. 1988).
Lane, P., et al., "CD40 Ligand-independent B Cell Activation Revealed by CD40 Ligand-deficient T Cell Clones: Evidence for Distinct Activation Requirements for Antibody Formation and B Cell Proliferation," European Journal of Immunology 25(6):1788-1793, Wiley-VCH, Germany (Jun. 1995).
Lanier, L.L., "NK Cell Receptors," Annual Review of Immunology 16:359-393, Annual Reviews Inc., United States (1998).
Lanier, L.L., et al., "Immunoreceptor DAP12 Bearing a Tyrosine-based Activation Motif Is Involved in Activating NK Cells," Nature 391(6668):703-707, Nature Publishing Group, England (Feb. 1998).
Lantz, M., et al., "Characterization in Vitro of a Human Tumor Necrosis Factor-binding Protein. A Soluble Form of a Tumor Necrosis Factor Receptor," The Journal of Clinical Investigation 86(5):1396-1402, American Society for Clinical Investigation, United States (Nov. 1990).
Larin, S.S., et al., "Immunotherapy with Autologous Tumor Cells Engineered to Secrete Tag7/PGRP, an Innate Immunity Recognition Molecule," Gene Medicine 6(7):798-808, John Wiley & Sons, England (Jul. 2004).
Lemaitre, M., et al., "Specific Antiviral Activity of a Poly (L-Lysine)-Conjugated Oligodeoxyribonucleotide Sequence Complementary to Vesicular Stomatitis Virus N Protein mRNA Initiation Site," Proceedings of the National Academy of Sciences 84(3):648-652, National Academy of Science, United States (Feb. 1987).
Letsinger, R.L., et al., "Cholesteryl-conjugated Oligonucleotides: Synthesis, Properties, and activity as Inhibitors of Replication of Human Immunodeficiency Virus in Cell Culture," Proceedings of the National Academy of Sciences USA 86(17):6553-6556, National Academy of Science, United States (Sep. 1989).
Li, E., et al., "Targeted Mutation of the DNA Methyltransferase Gene Results in Embryonic Lethality," Cell 69(6):915-926, Cell Press, United States (Jun. 1992).
Liu, J., et al., "Reversible Self-association Increases the Viscosity of a Concentrated Monoclonal Antibody in Aqueous Solution," Journal of Pharmaceutical Sciences 94(9):1928-1940, Elsevier, United States (2005).
Lizardi, M.P., et al., "Exponential Amplification of Recombinant—RNA Hybridization Probes," Nature Biotechnology 6:1197-1202 (1988).
Loeffler, J.P., et al., "Gene Transfer Into Primary and Established Mammalian Cell Lines With Lipopolyamine-coated DNA," Methods in Enzymology 217:599-618, Academic Press, United States (1993).
Lolis, E. and Bucala, R., "Therapeutic Approaches to Innate Immunity: Severe Sepsis and Septic Shock," Nature Reviews. Drug Discovery 2(8):635-645, Nature Pub. Group, England (Aug. 2003).
Lonberg, N. and Huszar, D., "Human Antibodies from Transgenic Mice," International Reviews of Immunology 13(1):65-93, Informa Healthcare, England (1995).
Lowy, I., et al., "Isolation of Transforming DNA: Cloning the Hamster aprt Gene," Cell 22(3):817-823, Cell Press, United States (Dec. 1980).
LS Bio/LifeSpan BioSciences, Inc., Pglyrp1 1 pgrp antibody (ls-c38137), accessed at http://www.lsbio .com/a nti bod ies/PG LY RP 1-PG RP-Antibody-LS-C38137/37645.
LS Bio/LifeSpan BioSciences, Inc., Pglyrp1/ Pgrp antibody (ls-c579), accessed at http://www.lsbio.com/Antibodies/PGLY RP1-PGRP-Antibody-LS-0579/2801.
LS Bio/LifeSpan BioSciences, Inc., Pglyrpl/ pgrp antibody (ls-b4940), accessed at http://www.lsbio.com/Antibodies/PGLY RP1-PGRP-Antibody-LS-B4940/128350.
LS Bio/LifeSpan BioSciences, Inc., Pglyrpl/ pgrp antibody (ls-c578), accessed at http://www.lsbio.com/Antibodies/PGLY RP1-PGRP-Antibody-LS-C578/2800.
Lucklow, V.A., et al., "High Level Expression of Nonfused Foreign Genes With Autographa Californica Nuclear Polyhedrosis Virus Expression Vectors," Virology 170(1):31-39 (1989).
Madura, K., et al., "N-recognin/Ubc2 interactions in the N-end rule pathway," The Journal of Biological Chemistry 268(16):12046-12054, The American Society for Biochemistry and Molecular Biology, Inc., United States (1993).
Mag, M., et al., "Synthesis and Selective Cleavage of Oligodeoxyribonucleotides Containing Non-chiral Internucleotide Phosphoramidate Linkages," Nucleic Acids Research 17(15):5973-5988 (Aug. 1989).
Maher, L.J., et al., "DNA Triple-helix Formation: an Approach to Artificial Gene Repressors?," BioEssays 14(12):807-815, Wiley, United States (Dec. 1992 ).
Malaviya, R., et al., "Mast Cell Modulation of Neutrophil Influx and Bacterial Clearance at Sites of Infection Through TNF-alpha," Nature 381(6577):77-80, Nature Publishing Group, England (May 1996).
Mandell, J.G., et al., "Identification of Protein-protein Interfaces by Decreased Amide Proton Solvent Accessibility," Proceedings of the National Academy of Sciences of the United States of America 95(25):14705-14710, National Academy of Sciences, United States (1998).
Mansart, A., et al., "Hemodynamic Effects of Early Versus Late Glucocorticosteroid Administration in Experimental Septic Shock," Shock 19(1):38-44, Lippincott Williams & Wilkins, United states (Jan. 2003).
Mastrangeli, A., et al., "Diversity of Airway Epithelial Cell Targets for In Vivo Recombinant Adenovirus-Mediated Gene Transfer," Journal of Clinical Investigation 91(1):225-234, American Society for Clinical Investigation, United States (Jan. 1993).
Maxam, A.M. And Gilbert, W., "A New Method for Sequencing DNA," Proceedings of the National Academy of Sciences USA 74(2):560-564, National Academy of Sciences, United States (Feb. 1977).
McNamara, M.J., et al., "Interleukin-1 Receptor Antibody (Il-1rab) Protection and Treatment Against Lethal Endotoxemia in Mice," Journal of Surgical Research 54(4):316-321, Academic Press, United States (Apr. 1993).
Medzhitov, R., et al., "Innate Immunity," The New England Journal of Medicine 343(5):338-344, Massachusetts Medical Society, United States (Aug. 2000).
Micanovic, R., et al., "Different Roles of N- and C-Termini in the Functional Activity of FGF21 ," Journal of Cellular Physiology 219(2):227-234, Wiley-Liss, United States (May 2009).
Michael, S.F., et al., "Mutagenesis by Incorporation of a Phosphorylated Oligo During PCR Amplification," BioTechniques 16(3):410-412, Informa Healthcare USA, England (Mar. 1994).
Miller, A.D., et al., "Use of Retroviral Vectors for Gene Transfer and Expression," Methods in Enzymology 217:581-599, Academic Press, United States (1993).
Mohamadzadeh, M., et al., "Activation of Triggering Receptor Expressed on Myeloid Cells-1 on Human Neutrophils by Marburg and Ebola Viruses," Journal of Virology 80(14):7235-7244, American Society for Microbiology, United States (Jul. 2006).
Molloy, E.J., "Triggering Receptor Expressed on Myeloid Cells (TREM) Family and the Application of its Antagonists," Recent

(56) References Cited

OTHER PUBLICATIONS

Patents on Anti-infective Drug Discovery 4(1):51-56, Bentham Science Publishers, Netherlands (2009).
Morgan, R.A. and Anderson, W.F., "Human Gene Therapy," Annual Review of Biochemistry 62:191-217, Annual Reviews, United States (1993).
Mori, S.I., et al., "A Novel Amino Acid Substitution at the Receptor-binding Site on the Hemagglutinin of H3N2 Influenza a Viruses Isolated From 6 Cases With Acute Encephalopathy During the 1997-1998 Season in Tokyo," Archives of Virology 144(1):147-155, Springer-Verlag, Austria (1999).
Morrison, D.C., et al., "Endotoxins and Disease Mechanisms," Annual Review of Medicine 38:417-432, Annual Reviews, United States (1987).
Morrison, S.L., "Transfectomas Provide Novel Chimeric Antibodies," Science 229(4719):1202-1207, Association for the Advancement of Science, United States (Sep. 1985).
Mulligan, R.C. and Berg, P., "Selection for Animal Cells that Express the *Escherichia coli* Gene Coding for Xanthine-guanine Phosphoribosyltransferase," Proceedings of the National Academy of Sciences USA 78(4):2072-2076, National Academy of Sciences, United States (Apr. 1981).
Mulligan, R.C., "The Basic Science of Gene Therapy," Science 260(5110):926-932, American Association for the Advancement of Science, United States (1993).
Mullinax, R.L., et al., "Expression of a Heterodimeric Fab Antibody Protein in One Cloning Step," BioTechniques 12(6):864-869, Informa Healthcare, England (1992).
Murakami, Y., et al., "Intervention of an Inflammation Amplifier, Triggering Receptor Expressed on Myeloid Cells 1, for Treatment of Autoimmune Arthritis," Arthritis and Rheumatism 60(6):1615-1623, Wiley-Blackwell, United States (Jun. 2009).
Murshudov, G.N., et al., "Refinement of Macromolecular Structures by the Maximum-likelihood Method," Acta Crystallographica. Section D, Biological Crystallography 53(Pt 3):240-255, Wiley-Blackwell, United States (1997).
Myers, R.M., et al., "Detection of Single Base Substitutions by Ribonuclease Cleavage at Mismatches in RNA:DNA Duplexes," Science 230(4731):1242-1246, American Association for the Advancement of Science, United States (Dec. 1985 ).
Myers, R.M., et al., "Detection of Single Base Substitutions in Total Genomic DNA," Nature 313(6002):495-498, Nature Publishing Group, England (Feb. 1985).
Nakajima, H., et al., "2B4: an Nk Cell Activating Receptor With Unique Specificity and Signal Transduction Mechanism," Human Immunology 61(1):39-43, Elsevier/North-Holland, United States (Jan. 2000).
Nakajima, H., et al., "Cutting Edge: Human Myeloid Cells Express an Activating Ilt Receptor (ILT1) That Associates With Fc Receptor Gamma-chain," Journal of Immunology 162(1):5-8, American Association of Immunologists, United States (Jan. 1999).
Nakazawa, H., et al., "UV and Skin Cancer: Specific P53 Gene Mutation in Normal Skin as a Biologically Relevant Exposure Measurement," Proceedings of the National Academy of Sciences USA 91(1):360-364 (Jan. 1994).
Naramura, M., et al., "Mechanisms of Cellular Cytotoxicity Mediated by a Recombinant Antibody-IL2 Fusion Protein Against Human Melanoma Cells," Immunology Letters 39(1):91-99 (Dec. 1993).
Nathan, C. and Ding, A., "TREM-1: A New Regulator of Innate Immunity in Sepsis Syndrome," Nature Medicine 7(5):530-532, Nature Publishing Company, United States (May 2001).
Nauck, M.A. and Meier, J.J., "Glucagon-like Peptide 1 and Its Derivatives in the Treatment of Diabetes," Regulatory Peptides 128(2):135-148, Elsevier/North Holland, Netherlands (Jun. 2005).
Nederman, T., et al., "An in Vitro Bioassay for Quantitation of Human Interferons by Measurements of Antiproliferative Activity on a Continuous Human Lymphoma Cell Line," Biologicals 18(1):29-34, Academic Press, England (Jan. 1990).
Ngo, J.T., et al., "The Protein Folding Problem and Tertiary Structure Prediction, Chapter 14: Computational Complexity Protein Structure Prediction, and the Levinthal Paradox," 492-495 (Mar. 1995).
Nicoletti, I., et al., "A Rapid and Simple Method for Measuring Thymocyte Apoptosis by Propidium Iodide Staining and Flow Cytometry," Journal of Immunological Methods 139(2):271-279, Elsevier, Netherlands (Jun. 1991).
O'Gorman, S., et al., "Recombinase-Mediated Gene Activation and Site-specific Integration in Mammalian Cells," Science 251(4999):1351-1355, American Association for the Advancement of Science, United States (Mar. 1991).
O'Hare, K., et al., "Transformation of Mouse Fibroblasts to Methotrexate Resistance by a Recombinant Plasmid Expressing a Prokaryotic Dihydrofolate Reductase," Proceedings of the National Academy of Sciences USA 78(3):1527-1531, National Academy of Sciences, United States (Mar. 1981).
Ohlsson, K., et al., "Interleukin-1 Receptor Antagonist Reduces Mortality from Endotoxin Shock," Nature 348(6301):550-552, Nature Publishing Group, England (Dec. 1990).
Oi, V.T. and Morrison, S.L., "Chimeric Antibodies," BioTechniques 4(3):214-221 (1986).
Oishi, K., et al., "Inhibition of Neutrophil Apoptosis by Antioxidants in Culture Medium," Scandinavian Journal of Immunology 45(1):21-27, Blackwell Scientific Publications, England (Jan. 1997 ).
Oliveira, J.S., et al., "Fungal Infections in Marrow Transplant Recipients Under Antifungal Prophylaxis With Fluconazol," Brazilian Journal of Medical and Biological Research 35(7):789-798, Brazilian Association of Scientific Dissemination, Brazil ( Jul. 2002 ).
Olopade, O.I., et al., "Molecular Analysis of Deletions of the Short Arm of Chromosome 9 in Human Gliomas," Cancer Research 52(9):2523-2529, American Association for Cancer Research, United States (May 1992).
Orita, M., et al., "Detection of Polymorphisms of Human DNA by Gel Electrophoresis as Single-strand Conformation Polymorphisms," Proceedings of the National Academy of Sciences USA 86(8):2766-2770, National Academy of Sciences, United States (Apr. 1989 ).
Osanai, A., et al., "Mouse Peptidoglycan Recognition Protein PGLYRP-1 Plays a Role in the Host Innate Immune Response Against Listeria Monocytogenes Infection," Infection and Immunity 79(2):858-866, American Society for Microbiology, United States (Feb. 2011).
Owerbach, D., et al., "Genetics of the Large, External, Transformation-sensitive(LETS) Protein: Assignment of a Gene Coding for Expression of Lets to Human Chromosome 8," Proceedings of the National Academy of Sciences USA 75(11):5640-5644, National Academy of Sciences, United States (Nov. 1978 ).
Padlan, E.A., "A Possible Procedure for Reducing the Immunogenicity of Antibody Variable Domains While Preserving their Ligand-binding Properties," Molecular Immunology 28(4-5):489-498, Pergamon Press., England (Apr. 1991).
Pajunen, L., et al., "Assignment of the Gene Coding for Both the Beta-subunit of Prolyl 4-hydroxylase and the Enzyme Disulfide Isomerase to Human Chromosome Region 17p11---- qter," Cytogenetics and Cell Genetics 47(1-2):37-41, Karger, Switzerland (1988).
Pant, S.,D., et al. "Bovine PGLYRP1 Polymorphisms and their Association with Resistance to *Mycobacterium avium* ssp. *Paratuberculosis*," Animal Genetics 42(4):354-360, Wiley-Blackwell, England (Aug. 2011).
Perry-O'Keefe, H., et al., "Peptide Nucleic Acid Pre-gel Hybridization: an Alternative to Southern Hybridization," Proceedings of the National Academy of Sciences of the United States of America 93(25):14670-14675, National Academy of Sciences, United States (1996).
Persic, L., et al., "An Integrated Vector System for the Eukaryotic Expression of Antibodies or Their Fragments After Selection From Phage Display Libraries," Gene 187(1):9-18, Elsevier/North-Holland, Netherlands (1997).
Peschon, J.J., et al., "TNF Receptor-Deficient Mice Reveal Divergent Roles for P55 and P75 in Several Models of Inflammation," Journal of Immunology 160(2):943-952, American Association of Immunologists, United States (Jan. 1998 ).

(56) References Cited

OTHER PUBLICATIONS

Petersen, K.H., et al., "A Pna-Dna Linker Synthesis of N-((4,4'-dimethoxytrityloxy)ethyl)-N-(Thymin-1-ylacetyl)glycine," Bioorganic & Medicinal Chemistry Letters 5:1119-1124 (1995).
Pfeffer, K., et al., "Mice Deficient for the 55 Kd Tumor Necrosis Factor Receptor are Resistant to Endotoxic Shock, Yet Succumb to L. Monocytogenes Infection," Cell 73(3):457-467, Cell Press, United States (May 1993 ).
Phua, J., et al., "Soluble Triggering Receptor Expressed on Myeloid Cells-1 in Acute Respiratory Infections," The European Respiratory Journal 28(4):695-702, European Respiratory Society, England (Oct. 2006).
Pinkert, C.A., et al., "An Albumin Enhancer Located 10 Kb Upstream Functions Along With Its Promoter to Direct Efficient, Liver-specific Expression in Transgenic Mice," Genes & Development 1(3):268-276, Cold Spring Harbor Laboratory Press, United States (May 1987).
Pittelkow, M.R. and Scott, R.E., "New Techniques for the in Vitro Culture of Human Skin Keratinocytes and Perspectives on Their Use for Grafting of Patients With Extensive Burns," Mayo Clinic Proceedings 61(10):771-777, Elsevier, England (Oct. 1986).
Potterton, E., et al., "A Graphical User Interface to the CCP4 Program Suite," Acta Crystallographica. Section D, Biological Crystallography 59(Pt 7):1131-1137, Wiley-Blackwell, United States (2003).
Poukoulidou, T., et al., "TREM-1 Expression on Neutrophils and Monocytes of Septic Patients: Relation to the Underlying Infection and the Implicated Pathogen," BMC Infectious Diseases 11(1): 8 pages, BioMed Central, England (Nov. 2011).
Prosser, J., "Detecting Single-base Mutations," Trends in Biotechnology 11(6):238-246, Elsevier Science Publishers, England (Jun. 1993).
Proudfoot, N.J., "Transcriptional Interference and Termination Between Duplicated Alpha-globin Gene Constructs Suggests a Novel Mechanism for Gene Regulation," Nature 322(6079):562-565, Nature Publishing Group, England (1986).
Purified anti-human CD354 TREM-1 Antibody, accessed at, https//www.biolegend.com/en-us/products/purified-anti-human-cd354-trem-1 -- antibody-2826, last accessed on Jun. 12, 2018, 3 pages.
Queen, C. and Baltimore, D., "Immunoglobulin Gene Transcription Is Activated by Downstream Sequence Elements," Cell 33(3):741-748, Cell Press, United States (Jul. 1983).
R&D Systems: "Human TREM-1 Antibody," Retrieved from the internet< URL: http://www.mdsystems.com/Products/MAB1278> on Oct. 26, 2010, p. 1, XP002688074.
Radaev, S., et al., "Crystal Structure of the Human Myeloid Cell Activating Receptor TREM-1," Structure 11(12):1527-1535, Cell Press, United States (Dec. 2003).
Radany, E.H., et al., "Directed Establishment of Rat Brain Cell Lines With the Phenotypic Characteristics of Type 1 Astrocytes," Proceedings of the National Academy of Sciences of the United States of America 89(14):6467-6471, National Academy of Sciences, United States (Jul. 1992).
Ramanathan, B., et al., "Cloning of Porcine Triggering Receptor Expressed on Myeloid Cells-1 (TREM-1) and its Induction by Lipopolysaccharide, Peptidoglycan, and *Salmonella enterica* Serovar *Typhimurium* Infection," Developmental and Comparative Immunology 29(1):1-7, Elsevier Science, United States (2005).
Redl, H., et al., "Animal Models as the Basis of Pharmacologic Intervention in Trauma and Sepsis Patients," World Journal of Surgery 20(4):487-492, Springer International, United States (May 1996).
Rheinwald, J.G., "Chapter 15 Serial Cultivation of Normal Human Epidermal Keratinocytes," Methods in Cell Biology 21A:229-254, Academic Press, United States (1980).
Riechmann, L., et al., "Reshaping Human Antibodies for Therapy," Nature 332(6162):323-327, Nature Publishing Group, United States (Mar. 1988).
Riedemann, N.C., et al., "Novel Strategies for the Treatment of Sepsis," Nature Medicine 9(5):517-524, Nature Publishing Company, United States (May 2003).
Roguska, M.A., et al., "Humanization of Murine Monoclonal Antibodies through Variable Domain Resurfacing," Proceedings of the National Academy of Sciences USA 91(3):969-973, National Academy of Sciences, United States (Feb. 1994).
Rosenbaum, V. and Riesner, D., "Temperature-gradient Gel Electrophoresis. Thermodynamic Analysis of Nucleic Acids and Proteins in Purified Form and in Cellular Extracts," Biophysical Chemistry 26(2-3):235-246, Elsevier Science B.V, Netherlands (May 1987).
Rosenberg, H.F, and Gallin, J.I., "Inflammation," In Fundamental Immunology, 4th Ed. W. E. Paul, ed., Chapter 32, p. 1051-1058, Lippincott-Raven Publishers, 1999.
Rosenfeld, M.A., et al., "Adenovirus-mediated Transfer of a Recombinant alpha 1-antitrypsin Gene to the Lung Epithelium in Vivo," Science 252(5004):431-434, American Association for the Advancement of Science, United States (Apr. 1991).
Rosenfeld, M.A., et al., "In Vivo Transfer of the Human Cystic Fibrosis Transmembrane Conductance Regulator Gene to the Airway Epithelium," Cell 68(1):143-155, Cell Press, United States (Jan. 1992).
Rothe, J., et al., "Mice Lacking the Tumour Necrosis Factor Receptor 1 are Resistant to TNF-mediated Toxicity but Highly Susceptible to Infection by Listeria Monocytogenes," Nature 364(6440):798-802, Nature Publishing Group, England (Aug. 1993).
Royet, J., et al., "Peptidoglycan Recognition Proteins: Modulators of the Microbiome and Inflammation," Nature Reviews Immunology 11(12):837-851, Nature Pub. Group, England (Nov. 2011).
Saha, S., et al, "Peptidoglycan Recognition Proteins Protect Mice from Experimental Colitis by Promoting Normal Gut Flora and Preventing Induction of Interferon-Gamma," Cell Host & Microbe 8(2):147-162, Cell Press, United States (Aug. 2010).
Saha, S, et al., "PGLYRP-2 and Nod2 are both Required for Peptidoglycan-Induced Arthritis and Local Inflammation," Cell Host & Microbe 5(2):137-150, Cell Press, United States (Feb. 2009).
Saiki, R.K., et al., "Analysis of Enzymatically Amplified Beta-globin and HLA-DQ Alpha DNA With Allele-specific Oligonucleotide Probes," Nature 324(6093):163-166, Nature Publishing Group, England (Nov. 1986).
Saiki, R.K., et al., "Genetic Analysis of Amplified DNA With Immobilized Sequence-specific Oligonucleotide Probes," Proceedings of the National Academy of Sciences of the United States of America 86(16):6230-6234, National Academy of Sciences, United States (Aug. 1989).
Saleeba, J.A. and Cotton, R.G., "Chemical Cleavage of Mismatch to Detect Mutations," Methods in Enzymology 217:286-295, Academic Press, United States (1993).
Sallusto, F., et al., "Efficient Presentation of Soluble Antigen by Cultured Human Dendritic Cells Is Maintained by Granulocyte/macrophage Colony-stimulating Factor Plus Interleukin 4 and Downregulated by Tumor Necrosis Factor Alpha," The Journal of Experimental Medicine 179(4):1109-1118, Rockefeller University Press, United States (1994).
Salmons, B. and Gunzburg, W.H., "Targeting of Retroviral Vectors for Gene Therapy," Human Gene Therapy 4(2):129-141, Liebert, United States (Apr. 1993).
Sanger, F., et al., "DNA Sequencing With Chain-terminating Inhibitors," Proceedings of the National Academy of Sciences of the United States of America 74(12):5463-5467, National Academy of Sciences, United States (Dec. 1977).
Santerre, R.F., et al., "Expression of Prokaryotic Genes for Hygromycin B and G418 Resistance as Dominant-selection Markers in Mouse L Cells," Gene 30(1-3):147-156, Elsevier/North-Holland, Netherlands (Oct. 1984).
Sawai, H., et al., "Direct Production of the Fab Fragment Derived From the Sperm Immobilizing Antibody Using Polymerase Chain Reaction and cDNA Expression Vectors," American Journal of reproductive immunology 34(1):26-34, Wiley-Blackwell, Denmark (1995).

(56) References Cited

OTHER PUBLICATIONS

Schultz, L.D., et al., "Expression and Secretion in Yeast of a 400-kDa Envelope Glycoprotein Derived From Epstein-Barr Virus," Gene 54(1):113-123, Elsevier/North-Holland, Netherlands (1987).
Scott, J.K. and Smith, G.P., "Searching for peptide ligands with an epitope library," Science 249(4967):386-390, American Association for the Advancement of Science, United States (1990).
Seed, B., "An LFA-3 cDNA Encodes a Phospholipid-linked Membrane Protein Homologous to its Receptor CD2," Nature 329(6142):840-842, Nature Publishing Group, England (Oct. 1987).
Sharif, O. and Knapp, S., "From Expression to Signaling: Roles of TREM-1 and TREM-2 in Innate Immunity and Bacterial Infection," Immunobiology 213(9-10):701-713, Elsevier, Netherlands (2008).
Shu, L., et al., "Secretion of a Single-gene-encoded Immunoglobulin From Myeloma Cells," Proceedings of the National Academy of Sciences of the USA 90(17):7995-7999, National Academy of Sciences, United States (1993).
Skerra, A. and Pluckthun, A., "Assembly of a Functional Immunoglobulin Fv Fragment in *Escherichia coli*," Science 240(4855):1038-1041, Association for the Advancement of Science, United States (May 1988).
Skolnick, "From Genes to Protein Stucture and Function: Novel Applications of Computational Approaches in the Genomic era," Trends in Biotechnology 18:34-39, Elsevier Science Publishers, London (Jan. 2000).
Smith, D.B. and Johnson, K.S., "Single-step Purification of Polypeptides Expressed in *Escherichia coli* as Fusions with Glutathione 5-transferase," Gene 67(1):31-40, Elsevier, Netherlands (Jul. 1988).
Smith, G.E., et al., "Production of Human Beta Interferon in Insect Cells Infected With a Baculovirus Expression Vector," Molecular and Cellular Biology 3(12):2156-2165, American Society for Microbiology, United States (Dec. 1983).
Smith, T.F. and Zhang, X., "The Challenges of Genome Sequence Annotation or "The Devil is in the Details"," Nature Biotechnology 15(12):1222-1223, Nature America Publishing, United States (Nov. 1997).
Springer, T.A., "Traffic Signals for Lymphocyte Recirculation and Leukocyte Emigration: The Multistep Paradigm," Cell 76(2):301-314, Cell Press, United States (Jan. 1994).
Standen, J. and Bihari, D., "Septic Shock," The New England Journal of Medicine 343:447-448 (Aug. 2010).
Steiner, H., "Peptidoglycan Recognition Proteins: On and Off Switches for Innate Immunity," Immunological Reviews 198:83-96, Blackwell, England (Apr. 2004).
Stemple, D.L. and Anderson, D.J., "Isolation of a Stem Cell for Neurons and Glia From the Mammalian Neural Crest," Cell 71(6):973-985, Cell Press, United States (Dec. 1992).
Stone, R., "Search for Sepsis Drugs Goes on Despite Past Failures," Science 264(5157):365-367, American Association for the Advancement of Science, United States (Apr. 1994).
Studnicka, G.M., et al., "Human-Engineered Monoclonal Antibodies Retain Full Specific Binding Activity by Preserving Non-CDR Complementarity-Modulating Residues," Protein Engineering 7(6):805-814, Oxford University Press, England (1994).
Sugimoto, T., et al., "Determination of Cell Surface Membrane Antigens Common to Both Human Neuroblastoma and Leukemia-lymphoma Cell Lines by a Panel of 38 Monoclonal Antibodies," Journal of the National Cancer Institute 73(1):51-57, Oxford University Press, United States (Jul. 1984).
Sullivan, G.W., et al., "Interaction of Tumor Necrosis Factor-alpha and Granulocyte Colony-stimulating Factor on Neutrophil Apoptosis, Receptor Expression, and Bactericidal Function," Proceedings of the Association of American Physicians 108(6):455-466, Blackwell Science, Inc., United States (Nov. 1996).
Szybalska, E.H. and Szybalski, W., "Genetics of Human Cess Line IV DNA-mediated Heritable Transformation of a Biochemical Trait," Proceedings of the National Academy of Sciences USA 48:2026-2034, National Academy of Sciences, United States (Dec. 1962).
Tessarz, A.S. and Cerwenka, A., "The TREM-1/DAP12 Pathway," Immunology Letters 116(2):111-116, Elsevier/North-Holland Biomedical Press, Netherlands (Mar. 2008).
Thomas, K.R. and Capecchi, M.R., "Site-directed Mutagenesis by Gene Targeting in Mouse Embryo-derived Stem Cells," Cell 51(3):503-512, Cell Press, United States (Nov. 1987).
Thoma-Uszynski, S., et al., "Induction of Direct Antimicrobial Activity Through Mammalian Toll-like Receptors," Science 291(5508):1544-1547, American Association for the Advancement of Science, United States (Feb. 2001).
Thorpe, Antibody Carriers of Cytotoxic Agents in Cencer Therapy: A Review, in Monoclonal Antibodies 84: Biological and Clinical Applications, Pinchera et al., eds., pp. 475-506 (1985).
Thorpe, P.E. and Ross, W.C., "The Preparation and Cytotoxic Properties of Antibody-toxin Conjugates," Immunological Reviews 62:119-158, Blackwell, England (1982).
Tolstoshev, P., "Gene Therapy, Concepts, Current Trials and Future Directions," Annual Review of Pharmacology and Toxicology 33:573-596, Annual Reviews, United States (1993).
Tomasello, E., et al., "Combined Natural Killer Cell and Dendritic Cell Functional Deficiency in KARAP/DAP12 Loss-of-function Mutant Mice," Immunity 13(3):355-364, Cell Press, United States (Sep. 2000).
Tomic, M., et al., "A Rapid and Simple Method for Introducing Specific Mutations Into Any Position of DNA Leaving All Other Positions Unaltered," Nucleic Acids Research 18(6):1656, Oxford University Press, England (Mar. 1990 ).
Tracey, K.J., et al., "Shock and Tissue Injury Induced by Recombinant Human Cachectin," Science 234(4775):470-474, American Association for the Advancement of Science, United States (1986).
Traunecker, A., et al., "Myeloma Based Expression System for Production of Large Mammalian Proteins," Trends in Biotechnology 9(4):109-113, Elsevier Science Publisher, England ( Apr. 1991).
Trowbridge, R.S., et al. , "Establishment and Characterization of Ferret Cells in Culture," In Vitro 18(11):952-960, Tissue Culture Assn, United States (Nov. 1982).
Tsuji, E., et al., "Simultaneous Onset of Acute Inflammatory Response, Sepsis-like Symptoms and Intestinal Mucosal Injury After Cancer Chemotherapy," International Journal of Cancer 107(2):303-308, Wiley-Liss, United States (Nov. 2003).
Turnbull, I.R., et al., "Cutting Edge: TREM-2 Attenuates Macrophage Activation," Journal of Immunology 177(6):3520-3524, American Association of Immunologists, United States (Sep. 2006).
Ulevitch, R.J., et al. , "Recognition of Gram-negative Bacteria and Endotoxin by the Innate Immune System," Current Opinion in Immunology 11(1):19-22, Elsevier, England (Feb. 1999 ).
Upender, M., et al. , "Megaprimer Method for in Vitro Mutagenesis Using Parallel Templates," Biotechniques 18(1):29-30, Informa Healthcare USA, Inc, England (Jan. 1995).
Urban, M.B., et al., "NF-kappa B Contacts DNA by a Heterodimer of the p50 and p65 Subunit," The EMBO Journal 10(7):1817-1825, Wiley Blackwell, England (Jul. 1991).
Van Der Krol, A.R., et al., "Modulation of Eukaryotic Gene Expression by Complementary RNA or DNA Sequences," Biotechniques 6(10):958-976, Informa Healthcare, United States (Nov. 1988).
Van Keuren, M., et al. , "Regional Assignment of Human Liver-Type 6-Phosphofructokinase to Chromosome 21q22.3 by Using Somatic Cell Hybrids and a Monoclonal Anti-L Antibody," Human Genetics 74(1):34-40, Springer Verlag, Germany (Sep. 1986 ).
Van Zee, K.J., et al., "Tumor Necrosis Factor Soluble Receptors Circulate During Experimental and Clinical Inflammation and Can Protect Against Excessive Tumor Necrosis Factor Alpha in Vitro and in Vivo," Proceedings of the National Academy of Sciences of the United States of America 89(11):4845-4849, National Academy of Sciences, United States (Jun. 1992).
Vincent, J.L., et al., "Clinical Trials of Immunomodulatory Therapies in Severe Sepsis and Septic Shock," Clinical Infectious Diseases 34(8):1084-1093, Oxford University Press, United States (Apr. 2002).
Wada, K.N., et al. , "Codon Usage Tabulated From the Genbank Genetic Sequence Data," Nucleic Acids Research 20:2111-2118, Oxford University Press, England (May 1992).

(56) References Cited

OTHER PUBLICATIONS

Wakayama, T., et al., "Mice Cloned From Embryonic Stem Cells," Proceedings of the National Academy of Sciences of the United States of America 96(26):14984-14989, National Academy of Sciences, United States (Dec. 1999).
Walsh, C.E., et al., "Gene Therapy for Human Hemoglobinopathies," Proceedings of the Society for Experimental Biology and Medicine 204(3):289-300, Blackwell Science, United States (Dec. 1993).
Wang, H., et al., "HMG-1 as a Late Mediator of Endotoxin Lethality in Mice," Science 285(5425):248-251, American Association for the Advancement of Science, United States (1999).
Wang, Q., et al., "A Packaging Cell Line for Propagation of Recombinant Adenovirus Vectors Containing Two Lethal Gene-region Deletions," Gene Therapy 2(10):775-783, Nature Publishing Group, England (Dec. 1995).
Warren, H.S., "Strategies for the Treatment of Sepsis," The New England Journal of Medicine 336(13):952-953, Massachusetts Medical Society, United States (Mar. 1997).
Wasmuth, H.E., et al., "Patients With Acute on Chronic Liver Failure Display "Sepsis-like" Immune Paralysis," Journal of Hepatology 42(2):195-201, Elsevier, Netherlands (Feb. 2005).
Weintraub, H., et al., "Anti-sense RNA as a Molecular Tool for Genetic Analysis," Trends in Genetics 1:22-25 (1985).
Weis, D.D., et al., "Semi-automated Data Processing of Hydrogen Exchange Mass Spectra Using HX-express," Journal of the American Society for Mass Spectrometry 17(12):1700-1703, Springer, United States (2006).
Wells, J.A., "Additivity of Mutational Effects in Proteins," Biochemistry 29(37):8509-8517, American Chemical Society, United States (Sep. 1990).
Wheeler, A.P. and Bernard, G.R., "Treating Patients With Severe Sepsis," The New England Journal of Medicine 340(3):207-214, Massachusetts Medical Society, United States (Jan. 1999).
Wigler, M., et al., "Transfer of Purified Herpes Virus Thymidine Kinase Gene to Cultured Mouse Cells," Cell 11(1):223-232, Cell Press, United States (May 1977).
Wigler, M., et al., "Transformation of Mammalian Cells with an Amplifiable Dominant-Acting Gene," Proceedings of the National Academy of Sciences USA 77(6):3567-3570, National Academy of Sciences, United States (Jun. 1980).
Wilmut, I., et al., "Viable Offspring Derived From Fetal and Adult Mammalian Cells," Nature 385(6619):810-813, Nature Publishing Group, England (Feb. 1997).
Wilson, I.A., et al., "The Structure of an Antigenic Determinant in a Protein," Cell 37(3):767-778, Cell Press, United States (Jul. 1984).
Winoto, A. and Baltimore, D., "A Novel, Inducible and T Cell-specific Enhancer Located at the 3' End of the T Cell Receptor Alpha Locus," The EMBO Journal 8(3):729-733, Wiley Blackwell, England (Mar. 1989).
Wu, G.Y. and Wu, C.H., "Delivery Systems for Gene Therapy," Biotherapy 3(1):87-95, Kluwer Academic Publishers, Netherlands (1991).
Wu, G.Y. and Wu, C.H., "Receptor-mediated in Vitro Gene Transformation by a Soluble DNA Carrier System," The Journal of Biological Chemistry 262(10):4429-4432, American Society for Biochemistry and Molecular Biology, United States (1987).
Xu, J., et al., "Fibroblast Growth Factor 21 Reverses Hepatic Steatosis, Increases Energy Expenditure, and Improves Insulin Sensitivity in Diet-induced Obese Mice," Diabetes 58(1):250-259, American Diabetes Association, United States (2009).
Yadav, S., et al., "Specific Interactions in High Concentration Antibody Solutions Resulting in High Viscosity," Journal of Pharmaceutical Sciences 99(3):1152-1168, Elsevier, United States (2010).
Yadav, S., et al., "Viscosity Behavior of High-concentration Monoclonal Antibody Solutions: Correlation With Interaction Parameter and Electroviscous Effects," Journal of Pharmaceutical Sciences 101(3):998-1011, Elsevier, United States (2012).
Yadav, Sandeep, et al., "Establishing a Link Between Amino Acid Sequences and Self-Associating and Viscoelastic Behavior of Two Closely Related Monoclonal Antibodies", Pharmaceutical Research, 2011, vol. 28, pp. 1750-1764.
Yadav, Sandeep, et al., "The Influence of Charge Distribution on Self-Association and Viscosity Behavior of Monoclonal Antibody Solutions", Molecular Pharmaceutics, 2012, vol. 9, pp. 791-802.
Yamashita, Y., et al., "Inhibitory and Stimulatory Functions of Paired Ig-like Receptor (PIR) Family in RBL-2H3 Cells.," Journal of Immunology 161(8):4042-4047, American Association of Immunologists, United States (Oct. 1998).
Yie, J., et al., "FGF21 N- and C-termini Play Different Roles in Receptor Interaction and Activation," FEBS Letters 583(1):19-24, John Wiley & Sons Ltd, England (Jan. 2009).
Zervos, A.S., et al., Mxi1, a protein that specifically interacts with Max to bind Myc-Max recognition site, Cell 72(2):223-232, Elsevier Science, United States (1993).
Zijlstra, M., et al., "Germ-line Transmission of a Disrupted beta 2-microglobulin Gene Produced by Homologous Recombination in Embryonic Stem Cells," Nature 342(6248):435-438, Nature Publishing Group, England (Nov. 1989).
Zon, G., et al., "Oligonucleotide Analogues as Potential Chemotherapeutic Agents," Pharmaceutical Research 5(9):539-549, Kluwer Academic/Plenum Publishers, United States (Sep. 1988).
Zuckermann, R.N., et al., "Discovery of nanomolar ligands for 7-transmembrane G-protein-coupled receptors from a diverse N-(substituted)glycine peptoid librar," Journal of Medicinal Chemistry 37(17):2678-2685, ACS Publications, United Kingdom (1994).
Zwaveling, J.H., et al., "High Plasma Tumor Necrosis Factor (TNF)-alpha Concentrations and a Sepsis-like Syndrome in Patients Undergoing Hyperthermic Isolated Limb Perfusion With Recombinant TNF-alpha, Interferon-gamma, and Melphalan," Critical Care Medicine 24(5):765-770, Lippincott Williams & Wilkins, United States (May 1996).
Lee et al., "TREM-1, a negative regulator of human osteoclastogenesis," Immunology Letters, 171, Feb. 4, 2016, pp. 50-59.
Brynjolfsson et al., "An Antibody Against Triggering Receptor Expressed on Myeloid Cells 1 (TREM-1) Dampens Proinflammatory Cytokine Secretion by Lamina Propria Cells from Patients with IBD," Inflamm Bowel Dis, 22(8), pp. 1803-1811 (Aug. 2016).

* cited by examiner

FIG. 1

```
                                                            CDR1                       CDR2
P1--047248_VH   QVQLQESGPGLVKPSETLSLTCTVSGGSI-SSSYWSWVRQPPGKGLEWIGYT-HYSGISN
P1--047246_VH   QVQLQESGPGLVKPSETLSLTCTVSGGSI-TNYYWTWIRQPPGKGLEWIGYI-YDSGYTN
P1--047247_VH   QVQLQESGPGLVKPSETLSLTCTVSGGSI-TNYYWTWIRQPPGKGLEWIGYI-YDSGYTN
P1--047239_VH   QVQLVESGGGVVQPGRSLRLSCAATEFTF-SNYGMHWVRQAPGKGLEWVAVIWYDGSNKY
P1--047334_VH   QVQLVQSGAEVKRPGSSVKVSCKASGGTF-SSSAISWVRQAPGQGLEWMGGIIPIFGTTN
P1--047323_VH   QVQLVQSGAEVKKPGSSVKVSCKASGGTFINSEAINWVRQAPGQGLEWMGGIIPIFDITN
P1--047328_VH   QVQLVQSGAEVKKPGSSVKVSCKASGGTFINSEAINWVRQAPGQGLEWMGGIIPIFDITN
                :***  :**   :  :*. ::  ::*   :    :  ..   *:**  **:****:.        . .

                CDR2                                    CDR3
P1--047248_VH   YNPSLKSRVTISVDTSKNQFSLKLSSVTAADTAVYYCAREGYDILTGYEYYG-----MDV
P1--047246_VH   YNPSLKSRVTLSIDTSKNQFSLKLSSVTAADTAVYYCAR-G------VLWFGELLPLLDY
P1--047247_VH   YNPSLKSRVTLSIDTSKNQFSLKLSSVTAADTAVYYCAR-G------VLWFGELLPLLDY
P1--047239_VH   YADSVKGRFTISRDNSKNTLYLQLNSLSAEDSAVYYCARDGRHYYGSTSYFG-----MDV
P1--047334_VH   GAQKFQGRVTITADESTSTAYMELSSLRSEDTAVYYCAAMVRG--NYFYFYG-----MDV
P1--047323_VH   YAQKFQGRVTITADESMSTAYMELSSLRSEDTAVYYCAKTYYDILTYHYHYG-----MDV
P1--047328_VH   YAQKFQGRVTITADESMSTAYMELSSLRSEDTAVYYCATTYYDILTYHYHYG-----MDV
                  ..:.:.*:: : * .   :: .*: : *:*:****            *        *

P1--047248_VH   WGQGTTVTVSS
P1--047246_VH   WGQGTLVTVSS
P1--047247_VH   WGQGTLVTVSS
P1--047239_VH   WGQGTTVTVSS
P1--047334_VH   WGQGTTVTVSS
P1--047323_VH   WGQGTTVTVSS
P1--047328_VH   WGQGTTVTVSS
                **:** *****
```

FIG. 2

```
                                  CDR1                                     CDR2
                       |-----------|               |-----|
P1--047248_VL   EIVLTQSPGTLSLSPGERATLSCRASQSVSSSYLAWYQQKPGQAPRLLIYGASSRATGIP
P1--047247_VL   EIVLTQSPGTLSLSPGERATLSCRASQSVSSSYLAWYQQKPGQAPRLLIYGASSRATGIP
P1--047246_VL   AIQLTQSPSSLSASVGDRVTITCRASQGI-SSALAWYQQKPGKAPKLLIYDASSLESGVP
P1--047239_VL   AIQLTQSPSSLSASVGDRVTITCRASQGI-SSALAWYQQKPGKAPKLLIYDASSLESGVP
P1--047323_VL   AIQLTQSPSSLSASVGDRVTITCRASQGI-SSALAWYQQKPGKAPKLLIYDASSLESGVP
P1--047328_VL   AIQLTQSPSSLSASVGDRVTITCRASQGI-SSALAWYQQKPGKAPKLLIYDASSLESGVP
P1--047334_VL   AIQLTQSPSSLSASVGDRVTITCRASQGI-SSALAWYQQKPGKAPKLLIYAASSLQSGVP
                 * *****.:** *.*:*.*::*****.: ** ********:**:**:* ***  :*:*
```

```
                                             CDR3
                                             |-------|
P1--047248_VH   DRFSGSGSGTDFTLTISRLEPEDFAVYYCQQYGSSP-TFGGGTKVEIK
P1--047246_VH   ERFSGSGSGTDFTLTISRLEPEDFAVYYCQQYGSSPLTFGGGTKVEIK
P1--047247_VH   SRFSGSGSGTDFTLTISSLQPEDFATYYCQQFNSYPYTFGQGTKLEIK
P1--047239_VH   SRFSGSGSGTDFTLTISSLQPEDFATYYCQQFNSYPYTFGQGTKLEIK
P1--047334_VH   SRFSGSGSGTDFTLTISSLQPEDFATYYCQQFNSYPITFGQGTRLEIK
P1--047323_VH   SRFSGSGSGTDFTLTISSLQPEDFATYYCQQYNSYPITFGQGTRLEIK
P1--047328_VH   SRFSGSGSGTDFTLTISSLQPEDFATYYCQQYNSYPLTFGGGTKVEIK
                 **************** *:**** .***** .* * *** **::***
```

ANTIBODIES AGAINST HUMAN TREM-1 AND USES THEREOF

CROSS-REFERENCE TO RELATED APPLICATIONS

This application is the national stage of International Patent Application No. PCT/US2020/042172, filed on Jul. 15, 2020, which claims the priority benefit of U.S. Provisional Application No. 62/874,316, filed Jul. 15, 2019, each of which are incorporated herein by reference in their entirety.

REFERENCE TO SEQUENCE LISTING SUBMITTED ELECTRONICALLY VIA EFS-WEB

The content of the electronically submitted sequence listing in ASCII text file (Name: 105218-03-5008-US_Sequence_Listing_v2.txt; Size: 452,801 bytes; and Date of Creation: Jun. 4, 2025) filed with the application is herein incorporated by reference in its entirety.

BACKGROUND OF THE DISCLOSURE

TREM-1 is an activating receptor expressed on monocytes, macrophages, and neutrophils. These cells play a central role in chronic inflammatory diseases by releasing cytokines and other mediators that drive inflammation. TREM-1 mRNA and protein expression is up-regulated in patients with rheumatic arthritis (RA) and inflammatory bowel disease (IBD), and TREM-1-positive cells accumulate at sites of inflammation, correlating with disease severity. See Bouchon et al., *Nature* 410:1103-1107 (2001); Schenk et al., *Clin Invest* 117:3097-3106 (2007); and Kuai et al., *Rheumatology* 48:1352-1358 (2009). Peptidoglycan-recognition-protein 1 (PGLYRP1) expressed primarily by activated neutrophils is a ligand for TREM-1 and mediate TREM-1 signaling upon binding.

In vitro, engagement of TREM-1 triggers secretion of pro-inflammatory cytokines including TNF, IL-8, and monocyte chemotactic protein-1. In addition, TREM-1 signaling synergizes with multiple Toll-like Receptors (TLRs) to further boost pro-inflammatory signals. In turn, this up-regulates expression of TREM-1, leading to a vicious cycle amplifying the inflammation. See Bouchon et al., *J Immunol* 164:4991-4995 (2000). Increasing evidence indicates that TLRs contribute to the development and progression of chronic inflammatory diseases such as RA and IBD.

Humanized anti-TREM-1 mAbs that inhibit both human and cynomolgus TREM-1 function have been disclosed elsewhere. See WO 2013/120553 A1 and WO 2016/009086 A1. However, such antibodies either have viscosity profile that can hamper manufacturing process or have other issues that can limit their therapeutic potential (e.g., cytokine storm and ADCC). See Shire et al., *J. Pharm. Sci.* 93:1390-1402 (2004); and Warncke et al., *J Immunol.* 188:4405-11 (2012). Accordingly, there is a need for alternative anti-TREM-1 antibodies that can specifically bind to and inhibit TREM-1 function but without the issues of the earlier anti-TREM-1 antibodies.

SUMMARY OF THE DISCLOSURE

Provided herein are isolated antibodies, such as monoclonal antibodies (e.g., human monoclonal antibodies), that specifically bind to a triggering receptor expressed on myeloid cells-1 (TREM-1) and have desirable functional properties. In some embodiments, an antibody of the present disclosure comprises a heavy chain variable region (VH) and a light chain variable region (VL), wherein the antibody binds to TREM-1 at an epitope comprising amino acids E27 to L37 (EKYELKEGQTL, SEQ ID NO: 9), E88 to M100 (EDYHDHGLLRVRM, SEQ ID NO: 10), and/or K120 to R128 (KEPHMLFDR, SEQ ID NO: 11). In certain embodiments, an antibody of the present disclosure binds to TREM-1 at an epitope comprising amino acids E27 to L37 (EKYELKEGQTL, SEQ ID NO: 9). In other embodiments, an antibody of the present disclosure binds to TREM-1 at an epitope comprising amino acids E88 to M100 (EDYHDHGLLRVRM, SEQ ID NO: 10). In further embodiments, an antibody of the present disclosure binds to TREM-1 at an epitope comprising amino acids K120 to R128 (KEPHMLFDR, SEQ ID NO: 11).

In some aspects, the present disclosure provides an isolated antibody which specifically binds to TREM-1 and comprises a VH and a VL, wherein the antibody binds to TREM-1 at an epitope other than D38 to F48 of SEQ ID NO: 1.

In some aspects, the present disclosure provides an isolated antibody which specifically binds to TREM-1 and comprises a VH and a VL, wherein the antibody binds to TREM-1 at a different epitope than mAb 0170.

In some aspects, the present disclosure also provides an isolated antibody which specifically binds to a triggering receptor expressed on myeloid cells-1 (TREM-1) and comprises a VH and a VL, wherein the antibody cross-competes with a reference antibody for binding to TREM-1, and wherein the reference antibody comprises a heavy chain variable region (VH) comprising SEQ ID NO: 13, 15, 23, 25, or 130, and/or a light chain variable region (VL) comprising SEQ ID NO: 14, 16, 17, 24, 131, or 132.

In some embodiments, an antibody disclosed herein comprises a heavy chain CDR1, CDR2, and CDR3 in the VH and a light chain CDR1, CDR2, and CDR3 in the VL, wherein the heavy chain CDR3 comprises EGYDILTGYEYYGMDV (SEQ ID NO: 28), GVLWFGELLPLLDY (SEQ ID NO: 34), MVRGNYFYFYGMDV (SEQ ID NO: 47), DGRHYYGSTSYFGMDV (SEQ ID NO: 52), TYYDILTYHYHYGMDV (SEQ ID NO: 138).

In some embodiments, a heavy chain CDR1 of an antibody disclosed herein comprises X1, X2, X3, X4, and X5, wherein X1 is S or N; X2 is S, Y, or E; X3 is Y G, or A; X4 is W, M, or I; and X5 is S, T, H, or N.

In some embodiments, a heavy chain CDR1 of an antibody disclosed herein comprises NSEAIN (SEQ ID NO: 136).

In some embodiments, a heavy chain CDR2 of an antibody disclosed herein comprises X1, X2, X3, X4, X5, X6, X7, X8, X9, X10, X11, X12, X13, X14, X15, X16, and X17, wherein X1 is Y V, or G; X2 is T or I; X3 is W, I, or none; X4 is H, Y, or P; X5 is Y, D, or I; X6 is S, G, or F; X7 is G, S, or D; X8 is I, Y, N, or T; X9 is S, T, or K; X10 is N or Y; X11 is Y or G; X12 is N or A; X13 is P, D, or Q; X14 is S or K; X15 is L, V, or F; X16 is K or Q; and X17 is S or G.

In some embodiments, a light chain CDR1 of an antibody disclosed herein comprises R, A, S, Q, X1, X2, X3, S, S, X4, L, and A, wherein X1 is S or G; X2 is V or I; X3 is S or none; and X4 is Y or A (SEQ ID NO: 341). In some embodiments, the light chain CDR2 of an antibody disclosed herein comprises X1, A, S, S, X2, X3, and X4, wherein X1 is G, D or A; X2 is R or L; X3 is A, E, or Q; and X4 is T or S.

In some embodiments, a light chain CDR3 of an antibody disclosed herein comprises Q, Q, X1, X2, S, X3, P, X4, and T, wherein X1 is Y or F; X2 is G or N; X3 is S or Y; and X4 is L, Y, or none (SEQ ID NO: 342).

In some embodiments, a heavy chain CDR2 of an antibody disclosed herein comprises YTHYSGISNYNPSLKS (SEQ ID NO: 27), YIYDSGYTNYNPSLKS (SEQ ID NO: 33), GIIPIFGTTNGAQKFQG (SEQ ID NO: 46), VIWYDGSNKYYADSVKG (SEQ ID NO: 51), or GIIPIFDITNYAQKFQG (SEQ ID NO: 137).

In some embodiments, a heavy chain CDR1 of an antibody disclosed herein comprises SSYWS (SEQ ID NO: 26), NYYWT (SEQ ID NO: 32), SSAIS (SEQ ID NO: 45), or NYGMH (SEQ ID NO: 50).

In some embodiments, a light chain CDR1 of an antibody disclosed herein comprises RASQSVSSSYLA (SEQ ID NO: 29) or RASQGISSALA (SEQ ID NO: 35).

In some embodiments, a light chain CDR2 of an antibody disclosed herein comprises GASSRAT (SEQ ID NO: 30), DASSLES (SEQ ID NO: 36), or AASSLQS (SEQ ID NO: 48).

In some embodiments, a light chain CDR3 of an antibody disclosed herein comprises QQYGSSPT (SEQ ID NO: 31), QQFNSYPYT (SEQ ID NO: 37), QQYGSSPLT (SEQ ID NO: 38), QQYNSYPLT (SEQ ID NO: 49), or QQYNSYPIT (SEQ ID NO: 103).

In some embodiments, an antibody of the present disclosure comprises a heavy chain CDR1, CDR2, and CDR3 in the VH and a light chain CDR1, CDR2, and CDR3 in the VL, (a) the heavy chain CDR1, CDR2, and CDR3 comprise the amino acid sequence set forth as SEQ ID NOs: 26, 27, and 28, respectively, and the light chain CDR1, CDR2, and CDR3 comprise the amino acid sequence set forth as SEQ ID NOs: 29, 30, and 31, respectively;

(b) the heavy chain CDR1, CDR2, and CDR3 comprise the amino acid sequence set forth as SEQ ID NOs: 32, 33, and 34, respectively, and the light chain CDR1, CDR2, and CDR3 comprise the amino acid sequence set forth as SEQ ID NOs: 35, 36, and 37, respectively;

(c) the heavy chain CDR1, CDR2, and CDR3 comprise the amino acid sequence set forth as SEQ ID NOs: 32, 33, and 34, respectively, and the light chain CDR1, CDR2, and CDR3 comprise the amino acid sequence set forth as SEQ ID NOs: 29, 30, and 38, respectively;

(d) the heavy chain CDR1, CDR2, and CDR3 comprise the amino acid sequence set forth as SEQ ID NOs: 45, 46, and 47, respectively, and the light chain CDR1, CDR2, and CDR3 comprise the amino acid sequence set forth as SEQ ID NOs: 35, 48, and 49, respectively;

(e) the heavy chain CDR1, CDR2, and CDR3 comprise the amino acid sequence set forth as SEQ ID NOs: 50, 51, and 52, respectively, and the light chain CDR1, CDR2, and CDR3 comprise the amino acid sequence set forth as SEQ ID NOs: 35, 36, and 37, respectively;

(f) the heavy chain CDR1, CDR2, and CDR3 comprise the amino acid sequence set forth as SEQ ID NOs: 136, 137, and 138, respectively, and the light chain CDR1, CDR2, and CDR3 comprise the amino acid sequence set forth as SEQ ID NOs: 35, 36, and 139, respectively; or (g) the heavy chain CDR1, CDR2, and CDR3 comprise the amino acid sequence set forth as SEQ ID NOs: 136, 137, and 138, respectively, and the light chain CDR1, CDR2, and CDR3 comprise the amino acid sequence set forth as SEQ ID NOs: 35, 36, and 103, respectively.

In some embodiments, the heavy chain CDR1, CDR2, and CDR3 comprise the amino acid sequence set forth as SEQ ID NOs: 32, 33, and 34, respectively, and the light chain CDR1, CDR2, and CDR3 comprise the amino acid sequence set forth as SEQ ID NOs: 35, 36, and 37, respectively.

In some embodiments, the heavy chain CDR1, CDR2, and CDR3 comprise the amino acid sequence set forth as SEQ ID NOs: 32, 33, and 34, respectively, and the light chain CDR1, CDR2, and CDR3 comprise the amino acid sequence set forth as SEQ ID NOs: 29, 30, and 38, respectively.

In some embodiments, the heavy chain CDR1, CDR2, and CDR3 comprise the amino acid sequence set forth as SEQ ID NOs: 45, 46, and 47, respectively, and the light chain CDR1, CDR2, and CDR3 comprise the amino acid sequence set forth as SEQ ID NOs: 35, 48, and 49, respectively.

In some embodiments, the heavy chain CDR1, CDR2, and CDR3 comprise the amino acid sequence set forth as SEQ ID NOs: 50, 51, and 52, respectively, and the light chain CDR1, CDR2, and CDR3 comprise the amino acid sequence set forth as SEQ ID NOs: 35, 36, and 37, respectively.

In some embodiments, the heavy chain CDR1, CDR2, and CDR3 comprise the amino acid sequence set forth as SEQ ID NOs: 136, 137, and 138, respectively, and the light chain CDR1, CDR2, and CDR3 comprise the amino acid sequence set forth as SEQ ID NOs: 35, 36, and 139, respectively.

In some embodiments, the heavy chain CDR1, CDR2, and CDR3 comprise the amino acid sequence set forth as SEQ ID NOs: 136, 137, and 138, respectively, and the light chain CDR1, CDR2, and CDR3 comprise the amino acid sequence set forth as SEQ ID NOs: 35, 36, and 103, respectively.

In some embodiments, the VH comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 13, 15, 23, 25, or 130. In certain embodiments, the VL comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 14, 16, 17, 24, 131, or 132.

In some embodiments, an antibody of the present disclosure comprises a VH and a VL, wherein:

(a) the VH comprises SEQ ID NO: 13 and the VL comprises SEQ ID NO: 14;

(b) the VH comprises SEQ ID NO: 15 and the VL comprises SEQ ID NO: 16;

(c) the VH comprises SEQ ID NO: 15 and the VL comprises SEQ ID NO: 17;

(d) the VH comprises SEQ ID NO: 23 and the VL comprises SEQ ID NO: 24;

(e) the VH comprises SEQ ID NO: 25 and the VL comprises SEQ ID NO: 16;

(f) the VH comprises SEQ ID NO: 130 and the VL comprises SEQ ID NO: 131; or (g) the VH comprises SEQ ID NO: 130 and the VL comprises SEQ ID NO: 132.

In some embodiments, an antibody disclosed herein further comprises a heavy chain (HC) constant region and a light chain (LC) constant region, wherein the HC constant region comprises an amino acid sequence that is at least about 70%, at least about 80%, at least about 85%, at least about 90%, at least about 95%, at least about 96%, at least about 97%, at least about 98%, at least about 99%, or about 100% identical to SEQ ID NO: 123, SEQ ID NO: 122, SEQ ID NO: 124, or SEQ ID NO: 125. In some embodiments, the LC constant region comprises an amino acid sequence that is at least about 70%, at least about 80%, at least about 85%, at least about 90%, at least about 95%, at least about 96%, at least about 97%, at least about 98%, at least about 99%, or about 100% identical to SEQ ID NO: 126.

Also provided herein are bispecific molecules comprising an antibody of the present disclosure linked to a molecule having a second binding specificity.

Present disclosure further provides nucleic acids encoding an antibody disclosed herein, vectors comprising the nucleic acids, and cells comprising the vectors.

Provided herein are also immunoconjugates comprising an antibody or a bispecific molecule, as disclosed herein, linked to an agent.

Present disclosure provides compositions comprising an antibody, bispecific molecule, nucleic acid, vector, cell, or an immunoconjugate, as disclosed herein, and a carrier.

Also provided in the present disclosure are kits comprising an antibody, bispecific molecule, nucleic acid, vector, cell, or an immunoconjugate, as disclosed herein, and an instruction for use.

Provided herein is a method of inhibiting TREM-1 activity in a subject in need thereof, comprising administering an antibody, bispecific molecule, nucleic acid, vector, cell, or an immunoconjugate, as disclosed herein, to the subject.

Provided herein is a method of treating an inflammatory disease or an autoimmune disease in a subject in need thereof, comprising administering an antibody, bispecific molecule, nucleic acid, vector, cell, or an immunoconjugate, as disclosed herein, to the subject.

In some embodiments, the inflammatory disease or the autoimmune disease is selected from the group consisting of an inflammatory bowel disease (IBD), Crohn's disease (CD), ulcerative colitis (UC), irritable bowel syndrome, rheumatoid arthritis (RA), psoriasis, psoriatic arthritis, systemic lupus erythematosus (SLE), lupus nephritis, vasculitis, sepsis, systemic inflammatory response syndrome (SIRS), type I diabetes, Grave's disease, multiple sclerosis (MS), autoimmune myocarditis, Kawasaki disease, coronary artery disease, chronic obstructive pulmonary disease, interstitial lung disease, autoimmune thyroiditis, scleroderma, systemic sclerosis, osteoarthritis, atopic dermatitis, vitiligo, graft versus host disease, Sjogren's syndrome, autoimmune nephritis, Goodpasture syndrome, chronic inflammatory demyelinating polyneuropathy, allergy, asthma, other autoimmune diseases that are a result of either acute or chronic inflammation, and any combinations thereof.

In some embodiments, methods disclosed herein further comprise administering one or more additional therapeutics. In certain embodiments, the additional therapeutics is an anti-IP-10 antibody or an anti-TNF-α antibody.

BRIEF DESCRIPTION OF THE DRAWINGS/FIGURES

FIG. 1 shows a sequence alignment of the heavy chain variable region (VH) of different epitope-steered anti-TREM-1 antibodies disclosed herein. The antibodies shown include (i) P1-047248 (SEQ ID NO: 13); (ii) P1-047246 (SEQ ID NO: 15); (iii) P1-047247 (SEQ ID NO: 15); (iv) P1-047239 (SEQ ID NO: 25); (v) P1-047334 (SEQ ID NO: 23); (vi) P1-047323 (SEQ ID NO: 130); and (vii) P1-047328 (SEQ ID NO: 130). The heavy chain CDR1, CDR2, and CDR3 regions are boxed.

FIG. 2 shows a sequence alignment of the light chain variable region (VL) of different epitope-steered anti-TREM-1 antibodies disclosed herein. The antibodies shown include (i) P1-047248 (SEQ ID NO: 14); (ii) P1-047246 (SEQ ID NO: 16); (iii) P1-047247 (SEQ ID NO: 17); (iv) P1-047239 (SEQ ID NO: 16); (v) P1-047334 (SEQ ID NO: 24); (vi) P1-047323 (SEQ ID NO: 131); and (vii) P1-047328 (SEQ ID NO: 132). The light chain CDR1, CDR2, and CDR3 regions are denoted (boxed).

FIG. 3 shows a comparison of the epitope competition analysis (y-axis) and the THP1 inhibition assay results (x-axis) for the different anti-TREM-1 antibodies. The data for the epitope competition analysis is provided as percent inhibition of mAb170 binding to TREM-1. The diamonds represent different anti-TREM-1 antibodies generated from the non-epitope-steered clones. The circles represent different anti-TREM-1 antibodies generated from the epitope-steered clones.

Figure 4:
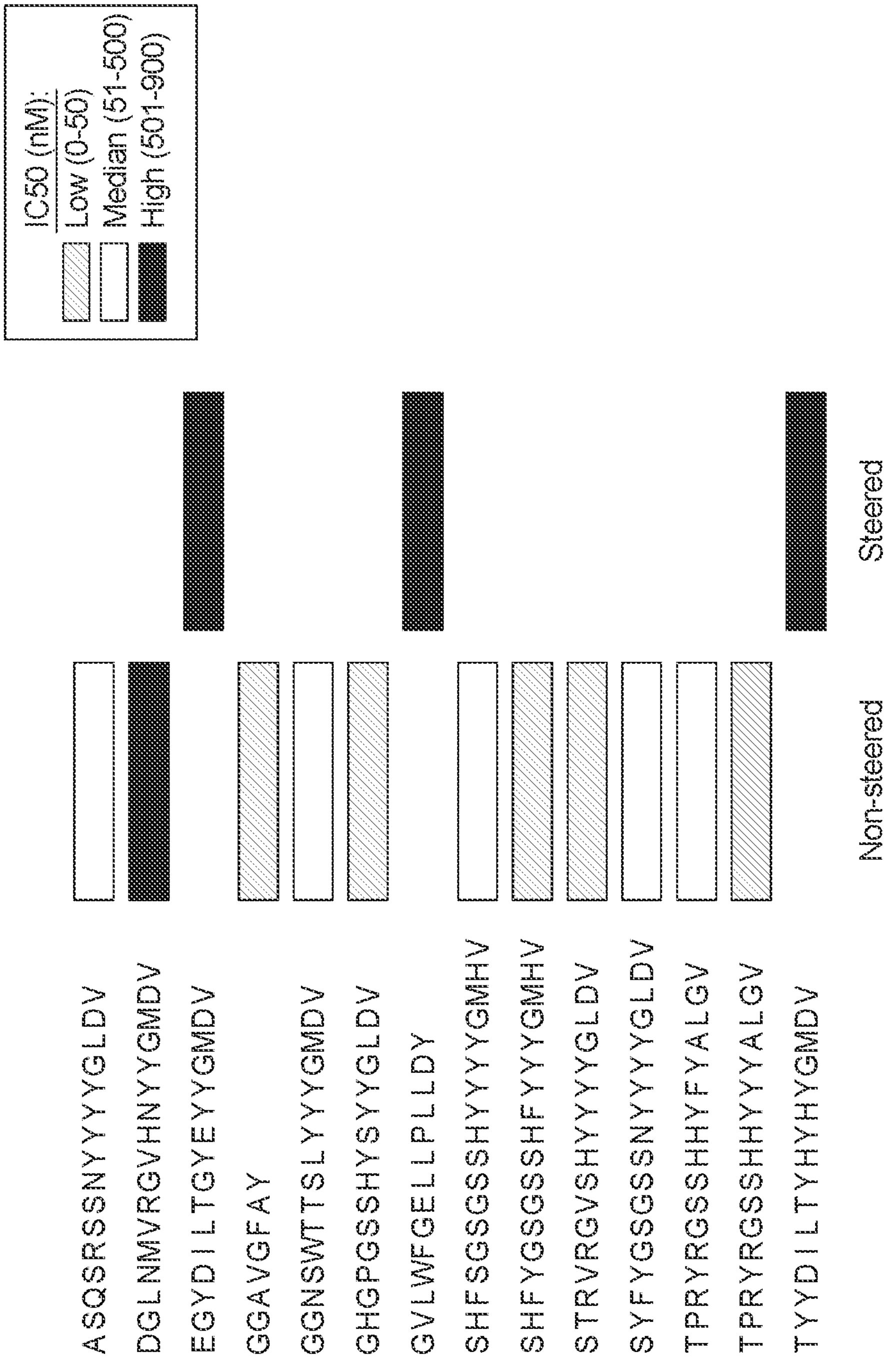

FIG. 4 shows how the steered and non-steered epitope bins correlate to antibodies grouped by the heavy chain CDR3 ("HCDR3") amino acid sequences. Each HCDR3 sequence provided represents an individual group, with each group consisting of one or more antibodies that share the same HCDR3 sequence. Based on the distribution of IL-1 Beta protein signal measured with Cisbio HTRF kit, the different HCDR3 groups were further grouped into Low (0-50, striped), Medium (51-500, gray), and High (501-900, black) nM IC50 categories. The bars shown to the left of the figure correspond to the anti-TREM-1 antibodies generated from the non-epitope-steered clones. The bars shown to the right of the figure correspond to the anti-TREM-1 antibodies generated from the epitope-steered clones. The HCDR3 amino acid sequences are listed in the following order, from top to bottom: SEQ ID NO: 120 (ASQSRSSNYYYYGLDV), SEQ ID NO: 142 (DG-LNMVRGVHNYYGMDV), SEQ ID NO: 28 (EGYDILTGYEYYGMDV), SEQ ID NO: 91 (GGAVGFAY), SEQ ID NO: 111 (GGNSWTTS-LYYYGMDV), SEQ ID NO: 95 (GHGPGSSHY-SYYGLDV), SEQ ID NO: 34 (GVLWFGELLPLLDY), SEQ ID NO: 108 (SHFSGSGSSHYYYYGMHV), SEQ ID NO:114 (SHFYGSGSSHFYYYGMHV), SEQ ID NO: 105 (STRVRGVSHYYYYGLDV), SEQ ID NO: 101 (SYFYGSGSSNYYYYGLDV), SEQ ID NO: 117 (TPRYRGSSHHYFYALGV), SEQ ID NO: 86 (TPRYRGSSHHYYYALGV), and SEQ ID NO: 138 (TYYDILTYHYHYGMDV).

Figure 5A:
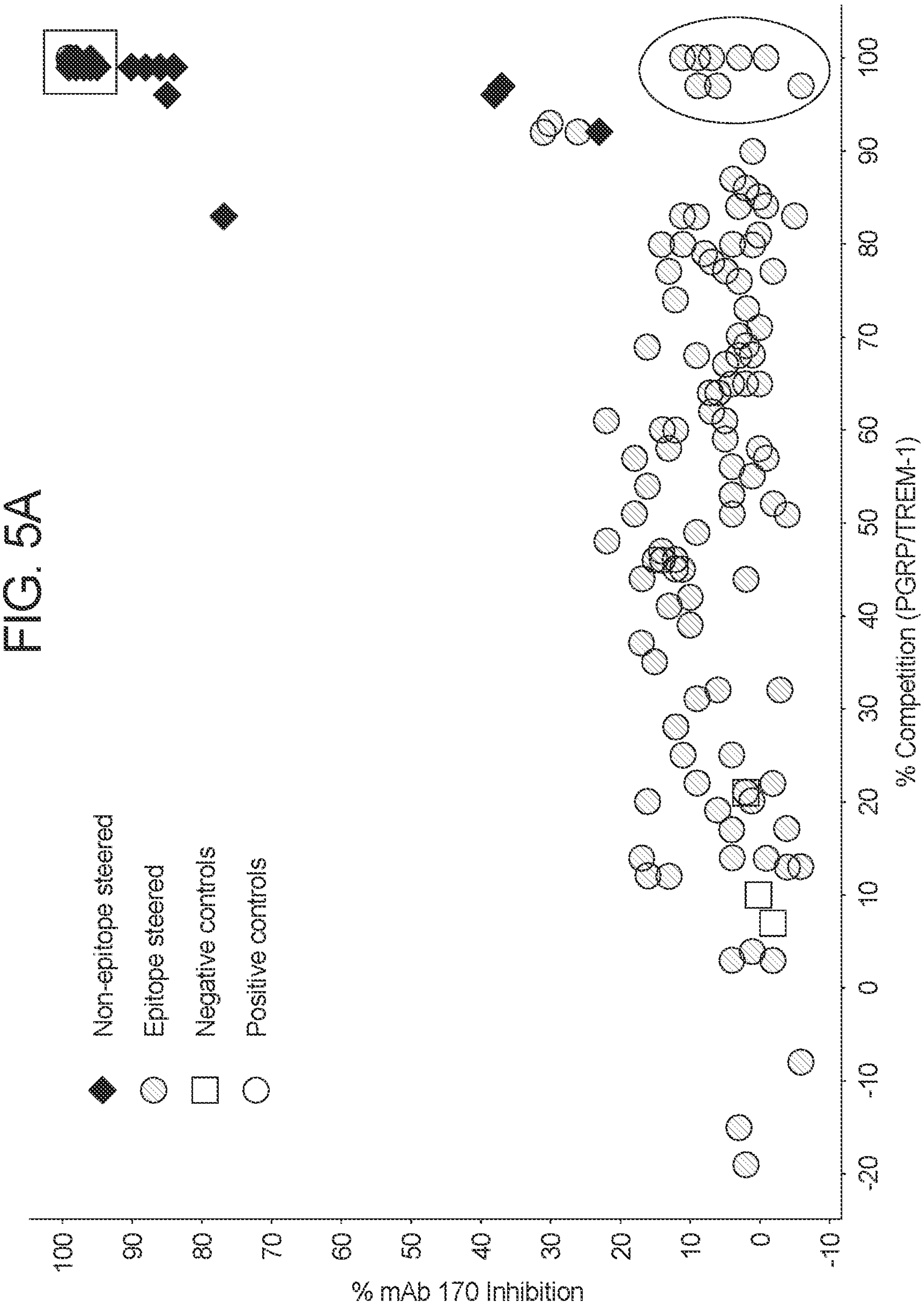

FIG. 5A shows a comparison of the binding analysis of the different anti-TREM-1 antibodies. The y-axis shows the ability of the different anti-TREM-1 antibodies to compete with mAb170 for binding to TREM-1. Data is shown as percent inhibition of mAb170 binding. The x-axis shows the ability of the different anti-TREM-1 antibodies to compete with PGRP for binding to TREM-1. Data is shown as percent inhibition of PGRP binding. The different anti-TREM-1 antibodies shown were generated from either non-epitope-steered clones (black diamonds) or epitope-steered clones (gray circle). The circled antibodies in FIG. 5A (lower right quadrant) correspond to epitope-steered TREM-1 antibodies that best inhibited the binding of PGRP to TREM-1. The boxed antibodies (upper right quadrant) correspond to non-epitope-steered antibodies that best inhibited the binding of both PGRP and mAb170 to TREM-1. HMEP (High Throughput Mammalian Expression and Purification) buffer (i.e., no antibody) was used as a negative control (open square). The mAb 0170 was used as a positive control (open circle).

Figure 5B:
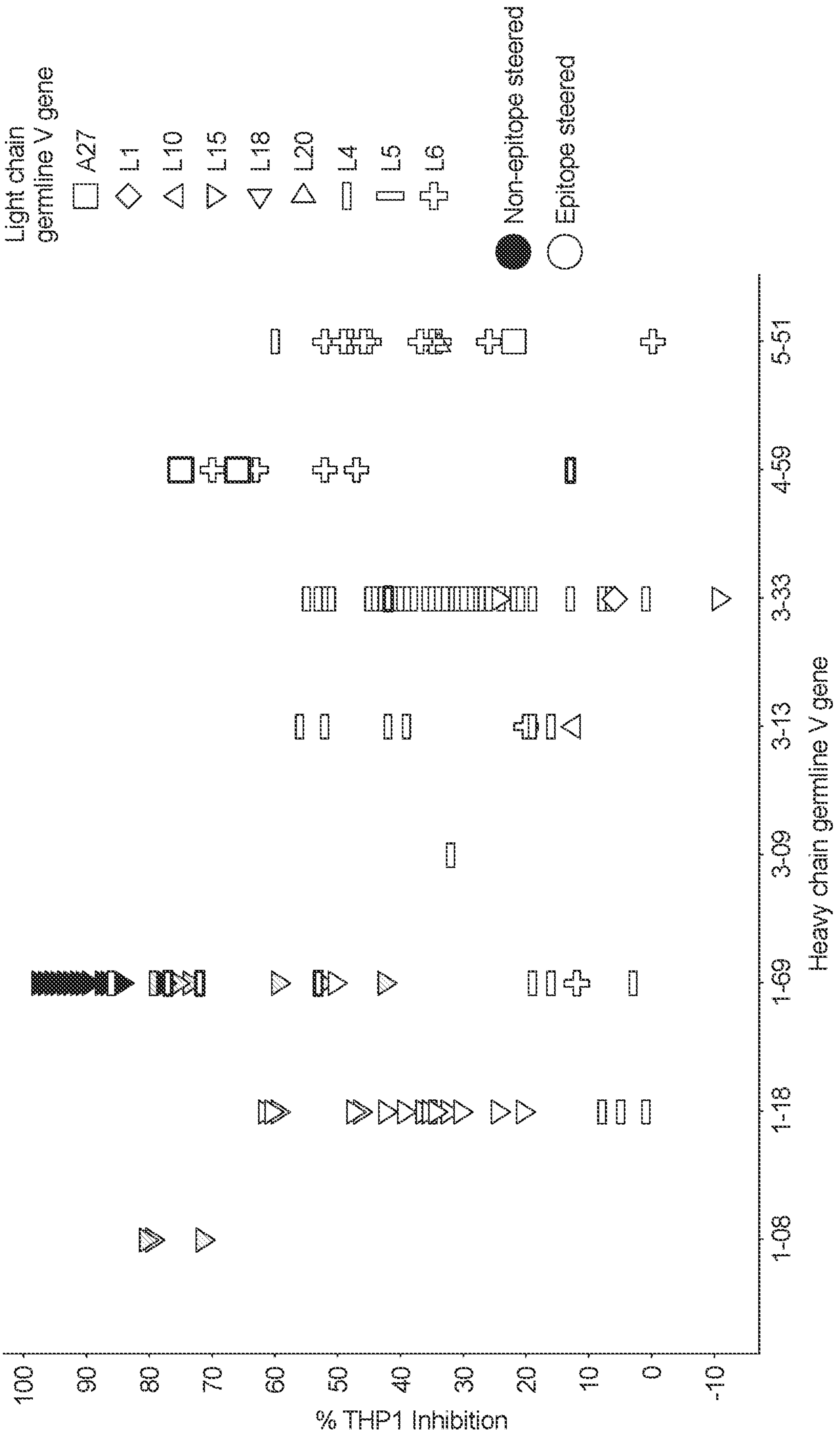

FIG. 5B shows both the THP1 inhibition assay results (y-axis) and the human germline genes (x-axis) corresponding to the heavy chain variable region (VH) of the different anti-TREM-1 antibodies shown in FIG. 5A. The human germline genes corresponding to the light chain variable region are also provided, with each shape representing a different germline gene. The THP1 inhibition assay results are shown as percent inhibition. The different anti-TREM-1 antibodies shown were generated from either non-epitope-steered clones (black/grey) or epitope-steered clones (white). The circled and boxed antibodies in FIG. 5A are shown in black outline and black shading, respectively.

DETAILED DESCRIPTION OF DISCLOSURE

In order that the present description can be more readily understood, certain terms are first defined. Additional definitions are set forth throughout the detailed description.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, nucleotide sequences are written left to right in 5 to Y orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The term "triggering receptor expressed on myeloid cells 1" (also known as TREM1, TREM-1, and CD354) refers to a receptor that is expressed on monocytes, macrophages, and neutrophils. Primary ligand for TREM-1 include peptidoglycan-recognition-protein 1 (PGLYRP1), which belongs to a family of peptidoglycan (PGN) binding proteins (PGRPs). When activated, TREM-1 associates with the ITAM-containing signaling adaptor protein, DAP12. Downstream signaling may include activation of the NFAT transcription factor, causing an up-regulation of pro-inflammatory cytokine production. The term "TREM-1" includes any variants or isoforms of TREM-1 which are naturally expressed by cells. Accordingly, in some embodiments, antibodies described herein can cross-react with TREM-1 from species other than human (e.g., cynomolgus TREM-1).

Three isoforms of human TREM-1 have been identified. Isoform 1 (Accession No. NP_061113.1; SEQ ID NO: 1) consists of 234 amino acids and represents the canonical sequence. Isoform 2 (Accession No. NP_001229518.1; SEQ ID NO: 2) consists of 225 amino acids and differ from the canonical sequence at amino acid residues 201-234. The amino acid residues encode part of the transmembrane domain and the cytoplasmic domain. Isoform 3 (Accession No. NP_001229519; SEQ ID NO: 3) consists of 150 amino acids, and is soluble. It lacks amino acid residues 151-234, which encode the transmembrane domain, the cytoplasmic domain, and part of the extracellular domain. The amino acid residues 138-150 also differ from the canonical sequence described above.

Below are the amino acid sequences of the three known human TREM-1 isoforms.

(A) Human TREM-1 isoform 1 (Accession No. NP_061113.1; SEQ ID NO: 1; encoded by the nucleotide sequence having Accession No. NM_018643; SEQ ID NO: 4):

<u>MRKIRLWGLIMMLEVSELRA</u>ATKLIEEKYELKEGQTLDVKCDYTLEKFASSQKAWQIIRDGEMPK

TLACTERPSKNSHPVQVGRIILEDYHDHGLLRVRMVNLQVEDSGLYQCVIYQPPKEPHMLFDRIR

LVVTKGFSGTPGSNENSTQNVYKIPPTTTKALCPLYTSPRTVTQAPPKSTADVSTPDSEINLTNV

TDIIRVPVFNIVILLAGGFLSKSLVFSVLFAVTLRSFVP (signal sequence is underlined);

-continued (B) Human TREM-1 isoform 2 (Accession No. NP_001229518.1; SEQ ID NO: 2; encoded by the nucleotide sequence having Accession No. NM_001242589; SEQ ID NO: 5):

```
MRKTRLWGLLWMLFVSELRAATKLTEEKYELKEGQTLDVKCDYTLEKFASSQKAWQIIRDGEMPK

TLACTERPSKNSHPVQVGRIILEDYHDHGLLRVRMVNLQVEDSGLYQCVIYQPPKEPHMLFDRIR

LVVTKGFSGTPGSNENSTQNVYKIPPTTTKALCPLYTSPRTVTQAPPKSTADVSTPDSEINLTNV

TDIIRYSFQVPGPLVWTLSPLFPSLCAERM
```

(signal sequence is underlined);

(C) Human TREM4 isoform 3 (Accession No. NP_001229519; SEQ ID NO: 3; encoded by the nucleotide sequence haying Accession No. NM_001242590; SEQ ID NO: 6):

```
MRKTRLWGLLWMLFVSELRAATKLTEEKYELKEGQTLDVKCDYTLEKFASSQKAWQIIRDGEMPK

TLACTERPSKNSHPVQVGRIILEDYHDHGLLRVRMVNLQVEDSGLYQCVIYQPPKEPHMLFDRIR

LVVTKGFRCSTLSFSWLVDS
```

(signal sequence is underlined).

Cynomolgus TREM-1 protein (Accession No. XP_001082517; SEQ ID NO: 7) is predicted to have the following amino acid sequence:

```
MRKTRLWGLLWMLFVSELRATTELTEEKYEYEEGQTLEVKCDYALEKYAN

SRKAWQKMEGKMPKILAKTERPSENSHPVQVGRITLEDYPDHGLLQVQMT

NLQVEDSGLYQCVIYQHPKESHVLFNPICLVVTKGSSGTPGSSENSTQNV

YRTPSTTAKALGPRYTSPRTVTQAPPESTVVVSTPGSEINLTNVTDIIRV

PVFNIVIIVAGGFLSKSLVFSVLFAVTLRSFGP
```

(signal sequence is underlined).

The present disclosure relates to antibodies that specifically bind and block the function of TREM-1. The antibodies block TREM-1 function by reducing/blocking TREM-1 activation and downstream signaling.

The anti-TREM-1 antibodies of the present disclosure block TREM-1 signaling by means of one or a combination of several different mechanisms, blocking TREM-1 directly or indirectly. In one embodiment, the antibodies prevent the natural ligand of TREM-1, peptidoglycan recognition protein 1 (PGLYRP1), from creating a functional complex with TREM-1. In another embodiment, the antibodies block TREM-1 by preventing individual TREM-1 molecules from forming dimers or multimers. In some embodiments, the TREM-1 dimerization or multimerization is reduced or prevented by anti-TREM-1 antibodies that are capable of binding to a portion of TREM-1 that would otherwise reside in the interface of a TREM-1 dimer, thus preventing individual TREM-1 molecules from associating with one another. In other embodiments, the TREM-1 dimerization or multimerization is reduced or prevented by anti-TREM-1 antibodies that interfere with the interaction of TREM-1 with its ligand.

In some embodiments, the anti-TREM-1 antibodies can block PGLYRP1-induced activation of TREM-1. PGLYRP1, a highly conserved, 196 amino acid long protein consisting of a signal peptide and a peptidoglycan binding domain, is expressed in neutrophils and released upon their activation. The amino acid sequence of PGLYRP1 (Accession No. NP_005082.1; SEQ ID NO: 8) is provided below:

```
MSRRSMLLAWALPSLLRLGAAQETEDPACCSPIVPRNEWKALASECAQHL

SLPLRYVVVSHTAGSSCNTPASCQQQARNVQHYHMKTLGWCDVGYNFLIG

EDGLVYEGRGWNFTGAHSGHLWNPMSIGISFMGNYMDRVPTPQAIRAAQG

LLACGVAQGALRSNYVLKGHRDVQRTLSPGNQLYHLIQNWPHYRSP
```

(signal sequence is underlined).

Accordingly, in some embodiments, the anti-TREM-1 antibodies of the present disclosure down-regulate or block the release of proinflammatory cytokines from myeloid cells, such as dendritic cells and monocytes (e.g., THP-1 cells). In some embodiments, the anti-TREM-1 antibodies block the release of TNF-α, MIP-1beta, MCP-1, IL-1beta, GM-CSF, IL-6 and/or IL-8 from macrophages, neutrophils, synovial tissue cells and/or a reporter cell, as disclosed herein.

In some embodiments, the anti-TREM-1 antibodies of the present disclosure bind both human TREM-1 and TREM-1 from another species. The term "TREM-1", as used herein, thus encompasses any naturally occurring form of TREM-1 which can be derived from any suitable organism. For example, TREM-1 for use as described herein can be vertebrate TREM-1, such as mammalian TREM-1, such as TREM-1 from a primate (such as a human, a chimpanzee, a cynomolgus monkey, or a rhesus monkey); a rodent (such as a mouse or a rat), a lagomorph (such as a rabbit), or an artiodactyl (such a cow, sheep, pig or camel). In certain embodiments, TREM-1 is SEQ ID NO: 1 (human TREM-1, isoform 1). The TREM-1 can be a mature form of TREM-1, such as a TREM-1 protein that has undergone post-translational processing within a suitable cell. Such a mature TREM-1 protein can, for example, be glycosylated. The TREM-1 can be a full length TREM-1 protein.

In some embodiments, the anti-TREM-1 antibodies of the present disclosure are monoclonal antibodies, in the sense that they are directly or indirectly derived from a single clone of a B lymphocyte. In some embodiments, the anti-TREM-1 antibodies are produced, screened, and purified using, for example, the methods described in the Examples of International Publ. No. WO 2013/120553. In brief, a suitable mouse such as a TREM-1 or TREM-V/TREM-3 knock-out (KO) mouse are immunized with TREM-1, a cell expressing TREM-1, or a combination of both. In another embodiment, the anti-TREM-1 antibodies are polyclonal antibodies, in the sense that they are mixture of monoclonal antibodies as disclosed herein.

In some embodiments, the anti-TREM-1 antibodies of the current disclosure are recombinantly expressed in prokaryotic or eukaryotic cells. In some embodiments, the prokaryotic cell is *E. coli*. In certain embodiments, the eukaryotic is a yeast, insect, or mammalian cell, such as a cell derived from an organism that is a primate (such as a human, a chimpanzee, a cynomolgus monkey or a rhesus monkey), a rodent (such as a mouse or a rat), a lagomorph (such as a rabbit) or an artiodactyl (such a cow, sheep, pig or camel). Suitable mammalian cell lines include, but are not limited to, HEK293 cells, CHO cells, and HELA cells. The anti-TREM-1 antibodies as disclosed herein can also be produced by means of other methods known to the person skilled in the art, such as a phage display or a yeast display. Once produced, the antibodies can be screened for binding to, for example, full length TREM-1 or mutants thereof using the methods described in the Examples of International Publ. No. WO 2013/120553.

In some embodiments, the anti-TREM-1 antibodies of the present disclosure are steered away from an epitope on human TREM-1 that is recognized by a reference antibody (e.g., mAb 0170). Accordingly, in some embodiments, the anti-TREM-1 antibodies disclosed herein do not compete with the reference antibody (e.g., mAb 0170) for binding to human TREM-1. In some embodiments, the anti-TREM-1 antibodies of the present disclosure do not bind to amino acids D38 to F48 of human TREM-1 (SEQ ID NO: 1). In certain embodiments, the anti-TREM-1 antibodies disclosed herein do not bind to amino acids D38 to L45, E46 to Q56, and/or Y90 to L96 of human TREM-1 (SEQ ID NO: 1). The binding epitope of the reference antibody mAb 0170 is known in the art. See, e.g., U.S. Pat. No. 9,000,127.

As used herein, the term "epitope-steered" refers to anti-TREM-1 antibodies that are selected to bind to epitopes other than D38 to L45, E46 to Q56, and/or Y90 to L96 of human TREM-1 (SEQ ID NO: 1). In some embodiments, the epitope-steered anti-TREM-1 antibodies bind to one or more epitope selected from the group consisting of (1) $^{27}$EKYELKEGQTL$^{37}$ (SEQ ID NO: 9), (2) $^{88}$EDYHDHGLLRVRM$^{100}$ (SEQ ID NO: 10), (3) $^{120}$KEPHMLFDR$^{128}$ (SEQ ID NO: 11), and any combination thereof of human TREM-1 (e.g., Isoform 1, SEQ ID NO: 1).

Epitope-steered anti-TREM-1 antibodies described herein can be produced by any method known in the art, such as those described in the Examples. In some embodiments, the epitope-steered anti-TREM-1 antibodies can be generated by immunizing an animal (e.g., mice) with a human TREM-1 polypeptide comprising mutations at one of above epitopes (e.g., amino acids residues 38-48 of SEQ ID NO: 1). Upon immunization, the antibodies generated can be further characterized for binding to human TREM-1. In some embodiments, synthetic peptides that comprise the epitope of interest can be synthesized and used to immunize an animal (e.g., mice). In some embodiments, alternative scaffolds (e.g., tenth human fibronectin type three domain, $^{10}$Fn3; or α3D, a highly thermostable three-helix bundle protein) that comprise the epitope of interest can be used.

In some embodiments, the anti-TREM-1 antibodies of the present disclosure are non-epitope-steered and therefore, can bind to the same epitope as the reference antibody (e.g., mAb170).

The term "antibody" as used herein refers to a protein, derived from a germline immunoglobulin sequence, which is capable of specifically binding to an antigen (TREM-1) or a portion thereof. The term includes full length antibodies of any class or isotype (that is, IgA, IgE, IgG, IgM and/or IgY) and any single chain or fragment thereof. An antibody that specifically binds to an antigen, or portion thereof, may bind exclusively to that antigen, or portion thereof, or it may bind to a limited number of homologous antigens, or portions thereof. Full-length antibodies usually comprise at least four polypeptide chains: two heavy (H) chains and two light (L) chains that are interconnected by disulfide bonds. One immunoglobulin sub-class of particular pharmaceutical interest is the IgG family. In humans, the IgG class may be sub-divided into 4 sub-classes: IgG1, IgG2, IgG3 and IgG4, based on the sequence of their heavy chain constant regions. The light chains can be divided into two types, kappa and lambda, based on differences in their sequence composition. IgG molecules are composed of two heavy chains, inter-linked by two or more disulfide bonds, and two light chains, each attached to a heavy chain by a disulfide bond. A heavy chain may comprise a heavy chain variable region (VH) and up to three heavy chain constant (CH) regions: CH1, CH2 and CH3. A light chain may comprise a light chain variable region (VL) and a light chain constant region (CL). VH and VL regions can be further subdivided into regions of hypervariability, termed complementarity determining regions (CDRs), interspersed with regions that are more conserved, termed framework regions (FR). VH and VL regions are typically composed of three CDRs and four FRs, arranged from amino-terminus to carboxy-terminus in the following order: FR1, CDR1, FR2, CDR2, FR3, CDR3, FR4. The hypervariable regions of the heavy and light chains form a binding domain that is capable of interacting with an antigen, whilst the constant region of an antibody may mediate binding of the immunoglobulin to host tissues or factors, including but not limited to various cells of the immune system (effector cells), Fc receptors and the first component (C1q) of the classical complement system. Antibodies of the current invention may be isolated. The term "isolated antibody" refers to an antibody that has been separated and/or recovered from (an)other component(s) in the environment in which it was produced and/or that has been purified from a mixture of components present in the environment in which it was produced. Certain antigen-binding fragments of antibodies may be suitable in the context of the current invention, as it has been shown that the antigen-binding function of an antibody can be performed by fragments of a full-length antibody.

The term "antigen-binding portion" of an antibody refers to one or more fragment(s) of an antibody that retain the ability to specifically bind to an antigen, such as TREM-1, as described herein. Examples of antigen-binding fragments include Fab, Fab', F(ab)2, F(ab')2, F(ab)S, Fv (typically the VL and VH domains of a single arm of an antibody), single-chain Fv (scFv; see, e.g., Bird et al., *Science* 242: 42S-426 (1988); Huston et al., *PNAS* 85: 5879-5883 (1988)), dsFv, Fd (typically the VH and CH1 domain), and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., Ill et al., *Protein Eng* 10:949-57 (1997)); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, *Nat Biotechnol* 2S:1126-1136 (2005); International Publ. No. WO 2005/040219, and U.S. Publ. Nos. 2005/0238646 and 2002/0161201. These antibody fragments may be obtained using conventional techniques known to those of skill in the art, and the fragments may be screened for utility in the same manner as intact antibodies.

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The anti-TREM-1 antibodies described herein can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies are used synonymously.

A "humanized" antibody refers to a human/non-human chimeric antibody that contains one or more sequences (CDR regions or parts thereof) that are derived from a non-human immunoglobulin. A humanized antibody is, thus, a human immunoglobulin (recipient antibody) in which at least residues from a hyper-variable region of the recipient are replaced by residues from a hyper-variable region of an antibody from a non-human species (donor antibody) such as from a mouse, rat, rabbit or non-human primate, which have the desired specificity, affinity, sequence composition and functionality. In some instances, FR residues of the human immunoglobulin are replaced by corresponding non-human residues. An example of such a modification is the introduction of one or more so-called back-mutations, which are typically amino acid residues derived from the donor antibody. Humanization of an antibody may be carried out using recombinant techniques known to the person skilled in the art (see, e.g., Antibody Engineering, Methods in Molecular Biology, vol. 248, edited by Benny K. C. Lo). A suitable human recipient framework for both the light and heavy chain variable domain may be identified by, for example, sequence or structural homology. Alternatively, fixed recipient frameworks may be used, e.g., based on knowledge of structure, biophysical and biochemical properties. The recipient frameworks can be germline derived or derived from a mature antibody sequence. CDR regions from the donor antibody can be transferred by CDR grafting. The CDR grafted humanized antibody can be further optimized for e.g., affinity, functionality and biophysical properties by identification of critical framework positions where re-introduction (backmutation) of the amino acid residue from the donor antibody has beneficial impact on the properties of the humanized antibody. In addition to donor antibody derived backmutations, the humanized antibody can be engineered by introduction of germline residues in the CDR or framework regions, elimination of immunogenic epitopes, site-directed mutagenesis, affinity maturation, etc.

Furthermore, humanized antibodies can comprise residues that are not found in the recipient antibody or in the donor antibody. These modifications are made to further refine antibody performance. In general, a humanized antibody will comprise at least one—typically two—variable domains, in which all or substantially all of the CDR regions correspond to those of a non-human immunoglobulin and in which all or substantially all of the FR residues are those of a human immunoglobulin sequence. The humanized antibody can, optionally, also comprise at least a portion of an immunoglobulin constant region (Fc), typically that of a human immunoglobulin. The term "humanized antibody derivative" refers to any modified form of the humanized antibody, such as a conjugate of the antibody and another agent or antibody.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg *Nature Biotech.* 23(9): 1117-1125 (2005)), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen cannot have sequence identity with the original nucleic acid molecules, but instead will be substantially identical or similar (i.e., have at least 80% identity).

A "chimeric antibody" refers to an antibody in which the variable regions are derived from one species and the constant regions are derived from another species, such as an antibody in which the variable regions are derived from a mouse antibody and the constant regions are derived from a human antibody.

In some embodiments, the anti-TREM-1 antibodies of the current disclosure are IgG antibodies. An "IgG antibody", e.g., a human IgG1, as used herein has, in certain embodiments, the structure of a naturally occurring IgG antibody, i.e., it has the same number of heavy and light chains and disulfide bonds as a naturally occurring IgG antibody of the same subclass. For example, the TREM-1 IgG1 antibody consists of two heavy chains (HCs) and two light chains (LCs), wherein the two heavy chains and light chains are linked by the same number and location of disulfide bridges that occur in naturally occurring IgG1antibody (unless the antibody has been mutated to modify the disulfide bridges).

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally occurring variants within a specific isotype group, which variants differ in a few amino acids (see, e.g., Jefferis et al., mAbs 1:1 (2009)). Anti-TREM-1 antibodies described herein can be of any allotype. In some embodiments, the anti-TREM-1 antibodies are of "IgG1.3f" allotype, which comprises one or more amino acid substitutions selected from the group consisting of L234A, L235E, and G237A, per EU numbering, as compared to a wild-type IgG1 isotype (e.g., SEQ ID NO: 12). In other embodiments, the anti-TREM-1 antibodies are of "IgG1.1f" allotype, which comprises one or more amino acid substitutions selected from the group consisting of L234A, L235E, G237A, A330S, and P331S, per EU numbering, as compared to a wild-type IgG1 isotype (e.g., SEQ ID NO: 12). In certain embodiments, the anti-TREM-1 antibodies are of "IgG1-Aba" allotype, which comprises one or more amino acid substitutions selected from the group consisting of K214R, C226S, C229S, and P238S, per EU numbering, as compared to a wild-type IgG1 isotype (e.g., SEQ ID NO: 12). In further embodiments, the anti-TREM-1 antibodies are of "IgG4-Aba" allotype, which comprises one or more amino acid substitutions selected from the group consisting of S131C, K133R, G137E, G138S, Q1% K, I199T, N203D, K214R, C226S, C229S, P238S, per EU numbering, as compared to a wild-type IgG1 isotype (e.g., SEQ ID NO: 12).

The phrases "an antibody recognizing an antigen" and "an antibody specific for an antigen" are used interchangeably herein with the term "an antibody which binds specifically to an antigen."

An "isolated antibody," as used herein, is intended to refer to an antibody that has been separated and/or recovered from (an)other component(s) in the environment in which it was produced and/or that has been purified from a mixture of components present in the environment in which it was produced.

An "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and downregulation of a cell surface receptor (e.g., the B cell receptor, BCR). Such effector functions generally require the Fc region to be combined with a binding domain (e.g., an antibody variable domain). In one embodiment, the anti-TREM-1 antibodies of the current disclosure comprise Fc regions that do not bind to one or more FcγRs and therefore, lack effector function (i.e., effectorless).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. Various properties of human FcγRs are known in the art. The majority of innate effector cell types coexpress one or more activating FcγR and the inhibitory FcγRIIB, whereas natural killer (NK) cells selectively express one activating Fc receptor (FcγRIII in mice and FcγRIIIA in humans) but not the inhibitory FcγRIIB in mice and humans. Human IgG1 binds to most human Fc receptors and is considered equivalent to murine IgG2a with respect to the types of activating Fc receptors that it binds to.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL).

In IgG, the Fc region comprises immunoglobulin domains CH2 and CH3 and the hinge between CH1 and CH2 domains. Although the definition of the boundaries of the Fc region of an immunoglobulin heavy chain might vary, as defined herein, the human IgG heavy chain Fc region is defined to stretch from an amino acid residue D221 for IgG1, V222 for IgG2, L221 for IgG3 and P224 for IgG4 to the carboxy-terminus of the heavy chain, wherein the numbering is according to the EU index as in Kabat. The CH2 domain of a human IgG Fc region extends from amino acid 237 to amino acid 340, and the CH3 domain is positioned on C-terminal side of a CH2 domain in an Fc region, i.e., it extends from amino acid 341 to amino acid 447 or 446 (if the C-terminal lysine residue is absent) or 445 (if the C-terminal glycine and lysine residues are absent) of an IgG. As used herein, the Fc region can be a native sequence Fc, including any allotypic variant, or a variant Fc (e.g., a non-naturally occurring Fc). Fc can also refer to this region in isolation or in the context of an Fc-comprising protein polypeptide such as a "binding protein comprising an Fc region," also referred to as an "Fc fusion protein" (e.g., an antibody or immunoadhesion).

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof. Native sequence Fc include the various allotypes of Fcs (see, e.g., Jefferis et al., *mAbs* 1: 1 (2009)).

A "variant sequence Fc region" or "non-naturally occurring Fc" comprises a modification, typically to alter one or more of its functional properties, such as serum half-life, complement fixation, Fc-receptor binding, protein stability and/or antigen-dependent cellular cytotoxicity, or lack thereof, among others. In some embodiments, the anti-TREM-1 antibodies of the present disclosure can be chemically modified (e.g., one or more chemical moieties can be attached to the antibody) or be modified to alter its glycosylation, again to alter one or more functional properties of the antibody. In one embodiment, the anti-TREM-1 antibody is an IgG1 isotype and carries a modified Fc domain comprising one or more, and perhaps all of the following mutations that will result in decreased affinity to certain Fc receptors (L234A, L235E, and G237A) and in reduced C1q-mediated complement fixation (A330S and P331S), respectively (residue numbering according to the EU index).

The terms "hinge," "hinge domain," "hinge region," and "antibody hinge region" refer to the domain of a heavy chain constant region that joins the CH1 domain to the CH2 domain and includes the upper, middle, and lower portions of the hinge (Roux et al., *J Immunol* 161:4083 (1998)). The hinge provides varying levels of flexibility between the binding and effector regions of an antibody and also provides sites for intermolecular disulfide bonding between the two heavy chain constant regions. As used herein, a hinge starts at Glu216 and ends at Gly237 of all IgG isotypes (Roux et al., *J Immunol* 161:4083 (1998)). The sequences of wildtype IgG1, IgG2, IgG3, and IgG4 hinges are known in the art (e.g., International PCT publication no. WO 2017/087678). In one embodiment, the hinge region of CH1 of the anti-TREM-1 antibodies is modified such that the number of cysteine residues in the hinge region is altered, e.g., increased or decreased. This approach is described further for instance in U.S. Pat. No. 5,677,425.

The constant region may be modified to stabilize the antibody, e.g., to reduce the risk of a bivalent antibody separating into two monovalent VH-VL fragments. For example, in an IgG4 constant region, residue S228 (residue numbering according to the EU index) may be mutated to a proline (P) residue to stabilize inter heavy chain disulfide bridge formation at the hinge (see, e.g., Angal et al., *Mol Immunol.* 30: 105-8(1995)). Antibodies or fragments thereof can also be defined in terms of their complementarity-determining regions (CDRs). The term "complementarity-determining region" or "hypervariable region", when used herein, refers to the regions of an antibody in which amino acid residues involved in antigen binding are situated. The region of hypervariability or CDRs can be identified as the regions with the highest variability in amino acid alignments of antibody variable domains. Databases can be used for CDR identification such as the Kabat database, the CDRs e.g., being defined as comprising amino acid residues 24-34 (CDR1), 50-59 (CDR2) and 89-97 (CDR3) of the light-chain variable domain, and 31-35 (CDR1), 50-65 (CDR2) and 95-102 (CDR3) in the heavy-chain variable domain; (Kabat et al. 1991; Sequences of Proteins of Immunological Interest, Fifth Edition, U.S. Department of Health and Human Services, NIH Publication No. 91-3242). Alternatively CDRs can be defined as those residues from a "hypervariable loop" (residues 26-33 (L1), 50-52 (L2) and 91-96 (L3) in the light-chain variable domain and 26-32 (H1), 53-55 (H2) and 96-101 (H3) in the heavy-chain variable domain (Chothia and Lesk, *J. Mol. Biol* 196: 901-917 (1987)). Typically, the numbering of amino acid residues in this region is performed by the method described in Kabat et al., supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "epitope" or "antigenic determinant" refers to a site on an antigen (e.g., TREM-1) to which an immunoglobulin or antibody specifically binds, e.g., as defined by the specific method used to identify it. Epitopes can be formed both from contiguous amino acids (usually a linear epitope) or noncontiguous amino acids juxtaposed by tertiary folding of a protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from (e.g., from TREM-1) are tested for reactivity with a given antibody (e.g., anti-TREM-1 antibody). Methods of determining spatial conformation of epitopes include techniques in the art and those described herein, for example, x-ray crystallography, antigen mutational analysis, 2-dimensional nuclear magnetic resonance and HDX-MS (see, e.g., Epitope Mapping Protocols in Methods in Molecular Biology, Vol. 66, G. E. Morris, Ed. (1996)).

The term "binds to the same epitope" with reference to two or more antibodies means that the antibodies bind to the same segment of amino acid residues, as determined by a given method. Techniques for determining whether antibodies bind to the "same epitope on TREM-1" with the antibodies described herein include, for example, epitope mapping methods, such as, x-ray analyses of crystals of antigen: antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, can be determined using known competition experiments, e.g., BIACORE® surface plasmon resonance (SPR) analysis. In certain embodiments, an antibody competes with, and inhibits binding of another antibody to a target by at least 50%, 60%, 70%, 80%, 90% or 100%. The level of inhibition or competition can be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi: 10.1101/pdb.prot4277 or in Chapter 11 of "Using Antibodies" by Ed Harlow and David Lane, Cold Spring Harbor Laboratory Press, Cold Spring Harbor, NY, USA 1999. Two antibodies "cross-compete" if antibodies block each other both ways by at least 50%, i.e., regardless of whether one or the other antibody is contacted first with the antigen in the competition experiment.

As used herein, the terms "specific binding," "selective binding," "selectively binds," and "specifically binds," refer to antibody binding to an epitope on a predetermined antigen. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE® 2000 instrument using the predetermined antigen, e.g., recombinant human TREM-1, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Accordingly, an antibody that "specifically binds to human TREM-1" refers to an antibody that binds to soluble or cell bound human TREM-1 with a $K_D$ of $10^{-7}$ M or less, such as approximately less than $10^{-8}$ M, $10^{-9}$ M or $10^{-10}$ M or even lower. An antibody that "cross-reacts with cynomolgus TREM-1" refers to an antibody that binds to cynomolgus TREM-1 with a $K_D$ of $10^{-7}$ M or less, such as approximately less than $10^{-8}$ M, $10^{-9}$ M or $10^{-10}$ M or even lower. In certain embodiments, such antibodies that do not cross-react with TREM-1 from a non-human species exhibit essentially undetectable binding against these proteins in standard binding assays.

The term "binding specificity" herein refers to the interaction of a molecule such as an antibody, or fragment thereof, with a single exclusive antigen, or with a limited number of highly homologous antigens (or epitopes). In contrast, antibodies that are capable of specifically binding to TREM-1 are not capable of binding dissimilar molecules. Antibodies according to the invention may not be capable of binding Nkp44, the Natural killer cell p44-related protein.

The specificity of an interaction and the value of an equilibrium binding constant can be determined directly by well-known methods. Standard assays to evaluate the ability of ligands (such as antibodies) to bind their targets are known in the art and include, for example, ELISAs, Western blots, RIAs, and flow cytometry analysis. The binding kinetics and binding affinity of the antibody also can be assessed by standard assays known in the art, such as SPR.

Competitive binding assays for determining whether two antibodies compete or cross-compete for binding include: competition for binding to myeloid cells expressing TREM-1, e.g., by flow cytometry, such as described in the Examples. Other methods include: SPR (e.g., BIACORE®), solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

As used herein, the term "bin" is defined using a reference antibody. If a second antibody is unable to bind to an antigen at the same time as the reference antibody, the second antibody is said to belong to the same "bin" as the reference antibody. In this case, the reference and the second antibody competitively bind the same part of an antigen and are coined "competing antibodies". If a second antibody is capable of binding to an antigen at the same time as the reference antibody, the second antibody is said to belong to a separate "bin". In this case, the reference and the second antibody do not competitively bind the same part of an antigen and are coined "non-competing antibodies".

Antibody "binning" does not provide direct information about the epitope. Competing antibodies, i.e., antibodies belonging to the same "bin" can have identical epitopes, overlapping epitopes, or even separate epitopes. The latter is the case if the reference antibody bound to its epitope on the antigen takes up the space required for the second antibody to contact its epitope on the antigen ("steric hindrance"). Non-competing antibodies generally have separate epitopes.

The term "binding affinity" herein refers to a measurement of the strength of a non-covalent interaction between two molecules, e.g., an antibody, or fragment thereof, and an antigen. The term "binding affinity" is used to describe monovalent interactions (intrinsic activity).

The binding affinity between two molecules, e.g., an antibody, or fragment thereof, and an antigen, through a monovalent interaction may be quantified by determination of the equilibrium dissociation constant ($K_D$). In turn, $K_D$ can be determined by measurement of the kinetics of complex formation and dissociation, e.g., by the SPR method. The rate constants corresponding to the association and the dissociation of a monovalent complex are referred to as the association rate constant $k_a$ (or $k_{on}$) and dissociation rate constant $k_d$ (or $k_{Off}$), respectively. $K_D$ is related to $k_a$ and $k_d$ through the equation $K_D=k_d/k_a$. Following the above definition, binding affinities associated with different molecular interactions, such as comparison of the binding affinity of different antibodies for a given antigen, may be compared by comparison of the $K_D$ values for the individual antibody/antigen complexes.

As used herein, the term "high affinity" for an IgG antibody refers to an antibody having a $K_D$ of $10^{-8}$ M or less, $10^{-9}$ M or less, or $10^{-10}$ M or less for a target antigen. However, "high affinity" binding can vary for other antibody isotypes. For example, "high affinity" binding for an IgM isotype refers to an antibody having a $K_D$ of $10^{-10}$ M or less, or $10^{-8}$ M or less.

The term "$EC_{50}$" in the context of an in vitro or in vivo assay using an antibody or antigen binding fragment thereof, refers to the concentration of an antibody or an antigen-binding portion thereof that induces a response that is 50% of the maximal response, i.e., halfway between the maximal response and the baseline.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" can comprise one or more polypeptides.

The term "nucleic acid molecule," as used herein, is intended to include DNA molecules and RNA molecules. A nucleic acid molecule can be single-stranded or double-stranded, and can be cDNA.

"Conservative amino acid substitutions" refer to substitutions of an amino acid residue with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, a predicted nonessential amino acid residue in an anti-TREM-1 antibody is replaced with another amino acid residue from the same side chain family. Methods of identifying nucleotide and amino acid conservative substitutions which do not eliminate antigen binding are well-known in the art (see, e.g., Brummell et al., *Biochem.* 32: 1180-1187

(1993); Kobayashi et al. *Protein Eng.* 12(10):879-884 (1999); and Burks et al. *Proc. Natl. Acad. Sci. USA* 94:412-417 (1997)).

For nucleic acids, the term "substantial homology" indicates that two nucleic acids, or designated sequences thereof, when optimally aligned and compared, are identical, with appropriate nucleotide insertions or deletions, in at least about 80% of the nucleotides, at least about 90% to 95%, or at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, at least about 90% to 95%, or at least about 98% to 99.5% of the amino acids.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at worldwideweb.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*CABIOS,* 4: 11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at worldwideweb.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See worldwideweb.ncbi.nlm.nih.gov.

The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

Nucleic acids, e.g., cDNA, can be mutated, in accordance with standard techniques to provide gene sequences. For coding sequences, these mutations, can affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "vector," as used herein, is intended to refer to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" can be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and can be a cell into which a recombinant expression vector has been introduced. It should be understood that such terms are intended to refer not only to the particular subject cell but to the progeny of such a cell. Because certain modifications can occur in succeeding generations due to either mutation or environmental influences, such progeny cannot, in fact, be identical to the parent cell, but are still included within the scope of the term "host cell" as used herein.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, "administering" refers to the physical introduction of a composition comprising a therapeutic agent to a subject, using any of the various methods and delivery systems known to those skilled in the art. Different routes of administration for the anti-TREM-1 antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, the terms "inhibits" or "blocks" (e.g., referring to inhibition/blocking of binding of TREM-1 ligand to TREM-1 on cells) are used interchangeably and encompass both partial and complete inhibition/blocking. In some embodiments, the anti-TREM-1 antibody inhibits binding of TREM-1 ligand to TREM-1 by at least about 50%, for example, about 60%, 70%, 80%, 90%, 95%, 99%, or 100%, determined, e.g., as further described herein. In some embodiments, the anti-TREM-1 antibody inhibits binding of TREM-1 ligand to TREM-1 by no more than 50%, for example, by about 40%, 30%, 20%, 10%, 5% or 1%, determined, e.g., as further described herein.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease or enhancing overall survival. Treatment can be of a subject having a disease or a subject who does not have a disease (e.g., for prophylaxis).

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

The term "patient" includes human and other mammalian subjects that receive either prophylactic or therapeutic treatment.

As used herein, the term "subject" includes any human or non-human animal. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc.

As used herein, the terms "ug" and "uM" are used interchangeably with "μg" and "μM," respectively.

Various aspects described herein are described in further detail in the following subsections.

I. Anti-TREM-1 Antibodies

Described herein are antibodies, e.g., fully human antibodies, which are characterized by particular functional features or properties. For example, the antibodies of the present disclosure specifically bind human TREM-1, and more specifically, a particular domain (e.g., a functional domain) within the extracellular domain of human TREM-1. In some embodiments, the antibodies specifically bind to the site on TREM-1 to which the TREM-1 ligand (e.g., PGLYRP1) binds. In some embodiments, the antibodies are antagonist antibodies, i.e., they inhibit or suppress the activity of TREM-1 (i.e., do not agonize upon binding) on cells, e.g., monocytes, macrophages, and neutrophils. In some embodiments, the anti-TREM-1 antibodies cross-react with TREM-1 from one or more non-human primates, such as cynomolgus TREM-1. In some embodiments, the anti-TREM-1 antibodies block the production of inflammatory cytokines (e.g., IL-6, TNF-α, IL-8, IL-1β, IL-12, and combinations thereof) by cells (e.g., macrophages, dendritic cells, neutrophils) upon activation. In some embodiments, the particular anti-TREM-1 antibodies described herein are antibodies, e.g., monoclonal, recombinant, and/or human antibodies, that bind to human TREM-1 at a different epitope than a reference antibody (e.g., mAb170) (i.e., epitope-steered). Accordingly, in some embodiments, the anti-TREM-1 antibody does not cross-compete with the reference antibody (e.g., mAb170) for binding to human TREM-1. In other words, in some embodiments, the anti-TREM-1 antibodies of the present disclosure belong to a different "bin" as the reference antibody (e.g., mAb170).

In some embodiments, the epitope-steered anti-TREM-1 antibodies of the present disclosure comprise a heavy chain variable region (VH) and/or a light chain variable region (VL) from Table 1. In certain embodiments, the VH comprises an amino acid sequence set forth as SEQ ID NO: 13, 15, 23, 25, or 130. In certain embodiments, the VL comprises an amino acid sequence set forth as SEQ ID NO: 14, 16, 17, 24, 131, or 132.

In some embodiments, the epitope-steered anti-TREM-1 antibodies of the present disclosure comprise a VH and a VL, wherein:

(a) the VH and VL comprises amino acid sequences set forth as SEQ ID NOs: 13 and 14, respectively;

(b) the VH and VL comprises amino acid sequences set forth as SEQ ID NOs: 15 and 16, respectively;

(c) the VH and VL comprises amino acid sequences set forth as SEQ ID NOs: 15 and 17, respectively;

(d) the VH and VL comprises amino acid sequences set forth as SEQ ID NOs: 23 and 24, respectively;

(e) the VH and VL comprises amino acid sequences set forth as SEQ ID NOs: 25 and 16, respectively;

the VH and VL comprises amino acid sequences set forth as SEQ ID NOs: 130 and 131, respectively; or (f) the VH and VL comprises amino acid sequences set forth as SEQ ID NOs: 130 and 132, respectively.

In some embodiments, the epitope-steered anti-TREM-1 antibodies disclosed herein comprise CDRs of a heavy chain variable region selected from the group consisting of SEQ ID NOs: 13, 15, 23, 25, and 130. In some embodiments, the epitope-steered anti-TREM-1 antibodies disclosed herein comprise CDRs of a light chain variable region selected from the group consisting of SEQ ID NOs: 14, 16, 17, 24, 131, and 132.

In some embodiments, the epitope-steered anti-TREM-1 antibodies of the present disclosure comprise heavy chain variable region (VH) CDR1, CDR2, and CDR3 and a light chain variable region (VL) CDR1, CDR2, and CDR3, wherein:

(a) the VH CDR1 comprises an amino acid sequence selected from the group consisting of SEQ ID NOs: 26, 32, 45, 50, and 136;
(b) the VH CDR2 comprises an amino acid sequence selected from the group consisting of SEQ ID NOs: 27, 33, 46, 51, and 137;
(c) the VH CDR3 comprises an amino acid sequence selected from the group consisting of SEQ ID NOs: 28, 34, 47, 52, and 138;
(d) the VL CDR1 comprises an amino acid sequence selected from the group consisting of SEQ ID NOs: 29 and 35;
(e) the VL CDR2 comprises an amino acid sequence selected from the group consisting of SEQ ID NOs: 30, 36, and 48; and/or
(f) the VL CDR3 comprises an amino acid sequence selected from the group consisting of SEQ ID NOs: 31, 37, 38, 39, 103, and 139.

In some embodiments, the epitope-steered anti-TREM-1 antibodies disclosed herein comprise heavy chain variable region (VH) CDR1, CDR2, and CDR3 and a light chain variable region (VL) CDR1, CDR2, and CDR3, wherein:

(a) the VH CDR1 comprises the amino acid sequence set forth as SEQ ID NO: 26, the VH CDR2 comprises the amino acid sequence set forth as SEQ ID NO: 27, and the VH CDR3 comprises the amino acid sequence set forth as SEQ ID NO: 28, the VL CDR1 comprises the amino acid sequence set forth in SEQ ID NO: 29, the VL CDR2 comprises the amino acid sequence set forth in SEQ ID NO: 30, and the VL CDR3 comprises the amino acid sequence set forth in SEQ ID NO: 31;
(b) the VH CDR1 comprises the amino acid sequence set forth as SEQ ID NO: 32, the VH CDR2 comprises the amino acid sequence set forth as SEQ ID NO: 33, and the VH CDR3 comprises the amino acid sequence set forth as SEQ ID NO: 34, the VL CDR1 comprises the amino acid sequence set forth in SEQ ID NO: 35, the VL CDR2 comprises the amino acid sequence set forth in SEQ ID NO: 36, and the VL CDR3 comprises the amino acid sequence set forth in SEQ ID NO: 37;
(c) the VH CDR1 comprises the amino acid sequence set forth as SEQ ID NO: 32, the VH CDR2 comprises the amino acid sequence set forth as SEQ ID NO: 33, and the VH CDR3 comprises the amino acid sequence set forth as SEQ ID NO: 34, the VL CDR1 comprises the amino acid sequence set forth in SEQ ID NO: 29, the VL CDR2 comprises the amino acid sequence set forth in SEQ ID NO: 30, and the VL CDR3 comprises the amino acid sequence set forth in SEQ ID NO: 38;
(d) the VH CDR1 comprises the amino acid sequence set forth as SEQ ID NO: 45, the VH CDR2 comprises the amino acid sequence set forth as SEQ ID NO: 46, and the VH CDR3 comprises the amino acid sequence set forth as SEQ ID NO: 47, the VL CDR1 comprises the amino acid sequence set forth in SEQ ID NO: 35, the VL CDR2 comprises the amino acid sequence set forth in SEQ ID NO: 48, and the VL CDR3 comprises the amino acid sequence set forth in SEQ ID NO: 49;
(e) the VH CDR1 comprises the amino acid sequence set forth as SEQ ID NO: 50, the VH CDR2 comprises the amino acid sequence set forth as SEQ ID NO: 51, and the VH CDR3 comprises the amino acid sequence set forth as SEQ ID NO: 52, the VL CDR1 comprises the amino acid sequence set forth in SEQ ID NO: 35, the VL CDR2 comprises the amino acid sequence set forth in SEQ ID NO: 36, and the VL CDR3 comprises the amino acid sequence set forth in SEQ ID NO: 37;
(f) the VH CDR1 comprises the amino acid sequence set forth as SEQ ID NO: 136, the VH CDR2 comprises the amino acid sequence set forth as SEQ ID NO: 137, and the VH CDR3 comprises the amino acid sequence set forth as SEQ ID NO: 138, the VL CDR1 comprises the amino acid sequence set forth in SEQ ID NO: 35, the VL CDR2 comprises the amino acid sequence set forth in SEQ ID NO: 36, and the VL CDR3 comprises the amino acid sequence set forth in SEQ ID NO: 139; or
(g) VH CDR1 comprises the amino acid sequence set forth as SEQ ID NO: 136, the VH CDR2 comprises the amino acid sequence set forth as SEQ ID NO: 137, and the VH CDR3 comprises the amino acid sequence set forth as SEQ ID NO: 138, the VL CDR1 comprises the amino acid sequence set forth in SEQ ID NO: 35, the VL CDR2 comprises the amino acid sequence set forth in SEQ ID NO: 36, and the VL CDR3 comprises the amino acid sequence set forth in SEQ ID NO: 103.

In some embodiments, the epitope-steered anti-TREM-1 antibodies disclosed herein comprise heavy chain variable region (VH) CDR1, CDR2, and CDR3 and a light chain variable region (VL) CDR1, CDR2, and CDR3, wherein one or more of the CDRs comprise one or more amino acid mutations (e.g., substitution or deletion) relative to an anti-TREM-1 antibody disclosed herein. Accordingly, in certain embodiments, the epitope-steered anti-TREM-1 antibodies comprise a VH CDR1 comprising X1, X2, X3, X4, and X5, wherein X1 is S or N; X2 is S, Y, or E; X3 is Y G, or A; X4 is W, M or I; and X5 is S, T, H, or N. In some embodiments, the epitope-steered anti-TREM-1 antibodies comprise a VH CDR2 comprising X1, X2, X3, X4, X5, X6, X7, X8, X9, X10, X11, X12, X13, X14, X15, X16, and X17, wherein X1 is Y V, or G; X2 is T or I; X3 is W, I, or none; X4 is H, Y, or P; X5 is Y, D, or I; X6 is S, G, or F; X7 is G, S, or D; X8 is I, Y, N, or T; X9 is S, T, or K; X10 is N or Y; XII is Y or G; X12 is N or A; X13 is P, D, or Q; X14 is S or K; X15 is L, V, or F; X16 is K or Q; and X17 is S or G. In some embodiments, the epitope-steered anti-TREM-1 antibodies comprise a VH CDR3 comprising X1, X2, X3, X4, X5, X6, X7, X8, X9, X10, X11, X12, G, X13, X14, X15, X16, X17, X18, D, and X19, wherein X1 is E, D, M, T, or none; X2 is G, V, or Y; X3 is Y, R, or none; X4 is D, H, G, or none; X5 is I, Y, or none; X6 is L, Y, or none; X7 is T, G, N, or none; X8 is G, S, Y, or none; X9 is Y, V, T, F, or H; X10 is E, L, S, or Y; X11 is Y, W, F, or H; X12 is Y or F; X13 is E or none; X14 is L or none; X15 is L or none; X16 is P or none; X17 is L or none; X18 is M or L; and X19 is V or Y. In certain embodiments, the epitope-steered anti-TREM-1 antibodies comprise a VL CDR1 comprising R, A, S, Q, X1, X2, X3, S, S, X4, L, and A, wherein X1 is S or G; X2 is V or I; X3 is S or none; and X4 is Y or A (SEQ ID NO: 341). In some embodiments, the epitope-steered anti-TREM-1 antibodies disclosed herein comprise a VL CDR2 comprising X1, A, S, S, X2, X3, and X4, wherein X1 is G, D or A; X2 is R or L; X3 is A, E, or Q; and X4 is T or S. In certain embodiments, the epitope-steered anti-TREM-1 antibodies comprise a VL CDR3 comprising Q, Q, X1, X2, S, X3, P, X4, and T, wherein X1 is Y or F; X2 is G or N; X3 is S or Y; and X4 is L, Y, I, or none (SEQ ID NO: 343).

Also provided herein are anti-TREM-1 antibodies that bind to human TREM-1 at a same epitope as the reference antibody (e.g., mAb170) (i.e., non-epitope-steered), but the anti-TREM-1 antibody is not mAb170. Accordingly, in some embodiments, these non-epitope-steered anti-TREM-1 antibodies do cross-compete with the reference antibody (e.g., mAb170) for binding to human TREM-1. In other words, in some embodiments, the anti-TREM-1 antibodies of the present disclosure belong to the same "bin" as the reference antibody (e.g., mAb170), wherein the anti-TREM-1 antibody is not mAb170. The amino acid sequences of the heavy chain variable region (VH) and the light chain variable region (VL) of the reference antibody mAb 0170 are as follows:

```
(A) Heavy chain variable region:
                                    (SEQ ID NO: 193)
EVQLVESGGGLVQPGGSLKLSCAAEGFTFSTYAMHWVRQASGKGLEWVGR

IRTKSSNYATYYAASVKGRFTISRDDSKNTAYLOMNSLKTEDTAVYYCTR

DMGIRRQFAYWGQGTLVTVSSASTKGPSVFPLAPCSRSTSESTAALGCLV

KDYFPEPVTVSWNSGALTSGVHTFPAVIQSSGLYSLSSVVTVPSSSLGTK

TYTCNVDHKPSNTKVDKRVESKYGPPCPPCPAPEFLGGPSVFLFPPKPKD

TLMISRTPEVTCVVVDVSQEDPEVQFNWYVDGVEVHNAKTKPREEQFNST

YRVVSVLTVLIQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK

(B) Light chain variable region:
                                    (SEQ ID NO: 194)
DIVLTQSPDSLAVSLGERATINCRASESVDTFDYSFLHWYQQKPGQPPKL

LIYRASNLESGVPDRFSGSGSGTDFTLTISSLQAEDVAVYYCQQSNEDPY

TFGQGTKLEIKRTVAAPSVFIFPPSDEQLKSGTASVVCLLNNFYPREAEV

QWKVDNALQSGNSQESVTEQDSKDSTYSLSSTLTLSKADYEKHKVYACEV

THQGLSSPVTKSFNRGEC.
See international Publ. No. WO 2016/009086 A1.
```

In some embodiments, the non-epitope-steered anti-TREM-1 antibodies disclosed herein comprise a heavy chain variable region (VH) and/or a light chain variable region (VL) from Table 2. In certain embodiments, the VH comprises an amino acid sequence set forth as SEQ ID NO: 53, 55, 57, 59, 62, 64, 66, 68, 73, 74, 75, 76, 78, 80, 81, 83, or 133. In certain embodiments, the VL comprises an amino acid sequence set forth as SEQ ID NO: 54, 56, 58, 60, 61, 63, 65, 67, 69, 70, 71, 72, 77, 79, 82, 134, or 135.

In some embodiments, the non-epitope-steered anti-TREM-1 antibodies disclosed herein comprise a VH and a VL, wherein (a) the VH comprises the amino acid sequence set forth in SEQ ID NO: 53 and the VL comprises the amino acid sequence set forth in SEQ ID NO: 54;

(b) the VH comprises the amino acid sequence set forth in SEQ ID NO: 55 and the VL comprises the amino acid sequence set forth in SEQ ID NO: 56;

(c) the VH comprises the amino acid sequence set forth in SEQ ID NO: 57 and the VL comprises the amino acid sequence set forth in SEQ ID NO: 58;

(d) the VH comprises the amino acid sequence set forth in SEQ ID NO: 59 and the VL comprises the amino acid sequence set forth in SEQ ID NO: 60;

(e) the VH comprises the amino acid sequence set forth in SEQ ID NO: 59 and the VL comprises the amino acid sequence set forth in SEQ ID NO: 61;

(f) the VH comprises the amino acid sequence set forth in SEQ ID NO: 59 and the VL comprises the amino acid sequence set forth in SEQ ID NO: 54;

(g) the VH comprises the amino acid sequence set forth in SEQ ID NO: 62 and the VL comprises the amino acid sequence set forth in SEQ ID NO: 61;

(h) the VH comprises the amino acid sequence set forth in SEQ ID NO: 59 and the VL comprises the amino acid sequence set forth in SEQ ID NO: 63;

(i) the VH comprises the amino acid sequence set forth in SEQ ID NO: 64 and the VL comprises the amino acid sequence set forth in SEQ ID NO: 65;

(j) the VH comprises the amino acid sequence set forth in SEQ ID NO: 66 and the VL comprises the amino acid sequence set forth in SEQ ID NO: 67;

(k) the VH comprises the amino acid sequence set forth in SEQ ID NO: 68 and the VL comprises the amino acid sequence set forth in SEQ ID NO: 54;

(l) the VH comprises the amino acid sequence set forth in SEQ ID NO: 68 and the VL comprises the amino acid sequence set forth in SEQ ID NO: 69;

(m) the VH comprises the amino acid sequence set forth in SEQ ID NO: 68 and the VL comprises the amino acid sequence set forth in SEQ ID NO: 70;

(n) the VH comprises the amino acid sequence set forth in SEQ ID NO: 68 and the VL comprises the amino acid sequence set forth in SEQ ID NO: 71;

(o) the VH comprises the amino acid sequence set forth in SEQ ID NO: 68 and the VL comprises the amino acid sequence set forth in SEQ ID NO: 72;

(p) the VH comprises the amino acid sequence set forth in SEQ ID NO: 68 and the VL comprises the amino acid sequence set forth in SEQ ID NO: 60;

(q) the VH comprises the amino acid sequence set forth in SEQ ID NO: 73 and the VL comprises the amino acid sequence set forth in SEQ ID NO: 54;

(r) the VH comprises the amino acid sequence set forth in SEQ ID NO: 73 and the VL comprises the amino acid sequence set forth in SEQ ID NO: 63;

(s) the VH comprises the amino acid sequence set forth in SEQ ID NO: 74 and the VL comprises the amino acid sequence set forth in SEQ ID NO: 54;

(t) the VH comprises the amino acid sequence set forth in SEQ ID NO: 75 and the VL comprises the amino acid sequence set forth in SEQ ID NO: 54;

(u) the VH comprises the amino acid sequence set forth in SEQ ID NO: 76 and the VL comprises the amino acid sequence set forth in SEQ ID NO: 77;

(v) the VH comprises the amino acid sequence set forth in SEQ ID NO: 78 and the VL comprises the amino acid sequence set forth in SEQ ID NO: 79;

(w) the VH comprises the amino acid sequence set forth in SEQ ID NO: 80 and the VL comprises the amino acid sequence set forth in SEQ ID NO: 54;

(x) the VH comprises the amino acid sequence set forth in SEQ ID NO: 81 and the VL comprises the amino acid sequence set forth in SEQ ID NO: 82;

(y) the VH comprises the amino acid sequence set forth in SEQ ID NO: 83 and the VL comprises the amino acid sequence set forth in SEQ ID NO: 60;

(z) the VH comprises the amino acid sequence set forth in SEQ ID NO: 133 and the VL comprises the amino acid sequence set forth in SEQ ID NO: 134;

(aa) the VH comprises the amino acid sequence set forth in SEQ ID NO: 133 and the VL comprises the amino acid sequence set forth in SEQ ID NO: 54; or (bb) the VH comprises the amino acid sequence set forth in SEQ ID NO: 59 and the VL comprises the amino acid sequence set forth in SEQ ID NO: 135.

In some embodiments, the non-epitope-steered anti-TREM-1 antibodies comprise CDRs of a heavy chain variable region selected from the group consisting of 53, 55, 57, 59, 62, 64, 66, 68, 73, 74, 75, 76, 78, 80, 81, 83, and 133. In some embodiments, the non-epitope-steered anti-TREM-1 antibodies comprise CDRs of a light chain variable region selected from the group consisting of 54, 56, 58, 60, 61, 63, 65, 67, 69, 70, 71, 72, 77, 79, 82, 134, and 135.

In some embodiments, the non-epitope-steered anti-TREM-1 antibodies of the present disclosure comprise heavy chain variable region (VH) CDR1, CDR2, and CDR3 and a light chain variable region (VL) CDR1, CDR2, and CDR3, wherein (a) the VH CDR1 comprises an amino acid sequence selected from the group consisting of SEQ ID NOs: 45, 84, 89, 93, 99, 106, 109, 112, and 140;

(b) the VH CDR2 comprises an amino acid sequence selected from the group consisting of SEQ ID NOs: 85, 90, 94, 97, 98, 100, 102, 104, 107, 110, 113, 116, 119, and 141;

(c) the VH CDR3 comprises an amino acid sequence selected from the group consisting of SEQ ID NOs: 86, 91, 95, 101, 105, 108, 111, 114, 115, 117, 120, and 142;

(d) the VL CDR1 comprises an amino acid sequence selected from the group consisting of SEQ ID NOs: 87 and 42;

(e) the VL CDR2 comprises an amino acid sequence selected from the group consisting of SEQ ID NOs: 48 and 30; and/or (f) the VL CDR3 comprises an amino acid sequence selected from the group consisting of SEQ ID NOs: 38, 49, 88, 92, %, 103, 118, and 143.

In some embodiments, the non-epitope-steered anti-TREM-1 antibodies disclosed herein comprise VH CDR1, CDR2, and CDR3 and VL CDR1, CDR2, and CDR3, wherein:

(a) the VH CDR1 comprises the amino acid sequence set forth as SEQ ID NOs: 84, the VH CDR2 comprises the amino acid sequence set forth as SEQ ID NO: 85, and the VH CDR3 comprises the amino acid sequence set forth as SEQ ID NO: 86, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 88;

(b) the VH CDR1 comprises the amino acid sequence set forth as SEQ ID NOs: 89, the VH CDR2 comprises the amino acid sequence set forth as SEQ ID NO: 90, and the VH CDR3 comprises the amino acid sequence set forth as SEQ ID NO: 91, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 92;

(c) the VH CDR1 comprises the amino acid sequence set forth as SEQ ID NOs: 93, the VH CDR2 comprises the amino acid sequence set forth as SEQ ID NO: 94, and the VH CDR3 comprises the amino acid sequence set forth as SEQ ID NO: 95, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 96;

(d) the VH CDR1 comprises the amino acid sequence set forth as SEQ ID NOs: 93, the VH CDR2 comprises the amino acid sequence set forth as SEQ ID NO: 97, and the VH CDR3 comprises the amino acid sequence set forth as SEQ ID NO: 95, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 49;

(e) the VH CDR1 comprises the amino acid sequence set forth as SEQ ID NOs: 93, the VH CDR2 comprises the amino acid sequence set forth as SEQ ID NO: 97, and the VH CDR3 comprises the amino acid sequence set forth as SEQ ID NO: 95, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 88;

(f) the VH CDR1 comprises the amino acid sequence set forth as SEQ ID NO: 93, the VH CDR2 comprises the amino acid sequence set forth as SEQ ID NO: 98, and the VH CDR3 comprises the amino acid sequence set forth as SEQ ID NO: 95, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 49;

(g) the VH CDR1 comprises the amino acid sequence set forth as SEQ ID NO: 99, the VH CDR2 comprises the amino acid sequence set forth as SEQ ID NO: 100, and the VH CDR3 comprises the amino acid sequence set forth as SEQ ID NO: 101, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 49;

(h) the VH CDR1 comprises the amino acid sequence set forth as SEQ ID NO: 99, the VH CDR2 comprises the amino acid sequence set forth as SEQ ID NO: 102, and the VH CDR3 comprises the amino acid sequence set forth as SEQ ID NO: 101, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 88;

(i) the VH CDR1 comprises the amino acid sequence set forth as SEQ ID NO: 99, the VH CDR2 comprises the amino acid sequence set forth as SEQ ID NO: 102, and the VH CDR3 comprises the amino acid sequence set forth as SEQ ID NO: 101, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 103;

(j) the VH CDR1 comprises the amino acid sequence set forth as SEQ ID NO: 99, the VH CDR2 comprises the amino acid sequence set forth as SEQ ID NO: 102, and the VH CDR3 comprises the amino acid sequence set forth as SEQ ID NO: 101, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 49;

(k) the VH CDR1 comprises the amino acid sequence set forth as SEQ ID NO: 93, the VH CDR2 comprises the amino acid sequence set forth as SEQ ID NO: 102, and the VH CDR3 comprises the amino acid sequence set forth as SEQ ID NO: 95, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 88;

(l) the VH CDR1 comprises the amino acid sequence set forth as SEQ ID NO: 45, the VH CDR2 comprises the amino acid sequence set forth as SEQ ID NO: 104, and the VH CDR3 comprises the amino acid sequence set forth as SEQ ID NO: 105, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 88;

(m) the VH CDR1 comprises the amino acid sequence set forth as SEQ ID NO: 106, the VH CDR2 comprises the amino acid sequence set forth as SEQ ID NO: 107, and the VH CDR3 comprises the amino acid sequence set forth as SEQ ID NO: 108, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 88;

(n) the VH CDR1 comprises the amino acid sequence set forth as SEQ ID NO: 109, the VH CDR2 comprises the amino acid sequence set forth as SEQ ID NO: 110, and the VH CDR3 comprises the amino acid sequence set forth as SEQ ID NO: 111, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 49;

(o) the VH CDR1 comprises the amino acid sequence set forth as SEQ ID NO: 112, the VH CDR2 comprises the amino acid sequence set forth as SEQ ID NO: 113, and the VH CDR3 comprises the amino acid sequence set forth as SEQ ID NO: 114, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: %;

(p) the VH CDR1 comprises the amino acid sequence set forth as SEQ ID NO: 112, the VH CDR2 comprises the amino acid sequence set forth as SEQ ID NO: 113, and the VH CDR3 comprises the amino acid sequence set forth as SEQ ID NO: 115, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 88;

(q) the VH CDR1 comprises the amino acid sequence set forth as SEQ ID NO: 45, the VH CDR2 comprises the amino acid sequence set forth as SEQ ID NO: 116, and the VH CDR3 comprises the amino acid sequence set forth as SEQ ID NO: 117, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 118;

(r) the VH CDR1 comprises the amino acid sequence set forth as SEQ ID NO: 45, the VH CDR2 comprises the amino acid sequence set forth as SEQ ID NO: 119, and the VH CDR3 comprises the amino acid sequence set forth as SEQ ID NO: 120, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 49;

(s) the VH CDR1 comprises the amino acid sequence set forth as SEQ ID NO: 140, the VH CDR2 comprises the amino acid sequence set forth as SEQ ID NO: 141, and the VH CDR3 comprises the amino acid sequence set forth as SEQ ID NO: 142, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 143;

(t) the VH CDR1 comprises the amino acid sequence set forth as SEQ ID NO: 140, the VH CDR2 comprises the amino acid sequence set forth as SEQ ID NO: 141, and the VH CDR3 comprises the amino acid sequence set forth as SEQ ID NO: 142, the VL CDR1 comprises the amino acid sequence set forth in SEQ ID NO: 87, the VL CDR2 comprises the amino acid sequence set forth in SEQ ID NO: 48, and the VL CDR3 comprises the amino acid sequence set forth in SEQ ID NO: 88; or (t) the VH CDR1 comprises the amino acid sequence set forth as SEQ ID NO: 93, the VH CDR2 comprises the amino acid sequence set forth as SEQ ID NO: 97, and the VH CDR3 comprises the amino acid sequence set forth as SEQ ID NO: 95, the VL CDR1 comprises the amino acid sequence set forth in SEQ ID NO: 42, the VL CDR2 comprises the amino acid sequence set forth in SEQ ID NO: 30, and the VL CDR3 comprises the amino acid sequence set forth in SEQ ID NO: 38.

In some embodiments, the anti-TREM-1 antibodies comprise CDR and/or variable region sequences that have at least 80% identity (e.g., at least 85%, at least 95%, at least 95%, or at least 99% identity) to the CDR and/or variable region sequences disclosed herein (e.g., Tables 1, 2, 5, and 6).

In some embodiments, the anti-TREM-1 antibody disclosed herein comprises a heavy chain and a light chain, wherein the heavy chain comprises a VH domain disclosed herein (e.g., those provided in Tables 1 and 2) fused to a heavy chain constant region described herein (e.g., SEQ ID NO: 122, 123, 124, or 125). In some embodiments, the anti-TREM-1 antibody disclosed herein comprises a heavy chain and a light chain, wherein the light chain comprises a VL domain disclosed herein (e.g., those provided in Tables 1 and 2) fused to a light chain constant region described herein (e.g., SEQ ID NO: 126).

In some embodiments, the anti-TREM-1 antibody of the present disclosure comprises a heavy chain and a light chain, wherein the heavy chain comprises an amino acid sequence selected from the group consisting of SEQ ID NOs: 197-207 and 209-232, and/or wherein the light chain comprises an amino acid sequence selected from the group consisting of SEQ ID NOs: 233-243 and 245-268.

Heavy and light chains comprising an amino acid sequence that is at least 99%, 98%, 97%, 96%, 95%, 90%, 85%, or 80% identical to any of the heavy or light chains described herein can be used for forming the anti-TREM-1 antibodies having the desired characteristics, e.g., those further described herein.

In some embodiments, the anti-TREM-1 antibody is capable of binding variants of human TREM-1 (e.g., TREM-1 isoforms 2 and 3, SEQ ID NOs: 2 and 3, respectively), as determined using, e.g., surface plasmon resonance. In some embodiments, the anti-TREM-1 antibody is capable of binding cynomolgus TREM-1 (SEQ ID NO: 7), as determined using, e.g., surface plasmon resonance.

In some embodiments, anti-TREM-1 antibodies described herein bind to human TREM-1 with high affinity, e.g., as determined by BIACORE™ (e.g., as described in the Examples), with a $K_D$ of $10^{-7}$ M or less, $10^{-8}$ M or less, $10^{-9}$ M (1 nM) or less, $10^{-10}$ M or less, $10^{-11}$ M or less, $10^{-12}$ M or less, $10^{-12}$ M to $10^{-7}$ M, $10^{-11}$ M to $10^{-7}$ M, $10^{-10}$ M to $10^{-7}$ M, or $10^{-9}$ M to $10^{-7}$ M. In some embodiments, anti-TREM-1 antibodies described herein bind to cyno TREM-1, e.g., as determined by BIACORE™ (e.g., as described in the Examples), with a $K_D$ of $10^{-7}$ M or less, $10^{-8}$ M or less, $10^{-9}$ M or less, $10^{-10}$ M or less, $10^{-11}$ M or less, $10^{-12}$ M or less, $10^{-12}$ M to $10^{-7}$ M, $10^{-11}$ M to $10^{-7}$ M, $10^{-10}$ M to $10^{-7}$ M, or $10^{-9}$ M to $10^{-7}$ M.

In some embodiments, the anti-TREM-1 antibodies bind to TREM-1 at a different epitope than a reference antibody (e.g., mAb 170) (i.e., epitope-steered), such that the anti-TREM-1 antibodies of the present disclosure do not compete with the reference antibody for binding to human TREM-1. Therefore, in certain embodiments, the anti-TREM-1 antibodies disclosed herein do not bind to amino acid D38 to L45, E46 to Q56, and/or Y90 to L96 of human TREM-1 (SEQ ID NO: 1). In some embodiments, the anti-TREM-1 antibody binds to one or more epitope selected from the group consisting of (1)$^{2}$EKYELKEGQTL$^{37}$ (SEQ ID NO: 9), (2) $^{88}$EDYHDHGLLRVRM$^{100}$ (SEQ ID NO: 10), and (3) $^{120}$KEPHMLFDR$^{128}$ (SEQ ID NO: 11) of human TREM-1 (e.g., Isoform 1, SEQ ID NO: 1). In some embodiments, the anti-TREM-1 antibody is capable of specifically binding at least one amino acid residue selected from the group consisting of (1) E27, K28, Y29, E30, L31, K32, E33, G34, Q35, T36, L37, and any combinations thereof; (2) E88, D89, Y90, H100, D101, H102, G103, L104, L105, R106, V107, R108, M109, and any combinations thereof; and (3) K120, E121, P122, H123, M124, L125, F126, D127, R128, and any combinations thereof of human TREM-1 (e.g., Isoform 1, SEQ ID NO: 1).

In some embodiments, the antibodies of the present disclosure bind TREM-1 at a same epitope as the reference antibody (e.g., mAb 170) (i.e., non-epitope-steered). In some embodiments, the anti-TREM-1 antibody is capable of specifically binding (i) at least one amino acid residue selected from the group consisting of the A21, T22, K23, L24, T25, E26, and any combination thereof and (ii) at least one amino acid residue selected from the group consisting of the A49, S50, S51, Q52, K53, A54, W55, Q56, 157, 158, R59, D60, G61, E62, M63, P64, K65, T66, L67, A68, C69, T70, E71, R72, P73, S74, K75, N76, S77, H78, P79, V80, Q81, V82, G83, R84, 185, and any combination thereof and (iii) at least one amino acid residue selected from the group consisting of the C113, V114, 1115, Y116, Q117, P118, P119, and any combination thereof of human TREM-1 (e.g., Isoform 1, SEQ ID NO: 1). See WO 2016/009086.

In some embodiments, the anti-TREM-1 antibody is capable of specifically binding to amino acids D38 to F48 of SEQ ID NO: 1 (human TREM-1), as determined using, e.g., HDX-MS or X-ray diffraction. In some embodiments, the anti-TREM-1 antibody has an epitope comprising one, two, three, four, five, six, seven, or all of the amino acid residues D38, V39, K40, C41, D42, Y43, T44, and L45 of SEQ ID NO: 1 (human TREM-1) and one, two, or all of the amino acid residues selected from the group consisting of the E46, K47, and F48 of SEQ ID NO: 1 (human TREM-1), as determined using, e.g., HDX-MS or X-ray diffraction. In certain embodiments, the anti-TREM-1 antibody has an epitope comprising one, two, three, or all of the amino acid residues selected from the group consisting of the D42, E46, D92, and H93 of SEQ ID NO: 1 (human TREM-1), as determined using variants of TREM-1 and surface plasmon resonance.

In some embodiments, the anti-TREM-1 antibody of the present disclosure has an epitope comprising at least the amino acid residues E46 and/or D92 of SEQ ID NO: 1 (human TREM-1), as determined using variants of TREM-1 and surface plasmon resonance. In another embodiment, the anti-TREM-1 antibody comprises one, two, or all of the amino acid residues selected from the group consisting of L31, I86, and V101 of SEQ ID NO: 1 (human TREM-1). In certain embodiments, the anti-TREM-1 antibody is capable of specifically binding a polypeptide comprising amino acid residues E19 to L26 of cynomolgus monkey TREM-1 (SEQ ID NO: 7), as determined using, e.g., HDX-MS or X-ray diffraction.

In some embodiments, the anti-TREM-1 antibody is capable of specifically binding human TREM-1, wherein the epitope of the antibody comprises one, two, three, four, five, six, seven, eight, nine, or all of the amino acid residues selected from the group consisting of the V39, K40, C41, D42, Y43, L45, E46, K47, F48, and A49 of SEQ ID NO: 1.

In some embodiments, the anti-TREM-1 antibody is capable of specifically binding human TREM-1, wherein the epitope of the antibody comprises the D42 of SEQ ID NO: 1. In other embodiments, the anti-TREM-1 antibody is capable of specifically binding human TREM-1, wherein the epitope of the antibody comprises the E46 of SEQ ID NO: 1. In some embodiments, the epitope of the antibody can comprise the V39, C41, D42, Y43, L45 of SEQ ID NO: 1. In further embodiments, The epitope of the antibody can comprise the E46, K47 and A49 of SEQ ID NO: 1. In a specific embodiment, the epitope of the anti-TREM-1 antibody can further comprise the F48 of SEQ ID NO: 1.

The variable regions of the anti-TREM-1 antibodies described herein can be linked (e.g., covalently linked or fused) to an Fc, e.g., an IgG1, IgG2, IgG3 or IgG4 Fc, which can be of any allotype or isoallotype, e.g., for IgG1: G1m, G1m1(a), G1m2(x), G1m3(f), G1m17(z); for IgG2: G2m, G2m23(n); for IgG3: G3m, G3m21(g1), G3m28(g5), G3m11(b0), G3m5(b1), G3m13(b3), G3m14(b4), G3m10 (b5), G3m15(s), G3m16(t), G3m6(c3), G3m24(c5), G3m26 (u), G3m27(v); and for K: Km, Km1, Km2, Km3 (see, e.g., Jeffries et al. (2009) *mAbs* 1:1). In some embodiments, the variable regions of the anti-TREM-1 antibodies disclosed herein are linked to an effectorless or mostly effectorless Fc, e.g., IgG1. In some embodiments, the variable regions of the anti-TREM-1 antibodies are linked to an Fc that has reduced binding or is incapable of binding to one or more FcγRs.

In some embodiments, the VH domain of the anti-TREM-1 antibodies described herein can be fused to the constant domain of a human IgG (i.e., Fc), e.g., IgG1, IgG2, IgG3, or IgG4, which is either naturally-occurring or modified, e.g., as further described herein. For example, a VH domain can comprise the amino acid sequence of any VH domain described herein fused to a human IgG, e.g., an IgG1, constant region, such as the following wild-type human IgG1 constant domain amino acid sequence:

(SEQ ID NO: 12)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVELFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKLSLSLPGK
or that of an allotypic variant of SEQ ID NO: 12 and have the following amino acid sequences:

ASTKGPSVFPLAPSSKSTSGGTAALGCLVKDYFPEPVTVSWNSGALTSGV

HTFPAVLQSSGLYSLSSVITVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVNNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSPN

WGNVFSCSVMHEAIHNHYTQKSLSLSPGK
(SEQ ID NO: 121; allotype specific amino acid residues are in bold and underlined).

In some embodiments, the VH domain of the anti-TREM-1 antibody described herein can comprise the amino acid sequence of any VH domain described herein fused to an effectorless constant region, e.g., the following effectorless human IgG1 constant domain amino acid sequences:

ASTKGPSVFPLAPSSKSTSGGTAALGCINKDYFPEPVTVSWNSGALTSGV

HTFPAVLQSSGLYSLSSVVTVPSSSLGTQTYICNVNHKPSNTKVDKRVEP

KSCDKTHTCPPCPAPEAEGAPSVFLFPPKPKDTLMISRTPEVTCVVVDVS

HEDPEVKFNWYVDGVEVRNAKTKPREEQYNSTYRVVSVLTVLHQDWLNGK

EYKCKVSNKALPSSIEKTISKAKGQPPEPQVYTLPPSREEMTKNQVSLTC

-continued

LVKGFYPSDTAVEWESNGQPENNYKTTPPVLDSDGSFFLYSKLTVDKSRW

QQGNVFSCSVMHEALHNHYTQKSLSLSPGK
(SEQ ID NO: 122; "IgG1.1f," comprising substitutions L234A, L235E, G237A, A330S and P331S, per EU numbering, which are are underlined) or

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPEAEGAPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVEKSRW

QOGNVFSCSVMHEALHNHYTOKSLSLSPGK
(SEQ ID NO: 123; "IgG1.1f", comprising substitutions L234A, L235E and G237A, per EU numbering, which are are underlined)

For example, an allotypic variant of IgG1 comprises an K97R, D239E, and/or L241 M (underlined and bolded above) and numbering according to that in SEQ ID NOs: 121-123. Within the full length heavy region and according to EU numbering, these amino acid substitutions are numbered K214R, D356E, and L358 M. In some embodiments, the constant region of an anti-TREM-1 antibody further comprises one or more mutations or substitutions at amino acids L117, A18, G120, A213, and P214 (underlined above) as numbered in SEQ ID NO: 121-123, or L234, A235, G237, A330 and P331, per EU numbering. In further embodiments, the constant region of the anti-TREM-1 antibody comprises one or more mutations or substitutions at amino acids L117A, A118E, G120A, A213S, and P214S of SEQ ID NO: 12, or L234A, L235E, G237A, A330S and P331S, per EU numbering. The constant region of the anti-TREM-1 antibody may also comprise one or more mutations or substitutions L117A, A118E and G120A of SEQ ID NO: 12, or L234A, L235E and G237A, per EU numbering.

In some embodiments, the VH domain of the anti-TREM-1 antibodies described herein comprises the amino acid sequence of any VH domain described herein fused to an IgG1 constant domain comprising the following amino acid sequences:

ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKRVEPKSCDKTHTSPPSPAPELLGGSSVFLFPPKPKDTLMISPTPEVTC

VVVDVSHEDPEVKFNWYVDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENNYKTTPPVLDSDGSFF

LYSKLTVDKSRWQQGNVFSCSVMHEALHNHYTQKSLSLSPGK
(SEQ ID NO: 124; "IgG1-Aba", comprising substitutions K214R, C2265, C2295, and P238S, per EU numbering, which are underlined);
or

ASTKGPSVFPLAPCSRSTSESTAALGCLVKDYFPEPVTVSWNSGALTSGVHTFPAVLQSSGLYSLSSVVTVP

SSSLGTKTYTCNVDHKPSNTKVDKRVEPKSCDKTHTSPPSPAPELLGGSSVFLFPPKPKDTLMISRTPEVTC

VVVDVSHEDPEVKFNWYVDGVEVHNAKTKPREEQYNSTYRVVSVLTVLHQDWLNGKEYKCKVSNKALPAPIE

-continued

```
KTISKAKGQPREPQVYTLPPSRDELTKNQVSLTCLVKGFYPSDIAVEWESNGQPENNYKTTPPVLDSDGSFF

LYSKIJUVDKSPWWGNVESCSVMHEALHNHYTQKSLSISPGK
(SEQ ID NO: 125; "IgG4-Aba", comprising substitutions S131C, K133R,
G137E, G1385, Q196K, I199T, N203D, K214R, C2265, C2295, P238S,
per EU numbering, which are underlined).
```

A VL domain described herein can be fused to the constant domain of a human Kappa or Lambda light chain. For example, a VL domain of an anti-TREM-1 antibody can comprise the amino acid sequence of any VL domain described herein fused to the following human IgG1 kappa light chain amino acid sequence:

```
                                    (SEQ ID NO: 126)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.
```

In certain embodiments, the heavy chain constant region comprises a lysine or another amino acid at the C-terminus, e.g., it comprises the following last amino acids: LSPGK (SEQ ID NO: 127) in the heavy chain. In certain embodiments, the heavy chain constant region is lacking one or more amino acids at the C-terminus, and has, e.g., the C-terminal sequence LSPG (SEQ ID NO: 128) or LSP.

Generally, variable regions described herein can be linked to an Fc comprising one or more modification, typically to alter one or more functional properties of the antibody, such as Fc receptor binding, inflammatory cytokine release, serum half-life, complement fixation, and/or antigen-dependent cellular cytotoxicity. Furthermore, an antibody described herein can be chemically modified (e.g., one or more chemical moieties can be attached to the antibody) or be modified to alter its glycosylation, to alter one or more functional properties of the antibody. Each of these embodiments is described in further detail below. The numbering of residues in the Fc region is that of the EU index of Kabat.

The Fc region encompasses domains derived from the constant region of an immunoglobulin (e.g., IgG1, IgG2, IgG3, IgG4, and other classes such as IgA, IgD, IgE and IgM), including a fragment, analog, variant, mutant or derivative of the constant region. The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in combination.

Ig molecules interact with multiple classes of cellular receptors. For example IgG molecules interact with three classes of Fcγ receptors (FcγR) specific for the IgG class of antibody, namely FcγRI, FcγRII, and FcγRIII. The important sequences for the binding of IgG to the FcγR receptors have been reported to be located in the CH2 and CH3 domains. The serum half-life of an antibody is influenced by the ability of that antibody to bind to an Fc receptor (FcR).

In one embodiment, the Fc region of the anti-TREM-1 antibodies is a variant Fc region, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity.

For example, one can make modifications in the Fc region in order to generate an Fc variant that (a) has increased or decreased antibody-dependent cell-mediated cytotoxicity (ADCC), (b) increased or decreased complement mediated cytotoxicity (CDC), (c) has increased or decreased affinity for C1q and/or (d) has increased or decreased affinity for a Fc receptor relative to the parent Fc. Such Fc region variants will generally comprise at least one amino acid modification in the Fc region. Combining amino acid modifications is thought to be particularly desirable. For example, the variant Fc region can include two, three, four, five, etc. substitutions therein, e.g., of the specific Fc region positions identified herein.

A variant Fc region can also comprise a sequence alteration wherein amino acids involved in disulfide bond formation are removed or replaced with other amino acids. Such removal can avoid reaction with other cysteine-containing proteins present in the host cell used to produce the anti-TREM-1 antibodies described herein. Even when cysteine residues are removed, single chain Fc domains can still form a dimeric Fc domain that is held together non-covalently. In other embodiments, the Fc region can be modified to make it more compatible with a selected host cell. For example, one can remove the PA sequence near the N-terminus of a typical native Fc region, which can be recognized by a digestive enzyme in *E. coli* such as proline iminopeptidase. In other embodiments, one or more glycosylation sites within the Fc domain can be removed. Residues that are typically glycosylated (e.g., asparagine) can confer cytolytic response. Such residues can be deleted or substituted with unglycosylated residues (e.g., alanine). In other embodiments, sites involved in interaction with complement, such as the C1q binding site, can be removed from the Fc region. For example, one can delete or substitute the EKK sequence of human IgG1. In certain embodiments, sites that affect binding to Fc receptors can be removed, preferably sites other than salvage receptor binding sites. In other embodiments, an Fc region can be modified to remove an ADCC site. ADCC sites are known in the art; see, e.g., Sarmay et al., *Molec. Immunol.* 29 (5): 633-9 (1992) with regard to ADCC sites in IgG1. Specific examples of variant Fc domains are disclosed, for example, in WO 97/34631 and WO 96/32478.

In one embodiment, the hinge region of Fc is modified such that the number of cysteine residues in the hinge region is altered, e.g., increased or decreased. This approach is described further in U.S. Pat. No. 5,677,425 by Bodmer et al. The number of cysteine residues in the hinge region of Fc is altered to, for example, facilitate assembly of the light and heavy chains or to increase or decrease the stability of the antibody. In one embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320, 322, 330, and/or 331 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region can be modified to decrease antibody dependent cellular cytotoxicity (ADCC) and/or to decrease the affinity for an Fcγ receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439. Exemplary substitutions include 236A, 239D, 239E, 268D, 267E, 268E, 268F, 324T, 332D, and 332E. Exemplary variants include 239D/332E, 236A/332E, 236A/239D/332E, 268F/324T, 267E/268F, 267E/324T, and 267E/268F/324T. Other modifications for enhancing FcγR and complement interactions include but are not limited to substitutions 298 A, 333A, 334A, 326A, 2471, 339D, 339Q, 280H, 290S, 298D, 298V, 243L, 292P, 300L, 3% L, 3051, and 396L. These and other modifications are reviewed in Strohl, 2009, Current Opinion in Biotechnology 20:685-691.

Other Fc modifications that can be made to Fcs are those for reducing or ablating binding to FcγR and/or complement proteins, thereby reducing or ablating Fc-mediated effector functions such as ADCC, ADCP, and CDC. Exemplary modifications include but are not limited substitutions, insertions, and deletions at positions 234, 235, 236, 237, 267, 269, 325, 328, 330, and/or 331 (e.g., 330 and 331), wherein numbering is according to the EU index. Exemplary substitutions include but are not limited to 234A, 235E, 236R, 237A, 267R, 269R, 325L, 328R, 330S, and 331S (e.g., 330S, and 331S), wherein numbering is according to the EU index. An Fc variant can comprise 236R/328R. Other modifications for reducing FcγR and complement interactions include substitutions 297A, 234A, 235A, 237A, 318A, 228P, 236E, 268Q, 309L, 330S, 331 S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, *Current Opinion in Biotechnology* 20:685-691.

Optionally, the Fc region can comprise a non-naturally occurring amino acid residue at additional and/or alternative positions known to one skilled in the art (see, e.g., U.S. Pat. Nos. 5,624,821; 6,277,375; 6,737,056; 6,194,551; 7,317,091; 8,101,720; International Publ. Nos. WO 00/42072; WO 01/58957; WO 02/06919; WO 04/016750; WO 04/029207; WO 04/035752; WO 04/074455; WO 04/099249; WO 04/063351; WO 05/070963; WO 05/040217, WO 05/092925, and WO 06/020114).

The affinities and binding properties of an Fc region for its ligand can be determined by a variety of in vitro assay methods (biochemical or immunological based assays) known in the art including but not limited to, equilibrium methods (e.g., enzyme-linked immunoabsorbent assay (ELISA), or radioimmunoassay (RIA)), or kinetics (e.g., BIACORE analysis), and other methods such as indirect binding assays, competitive inhibition assays, fluorescence resonance energy transfer (FRET), gel electrophoresis and chromatography (e.g., gel filtration). These and other methods can utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental immunology, 4th Ed., Lippincott-Raven, Philadelphia (1999), which focuses on antibody-immunogen interactions.

In some embodiments, the anti-TREM-1 antibody, as disclosed herein, has (a) an IgG1 isotype and comprises one or more amino acid substitutions in the Fc region at an amino acid residue selected from the group consisting of: N297A, N297Q, D270A, D265A, L234A, L235A, C226S, C229S, P238S, E233P, L234V, P238A, A327Q, A327G, P329A, K322A, L234F, L235E, P331S, T394D, A330L, M252Y, S254T, T256E, L328E, P238D, S267E, L328F, E233D, G237D, H268D, P271G, A330R, and any combination thereof, wherein the numbering of the residues is according to EU or Kabat numbering, or comprises an amino acid deletion in the Fc region at a position corresponding to glycine 236; (b) an IgG2 isotype and comprises one or more amino acid substitutions in the Fc region at an amino acid residue selected from the group consisting of: P238S, V234A, G237A, H268A, H268Q, H268E, V309L, N297A, N297Q, A330S, P331S, C232S, C233S, M252Y, S254T, T256E, and any combination thereof, wherein the numbering of the residues is according to EU or Kabat numbering; or (c) an IgG4 isotype and comprises one or more amino acid substitutions in the Fc region at an amino acid residue selected from the group consisting of: E233P, F234V, L234A/F234A, L235A, G237A, E318A, S228P, L236E, S241P, L248E, T394D, M252Y, S254T, T256E, N297A, N297Q, and any combination thereof, wherein the numbering of the residues is according to EU or Kabat numbering. In some embodiments, (a) the Fc region further comprises one or more additional amino acid substitutions at an amino acid residue selected from the group consisting of A330L, L234F; L235E, P331S, and any combination thereof, wherein the numbering of the residues is according to EU or Kabat numbering; (b) the Fc region further comprises one or more additional amino acid substitutions at a position selected from the group consisting of M252Y, S254T, T256E, and any combination thereof, wherein the numbering of the residues is according to EU or Kabat numbering; or (c) the Fc region further comprises a S228P amino acid substitution according to EU or Kabat numbering. See WO 2017/152102.

In certain embodiments, an Fc is chosen that has reduced complement fixation. An exemplary Fc, e.g., IgG1 Fc, with reduced complement fixation has the following two amino acid substitutions: A330S and P331S.

In certain embodiments, an Fc is chosen that has essentially no effector function, i.e., it has reduced binding to FcγRs and reduced complement fixation. An exemplary Fc, e.g., IgG1 Fc, that is effectorless comprises the following five mutations: L234A, L235E, G237A, A330S and P331S.

II. Nucleic Acids, Vectors, and Cells

Another aspect described herein pertains to nucleic acid molecules that encode the anti-TREM-1 antibodies described herein. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and can or cannot contain intronic sequences. In some embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

In some embodiments, the nucleic acids described herein are those encoding the VH and VL sequences of the anti-TREM-1 antibodies of the present disclosure. Exemplary DNA sequences encoding the VH sequences are set forth as SEQ ID NOs: 144-168. Exemplary DNA sequences encoding the VL sequences are set forth as SEQ ID NOs: 169-192, 195, and 1%. The sequences are also provided in Tables 3 and 4.

A method for making an anti-TREM-1 antibody as disclosed herein can comprise expressing the heavy chain and the light chains in a cell line comprising the nucleotide sequences encoding the heavy and light chains with a signal peptide, e.g., SEQ ID NOs: 269 and 305, SEQ ID NOs: 270 and 306, SEQ ID NOs: 271 and 307, SEQ ID NOs: 272 and 308, SEQ ID NOs: 273 and 309, SEQ ID NOs: 274 and 310, SEQ ID NOs: 275 and 311, SEQ ID NOs: 276 and 312, SEQ ID NOs: 277 and 313, SEQ ID NOs: 278 and 314, SEQ ID NOs: 279 and 315, SEQ ID NOs: 281 and 317, SEQ ID NOs: 282 and 318, SEQ ID NOs: 283 and 319, SEQ ID NOs: 284 and 320, SEQ ID NOs: 285 and 321, SEQ ID NOs: 286 and 322, SEQ ID NOs: 287 and 323, SEQ ID NOs: 288 and 324, SEQ ID NOs: 289 and 325, SEQ ID NOs: 290 and 326, SEQ ID NOs: 291 and 327, SEQ ID NOs: 292 and 328, SEQ ID NOs: 293 and 329, SEQ ID NOs: 294 and 330, SEQ ID NOs: 295 and 331, SEQ ID NOs: 2% and 332, SEQ ID NOs: 297 and 333, SEQ ID NOs: 298 and 334, SEQ ID NOs: 299 and 335, SEQ ID NOs: 300 and 336, SEQ ID NOs: 301 and 337, SEQ ID NOs: 302 and 338, SEQ ID NOs: 303 and 339, SEQ ID NOs: 304 and 340, respectively. Host cells comprising these nucleotide sequences are encompassed herein.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, for example, an IgG2 and/or IgG 4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

Another aspect described herein pertains to cells (e.g., host cells) expressing (e.g., recombinantly) anti-TREM-1 antibodies described herein and related polynucleotides and expression vectors. Provided herein are also vectors comprising polynucleotides comprising nucleotide sequences encoding anti-TREM-1 antibodies or a fragment thereof. In some embodiments, the vectors can be used for recombinantly expressing anti-TREM-1 antibodies described herein in host cells, e.g., in mammalian cells. Non-limiting examples of cells that can be used to express the anti-TREM-1 antibodies disclosed herein include Human embryonic kidney (HEK) cell lines (e.g., HEK293), Chinese hamster ovary (CHO) cell lines, Baby hamster kidney (BHK) cell lines, COS cell lines, Madin Darby canine kidney (MDCK) cell line, and HeLa cell lines. In some embodiments, the vectors can be used for gene therapy.

Suitable vectors for the disclosure include expression vectors, viral vectors, and plasmid vectors. In some embodiments, the vector is a viral vector.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the disclosure can include polynucleotides encoding the antibody or antigen binding portion thereof described herein. In some embodiments, the coding sequences for the antibody or antigen binding portion thereof is operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired antibody or antigen binding portion thereof.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; lentivirus; adenovirus; adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Clifton, N.J. (1991).

In some embodiments, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

III. Immunoconjugates

The present disclosure also provides immunoconjugates comprising any of the anti-TREM-1 antibodies disclosed herein. In some embodiments, the immunoconjugate comprises an antibody or an antigen binding portion linked to an agent. In some embodiments, the immunoconjugate comprises a bispecific molecule disclosed herein linked to an agent (e.g., as therapeutic agent or a diagnostic agent).

For diagnostic purposes, appropriate agents are detectable labels that include radioisotopes, for whole body imaging, and radioisotopes, enzymes, fluorescent labels and other suitable antibody tags for sample testing. The detectable labels that can be linked to any anti-TREM-1 antibody described herein can be any of the various types used currently in the field of in vitro diagnostics, including particulate labels including metal sols such as colloidal gold, isotopes such as $I^{125}$ or $Tc^{99}$ presented for instance with a peptidic chelating agent of the $N_2S_2$, $N_3S$ or $N_4$ type, chromophores including fluorescent markers, luminescent markers, phosphorescent markers and the like, as well as enzyme labels that convert a given substrate to a detectable marker, and polynucleotide tags that are revealed following amplification such as by polymerase chain reaction. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3,2'-(5'-chloro)tricyclo{3.3.1.1 3,7}decan}-4-yl) phenyl phosphate (CSPD), as well as CDP and CDP-STAR® or other luminescent substrates well-known to those in the art, for example the chelates of suitable lanthanides such as Terbium(III) and Europium(III). The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

In some embodiments, conjugation methods result in linkages which are substantially (or nearly) non-immunogenic, e.g., peptide- (i.e., amide-), sulfide-, (sterically hindered), disulfide-, hydrazone-, and ether linkages. These linkages are nearly non-immunogenic and show reasonable stability within serum (see, e.g., Senter, P. D., *Curr. Opin. Chem. Biol.* 13 (2009) 235-244; WO 2009/059278; WO 95/17886).

Depending on the biochemical nature of the moiety and the antibody, different conjugation strategies can be employed. In case the moiety is naturally-occurring or recombinant of between 50 to 500 amino acids, there are standard procedures in text books describing the chemistry for synthesis of protein conjugates, which can be easily followed by the skilled artisan (see, e.g., Hackenberger, C. P. R., and Schwarzer, D., *Angew. Chem. Int. Ed Engl.* 47 (2008) 10030-10074). In some embodiments the reaction of a maleimido moiety with a cysteine residue within the antibody or the moiety is used. This is an especially suited coupling chemistry in case e.g., a Fab or Fab'-fragment of an antibody is used. Alternatively, in some embodiments, coupling to the C-terminal end of the antibody or moiety is performed. C-terminal modification of a protein, e.g., of a Fab-fragment, can be performed as described (Sunbul, M. and Yin, J., *Org. Biomol. Chem.* 7 (2009) 3361-3371).

In general, site specific reaction and covalent coupling is based on transforming a natural amino acid into an amino acid with a reactivity which is orthogonal to the reactivity of the other functional groups present. For example, a specific cysteine within a rare sequence context can be enzymatically converted in an aldehyde (see Frese, M. A., and Dierks, T., *ChemBioChem.* 10 (2009) 425-427). It is also possible to obtain a desired amino acid modification by utilizing the specific enzymatic reactivity of certain enzymes with a natural amino acid in a given sequence context (see, e.g., Taki, M. et al., *Prot. Eng. Des. Sel.* 17 (2004) 119-126; Gautier, A. et al. *Chem. Biol.* 15 (2008) 128-136; and Protease-catalyzed formation of C—N bonds is used by Bordusa, F., Highlights in Bioorganic Chemistry (2004) 389-403). Site specific reaction and covalent coupling can also be achieved by the selective reaction of terminal amino acids with appropriate modifying reagents.

The reactivity of an N-terminal cysteine with benzonitriles (see Ren, H. et al., *Angew. Chem. Int. Ed. Engl.* 48 (2009) 9658-9662) can be used to achieve a site-specific covalent coupling.

Native chemical ligation can also rely on C-terminal cysteine residues (Taylor, E. Vogel; Imperiali, B, *Nucleic Acids and Molecular Biology* (2009), 22 (Protein Engineering), 65-96).

U.S. Pat. No. 6,437,095 B1 describes a conjugation method which is based on the faster reaction of a cysteine within a stretch of negatively charged amino acids with a cysteine located in a stretch of positively charged amino acids.

The moiety can also be a synthetic peptide or peptide mimic. In case a polypeptide is chemically synthesized, amino acids with orthogonal chemical reactivity can be incorporated during such synthesis (see e.g., de Graaf, A. J. et al., *Bioconjug. Chem.* 20 (2009) 1281-1295). Since a great variety of orthogonal functional groups is at stake and can be introduced into a synthetic peptide, conjugation of such peptide to a linker is standard chemistry.

In order to obtain a mono-labeled polypeptide, the conjugate with 1:1 stoichiometry can be separated by chromatography from other conjugation side-products. This procedure can be facilitated by using a dye labeled binding pair member and a charged linker. By using this kind of labeled and highly negatively charged binding pair member, mono conjugated polypeptides are easily separated from non-labeled polypeptides and polypeptides which carry more than one linker, since the difference in charge and molecular weight can be used for separation. The fluorescent dye can be useful for purifying the complex from un-bound components, like a labeled monovalent binder.

In some embodiments, the moiety attached to an anti-TREM-1 antibody is selected from the group consisting of a binding moiety, a labeling moiety, and a biologically active moiety.

Anti-TREM-1 antibodies described herein can also be conjugated to a therapeutic agent to form an immunoconjugate such as an antibody-drug conjugate (ADC). Suitable therapeutic agents include antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. In some embodiments, the linker is a peptidyl linker such as Val-Cit, Ala-Val, Val-Ala-Val, Lys-Lys, Pro-Val-Gly-Val-Val (SEQ ID NO: 129), Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038658; WO 07/051081; WO 07/059404; WO 08/083312; and WO 08/103693; U.S. Patent Publications 20060024317; 20060004081; and 20060247295.

Anti-TREM-1 antibodies, e.g., those described herein, can also be used for detecting TREM-1, such as human TREM-1, e.g., human TREM-1 in tissues or tissue samples. The antibodies can be used, e.g., in an ELISA assay or in flow cytometry. In some embodiments, an anti-TREM-1 antibody is contacted with cells, e.g., cells in a tissue, for a time appropriate for specific binding to occur, and then a reagent, e.g., an antibody that detects the anti-TREM-1 antibody, is added. Exemplary assays are provided in the Examples. The anti-TREM-1 antibody can be a fully human antibody, or it can be a chimeric antibody, such as an antibody having human variable regions and murine constant regions or a portion thereof. Exemplary methods for detecting TREM-1, e.g., human TREM-1, in a sample (cell or tissue sample) comprise (i) contacting a sample with an anti-TREM-1 antibody, for a time sufficient for allowing specific binding of the anti-TREM-1 antibody to TREM-1 in the sample, and (2) contacting the sample with a detection reagent, e.g., an antibody, that specifically binds to the anti-TREM-1 antibody, such as to the Fc region of the anti-TREM-1 antibody, to thereby detect TREM-1 bound by the anti-TREM-1 antibody. Wash steps can be included after the incubation with the antibody and/or detection reagent. Anti-TREM-1 antibodies for use in these methods do not have to be linked to a label or detection agents, as a separate detection agent can be used.

Other uses for anti-TREM-1 antibodies, e.g., as monotherapy or combination therapy, are provided elsewhere herein, e.g., in the section pertaining to combination treatments.

IV. Bispecific Molecules

Anti-TREM-1 antibodies described herein can be used for forming bispecific molecules. An anti-TREM-1 antibody, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. For example, an anti-TREM-1 antibody can be linked to an antibody or scFv that binds specifically to any protein that can be used as potential targets for combination treatments, such as the proteins described herein (e.g., antibodies to IP-10 or TNF-α). The antibody described herein can in fact be derived or linked to more than one other functional molecule to generate multispecific molecules that bind to more than two different binding sites and/or target molecules; such multispecific molecules are also intended to be encompassed by the term "bispecific molecule" as used herein. To create a bispecific molecule described herein, an antibody described herein can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, provided herein are bispecific molecules comprising at least one first binding specificity for TREM-1 and a second binding specificity for a second target epitope. In some embodiments described herein in which the bispecific molecule is multispecific, the molecule can further include a third binding specificity.

In some embodiments, the bispecific molecules described herein comprise as a binding specificity at least one antibody, or an antibody fragment thereof, including, e.g., an Fab, Fab', F(ab)2, Fv, or a single chain Fv (scFv). The antibody can also be a light chain or heavy chain dimer, or any minimal fragment thereof such as a Fv or a single chain construct as described in Ladner et al. U.S. Pat. No. 4,946,778.

While human monoclonal antibodies are preferred, other antibodies which can be employed in the bispecific molecules described herein are murine, chimeric and humanized monoclonal antibodies.

The bispecific molecules described herein can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohexane-1-carboxylate (sulfo-SMCC) (see, e.g., Karpovsky et al. (1984) *J. Exp. Med.* 160: 1686; Liu, M A et al. (1985) *Proc. Natl. Acad Sci. USA* 82:8648). Other methods include those described in Paulus (1985) *Behring Ins. Mitt.* No. 78, 118-132; Brennan et al. (1985) *Science* 229:81-83), and Glennie et al. (1987) *J. Immunol.* 139: 2367-2375). Some conjugating agents are SATA and sulfo-SMCC, both available from Pierce Chemical Co. (Rockford, IL).

When the binding specificities are antibodies, they can be conjugated via sulfhydryl bonding of the C-terminus hinge regions of the two heavy chains. In some embodiments, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, mAb×$(scFv)_2$, Fab×$F(ab)_2$ or ligand x Fab fusion protein. A bispecific antibody can comprise an antibody comprising an scFv at the C-terminus of each heavy chain. A bispecific molecule described herein can be a single chain molecule comprising one single chain antibody and a binding determinant, or a single chain bispecific molecule comprising two binding determinants. Bispecific molecules can comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed using art-recognized methods, such as enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

V. Kits

Provided herein are kits comprising one or more anti-TREM-1 antibodies described herein, or antigen-binding portions thereof, bispecific molecules, or immunoconjugates thereof. In some embodiments, provided herein is a pharmaceutical pack or kit comprising one or more containers filled with one or more of the ingredients of the pharmaceutical compositions described herein, such as one or more antibodies provided herein or an antigen-binding portion thereof, optional an instructing for use. In some embodiments, the kits contain a pharmaceutical composition described herein and any prophylactic or therapeutic agent, such as those described herein.

VI. Compositions and Formulations

Further provided herein are compositions (e.g., pharmaceutical compositions) and formulations comprising one or more of the anti-TREM-1 antibodies (including polynucleotides, vectors, and cells that encode and/or express the anti-TREM-1 antibodies) disclosed herein. For example, in one embodiment, the present disclosure provides a pharmaceutical composition comprising one or more anti-TREM-1 antibodies as disclosed herein, formulated together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. In some embodiments, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, can be coated in a material to protect the compound from the action of acids and other natural conditions that can inactivate the compound.

Accordingly, one object of the present disclosure is to provide a pharmaceutical formulation, which improves the stability of the anti-TREM-1 antibodies and thus, allows for their long-term storage. In some embodiments, the pharmaceutical formulation disclosed herein comprises: (a) an anti-TREM-1 antibody; (b) a buffering agent; (c) a stabilizing agent; (d) a salt; (e) a bulking agent; and/or (f) a surfactant. In some embodiments, the pharmaceutical formulation is stable for at least 1 month, at least 2 months, at least 3 months, at least 6 months, at least 1 year, at least 2 years, at least 3 years, at least 5 years or more. In some embodiments, the formulation is stable when stored at 4° C., 25° C., or 40° C.

Buffering Agent

Buffering agents useful for the present invention can be a weak acid or base used to maintain the acidity (pH) of a solution near a chosen value after the addition of another acid or base. Suitable buffering agents can maximize the stability of the pharmaceutical formulations by maintaining pH control of the formulation. Suitable buffering agents can also ensure physiological compatibility or optimize solubility. Rheology, viscosity and other properties can also dependent on the pH of the formulation. Common buffering agents include, but are not limited to, histidine, citrate, succinate, acetate and phosphate. In some embodiments, a buffering agent comprises histidine (e.g., L-histidine) with isotonicity agents and potentially pH adjustment with an acid or a base known in the art. In certain embodiments, the buffering agent is L-histidine. In certain embodiments, the pH of the formulation is maintained between about 2 and about 10, or between about 4 and about 8.

Stabilizing Agent

Stabilizing agents are added to a pharmaceutical product in order to stabilize that product. Such agents can stabilize proteins in a number of different ways. Common stabilizing agents include, but are not limited to, amino acids such as glycine, alanine, lysine, arginine, or threonine, carbohydrates such as glucose, sucrose, trehalose, raffmose, or maltose, polyols such as glycerol, mannitol, sorbitol, cyclodextrins or dextrans of any kind and molecular weight, or PEG. In one aspect of the invention, the stabilizing agent is chosen in order to maximize the stability of FIX polypeptide in lyophilized preparations. In certain embodiments, the stabilizing agent is sucrose and/or arginine.

Bulking Agent

Bulking agents can be added to a pharmaceutical product in order to add volume and mass to the product, thereby facilitating precise metering and handling thereof. Common bulking agents include, but are not limited to, lactose, sucrose, glucose, mannitol, sorbitol, calcium carbonate, or magnesium stearate.

Surfactant

Surfactants are amphipathic substances with lyophilic and lyophobic groups. A surfactant can be anionic, cationic, zwitterionic, or nonionic. Examples of nonionic surfactants include, but are not limited to, alkyl ethoxylate, nonylphenol ethoxylate, amine ethoxylate, polyethylene oxide, polypropylene oxide, fatty alcohols such as cetyl alcohol or oleyl alcohol, cocamide MEA, cocamide DEA, polysorbates, or dodecyl dimethylamine oxide. In some embodiments, the surfactant is polysorbate 20 or polysorbate 80.

In some embodiments, the pharmaceutical formulation of the present disclosure comprises:

(a) about 0.25 mg/mL to 250 mg/mL (e.g., 10 to 200 mg/mL) of an anti-TREM-1 antibody;
(b) about 20 mM histidine;
(c) about 150 mM sucrose;
(d) about 25 mM arginine; and
(e) about 50 mM NaCl.

The formulation can further comprise one or more of a buffer system, a preservative, a tonicity agent, a chelating agent, a stabilizer and/or a surfactant, as well as various combinations thereof. The use of preservatives, isotonic agents, chelating agents, stabilizers and surfactants in pharmaceutical compositions is well-known to the skilled person. Reference may be made to Remington: The *Science* and Practice of Pharmacy, $19^{th}$ edition, 1995.

In some embodiments, the pharmaceutical formulation is an aqueous formulation. Such a formulation is typically a solution or a suspension, but may also include colloids, dispersions, emulsions, and multi-phase materials. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In some embodiments, the pharmaceutical formulation is a freeze-dried formulation, to which the physician or the patient adds solvents and/or diluents prior to use.

Pharmaceutical compositions described herein also can be administered in combination therapy, i.e., combined with other agents. For example, the combination therapy can include an anti-anti-TREM-1 antibody described herein combined with at least one other therapeutic agent. Examples of therapeutic agents that can be used in combination therapy can include other compounds, drugs, and/or agents used for the treatment of a disease or disorder (e.g., an inflammatory disorder). Such compounds, drugs, and/or agents can include, for example, anti-inflammatory drugs or antibodies that block or reduce the production of inflammatory cytokines. In some embodiments, therapeutic agents can include an anti-IP-10 antibody, an anti-TNF-α antibody (e.g., adalimumab (HUMIRA®), golimumab (SIMPONI®), infliximab (REMICADE®), certolizumab pegol (CIMZIA®)), interferon beta-1a (e.g., AVONEX®, REBIF®), interferon beta-1b (e.g., BETASERON®, EXTAVIA®), glatiramer acetate (e.g., COPAXONE®, GLATOPA®), mitoxantrone (e.g., NOVANTRONE®), non-steroidal anti-inflammatory drugs (NSAIDs), analgesics, corticosteroids, and combinations thereof.

The pharmaceutical compounds described herein can include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein can also include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that can be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of presence of microorganisms can be ensured both by sterilization procedures, supra, and by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. A pharmaceutical composition can comprise a preservative or can be devoid of a preservative. Supplementary active compounds can be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, the compositions can include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated herein. In the case of sterile powders for the preparation of sterile injectable solutions, some methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals.

For administration of an anti-TREM-1 antibody, e.g., described herein, the dosage ranges from about 0.0001 to 100 mg/kg, and more usually 0.01 to 5 or 10 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Exemplary dosage regimens for an anti-TREM-1 antibody described herein include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some embodiments, the anti-TREM-1 antibody is administered at a flat dose (flat dose regimen). In other embodiments, the anti-TREM-1 antibody is administered at a fixed dose with another antibody. In certain embodiments, the anti-TREM-1 antibody is administered at a dose based on body weight.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

An antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and until the patient shows partial or complete amelioration of symptoms of disease. Thereafter, the patient can be administered a prophylactic regime.

Actual dosage levels of the active ingredients in the pharmaceutical compositions described herein can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A composition described herein can be administered via one or more routes of administration using one or more of a variety of methods known in the art. As will be appreciated by the skilled artisan, the route and/or mode of administration will vary depending upon the desired results. Routes of administration for the anti-TREM-1 antibodies described herein can include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody described herein could potentially be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a particular embodiment, a therapeutic composition described herein can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules for use with anti-TREM-1 antibodies described herein include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In some embodiments, the anti-TREM-1 antibodies described herein can be formulated to ensure proper distribution in vivo. For example, the blood-brain barrier (BBB) excludes many highly hydrophilic compounds. To ensure that the therapeutic compounds described herein cross the BBB (if desired, e.g., for brain cancers), they can be formulated, for example, in liposomes. For methods of manufacturing liposomes, see, e.g., U.S. Pat. Nos. 4,522, 811; 5,374,548; and 5,399,331. The liposomes can comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al); mannosides (Umezawa et al., (1988) *Biochem.* Biophys. Res. Commun. 153: 1038); antibodies (P. G. Bloeman et al. (1995) *FEBS Lett.* 357: 140; M. Owais et al. (1995) *Antimicrob. Agents Chemother.* 39: 180); surfactant protein A receptor (Briscoe et al. (1995) *Am. J. Physiol.* 1233: 134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

VII. Uses and Methods

The anti-TREM-1 antibodies of the present disclosure and the compositions comprising such antibodies (e.g., pharmaceutical composition, formulations, polynucleotides, vectors, and cells) can be used for the treatment of an inflammatory disease (e.g., by inhibiting TREM-1 activity).

Accordingly, in one aspect, the present disclosure provides methods for treating an inflammatory disease in a subject in need thereof, comprising administering a therapeutically effective dose of the anti-TREM-1 antibody to the subject. Examples of inflammatory diseases that can be treated with the present anti-TREM-1 antibodies include, but not limited to, inflammatory bowel disease (IBD), Crohn's disease (CD), ulcerative colitis (UC), irritable bowel syndrome, rheumatoid arthritis (RA), psoriasis, psoriatic arthritis, systemic lupus erythematosus (SLE), lupus nephritis, type I diabetes, Grave's disease, multiple sclerosis (MS), autoimmune myocarditis, Kawasaki disease, coronary artery disease, chronic obstructive pulmonary disease, interstitial lung disease, autoimmune thyroiditis, scleroderma, systemic sclerosis, osteoarthritis, atopic dermatitis, vitiligo, graft versus host disease, Sjogren's syndrome, autoimmune nephritis, Goodpasture syndrome, chronic inflammatory demyelinating polyneuropathy, allergy, asthma and other autoimmune diseases that are a result of either acute or chronic inflammation.

In one embodiment, the anti-TREM-1 antibodies are suitable for use in the treatment of individuals with inflammatory bowel disease. Inflammatory Bowel Disease (IBD)

is a disease that may affect any part of the gastrointestinal tract from mouth to anus, causing a wide variety of symptoms. IBD primarily causes abdominal pain, diarrhoea (which may be bloody), vomiting or weight loss, but may also cause complications outside of the gastrointestinal tract such as skin rashes, arthritis, inflammation of the eye, fatigue and lack of concentration. Patients with IBD can be divided into two major classes, those with ulcerative colitis (UC) and those with Crohn's disease (CD). CD generally involves the ileum and colon, it can affect any region of the intestine but is often discontinuous (focused areas of disease spread throughout the intestine). UC always involves the rectum (colonic) and is more continuous. In CD, the inflammation is transmural, resulting in abscesses, fistulas and strictures, whereas in UC, the inflammation is typically confined to the mucosa. There is no known pharmaceutical or surgical cure for Crohn's disease, whereas some patients with UC can be cured by surgical removal of the colon. Treatment options are restricted to controlling symptoms, maintaining remission and preventing relapse. Efficacy in inflammatory bowel disease in the clinic may be measured as a reduction in the Crohn's Disease Activity Index (CDAI) score for CD which is scoring scale based on laboratory tests and a quality of life questionnaire. In animal models, efficacy is mostly measured by increase in weight and also a disease activity index (DAI), which is a combination of stool consistency, weight and blood in stool.

In one embodiment, the anti-TREM-1 antibodies of the present disclosure are suitable for use in the treatment of individuals with rheumatoid arthritis. Rheumatoid arthritis (RA) is a systemic disease that affects nearly if not all of the body and is one of the most common forms of arthritis. It is characterized by inflammation of the joint, which causes pain, stiffness, warmth, redness and swelling. This inflammation is a consequence of inflammatory cells invading the joints, and these inflammatory cells release enzymes that may digest bone and cartilage. As a result, this inflammation can lead to severe bone and cartilage damage and to joint deterioration and severe pain, among other physiologic effects. The involved joint can lose its shape and alignment, resulting in pain and loss of movement. There are several animal models for rheumatoid arthritis known in the art. For example, in the collagen-induced arthritis (CIA) model, mice develop an inflammatory arthritis that resembles human rheumatoid arthritis. Since CIA shares similar immunological and pathological features with RA, this makes it a suitable model for screening potential human anti-inflammatory compounds. Efficacy in this model is measured by decrease in joint swelling. Efficacy in RA in the clinic is measured by the ability to reduce symptoms in patients which is measured as a combination of joint swelling, erythrocyte sedimentation rate, C-reactive protein levels and levels of serum factors, such as anti-citrullinated protein antibodies.

In one embodiment, the anti-TREM-1 antibodies as disclosed herein are suitable for use in the treatment of individuals with psoriasis. Psoriasis is a T-cell mediated inflammatory disorder of the skin that can cause considerable discomfort. It is a disease for which there is currently no cure and it affects people of all ages. Although individuals with mild psoriasis can often control their disease with topical agents, more than one million patients worldwide require ultraviolet light treatments or systemic immunosuppressive therapy. Unfortunately, the inconvenience and risks of ultraviolet radiation and the toxicities of many therapies limit their long-term use. Moreover, patients usually have recurrence of psoriasis, and in some cases rebound shortly after stopping immunosuppressive therapy. A recently developed model of psoriasis based on the transfer of CD4+ T cells mimics many aspects of human psoriasis and therefore can be used to identify compounds suitable for use in treatment of psoriasis (Davenport et al., *Internat. Immunopharmacol* 2: 653-672, 2002). Efficacy in this model is a measured by reduction in skin pathology using a scoring system. Similarly, efficacy in patients is measured by a decrease in skin pathology.

In one embodiment, the anti-TREM-1 antibodies are suitable for use in the treatment of individuals with psoriatic arthritis. Psoriatic arthritis (PA) is a type of inflammatory arthritis that occurs in a subset of patients with psoriasis. In these patients, the skin pathology/symptoms are accompanied by a joint swelling similar to that seen in rheumatoid arthritis. It features patchy, raised, red areas of skin inflammation with scaling. Psoriasis often affects the tips of the elbows and knees, the scalp, the navel and around the genital areas or anus. Approximately 10% of patients who have psoriasis also develop an associated inflammation of their joints.

In terms of the present disclosure, prophylactic, palliative, symptomatic and/or curative treatments may represent separate aspects of the disclosure. An antibody of the invention can be administered parenterally, such as intravenously, such as intramuscularly, such as subcutaneously. Alternatively, an antibody of the invention can be administered via a non-parenteral route, such as orally or topically. An antibody of the invention can be administered prophylactically. An antibody of the invention can be administered therapeutically (on demand).

The following examples are offered by way of illustration and not by way of limitation. The contents of all references cited throughout this application are expressly incorporated herein by reference.

EXAMPLES

Example 1: Generation of Anti-TREM-1 Antibodies

Six cohorts of transgenic mice expressing human antibodies (each cohort containing 2-4 mice) were immunized with either recombinant TREM-1 extracellular domain, TREM-1 Jurkat cell line, or plasma membrane preps of the TREM-1 Jurkat cell line. The spleens, lymph nodes, and bone marrow of the immunized animals were harvested and used to generate four immune antibody scFv (single chain variable fragment) libraries. Briefly, the mRNA was extracted from the harvested cells and reverse transcribed to generate cDNA. The antibody variable region genes were PCR amplified from the cDNA using a cocktail of primers and assembled using overlap extension PCR to generate the scFv libraries. The scFv libraries were expressed and selected using mRNA display (Xu L et al. (2002) *Chemistry & Biology* 9: 933; Roberts R W and J W Szostak (1997) *Proc. Natl. Acad. Sci. USA* 94:12297; Kurz et al. (2000) *Nucleic Acids Res.* 28(18):E83). The first round was conducted to enrich for TREM-1 specific antibodies by selecting the mRNA display scFv libraries against recombinant TREM-1 extracellular domain Fc fusion protein, followed by capture on Protein G magnetic beads. The output of the first round was taken through subsequent rounds of mRNA display, with the libraries split between 2 arms: (1) successive rounds of selection against recombinant TREM-1 extracellular domain Fc fusion protein, followed by capture on Protein G magnetic beads, to enrich for all TREM-1-binding scFvs, and (2) successive rounds of selection against recombinant TREM-1 extracellular domain Fc fusion protein pre-incubated with mAb 170, followed by capture on Protein G magnetic beads, to enrich for antibodies against novel epitopes ("epitope steering arm"). The final output of both selection arms was sequenced, and unique clones of interest were cloned and expressed as full-length immunoglobulin G (IgG) antibodies, with an IgG1.1f constant region that contains mutations to reduce effector function. These IgG antibodies were used for subsequent characterization and assays.

Example 2: Binding Competition Analysis of the Epitope-Steered Anti-TREM-1 Antibodies to Human TREM-1

To characterize the functional properties of the epitope-steered anti-TREM-1 antibodies, the ability of these antibodies to inhibit the binding of mAb 170 and PGRP to human TREM-1 was assessed. Briefly, mAb 170 was directly labeled with AlexaFluor 647 dye using reagent manufacturer's protocol. Antibodies to be tested against mAb 170 were bound on Jurkat cells expressing huTREM1 for 1 hour at 4° C. After washing the cells, directly labelled mAb 170 was added at 300 pM to the cells. After incubation at 4° C. for an additional 30 minutes, cells were washed and analyzed by FACS using standard methods. Unlabeled mAb 170 was used as a control for 100% inhibition.

As shown in FIGS. 3 and 5A, the non-epitope-steered anti-TREM-1 antibodies (black diamonds in both FIGS. 3 and 5A) inhibited the binding of mAb 170 to TREM-1 as expected. In contrast, the epitope-steered anti-TREM-1 antibodies (gray circles in both FIGS. 3 and 5A), were not able to inhibit the binding of mAb 170 to TREM-1. This result confirms that the epitope-steered anti-TREM-1 antibodies bind to human TREM-1 at an epitope that is distinct from that of the mAb 170 antibody.

The ability of the epitope-steered anti-TREM-1 antibodies to inhibit the binding of PGRP to human TREM-1 was much more varied compared to mAb 170. As shown in FIG. 5A, the mAb 170, along with majority of the non-epitope-steered antibodies, were able to effectively inhibit the interaction between TREM-1 and its natural ligand PGRP. However, for the epitope-steered antibodies, only a small fraction of the antibodies was able to inhibit the binding of PGRP to TREM1 (circled in FIG. 5A) as effectively as mAb 170. For majority of the epitope-steered antibodies, percent inhibition ranged from about 90% to as low as less than 10%.

Example 3: Analysis of the Epitope-Steered Anti-TREM-1 Antibodies to Inhibit THP-1 Cell Activation To assess the antagonistic properties of the epitope-steered anti-TREM-1 antibodies, the potency of these antibodies to block the release of inflammatory cytokines from activated human cells was assessed. Briefly, human monocytic THP-1 cells were stimulated in culture with plate-bound PGRP1 and soluble peptidoglycan that lack TLR2 activity either in the presence or absence of the anti-TREM-1 antibodies (epitope-steered or non-epitope-steered).

As shown in FIG. 3, majority of the non-epitope-steered anti-TREM-1 antibodies (black circle) inhibited the activation of the THP-1 cells with an IC50 value of less about 100 nM. However, only one of the epitope-steered anti-TREM-1 antibodies (gray circle) tested had an IC50 value of less than 100 nM. This appears to be in line with the data from Example 2, which showed that only a small fraction of the epitope-steered antibodies were able to effectively inhibit the binding of the PGRP to human TREM-1. FIG. 4 provides the amino acid sequence of the heavy chain variable region CDR3 for the anti-TREM-1 antibodies shown in FIG. 3.

Example 4: Sequence Analysis of the Epitope-Steered Anti-TREM-1 Antibodies

To further characterize the epitope-steered anti-TREM-1 antibodies, the human germline genes corresponding to the VH and VK regions of the antibodies were determined. The sequences were then grouped according to heavy chain V gene family and HCDR3 sequence.

As shown in FIG. 5B, the VH of the epitope-steered antibodies (gray circles in FIG. 5A) corresponded to human germline genes 1-18, 1-69, 3-09, 3-13, 3-33, 4-59, and 5-51. The VL region corresponded mostly to human germline genes L15, L4, L6, L10, L1, and A27. The epitope-steered antibodies that best inhibited the binding of PGRP to TREM-1 (circled in FIG. 5A—see lower right quadrant) had VH corresponding to human germline genes 1-69, 3-33, and 4-59, and VL corresponding to human germline genes L4 and A27.

In contrast, the non-epitope-steered anti-TREM-1 antibodies shown in FIG. 5A (black diamonds) had VH corresponding to human germline genes 1-08 and 1-69 and VL corresponding to human germline genes L15 and L4. Of those, the antibodies that best inhibited the binding of both PGRP and mAb170 to TREM-1 (boxed in FIG. 5A—see upper right quadrant) had VH and VL corresponding to human germline genes 1-69 and L15, respectively. For comparison, the VH and VL of mAb 170 correspond to 3-73 and B3, respectively.

TABLE 1

Exemplary NTH and VL Amino Acid Sequences for Epitope-Steered Anti-TREM-1 Antibodies

| SEQ ID No. | Description | Sequences |
|---|---|---|
| 13 | P1-047248 VH | QVQLQESGPGLVKPSETLSLTCTVSGGSISSSYWSWVRQPPGKGLEWIGYTHYSGISNY NPSLKSRVTISVDTSKNQFSLKLSSVTAADTAVYYCAREGYDILTGYEYYGMDVWGQGT TVTVSS |
| 14 | P1-047248 VL | EIVLTQSPGTLSLSPGERATLSCRASQSVSSSYLAWYQQKPGQAPRLLIYGASSRATGI PDRFSGSGSGTDFTLTISRLEPEDFAVYYCQQYGSSPTFGGGTKVEIK |

TABLE 1 -continued

Exemplary NTH and VL Amino Acid Sequences for Epitope-Steered Anti-TREM-1 Antibodies

| SEQ ID No. | Description | Sequences |
|---|---|---|
| 15 | P1-047246 VH | QVQLQESGPGLVKPSETLSLTCTVSGGSITNYYWTWIRQPPGKGLEWIGYIHYSGYTNYNPSLKSRVTLSIDTSKNQFSLKLSSVTAADTAVYYCARGVLWFGELLPLLDYWGQGTLVTVTVSS |
| 16 | P1-047246 VL | AIQLTQSPSSLSASVGDRVTITCRASQGISSALAWYQQKPGKAPKLLIYDASSLESGVPSRFSGSGSGTDFTLTISSLQPEDFATYYCQQFNSYPYTFGQGTKLEIK |
| 15 | P1-047247 VH | QVQLQESGPGLVKPSETLSLTCTVSGGSITNYYWTWIRQPPGKGLEWIGYIYDSGYTNYNPSLKSRVTLSIDTSKNQFSLKLSSVTAADTAVYYCARGVLWFGELLPLLDYWGQGTLVTVSS |
| 17 | P1-047247 VL | EIVLTQSPGTLSLSPGERATLSCRASQSVSSSYLAWYQQKPGQAPRLLIYGASSRATGIPERFSGSGSGTDFTLTISRLEPEDFAVYYCQQYGSSPLTFGGGTKVEIK |
| 23 | P1-047334 VH | QVQLVQSGAEVKRPGSSVKVSCKASGGTFSSSAISWVRQAPGQGLEWMGGIIPIFGTTNGAQKFQGRVTITADESTSTAYMELSSLRSEDTAVYYCAAMVRGNYFYFYGMDVWGQGTTVTVSS |
| 24 | P1-047334 VL | AIQLTQSPSSLSASVGDRVTITCRASQGISSALAWYQQKPGKAPKLLIYDASSLQSGVPSRFSGSGSGTDFTLTISSLQPEDFATYYCQQYNSYPYTFGQGTKVEIK |
| 25 | P1-047239 VH | QVQLVESGGGVVQPGRSLRLSCAATEFTFSNYGMHWVRQAPGKGLEWVAVIWYDGSNKYYADSVKGRFTISRDNSKNTLYLQLNSLSAEDSAVYYCARDGRHYYGSTSYFGMDVWGQGTTVTVSS |
| 16 | P1-047239 VL | AIQLTQSPSSLSASVGDRVTITCRASQGISSALAWYQQKPGKAPKLLIYDASSLESGVPSRFSGSGSGTDFTLTISSLQPEDFATYYCQQFNSYPYTFGQGTKLEIK |
| 130 | P1-047323 VH | QVQLVQSGAEVKKPGSSVKVSCKASGGTFINSEAINWVRQAPGQGLEWMGGIIPIFDITNYAQKFQGRVTITADESMSTAYMELSSLRSEDTAVYYCAKTYYDILTYHYHYGMDVWGQGTTVTVSS |
| 131 | P1-047323 VL | AIQLTQSPSSLSASVGDRVTITCRASQGISSALAWYQQKPGKAPKLLIYDASSLESGVPSRFSGSGSGTDFTLTISSLQPEDFATYYCQQFNSYPITFGQGTRLEIK |
| 130 | P1-047328 VH | QVQLVQSGAEVKKPGSSVKVSCKASGGTFINSEAINWVRQAPGQGLEWMGGIIPIFDITNYAQKFQGRVTITADESMSTAYMELSSLRSEDTAVYYCAKTYYDILTYHYHYGMDVWGQGTTVTVSS |
| 132 | P1-047328 VL | AIQLTQSPSSLSASVGDRVTITCRASQGISSALAWYQQKPGKKAPLLIYDASSLESGVPSRFSGSGSGTDFTLTISSLQPEDFATYYCQQYNSYPITFGQGTRLEIK |

TABLE 2

Exemplary VH and VL Sequences for Non-Epitope-Steered Anti-TREM-1 Antibodies

| SEQ ID No. | Description | Sequences |
|---|---|---|
| 53 | P1-047305 VH | QVQLVQSGAEVKKPGSSVKVSCKASGGTFSSSAVSWVRQAPGQGLEWMGGITPIFGTADYAQKFQGRVTITADASTSTGYMELSSLRSEDTAVYYCAFTPRYRGSSHHYYYALGVWGQGTTVTVSS |
| 54 | P1-047305 VL | DIQMTQSPTSLSASVGDRVTITCRASQGISSWLAWYQQKPEKAPKSLIYAASSLQSGVPSRFSGSGSGTDFTLTISSLQPEDFATYYCQQYNSYPYTFGQGTKLEIK |
| 55 | P1-047309 VH | QVQLVQSGAEVKKPGSSVKVSCNPSGGTFSTYAISWVRQAPGQGLEWMGGINPIFGTANYAQKFQGRVTITADESTSPGYLELSSLRSEDTAVYYCARGGAVGFAYWGQGTLVTVSS |
| 56 | P1-047309 VL | DIQMTQSPSSVSASVGDRVTITCRASQGISSWLAWYQHKPGKAPKLLIYAASSLQSGVPSRFSGSGSGTDFTLTISSLQPEDFATYYCQQANSFPFTFGGGTKVEIK |
| 57 | P1-047313 VH | QVQLVQSGAEVKRPGSSVKVSCKASGGTFSIYVISWVRQAPGQGLEWMGGIIPLFGTPNYAQRFQDRVTITADESTRTAYMELSSLRSEDTAVYYCARGHGPGSSHYSYYGLDVWGQGTTVTVSS |

TABLE 2 -continued

| SEQ ID No. | Description | Sequences |
| --- | --- | --- |
| | | Exemplary VH and VL Sequences for Non-Epitope-Steered Anti-TREM-1 Antibodies |
| 58 | P1-047313 VL | DIQMTQSPTSLSASVGDRVTITCRASQGISSWLAWYQHKPGKAPKLLIYAASSLQSGVP SRFSGSGSGTDFTLTISSLQPEDFATYYCQQYNSYPWTFGQGTKLEIK |
| 59 | P1-047307 VH | QVQLVQSGAEVKRPGSSVKVSCKASGGTFSIYVISWVRQAPGQGLEWMGGIIPLFGTPN YAQQFQDRVTITADESTRTAYMELNSLKSEDTAVYYCARGHGPGSSHYSYYGLDVWGQG TTVTVSS |
| 60 | P1-047307 VL | DIQMTQSPTSLSASVGDRVTITCRASQGISSWLAWYQHKPGKAPKSLIYAASSLQSGVP SRFSGSGSGTDFTLTISSLQPEDFATYYCQQYNSYPLTFGGGTKVEIK |
| 59 | P1-047312 VH | QVQLVQSGAEVKRPGSSVKVSCKASGGTFSIYVISWVRQAPGQGLEWMGGIIPLFGTPN YAQQFQDRVTITADESTRTAYMELNSLKSEDTAVYYCARGHGPGSSHYSYYGLDVWGQG TTVTVSS |
| 61 | P1-047312 VL | DIQMTQSPTSLSASVGDRVTITCRASQGISSWLAWYQHKPGKAPKLLIYAASSLQSGVP SRFSGSGSGTDFTLTISSLQPEDFATYYCQQYNSYPYTFGQGTKLEIK |
| 59 | P1-047314 VH | QVQLVQSGAEVKRPGSSVKVSCKASGGTFSIYVISWVRQAPGQGLEWMGGIIPLFGTPN YAQQFQDRVTITADESTRTAYMELNSLKSEDTAVYYCARGHGPGSSHYSYYGLDVWGQG TTVTVSS |
| 54 | P1-047314 VL | DIQMTQSPTSLSASVGDRVTITCRASQGISSWLAWYQQKPEKAPKSLIYAASSLQSGVP SRFSGSGSGTDFTLTISSLQPEDFATYYCQQYNSYPYTFGQGTKLEIK |
| 62 | P1-047318 VH | QVQLVQSGAEVKRPGSSVKVSCKASGGTFSIYVISWVRQAPGQGLEWMGGIIPLFGTPN YAQQFQDRVTITADESTRTAYMELNSLKSEDTAVYYCARGHGPGSSHYSYYGLDVWGQG TTVTVSS |
| 61 | P1-047318 VL | DIQMTQSPTSLSASVGDRVTITCRASQGISSWLAWYQHKPGKAPKLLIYAASSLQSGVP SRFSGSGSGTDFTLTISSLQPEDFATYYCQQYNSYPYTFGQGTKLEIK |
| 59 | P1-047320 VH | QVQLVQSGAEVKRPGSSVKVSCKASGGTFSIYVISWVRQAPGQGLEWMGGIIPLFGTPN YAQQFQDRVTITADESTRTAYMELNSLKSEDTAVYYCARGHGPGSSHYSYYGLDVWGQG TTVTVSS |
| 63 | P1-047320 VL | DIQMTQSPTSLSASVGDRVTITCRASQGISSWLAWYQHKPGKAPKSLIYAASSLQSGVP SRFSGSGSGTDFTLTISSLQPEDFATYYCQQYNSYPYTFGQGTKLEIK |
| 64 | P1-047311 VH | QVQLVQSGAEVKKPGSSVKVSCKASGGTFSIYVISWVRQAPGQGLEWMGGIIPLFGTAN YAQQFQDRVTITADESTRTAYMELNSLKSEDTAVYYCARGHGPGSSHYSYYGLDVWGQG TTVTVSS |
| 65 | P1-047311 VL | DIQMTQSPTSLSASVGDRVTITCRASQGISSWLAWYQQKPGKAPKSLIYAASSLQSGVP SRFSGSGSGTDFTLTISSLQPEDFATYYCQQYNSYPYTFGGGTKVEIK |
| 66 | P1-047294 VH | QVQLVQSGAEVKKPGSSVKVSCKASGGTFNRHAISWVRQAPGQGLEWMGGIIPLFGTAN YAQEFQGRVTIAADEPTSTTYMELRSLRSEDTAVYYCASSYFYGSGSSNYYYYGLDVWG QGTTVTVSS |
| 67 | P1-047294 VL | DIQMTQSPTSLSASVGDRVTITCRASQGISSWLAWYQQKPEKAPKSLIYAASSLQSGVP SRFSGGGSGTDFTLTISSLQPEDFATYYCQQYNSYPLTFGGGTKVEIK |
| 68 | P1-047290 VH | QVQLVQSGAEVKKPGSSVKVSCKASGGTFNRHAISWVRQAPGQGLEWMGGIIPLFGTAN YAQKFQGRVTIAADEPTSTTYMELRSLRSEDTAVYYCASSYFYGSGSSNYYYYGLDVWG QGTTVTVSS |
| 54 | P1-047290 VL | DIQMTQSPTSLSASVGDRVTITCRASQGISSWLAWYQQKPEKAPKSLIYAASSLQSGVP SRFSGSGSGTDFTLTISSLQPEDFATYYCQQYNSYPLTFGGGTKVEIK |
| 68 | P1-047291 VH | QVQLVQSGAEVKKPGSSVKVSCKASGGTFNRHAISWVRQAPGQGLEWMGGIIPLFGTAN YAQKFQGRVTIAADEPTSTTYMELRSLRSEDTAVYYCASSYFYGSGSSNYYYYGLDVWG QGTTVTVSS |
| 69 | P1-047291 VL | DIQMTQSPTSLSASVGDRVTITCRASQGISSWLAWYQQKPEKAPKSLIYAASSLQSGVP SRFSGSGSGTDFTLTISSLQPDDFATYYCQQYNSYPLTFGQGTKVEIK |
| 68 | P1-047296 VH | QVQLVQSGAEVKKPGSSVKVSCKASGGTFNRHAISWVRQAPGQGLEWMGGIIPLFGTAN YAQKFQGRVTIAADEPTSTTYMELRSLRSEDTAVYYCASSYFYGSGSSNYYYYGLDVWG QGTTVTVSS |
| 70 | P1-047296 VL | DIQMTQSPTSLSASVGDRVTITCRASQGISSWLAWYQQKPEKAPKSLIYAASSLQSGVP SRFSGSGSGTDFTLTISSLQPEDFATYYCQQYNSYPLTFGQGTKVEIK |

TABLE 2 -continued

Exemplary VH and VL Sequences for Non-Epitope-Steered Anti-TREM-1 Antibodies

| SEQ ID No. | Description | Sequences |
|---|---|---|
| 68 | P1-047297 VH | QVQLVQSGAEVKKPGSSVKVSCKASGGTFNRHAISWVRQAPGQGLEWMGGIIPLFGTAN YAQKFQGRVTIAADEPTSTTYMELRSLRSEDTAVYYCASSYFYGSGSSNYYYYGLDVWG QGTTVTVSS |
| 71 | P1-047297 VL | DIQMTQSPTSLSASVGDRVTITCRASQGISSWLAWYQQKPEKAPKSLIYAASSLQSGVP SRFSGSGSGTDFTLTISSLQPEDFATYYCQQYNSYPLTFGGGTKVEIK |
| 68 | P1-047300 VH | QVQLVQSGAEVKKPGSSVKVSCKASGGTFNRHAISWVRQAPGQGLEWMGGIIPLFGTAN YAQKFQGRVTIAADEPTSTTYMELRSLRSEDTAVYYCASSYFYGSGSSNYYYYGLDVWG QGTTVTVSS |
| 72 | P1-047300 VL | DIQMTQSPTSLSASVGDRVTITCRASQGISSWLAWYQQKPEKAPKSLIYAASSLQSGVP SRFSGSGSGTDFTLTISSLQPEDFATYYCQQYNSYPLTFGGGTKVEIK |
| 68 | P1-047302 VH | QVQLVQSGAEVKKPGSSVKVSCKASGGTFNRHAISWVRQAPGQGLEWMGGIIPLFGTAN YAQKFQGRVTIAADEPTSTTYMELRSLRSEDTAVYYCASSYFYGSGSSNYYYYGLDVWG QGTTVTVSS |
| 60 | P1-047302 VL | DIQMTQSPTSLSASVGDRVTITCRASQGISSWLAWYQQKPEKAPKSLIYAASSLQSGVP SRFSGSGSGTDFTLTISSLQPEDFATYYCQQYNSYPLTFGGGTKVEIK |
| 73 | P1-047308 VH | QVQLVQSGAEVKRPGSSVKVSCKASGGTFSIYVISWVRQAPGQGLEWMGGIIPLFGTAN YAQKFQGRVTITADESTNTAYMELRSLRSEDTAVYYCARGHGPGSSHYSYYGLDVWGQG TTVTVSS |
| 54 | P1-047308 VL | DIQMTQSPTSLSASVGDRVTITCRASQGISSWLAWYQQKPEKAPKSLIYAASSLQSGVP SRFSGSGSGTDFTLTISSLQPEDFATYYCQQYNSYPLTFGQGTKVEIK |
| 73 | P1-047319 VH | QVQLVQSGAEVKRPGSSVKVSCKASGGTFSIYVISWVRQAPGQGLEWMGGIIPLFGTAN YAQKFQGRVTITADESTNTAYMELRSLRSEDTAVYYCARGHGPGSSHYSYYGLDVWGQG TTVTVSS |
| 63 | P1-047319 VL | DIQMTQSPTSLSASVGDRVTITCRASQGISSWLAWYQHKPGKAPKSLIYAASSLQSGVP SRFSGSGSGTDFTLTISSLQPEDFATYYCQQYNSYPLTFGQGTKVEIK |
| 74 | P1-047292 VH | QVQLVQSGAEVKKPGSSVKVSCKASGGTFSSSAISWVRQAPGQGLEWMGGIIPLFSTGN YAQKFQGRVTITADESTNTAYMDLSSLRSEDTAVYYCARSTRVRGVSHYYYYGLDVWGQ GTTVTVSS |
| 54 | P1-047292 VL | DIQMTQSPTSLSASVGDRVTITCRASQGISSWLAWYQHKPEKAPKSLIYAASSLQSGVP SRFSGSGSGTDFTLTISSLQPEDFATYYCQQYNSYPLTFGQGTKVEIK |
| 75 | P1-047322 VH | QVQLVQSGAEVKKPGSSVKVSCKSSGGTFSSYAFTWVRQAPGQGLEWMGGIIPLFRTAN YAQKFQGRVTITADESTSTAYMELSSLRSEDTAVYYCASSHFSGSGSSHYYYYGMHVWG QGTTVTVSS |
| 54 | P1-047322 VL | DIQMTQSPTSLSASVGDRVTITCRASQGISSWLAWYQHKPEKAPKSLIYAASSLQSGVP SRFSGSGSGTDFTLTISSLQPEDFATYYCQQYNSYPLTFGQGTKVEIK |
| 76 | P1-047310 VH | QVQLVQSGAEVKRPGSSVKVSCKASGGTFSRYAISWVRQAPGQGLEWMGGIIPLFGTSN YAQKFQGRVTIKADESTNTAYMELSSLRSEDTAVYYCARGGNSWTTSLYYYGLDVWGQG TTVTVSS |
| 77 | P1-047310 VL | DIQMTQSPTSLSASVGDRVTITCRASQGISSWLAWYQQKPEKAPKSLIYAASSLQSGVP SRFSGSGSGTDYTLTISSLQPEDFATYYCQQYNSYPLTFGGGTKVEIK |
| 78 | P1-047299 VH | QVQLVQSGAEVKKPGSSVKVSCKSSGGTFSSYAFTWVRQAPGQGLEWMGGIIPLFRTPN YAQKFQGRVTITADESTSTAYMELSSLRSEDTAVYYCASSHFSGSGSSHYYYYGMHVWG QGTTVTVSS |
| 79 | P1-047299 VL | DIQMTQSPTSLSASVGDRVTITCRASQGISSWLAWYQQKPEKAPKSLIYAASSLQSGVP SRFSGSGSGTDYTLTISSLQPEDFATYYCQQYNSYPLTFGQGTKVEIK |
| 80 | P1-047301 VH | QVQLVQSGAEVKKPGSSVKVSCKSSGGTFSSSAISWVRQAPGQGLEWMGGIIPLFRTPN YAQKFQGRVTITADESTSTAYMELSSLISEDTAVYYCASSHFSGSGSSHYYYYGMHVWG QGTTVTVSS |
| 54 | P1-047301 VL | DIQMTQSPTSLSASVGDRVTITCRASQGISSWLAWYQQKPEKAPKSLIYAASSLQSGVP SRFSGSGSGTDFTLTISSLQPEDFATYYCQQYNSYPLTFGQGTKVEIK |

TABLE 2 -continued

| SEQ ID No. | Description | Sequences |
|---|---|---|
| | | Exemplary VH and VL Sequences for Non-Epitope-Steered Anti-TREM-1 Antibodies |
| 81 | P1-047289 VH | QVQLVQSGAEVKKPGSSVKVSCKASGGTFSSSAISWVRQAPGQGLEWMGGIIPIFDTAD SAQKFQGRVTITADESTSTAYMELNSLRSEDTAVYYCAFTPRYRGSSHHYFYALGVWGQ GTTVTVSS |
| 82 | P1-047289 VL | DIQMTQSPTSLSASVGDRVTITCRASQGISSWLAWYQQKPEKAPKSLIYAASSLQSGVP SRFSGSGSGTDFTLTISSLQPEDFATYYCQQYNSYPLTFGGGTKVEIK |
| 83 | P1-047306 VH | QVQLVQSGAEVKKPGSSVKVSCKASGGTFSSSAISWVRQAPGQGLEWMGGIIPLFGTAN YAQKFQGRVTIKADESTNTAYMELSSLRSEDTAVYYCARASQSRSSNYYYYGLDVWGQG TTVTVSS |
| 60 | P1-047306 VL | DIQMTQSPTSLSASVGDRVTITCRASQGISSWLAWYQQKPEKAPKSLIYAASSLQSGVP SRFSGSGSGTDFTLTISSLQPEDFATYYCQQYNSYPLTFGGGTKVEIK |
| 133 | P1-047263 VH | QVQLVQSGAEVKKPGSSVKVSCKASGYTFPTYDINWVRQATGQGLEWMGWVNPNSGNTG YAQKFQGRVTITADESTSTAYMELNSLRSEDTAVYYCAFTPRYRGSSHHYFYALGVWGQ GTTVTVSS |
| 134 | P1-047263 VL | DIQMTQSPTSLSASVGDRVTITCRASQGISSWLAWYQQKPEKAPKSLIYAASSLQSGVP SRFSGSGSGTDFTLTISSLQPEDFATYYCQQYNSYPLTFGQGTKLEIK |
| 133 | P1-047265 VH | QVQLVQSGAEVKKPGASVKVSCKASGYTFPTYDINWVRQATGQGLEWMGWVNPNSGNTG YAQKFQDRVTMTRNTSISTAYMELSSLRSEDTAVYYCASDGLNMVRGVHNYYGMDVWGQ GTTVTVSS |
| 54 | P1-047265 VL | DIQMTQSPTSLSASVGDRVTITCRASQGISSWLAWYQQKPEKAPKSLIYAASSLQSGVP SRFSGSGSGTDFTLTISSLQPEDFATYYCQQYNSYPLTFGQGTKLEIK |
| 59 | P1-047317 VH | QVQLVQSGAEVKKPGSSVKVSCKASGGTFSSSAISWVRQAPGQGLEWMGGIIPLFGTPN YAQQFQDRVTITADESTRTAYMELNSLKSEDTAVYYCARGHGPGSSHYSYYGLDVWGQG TTVTVSS |
| 135 | P1-047317 VL | EIVLTQSPGTLSLSPGERATLSCRASQSVSSYLAWYQQKPGQAPRLLIYGASSRATGIP DRFSGSGSGTDFTLTISRLEPEDFAVYYCQQYGSSPLTFGGGTKVEIK |

TABLE 3

| SEQ ID No. | Description | Sequences |
|---|---|---|
| | | Exemplary VH and VL Nucleotide Sequences for Epitope-Steered Anti-TREM-1 Antibodies |
| 146 | P1-047248 VH | CAGGTGCAGCTGCAGGAGTCGGGCCCAGGACTGGTGAAGCCTTCGGAGACCCTGTCCCT CACCTGCACTGTGTCTGGTGGCTCCATCAGTAGTTCCTACTGGAGCTGGGTCCGGCAGC CCCCAGGGAAGGGACTGGAGTGGATTGGATATACCCATTACAGTGGGATCAGCAACTAC AACCCCTCCCTCAAGAGTCGAGTCACCATATCAGTAGACACGTCCAAGAACCAGTTCTC CCTGAAGCTGAGCTCTGTGACCGCTGCGGACACGGCCGTGTATTACTGTGCGAGAGAAG GGTACGATATTTTGACTGGTTATGAGTACTACGGTATGGACGTCTGGGGCCAAGGGACC ACGGTCACCGTGTCCTCA |
| 171 | P1-047248 VL | GAAATTGTGTTGACGCAGTCTCCAGGCACCCTGTCTTTGTCTCCAGGGGAAAGAGCCAC CCTCTCCTGCAGGGCCAGTCAGAGTGTTAGCAGCAGCTACTTAGCCTGGTACCAGCAGA AACCTGGCCAGGCTCCCAGGCTCCTCATCTATGGTGCATCCAGCAGGGCCACTGGCATC CCAGACAGGTTCAGTGGCAGTGGGTCTGGGACAGACTTCACTCTCACCATCAGCAGACT GGAGCCTGAAGATTTTGCAGTGTATTACTGTCAGCAGTATGGTAGCTCACCTACTTTCG GCGGAGGGACCAAGGTGGAGATCAAA |
| 145 | P1-047246 VH | CAGGTGCAGCTGCAGGAGTCGGGCCCAGGACTGGTGAAGCCTTCGGAGACCCTGTCCCT CACCTGCACTGTCTCTGGTGGCTCCATCACTAATTACTACTGGACCTGGATCCGGCAGC CCCCAGGGAAGGGACTGGAGTGGATTGGGTATATCTATGACAGTGGGTACACCAACTAC AACCCCTCCCTCAAGAGTCGAGTCACCTTATCAATAGACACGTCCAAGAACCAGTTCTC CCTGAAGCTGAGCTCTGTGACCGCTGCGGACACGGCCGTTTATTACTGTGCGAGAGGGG TTCTATGGTTCGGGGAGTTATTACCTCTCCTTGACTACTGGGGCCAGGGAACCCTGGTC ACCGTCTCCTCA |

TABLE 3 -continued

Exemplary VH and VL Nucleotide Sequences for Epitope-Steered Anti-TREM-1 Antibodies

| SEQ ID No. | Description | Sequences |
| --- | --- | --- |
| 169 | P1-047246 VL | GCCATCCAGTTGACCCAGTCTCCATCCTCCCTGTCTGCATCTGTAGGAGACAGAGTCAC<br>CATCACTTGCCGGGCAAGTCAGGGCATTAGCAGTGCTTTAGCCTGGTATCAGCAGAAAC<br>CAGGGAAAGCTCCTAAGCTCCTGATCTATGATGCCTCCAGTTTGGAAAGTGGGGTCCCA<br>TCAAGGTTCAGCGGCAGTGGATCTGGGACAGATTTCACTCTCACCATCAGCAGCCTGCA<br>TCAAGGTTCAGCGGCAGTGGATCTGGGACAGATTTCACTCTCACCATCAGCAGCCTGCA<br>GCCTGAAGATTTTGCAACTTATTACTGTCAACAGTTTAATAGTTACCCGTACACTTTTG<br>GCCAGGGGACCAAGCTGGAGATCAAA |
| 145 | P1-047247 VH | CAGGTGCAGCTGCAGGAGTCGGGCCCAGGACTGGTGAAGCCTTCGGAGACCCTGTCCCT<br>CACCTGCACTGTCTCTGGTGGCTCCATCACTAATTACTACTGGACCTGGATCCGGCAGC<br>CCCCAGGGAAGGGACTGGAGTGGATTGGGTATATCTATGACAGTGGGTACACCAACTAC<br>AACCCCTCCCTCAAGAGTCGAGTCACCTTATCAATAGACACGTCCAAGAACCAGTTCTC<br>CCTGAAGCTGAGCTCTGTGACCGCTGCGGACACGGCCGTTTATTACTGTGCGAGAGGGG<br>TTCTATGGTTCGGGGAGTTATTACCTCTCCTTGACTACTGGGGCCAGGGAACCCTGGTC<br>ACCGTCTCCTCA |
| 170 | P1-047247 VL | GAAATTGTGTTGACGCAGTCTCCAGGCACCCTGTCTTTGTCTCCAGGGGAAAGAGCCAC<br>CCTCTCCTGCAGGGCCAGTCAGAGTGTTAGCAGCAGCTACTTAGCCTGGTACCAGCAGA<br>AACCTGGCCAGGCTCCCAGGCTCCTCATCTATGGTGCATCCAGCAGGGCCACTGGCATC<br>CCAGAGAGGTTCAGTGGCAGTGGGTCTGGGACAGACTTCACTCTCACCATCAGCAGACT<br>GGAGCCTGAAGATTTTGCAGTGTATTACTGTCAGCAGTATGGTAGCTCACCGCTCACTT<br>TCGGCGGAGGGACCAAGGTGGAGATCAAA |
| 148 | P1-047334 VH | CAGGTGCAGCTGGTGCAGTCTGGGGCTGAGGTGAAGAGGCCTGGGTCCTCTGTGAAGGT<br>CTCCTGCAAGGCTTCTGGAGGCACCTTCAGTAGTTCCGCTATCAGCTGGGTGCGACAGG<br>CCCCTGGACAAGGGCTTGAGTGGATGGGAGGGATCATCCCTATCTTTGGTACAACAAAC<br>GGCGCACAGAAGTTCCAGGGCAGAGTCACGATTACCGCGGACGAATCCACGAGCACAGC<br>CTACATGGAGCTGAGCAGCCTGAGATCTGAGGACACGGCCGTGTATTACTGTGCGGCTA<br>TGGTTCGGGGAAATTACTTCTACTTCTACGGTATGGACGTCTGGGGCCAAGGGACCACG<br>GTCACCGTCTCCTCA |
| 175 | P1-047334 VL | GCCATCCAGTTGACCCAGTCTCCATCCTCCCTGTCTGCATCTGTAGGAGACAGAGTCAC<br>CATCACTTGCCGGGCAAGTCAGGGCATTAGCAGTGCTTTAGCCTGGTATCAGCAGAAAC<br>CAGGGAAAGCCCCTAAGCTCCTGATCTATGCTGCATCCAGTTTGCAAAGTGGGGTCCCA<br>TCAAGGTTCAGCGGCAGTGGATCTGGGACAGATTTCACTCTCACCATCAGCAGCCTGCA<br>GCCTGAAGATTTTGCAACTTATTACTGCCAACAGTATAATAGTTACCCGCTCACTTTCG<br>GCGGAGGGACCAAGGTGGAGATCAAA |
| 144 | P1-047239 VH | CAGGTGCAGCTGGTGGAGTCTGGGGGAGGCGTGGTCCAGCCTGGGAGGTCCCTGAGACT<br>CTCCTGTGCAGCTACTGAATTCACCTTCAGTAACTATGGCATGCACTGGGTCCGCCAGG<br>CTCCAGGCAAGGGGCTGGAGTGGGTGGCAGTTATATGGTATGATGGAAGTAATAAATAC<br>TATGCAGACTCCGTGAAGGGCCGCTTCACCATCTCCAGAGACAATTCCAAGAACACGCT<br>GTATCTGCAATTGAACAGCCTGAGCGCCGAGGACTCGGCTGTGTATTACTGTGCGAGAG<br>ATGGGAGGCATTACTATGGTTCGACCTCCTACTTCGGCATGGACGTCTGGGGCCAAGGG<br>ACCACGGTCACCGTCTCCTCA |
| 169 | P1-047239 VL | GCCATCCAGTTGACCCAGTCTCCATCCTCCCTGTCTGCATCTGTAGGAGACAGAGTCAC<br>CATCACTTGCCGGGCAAGTCAGGGCATTAGCAGTGCTTTAGCCTGGTATCAGCAGAAAC<br>CAGGGAAAGCTCCTAAGCTCCTGATCTATGATGCCTCCAGTTTGGAAAGTGGGGTCCCA<br>TCAAGGTTCAGCGGCAGTGGATCTGGGACAGATTTCACTCTCACCATCAGCAGCCTGCA<br>GCCTGAAGATTTTGCAACTTATTACTGTCAACAGTTTAATAGTTACCCGTACACTTTTG<br>GCCAGGGGACCAAGCTGGAGATCAAA |
| 147 | P1-047323 VH | CAGGTGCAGCTGGTGCAGTCTGGGGCTGAGGTGAAGAAGCCTGGGTCCTCGGTGAAGGT<br>CTCCTGCAAGGCTTCTGGAGGCACCTTCATCAATAGCGAAGCTATCAACTGGGTGCGAC<br>AGGCCCCTGGACAAGGGCTTGAGTGGATGGGAGGGATCATCCCTATCTTTGACATTACA<br>AACTACGCACAGAAGTTCCAGGGCAGAGTCACGATTACCGCGGACGAATCCATGAGCAC<br>AGCCTACATGGAGCTGAGCAGCCTGAGATCTGAGGACACGGCCGTGTATTACTGTGCGA<br>AGACGTATTACGATATTTTGACTTATCACTATCACTACGGTATGGACGTCTGGGGCCAA<br>GGGACCACGGTCACCGTCTCCTCA |
| 172 | P1-047323 VL | GCCATCCAGTTGACCCAGTCTCCATCCTCCCTGTCTGCATCTGTAGGAGACAGAGTCAC<br>CATCACTTGCCGGGCAAGTCAGGGCATTAGCAGTGCTTTAGCCTGGTATCAGCAGAAAC<br>CAGGGAAAGCTCCTAAGCTCCTGATCTATGATGCCTCCAGTTTGGAAAGTGGGGTCCCA<br>TCAAGGTTCAGCGGCAGTGGATCTGGGACAGATTTCACTCTCACCATCAGCAGCCTGCA<br>GCCTGAAGATTTTGCAACTTATTACTGTCAACAGTTTAATAGTTACCCGATCACCTTCG<br>GCCAAGGGACACGACTGGAGATTAAA |
| 147 | P1-047328 VH | CAGGTGCAGCTGGTGCAGTCTGGGGCTGAGGTGAAGAAGCCTGGGTCCTCGGTGAAGGT<br>CTCCTGCAAGGCTTCTGGAGGCACCTTCATCAATAGCGAAGCTATCAACTGGGTGCGAC<br>AGGCCCCTGGACAAGGGCTTGAGTGGATGGGAGGGATCATCCCTATCTTTGACATTACA<br>AACTACGCACAGAAGTTCCAGGGCAGAGTCACGATTACCGCGGACGAATCCATGAGCAC |

TABLE 3 -continued

Exemplary VH and VL Nucleotide Sequences for Epitope-Steered Anti-TREM-1 Antibodies

| SEQ ID No. | Description | Sequences |
|---|---|---|
| | | AGCCTACATGGAGCTGAGCAGCCTGAGATCTGAGGACACGGCCGTGTATTACTGTGCGA AGACGTATTACGATATTTTGACTTATCACTATCACTACGGTATGGACGTCTGGGGCCAA GGGACCACGGTCACCGTCTCCTCA |
| 174 | P1-047328 VL | GCCATCCAGTTGACCCAGTCTCCATCCTCCCTGTCTGCATCTGTAGGAGACAGAGTCAC CATCACTTGCCGGGCAAGTCAGGGCATTAGCAGTGCTTTAGCCTGGTATCAGCAGAAAC CAGGGAAAGCTCCTAAGCTCCTGATCTATGATGCCTCCAGTTTGGAAAGTGGGGTCCCA TCAAGGTTCAGCGGCAGTGGATCTGGGACAGATTTCACTCTCACCATCAGCAGCCTGCA GCCTGAAGATTTTGCAACTTATTACTGCCAACAGTATAATAGTTACCCGATCACCTTCG GCCAAGGGACACGACTGGAGATTAAA |

TABLE 4

Exemplary VH and VL Nucleotide Sequences for Non-Epitope-Steered Anti-TREM-1 Antibodies

| SEQ ID No. | Description | Sequences |
|---|---|---|
| 158 | P1-047305 VH | CAGGTGCAGCTGGTGCAGTCTGGGGCTGAGGTGAAGAAGCCTGGGTCCTCGGTGAAGGT CTCCTGCAAGACTTCTGGAGGCACCTTCAGCAGCTCTGCTGTCAGCTGGGTGCGACAGG CCCCTGGACAAGGGCTTGAATGAATGGGAGGAATCACCCCTATTTTTGGTACAGCAGAC TACGCACAGAAGTTCCAGGGCAGAGTCACGATTACCGCGGACGCATCCACGAGCACAGG TTATATGGAACTGAGCAGCCTGAGATCTGAGGACACGGCCGTTTACTACTGTGCGTTCA CACCCCGATATCGTGGGAGCTCCCACCACTACTACTACGCTTTGGGCGTCTGGGGCCAA GGGACCACGGTCACCGTCTCCTCA |
| 176 | P1-047305 VL | GACATCCAGATGACCCAGTCTCCAACCTCACTGTCTGCATCTGTAGGAGACAGAGTCAC CATCACTTGTCGGGCGAGTCAGGGTATTAGCAGCTGGTTAGCCTGGTATCAGCAGAAAC CAGAGAAAGCCCCTAAGTCCCTGATCTATGCTGCATCCAGTTTGCAAAGTGGGGTCCCA TCAAGGTTCAGCGGCAGTGGATCTGGGACAGATTTCACTCTCACCATCAGCAGCCTGCA GCCTGAAGATTTTGCAACTTATTACTGCCAACAGTATAATAGTTACCCGTACACTTTTG GCCAGGGGACCAAGCTGGAGATCAAA |
| 162 | P1-047309 VH | CAGGTGCAGCTGGTGCAGTCTGGGGCTGAGGTGAAGAAGCCTGGGTCCTCGGTGAAGGT CTCCTGCAACCCTTCTGGAGGCACCTTCAGCACCTACGCTATCAGCTGGGTGCGACAGG CCCCTGGACAAGGGCTTGAGTGGATGGGAGGGATCAACCCTATCTTTGGAACAGCAAAC TACGCACAGAAGTTCCAGGGCAGAGTCACAATTACCGCGGACGAATCCACGAGTCCAGG CTACCTGGAGCTGAGCAGCCTGAGATCTGAGGACACGGCCGTTTATTACTGTGCGAGAG GGGGAGCAGTGGGTTTTGCCTATTGGGGCCAGGGAACCCTGGTCACCGTCTCCTCA |
| 186 | P1-047309 VL | GACATCCAGATGACCCAGTCTCCATCTTCCGTGTCTGCATCTGTAGGAGACAGAGTCAC CATCACTTGTCGGGCGAGTCAGGGTATTAGCAGCTGGTTAGCCTGGTATCAGCATAAAC CAGGGAAAGCCCCTAAGCTCCTGATCTATGCTGCATCCAGTTTGCAAAGTGGGGTCCCA TCAAGGTTCAGCGGCAGTGGATCTGGGACAGATTTCACTCTCACCATCAGCAGCCTGCA GCCTGAAGATTTTGCAACTTACTATTGTCAACAGGCTAATAGTTTCCCGTTCACTTTCG GCGGAGGGACCAAGGTGGAGATCAAA |
| 165 | P1-047313 VH | CAGGTGCAGCTGGTGCAGTCTGGGGCTGAGGTGAAGAGGCCTGGGTCCTCGGTGAAGGT CTCCTGCAAGGCTTCTGGAGGCACCTTCAGTATCTATGTTATCAGCTGGGTGCGACAGG CCCCTGGACAAGGGCTTGAGTGGATGGGAGGGATCATCCCTCTCTTTGGTACACCAAAC TACGCACAGCGGTTCCAGGACAGAGTCACGATTACCGCGGACGAATCCACGAGGACAGC CTACATGGAGCTGAGTAGCCTGAGATCTGAGGACACGGCCGTGTATTACTGTGCGAGGG GACATGGTCCGGGGAGTTCCCACTACTCCTACTACGGTTTGGACGTCTGGGGCCAAGGG ACCACGGTCACCGTCTCCTCA |
| 190 | P1-047313 VL | GACATCCAGATGACCCAGTCTCCAACCTCACTGTCTGCATCTGTAGGAGACAGAGTCAC CATCACTTGTCGGGCGAGTCAGGGTATTAGCAGCTGGTTAGCCTGGTATCAGCATAAAC CAGGGAAAGCCCCTAAGCTCCTGATCTATGCTGCATCCAGTTTGCAAAGTGGGGTCCCA TCAAGGTTCAGCGGCAGTGGATCTGGGACAGATTTCACTCTCACCATCAGCAGCCTGCA GCCTGAAGATTTTGCAACTTATTACTGCCAACAGTATAATAGTTACCCCTGGACGTTCG GCCAAGGGACCAAGGTGGAAATCAAA |
| 160 | P1-047307 VH | CAGGTGCAGCTGGTGCAGTCTGGGGCTGAGGTGAAGAGGCCTGGGTCCTCGGTGAAGGT CTCCTGCAAGGCTTCTGGAGGCACCTTCAGTATCTATGTTATCAGCTGGGTGCGACAGG CCCCTGGACAAGGGCTTGAGTGGATGGGAGGGATCATCCCTCTCTTTGGTACACCAAAC |

TABLE 4 -continued

Exemplary VH and VL Nucleotide Sequences for Non-Epitope-Steered Anti-TREM-1 Antibodies

| SEQ ID No. | Description | Sequences |
| --- | --- | --- |
| | | TACGCACAGCAGTTCCAGGACAGAGTCACGATTACCGCGGACGAATCCACGAGGACAGC<br>CTACATGGAGCTGAATAGCCTGAAATCTGAGGACACGGCCGTATATTACTGTGCGAGGG<br>GACATGGTCCGGGGAGTTCCCACTACTCCTACTACGGTTTGGACGTCTGGGGCCAAGGG<br>ACCACGGTCACCGTCTCCTCA |
| 184 | P1-047307 VL | GACATCCAGATGACCCAGTCTCCAACCTCACTGTCTGCATCTGTAGGAGACAGAGTCAC<br>CATCACTTGTCGGGCGAGTCAGGGTATTAGCAGCTGGTTAGCCTGGTATCAGCAGAAAC<br>CAGAGAAAGCCCCTAAGTCCCTGATCTATGCTGCATCCAGTTTGCAAAGTGGGGTCCCA<br>TCAAGGTTCAGCGGCAGTGGATCTGGGACAGATTTCACTCTCACCATCAGCAGCCTGCA<br>GCCTGAAGATTTTGCAACTTATTACTGCCAACAGTATAATAGTTACCCTCTCACTTTCG<br>GCGGAGGGACCAAGGTGGAGATCAAA |
| 160 | P1-047312 VH | CAGGTGCAGCTGGTGCAGTCTGGGGCTGAGGTGAAGAGGCCTGGGTCCTCGGTGAAGGT<br>CTCCTGCAAGGCTTCTGGAGGCACCTTCAGTATCTATGTTATCAGCTGGGTGCGACAGG<br>CCCCTGGACAAGGGCTTGAGTGGATGGGAGGGATCATCCCTCTCTTTGGTACACCAAAC<br>TACGCACAGCAGTTCCAGGACAGAGTCACGATTACCGCGGACGAATCCACGAGGACAGC<br>CTACATGGAGCTGAATAGCCTGAAATCTGAGGACACGGCCGTATATTACTGTGCGAGGG<br>GACATGGTCCGGGGAGTTCCCACTACTCCTACTACGGTTTGGACGTCTGGGGCCAAGGG<br>ACCACGGTCACCGTCTCCTCA |
| 189 | P1-047312 VL | GACATCCAGATGACCCAGTCTCCAACCTCACTGTCTGCATCTGTAGGAGACAGAGTCAC<br>CATCACTTGTCGGGCGAGTCAGGGTATTAGCAGCTGGTTAGCCTGGTATCAGCATAAAC<br>CAGGGAAAGCCCCTAAGCTCCTGATCTATGCTGCATCCAGTTTGCAAAGTGGGGTCCCA<br>TCAAGGTTCAGCGGCAGTGGATCTGGGACAGATTTCACTCTCACCATCAGCAGCCTGCA<br>GCCTGAAGATTTTGCAACTTATTACTGCCAACAGTATAATAGTTACCCGTACACTTTTG<br>GCCAGGGGACCAAGCTGGAGATCAAA |
| 160 | P1-047314 VH | CAGGTGCAGCTGGTGCAGTCTGGGGCTGAGGTGAAGAGGCCTGGGTCCTCGGTGAAGGT<br>CTCCTGCAAGGCTTCTGGAGGCACCTTCAGTATCTATGTTATCAGCTGGGTGCGACAGG<br>CCCCTGGACAAGGGCTTGAGTGGATGGGAGGGATCATCCCTCTCTTTGGTACACCAAAC<br>TACGCACAGCAGTTCCAGGACAGAGTCACGATTACCGCGGACGAATCCACGAGGACAGC<br>CTACATGGAGCTGAATAGCCTGAAATCTGAGGACACGGCCGTATATTACTGTGCGAGGG<br>GACATGGTCCGGGGAGTTCCCACTACTCCTACTACGGTTTGGACGTCTGGGGCCAAGGG<br>ACCACGGTCACCGTCTCCTCA |
| 176 | P1-047314 VL | GACATCCAGATGACCCAGTCTCCAACCTCACTGTCTGCATCTGTAGGAGACAGAGTCAC<br>CATCACTTGTCGGGCGAGTCAGGGTATTAGCAGCTGGTTAGCCTGGTATCAGCAGAAAC<br>CAGAGAAAGCCCCTAAGTCCCTGATCTATGCTGCATCCAGTTTGCAAAGTGGGGTCCCA<br>TCAAGGTTCAGCGGCAGTGGATCTGGGACAGATTTCACTCTCACCATCAGCAGCCTGCA<br>GCCTGAAGATTTTGCAACTTATTACTGCCAACAGTATAATAGTTACCCGTACACTTTTG<br>GCCAGGGGACCAAGCTGGAGATCAAA |
| 166 | P1-047318 VH | CAGGTGCAGCTGGTGCAGTCTGGGGCTGAGGTGAAGAGGCCTGGGTCCTCGGTGAAGGT<br>CTCCTGCAAGGCTTCTGGAGGCACCTTCAGTATCTATGTTATCAGCTGGGTCCGACAGG<br>CCCCTGGACAAGGGCTTGAGTGGATGGGAGGGATCATCCCTCTCTTTGGTACACCAAAC<br>TACGCACAGCAGTTCCAGGACAGAGTCACGATTACCGCGGACGAATCCACGAGGACAGC<br>CTACATGGAGCTGAGTAGCCTGAGATCTGAGGACACGGCCGTGTATTACTGTGCGAGGG<br>GACATGGTCCGGGGAGTTCCCACTACTCCTACTACGGTTTGGACGTCTGGGGCCAAGGG<br>ACCACGGTCACCGTCTCCTCA |
| 189 | P1-047318 VL | GACATCCAGATGACCCAGTCTCCAACCTCACTGTCTGCATCTGTAGGAGACAGAGTCAC<br>CATCACTTGTCGGGCGAGTCAGGGTATTAGCAGCTGGTTAGCCTGGTATCAGCATAAAC<br>CAGGGAAAGCCCCTAAGCTCCTGATCTATGCTGCATCCAGTTTGCAAAGTGGGGTCCCA<br>TCAAGGTTCAGCGGCAGTGGATCTGGGACAGATTTCACTCTCACCATCAGCAGCCTGCA<br>GCCTGAAGATTTTGCAACTTATTACTGCCAACAGTATAATAGTTACCCGTACACTTTTG<br>GCCAGGGGACCAAGCTGGAGATCAAA |
| 160 | P1-047320 VH | CAGGTGCAGCTGGTGCAGTCTGGGGCTGAGGTGAAGAGGCCTGGGTCCTCGGTGAAGGT<br>CTCCTGCAAGGCTTCTGGAGGCACCTTCAGTATCTATGTTATCAGCTGGGTGCGACAGG<br>CCCCTGGACAAGGGCTTGAGTGGATGGGAGGGATCATCCCTCTCTTTGGTACACCAAAC<br>TACGCACAGCAGTTCCAGGACAGAGTCACGATTACCGCGGACGAATCCACGAGGACAGC<br>CTACATGGAGCTGAATAGCCTGAAATCTGAGGACACGGCCGTATATTACTGTGCGAGGG<br>GACATGGTCCGGGGAGTTCCCACTACTCCTACTACGGTTTGGACGTCTGGGGCCAAGGG<br>ACCACGGTCACCGTCTCCTCA |
| 183 | P1-047320 VL | GACATCCAGATGACCCAGTCTCCAACCTCACTGTCTGCATCTGTAGGAGACAGAGTCAC<br>CATCACTTGTCGGGCGAGTCAGGGTATTAGCAGCTGGTTAGCCTGGTATCAGCATAAAC<br>CAGGGAAAGCCCCTAAGTCCCTGATCTATGCTGCATCCAGTTTGCAAAGTGGGGTCCCA<br>TCAAGGTTCAGCGGCAGTGGATCTGGGACAGATTTCACTCTCACCATCAGCAGCCTGCA<br>GCCTGAAGATTTTGCAACTTATTACTGCCAACAGTATAATAGTTACCCGTACACTTTTG<br>GCCAGGGGACCAAGCTGGAGATCAAA |

TABLE 4 -continued

Exemplary VH and VL Nucleotide Sequences for Non-Epitope-Steered Anti-TREM-1 Antibodies

| SEQ ID No. | Description | Sequences |
|---|---|---|
| 164 | P1-047311 VH | CAGGTGCAGCTGGTGCAGTCTGGGGCTGAGGTGAAGAAGCCTGGGTCCTCGGTGAAGGT CTCCTGCAAGGCTTCTGGAGGCACCTTCAGTATCTATGTTATCAGCTGGGTGCGACAGG CCCCTGGACAAGGGCTTGAGTGGATGGGAGGGATCATCCCTCTCTTTGGTACAGCAAAC TACGCACAGCAGTTCCAGGACAGAGTCACGATTACCGCGGACGAATCCACGAGGACAGC CTACATGGAGCTGAATAGCCTGAAATCTGAGGACACGGCTGTATATTACTGTGCGAGGG GACATGGTCCGGGGAGTTCCCACTACTCCTACTACGGTTTGGACGTCTGGGGCCAAGGG ACCACGGTCACCGTCTCCTCA |
| 188 | P1-047311 VL | GACATCCAGATGACCCAGTCTCCAACCTCACTGTCTGCATCTGTAGGAGACAGAGTCAC CATCACTTGTCGGGCGAGTCAGGGTATTAGCAGCTGGTTAGCCTGGTATCAGCAGAAAC CAGGGAAAGCCCCTAAGTCCCTGATCTATGCTGCATCCAGTTTGCAAAGTGGGGTCCCA TCAAGGTTCAGCGGCAGTGGATCTGGGACAGATTTCACTCTCACCATCAGCAGCCTGCA GCCTGAAGATTTTGCAACTTATTACTGCCAACAGTATAATAGTTACCCGCTCACTTTCG GCGGAGGGACCAAGGTGGAGATCAAA |
| 153 | P1-047294 VH | CAGGTGCAGCTGGTGCAGTCTGGGGCTGAGGTGAAGAAGCCTGGGTCCTCGGTGAAGGT CTCCTGCAAGGCTTCTGGAGGCACCTTCAACAGACATGCTATCAGCTGGGTGCGACAGG CCCCTGGACAAGGGCTTGAGTGGATGGGAGGGATCATCCCTCTCTTTGGTACAGCAAAC TACGCGCAGGAGTTCCAGGGCAGAGTCACGATTGCCGCGGACGAACCCACGAGCACAAC CTACATGGAGCTGCGCAGCCTGAGATCTGAGGACACGGCCGTGTATTACTGTGCGAGTT CGTATTTCTATGGTTCGGGGAGTTCCAACTACTACTACTACGGTTTGGACGTCTGGGGC CAAGGGACCACGGTCACCGTCTCCTCA |
| 180 | P1-047294 VL | GACATCCAGATGACCCAGTCTCCAACCTCACTGTCTGCATCTGTAGGAGACAGAGTCAC CATCACTTGTCGGGCGAGTCAGGGTATTAGCAGCTGGTTAGCCTGGTATCAGCAGAAAC CAGAGAAAGCCCCTAAGTCCCTGATCTATGCTGCATCCAGTTTGCAAAGTGGGGTCCCA TCAAGGTTCAGCGGCGGTGGATCTGGGACAGATTTCACTCTCACCATCAGCAGCCTGCA GCCTGAAGATTTTGCAACTTATTACTGCCAACAGTATAATAGTTACCCGCTCACTTTCG GCGGAGGGACCAAGGTGGAGATCAAA |
| 151 | P1-047290 VH | CAGGTGCAGCTGGTGCAGTCTGGGGCTGAGGTGAAGAAGCCTGGGTCCTCGGTGAAGGT CTCCTGCAAGGCTTCTGGAGGCACCTTCAACAGACATGCTATCAGCTGGGTGCGACAGG CCCCTGGACAAGGGCTTGAGTGGATGGGAGGGATCATCCCTCTCTTTGGTACAGCAAAC TACGCGCAGAAGTTCCAGGGCAGAGTCACGATTGCCGCGGACGAACCCACGAGCACAAC CTACATGGAGCTGCGCAGCCTGAGATCTGAGGACACGGCCGTGTATTACTGTGCGAGTT CGTATTTCTATGGTTCGGGGAGTTCCAACTACTACTACTACGGTTTGGACGTCTGGGGC CAAGGGACCACGGTCACCGTCTCCTCA |
| 176 | P1-047290 VL | GACATCCAGATGACCCAGTCTCCAACCTCACTGTCTGCATCTGTAGGAGACAGAGTCAC CATCACTTGTCGGGCGAGTCAGGGTATTAGCAGCTGGTTAGCCTGGTATCAGCAGAAAC CAGAGAAAGCCCCTAAGTCCCTGATCTATGCTGCATCCAGTTTGCAAAGTGGGGTCCCA TCAAGGTTCAGCGGCAGTGGATCTGGGACAGATTTCACTCTCACCATCAGCAGCCTGCA GCCTGAAGATTTTGCAACTTATTACTGCCAACAGTATAATAGTTACCCGTACACTTTTG GCCAGGGGACCAAGCTGGAGATCAAA |
| 151 | P1-047291 VH | CAGGTGCAGCTGGTGCAGTCTGGGGCTGAGGTGAAGAAGCCTGGGTCCTCGGTGAAGGT CTCCTGCAAGGCTTCTGGAGGCACCTTCAACAGACATGCTATCAGCTGGGTGCGACAGG CCCCTGGACAAGGGCTTGAGTGGATGGGAGGGATCATCCCTCTCTTTGGTACAGCAAAC TACGCGCAGAAGTTCCAGGGCAGAGTCACGATTGCCGCGGACGAACCCACGAGCACAAC CTACATGGAGCTGCGCAGCCTGAGATCTGAGGACACGGCCGTGTATTACTGTGCGAGTT CGTATTTCTATGGTTCGGGGAGTTCCAACTACTACTACTACGGTTTGGACGTCTGGGGC CAAGGGACCACGGTCACCGTCTCCTCA |
| 179 | P1-047291 VL | GACATCCAGATGACCCAGTCTCCAACCTCACTGTCTGCATCTGTAGGAGACAGAGTCAC CATCACTTGTCGGGCGAGTCAGGGTATTAGCAGCTGGTTAGCCTGGTATCAGCAGAAAC CAGAGAAAGCCCCTAAGTCCCTGATCTATGCTGCATCCAGTTTGCAAAGTGGGGTCCCA TCAAGGTTCAGCGGCAGTGGATCTGGGACAGATTTCACTCTCACCATCAGCAGCCTGCA GCCTGATGATTTTGCAACTTATTACTGCCAACAGTATAATAGTTACCCGTACACTTTTG GCCAGGGGACCAAGCTGGAGATCAAA |
| 151 | P1-047296 VH | CAGGTGCAGCTGGTGCAGTCTGGGGCTGAGGTGAAGAAGCCTGGGTCCTCGGTGAAGGT CTCCTGCAAGGCTTCTGGAGGCACCTTCAACAGACATGCTATCAGCTGGGTGCGACAGG CCCCTGGACAAGGGCTTGAGTGGATGGGAGGGATCATCCCTCTCTTTGGTACAGCAAAC TACGCGCAGAAGTTCCAGGGCAGAGTCACGATTGCCGCGGACGAACCCACGAGCACAAC CTACATGGAGCTGCGCAGCCTGAGATCTGAGGACACGGCCGTGTATTACTGTGCGAGTT CGTATTTCTATGGTTCGGGGAGTTCCAACTACTACTACTACGGTTTGGACGTCTGGGGC CAAGGGACCACGGTCACCGTCTCCTCA |
| 182 | P1-047296 VL | GACATCCAGATGACCCAGTCTCCAACCTCACTGTCTGCATCTGTAGGAGACAGAGTCAC CATCACTTGTCGGGCGAGTCAGGGTATTAGCAGCTGGTTAGCCTGGTATCAGCAGAAAC CAGAGAAAGCCCCTAAGTCCCTGATCTATGCTGCATCCAGTTTGCAAAGTGGGGTCCCA TCAAGGTTCAGCGGCAGTGGATCTGGGACAGATTTCACTCTCACCATCAGCAGCCTGCA |

TABLE 4 -continued

Exemplary VH and VL Nucleotide Sequences for Non-Epitope-Steered Anti-TREM-1 Antibodies

| SEQ ID No. | Description | Sequences |
|---|---|---|
| | | GCCTGAAGATTTTGCAACTTATTACTGCCAACAGTATAATAGTTACCCGATCACCTTCG<br>GCCAAGGGACACGACTGGAGATTAAA |
| 151 | P1-047297 VH | CAGGTGCAGCTGGTGCAGTCTGGGGCTGAGGTGAAGAAGCCTGGGTCCTCGGTGAAGGT<br>CTCCTGCAAGGCTTCTGGAGGCACCTTCAACAGACATGCTATCAGCTGGGTGCGACAGG<br>CCCCTGGACAAGGGCTTGAGTGGATGGGAGGGATCATCCCTCTCTTTGGTACAGCAAAC<br>TACGCGCAGAAGTTCCAGGGCAGAGTCACGATTGCCGCGGACGAACCCACGAGCACAAC<br>CTACATGGAGCTGCGCAGCCTGAGATCTGAGGACACGGCCGTGTATTACTGTGCGAGTT<br>CGTATTTCTATGGTTCGGGGAGTTCCAACTACTACTACTACGGTTTGGACGTCTGGGGC<br>CAAGGGACCACGGTCACCGTCTCCTCA |
| 181 | P1-047297 VL | GACATCCAGATGACCCAGTCTCCAACCTCACTGTCTGCATCTGTAGGAGACAGAGTCAC<br>CATCACTTGTCGGGCGAGTCAGGGTATTAGCAGCTGGTTAGCCTGGTATCAGCATAAAC<br>CAGGGAAAGCCCCTAAGTCCCTGATCTATGCTGCATCCAGTTTGCAAAGTGGGGTCCCA<br>TCAAGGTTCAGCGGCAGTGGATCTGGGACAGATTTCACTCTCACCATCAGCAGCCTGCA<br>GCCTGAAGATTTTGCAACTTATTACTGCCAACAGTATAATAGTTACCCGCTCACTTTCG<br>GCGGAGGGACCAAGGTGGAGATCAAA |
| 155 | P1-047300 VH | CAGGTGCAGCTGGTGCAGTCTGGGGCTGAGGTGAAGAAGCCTGGGTCCTCGGTGAAGGT<br>CTCCTGCAAGGCTTCTGGAGGCACCTTCAACAGACATGCTATCAGCTGGGTGCGACAGG<br>CCCCTGGACAAGGGCTTGAGTGGATGGGAGGGATCATCCCTCTCTTTGGTACAGCAAAC<br>TACGCGCAGAAGTTCCAGGGCAGAGTCACGATTGCCGCGGACGAACCCACGAGCACAAC<br>CTACATGGAGCTGCGCAGCCTGAGATCTGAGGACACGGCCGTGTATTACTGTGCAAGTT<br>CGTATTTCTATGGTTCGGGGAGTTCCAACTACTACTACTACGGTTTGGACGTCTGGGGC<br>CAAGGGACCACGGTCACCGTCTCCTCA |
| 185 | P1-047300 VL | GACATCCAGATGACCCAGTCTCCAACCTCACTGTCTGCATCTGTAGGAGACAGAGTCAC<br>CATCACTTGTCGGGCGAGTCAGGGTATTAGCAGCTGGTTAGCCTGGTATCAGCAGAAAC<br>CAGAGAAAGCCCCTAAGTCCCTGATCCATGCTGCATCCAGTTTGCAAAGTGGGGTCCCA<br>TCAAGGTTCAGCGGCAGTGGATCTGGGACAGATTTCACTCTCACCATCAGCAGCCTGCA<br>GCCTGAAGATTTTGCAACTTATTACTGCCAACAGTATAATAGTTACCCGCTCACTTTCG<br>GCGGAGGGACCAAGGTGGAGATCAAA |
| 157 | P1-047302 VH | CAGGTGCAGCTGGTGCAGTCTGGGGCTGAGGTGAAGAAGCCTGGGTCCTCGGTGAAGGT<br>CTCCTGCAAGGCTTCTGGAGGCACCTTCAACAGACATGCTATCAGCTGGGTGCGACAGG<br>CCCCTGGACAAGGGCTTGAGTGGATGGGAGGGATCATCCCTCTCTTTGGTACAGCAAAC<br>TACGCGCAGAAGTTCCAGGGCAGAGTCACGATTGCCGCGGACGAACCCACGAGCACAAC<br>CTACATGGAGCTGCGCAGCCTGAGATCTGAGGACACGGCCGTGTATTACTGTGCGAGTT<br>CGTATTTCTATGGTTCGGGGAGTTCCAACTATTACTACTACGGTTTGGACGTCTGGGGC<br>CAAGGGACCACGGTCACCGTCTCCTCA |
| 184 | P1-047302 VL | GACATCCAGATGACCCAGTCTCCAACCTCACTGTCTGCATCTGTAGGAGACAGAGTCAC<br>CATCACTTGTCGGGCGAGTCAGGGTATTAGCAGCTGGTTAGCCTGGTATCAGCAGAAAC<br>CAGAGAAAGCCCCTAAGTCCCTGATCTATGCTGCATCCAGTTTGCAAAGTGGGGTCCCA<br>TCAAGGTTCAGCGGCAGTGGATCTGGGACAGATTTCACTCTCACCATCAGCAGCCTGCA<br>GCCTGAAGATTTTGCAACTTATTACTGCCAACAGTATAATAGTTACCCTCTCACTTTCG<br>GCGGAGGGACCAAGGTGGAGATCAAA |
| 161 | P1-047308 VH | CAGGTGCAGCTGGTGCAGTCTGGGGCTGAGGTGAAGAGGCCTGGGTCCTCGGTGAAGGT<br>CTCCTGCAAGGCTTCTGGAGGCACCTTCAGTATCTATGTTATCAGCTGGGTGCGACAGG<br>CCCCTGGACAAGGGCTTGAGTGGATGGGAGGGATCATCCCTCTCTTTGGTACAGCAAAC<br>TACGCACAGAAGTTCCAGGGCAGAGTCACGATTACCGCGGACGAATCCACGAATACAGC<br>CTACATGGAGCTGAGTAGCCTGAGATCTGAGGACACGGCCGTGTATTACTGTGCGAGGG<br>GACATGGTCCGGGGAGTTCCCACTACTCCTACTACGGTTTGGACGTCTGGGGCCAAGGG<br>ACCACGGTCACCGTCTCCTCA |
| 176 | P1-047308 VL | GACATCCAGATGACCCAGTCTCCAACCTCACTGTCTGCATCTGTAGGAGACAGAGTCAC<br>CATCACTTGTCGGGCGAGTCAGGGTATTAGCAGCTGGTTAGCCTGGTATCAGCAGAAAC<br>CAGAGAAAGCCCCTAAGTCCCTGATCTATGCTGCATCCAGTTTGCAAAGTGGGGTCCCA<br>TCAAGGTTCAGCGGCAGTGGATCTGGGACAGATTTCACTCTCACCATCAGCAGCCTGCA<br>GCCTGAAGATTTTGCAACTTATTACTGCCAACAGTATAATAGTTACCCGTACACTTTTG<br>GCCAGGGGACCAAGCTGGAGATCAAA |
| 161 | P1-047319 VH | CAGGTGCAGCTGGTGCAGTCTGGGGCTGAGGTGAAGAGGCCTGGGTCCTCGGTGAAGGT<br>CTCCTGCAAGGCTTCTGGAGGCACCTTCAGTATCTATGTTATCAGCTGGGTGCGACAGG<br>CCCCTGGACAAGGGCTTGAGTGGATGGGAGGGATCATCCCTCTCTTTGGTACAGCAAAC<br>TACGCACAGAAGTTCCAGGGCAGAGTCACGATTACCGCGGACGAATCCACGAATACAGC<br>CTACATGGAGCTGAGTAGCCTGAGATCTGAGGACACGGCCGTGTATTACTGTGCGAGGG<br>GACATGGTCCGGGGAGTTCCCACTACTCCTACTACGGTTTGGACGTCTGGGGCCAAGGG<br>ACCACGGTCACCGTCTCCTCA |

TABLE 4 -continued

Exemplary VH and VL Nucleotide Sequences for Non-Epitope-Steered Anti-TREM-1 Antibodies

| SEQ ID No. | Description | Sequences |
|---|---|---|
| 183 | P1-047319 VL | GACATCCAGATGACCCAGTCTCCAACCTCACTGTCTGCATCTGTAGGAGACAGAGTCAC CATCACTTGTCGGGCGAGTCAGGGTATTAGCAGCTGGTTAGCCTGGTATCAGCATAAAC CAGGGAAAGCCCCTAAGTCCCTGATCTATGCTGCATCCAGTTTGCAAAGTGGGGTCCCA TCAAGGTTCAGCGGCAGTGGATCTGGGACAGATTTCACTCTCACCATCAGCAGCCTGCA GCCTGAAGATTTTGCAACTTATTACTGCCAACAGTATAATAGTTACCCGTACACTTTTG GCCAGGGGACCAAGCTGGAGATCAAA |
| 152 | P1-047292 VH | CAGGTGCAGCTGGTGCAGTCTGGGGCTGAGGTGAAGAAGCCTGGGTCCTCGGTGAAGGT CTCCTGCAAGGCTTCTGGAGGCACCTTCAGCAGCTCTGCTATCAGCTGGGTGCGACAGG CCCCTGGACAAGGGCTTGAGTGGATGGGAGGGATCATCCCTATCTTTAGTACAGGAAAC TACGCACAGAAGTTCCAGGGCAGAGTCACGATTACCGCGGACGAATCCACGAACACAGC CTACATGGATCTGAGCAGCCTGAGATCTGAGGACACGGCCGTGTATTACTGTGCGAGAT CCACTAGGGTTCGGGGAGTTTCCCACTACTACTACTACGGTTTGGACGTCTGGGGCCAA GGGACCACGGTCACCGTCTCCTCA |
| 176 | P1-047292 VL | GACATCCAGATGACCCAGTCTCCAACCTCACTGTCTGCATCTGTAGGAGACAGAGTCAC CATCACTTGTCGGGCGAGTCAGGGTATTAGCAGCTGGTTAGCCTGGTATCAGCAGAAAC CAGAGAAAGCCCCTAAGTCCCTGATCTATGCTGCATCCAGTTTGCAAAGTGGGGTCCCA TCAAGGTTCAGCGGCAGTGGATCTGGGACAGATTTCACTCTCACCATCAGCAGCCTGCA GCCTGAAGATTTTGCAACTTATTACTGCCAACAGTATAATAGTTACCCGTACACTTTTG GCCAGGGGACCAAGCTGGAGATCAAA |
| 168 | P1-047322 VH | CAGGTGCAGCTGGTGCAGTCTGGGGCTGAGGTGAAGAAGCCTGGGTCCTCGGTGAAGGT CTCCTGCAAGTCTTCTGGAGGCACCTTCAGCAGCTATGCTTTCACCTGGGTGCGACAGG CCCCTGGACAAGGGCTTGAGTGGATGGGAGGGATCATCCCTATCTTTCGTACAGCAAAC TACGCACAGAAGTTCCAGGGCAGAGTCACGATTACCGCGGACGAATCCACGAGCACAGC CTACATGGAGCTGAGCAGCCTGAGATCTGAGGACACGGCCGTGTATTACTGTGCGAGCA GCCATTTCTCTGGTTCGGGAAGTTCCCACTACTACTACTACGGTATGCACGTCTGGGGC CAAGGGACCACGGTCACCGTCTCCTCA |
| 192 | P1-047322 VL | GACATCCAGATGACCCAGTCTCCAACCTCACTGTCTGCATCTGTAGGAGACAGAGTCAC CATCACTTGTCGGGCGAGTCAGGGTATTAGCAGCTGGTTAGCCTGGTATCAGCAGAAAC CAGAGAAAGCCCCTAAGTCCCTGATCTATGCTGCATCCAGTTTGCAAAGTGGGGTCCCA TCAAGGTTTAGCGGCAGTGGATCTGGGACAGATTTCACTCTCACCATCAGCAGCCTGCA GCCTGAAGATTTTGCAACTTATTACTGCCAACAGTATAATAGTTACCCGTACACTTTTG GCCAGGGGACCAAGCTGGAGATCAAA |
| 163 | P1-047310 VH | CAGGTGCAGCTGGTGCAGTCTGGGGCTGAGGTGAAGAAGCCTGGGTCCTCGGTGAAGGT CTCCTGCAAGGCTTCTGGAGGCACCTTCAGCAGATATGCTATCAGCTGGGTGCGACAGG CCCCTGGACAAGGGCTTGAGTGGATGGGAGGGATCATCCCTATCTTTGGTACATCAAAC TACGCACAGAAGTTCCAGGGCAGAGTCACGATTAAAGCGGACGAATCCACGAGCACAGC CTACATGGAGCTGAGCAGCCTGAGATCTGAGGACACGGCCGTGTATTACTGTGCGAGAG GGGGCAACAGCTGGACCACTAGTTTGTACTACTACGGTATGGACGTCTGGGGCCAAGGG ACCACGGTCACCGTCTCCTCA |
| 187 | P1-047310 VL | GACATCCAGATGACCCAGTCTCCAACCTCACTGTCTGCATCTGTAGGAGACAGAGTCAC CATCACTTGTCGGGCGAGTCAGGGTATTAGCAGCTGGTTAGCCTGGTATCAGCAGAAAC CAGAGAAAGCCCCTAAGTCCCTGATCTATGCTGCATCCAGTTTGCAAAGTGGGGTCCCA TCAAGGTTCAGCGGCAGTGGATCTGGGACGGATTACACTCTCACCATCAGCAGCCTGCA GCCTGAAGATTTTGCAACTTATTACTGCCAACAGTATAATAGTTACCCGCTCACTTTCG GCGGAGGGACCAAGGTGGAGATCAAA |
| 154 | P1-047299 VH | CAGGTGCAGCTGGTGCAGTCTGGGGCTGAGGTGAAGAAGCCTGGGTCCTCGGTGAAGGT CTCCTGCAAGGCTTCTGGAGGCACCTTCAACAGATATGCTTTCAGCTGGGTGCGACAGG CCCCTGGACAAGGGCTTGAGTGGATGGGAGGGATCATCCCTATCTTTGGTACACCCAAC TACGCACAGAAGTTCCAGGGCAGAGTCACGATTACCGCGGACGAATCCACGAGCACGGC CTACATGGAGCTGAGCAGCCTGATATCTGAGGACACGGCCGTGTATTACTGTGCGAGCA GCCATTTCTATGGTTCGGGGAGTTCCCACTTTTACTACTACGGTATGCACGTCTGGGGC CAAGGGACCACGGTCACCGTCTCCTCA |
| 196 | P1-047299 VL | GACATCCAGATGACCCAGTCTCCAACCTCACTGTCTGCATCTGTAGGAGACAGAGTCAC CATCACTTGTCGGGCGAGTCAGGGTATTAGCAGCTGGTTAGCCTGGTATCAGCAGAAAC CAGAGAAAGCCCCTAAGTCCCTGATCTATGCTGCATCCAGTTTGCAAAGTGGGGTCCCA TCAAGGTTCAGCGGCAGTGGATCTGGGACAGATTTCACTCTCACCATCAGCAGCCTGCA GCCTGAAGATTTTGCAACTTATTACTGCCAACAGTATAATAGTTACCCGTGGACGTTCG GCCAAGGGACCAAGGTGGAAATCAAA |
| 156 | P1-047301 VH | CAGGTGCAGCTGGTGCAGTCTGGGGCTGAGGTGAAGAAGCCTGGGTCCTCGGTGAAGGT CTCCTGCAAGGCTTCTGGAGGCACCTTCAACAGATATGCTTTCAGCTGGGTGCGACAGG CCCCTGGACAAGGGCTTGAGTGGATGGGAGGGATCATCCCTATCTTTGGTACACCCAAC TACGCACAGAAGTTCCAGGGCAGAGTCACGATTACCGCGGACGAATCCACGAGCACGGC CTACATGGAGCTGAGCAGCCTGATATCTGAGGACACGGCCGTGTATTACTGTGCGAGCA |

TABLE 4 -continued

Exemplary VH and VL Nucleotide Sequences for Non-Epitope-Steered Anti-TREM-1 Antibodies

| SEQ ID No. | Description | Sequences |
|---|---|---|
| | | GCCATTTCTATGGTTCGGGGAGTTCCAACTACTACTACTACGGTTTGGACGTCTGGGGC CAAGGGACCACGGTCACCGTCTCCTCA |
| 176 | P1-047301 VL | GACATCCAGATGACCCAGTCTCCAACCTCACTGTCTGCATCTGTAGGAGACAGAGTCAC CATCACTTGTCGGGCGAGTCAGGGTATTAGCAGCTGGTTAGCCTGGTATCAGCAGAAAC CAGAGAAAGCCCCTAAGTCCCTGATCTATGCTGCATCCAGTTTGCAAAGTGGGGTCCCA TCAAGGTTCAGCGGCAGTGGATCTGGGACAGATTTCACTCTCACCATCAGCAGCCTGCA GCCTGAAGATTTTGCAACTTATTACTGCCAACAGTATAATAGTTACCCGTACACTTTTG GCCAGGGGACCAAGCTGGAGATCAAA |
| 150 | P1-047289 VH | CAGGTGCAGCTGGTGCAGTCTGGGGCTGAGGTGAAGAAGCCTGGGTCCTCGGTGAAGGT CTCCTGCAAGGCTTCTGGAGGCACCTTCAGCAGCTCTGCTATCAGCTGGGTGCGACAGG CCCCTGGACAAGGGCTTGAGTGGATGGGAGGAATCATCCCTATCTTCGGTACAGCAGAC TCCGCACAGAAGTTCCAGGGCAGAGTCACGATTACCGCGGACGAGTCCACGAGCACAGC CTACATGGAATTGAACAGCCTGAGATCTGAGGACACGGCCGTTTACTACTGTGCGTTCA CACCCCGGTATCGTGGGAGCTCCCACCACTACTTCTACGCTTTGGGCGTCTGGGGCCAA GGGACCACGGTCACCGTCTCCTCA |
| 195 | P1-047289 VL | GACATCCAGATGACCCAGTCTCCAACCTCACTGTCTGCATCTGTAGGAGACAGAGTCAC CATCACTTGTCGGGCGAGTCAGGGTATTAGCAGCTGGTTAGCCTGGTATCAGCAGAAAC CAGAGAAAGCCCCTAAGTCCCTGATCTATGCTGCATCCAGTTTGCAAAGTGGGGTCCCA TCAAGGTTCAGCGGCAGTGGATCTGGGACAGATTTCACTCTCACCATCAGCAGCCTGCA GCCTGAAGATTTTGCAACTTATTACTGTCAACAGTTTAATAGTTACCCTCTCACTTTCG GCGGAGGGACCAAGGTGGAGATCAAA |
| 159 | P1-047306 VH | CAGGTGCAGCTGGTGCAGTCTGGGGCTGAGGTGAAGAAGCCTGGGTCCTCGGTGAAGGT CTCCTGCAAGGCTTCTGGAGGCACCTTCAGCAGCTCTGCTATCAGCTGGGTACGACAGG CCCCTGGACAAGGGCTTGAGTGGATGGGAGGGATCATCCCTATCTTTGGTACAGCGAAC TACGCACAGAAGTTCCAGGGCAGAGTCACGATTACCGCGGACGAATCCACGAGCACAGC CTACATGGAGCTGAGCAGCCTGAGATCTGAGGACACGGCCGTGTATTACTGTGCGAGAG CCTCCCAAAGCAGGAGCTCGAACTACTACTACTACGGTCTGGACGTCTGGGGCCAAGGG ACCACGGTCACCGTCTCCTCA |
| 184 | P1-047306 VL | GACATCCAGATGACCCAGTCTCCAACCTCACTGTCTGCATCTGTAGGAGACAGAGTCAC CATCACTTGTCGGGCGAGTCAGGGTATTAGCAGCTGGTTAGCCTGGTATCAGCAGAAAC CAGAGAAAGCCCCTAAGTCCCTGATCTATGCTGCATCCAGTTTGCAAAGTGGGGTCCCA TCAAGGTTCAGCGGCAGTGGATCTGGGACAGATTTCACTCTCACCATCAGCAGCCTGCA GCCTGAAGATTTTGCAACTTATTACTGCCAACAGTATAATAGTTACCCTCTCACTTTCG GCGGAGGGACCAAGGTGGAGATCAAA |
| 149 | P1-047263 VH | CAGGTGCAGCTGGTGCAGTCTGGGGCTGAGGTGAAGAAGCCTGGGGCCTCAGTGAAGGT CTCCTGCAAGGCTTCTGGATACACCTTCCCCACTTATGATATCAACTGGGTGCGACAGG CCACTGGACAAGGGCTTGAGTGGATGGGATGGGTGAACCCTAACAGTGGTAACACAGGC TATGCACAGAAGTTCCAGGACAGAGTCACCATGACCAGGAACACCTCCATAAGCACAGC CTACATGGAGCTGAGCAGCCTGAGATCTGAGGACACGGCCGTGTATTACTGTGCGAGTG ACGGCCTTAATATGGTTCGGGGAGTTCACAACTACTACGGTATGGACGTCTGGGGCCAA GGGACCACGGTCACCGTCTCCTCA |
| 177 | P1-047263 VL | GACATCCAGATGACCCAGTCTCCAACCTCACTGTCTGCATCTGTAGGAGACAGAGTCAC CATCACTTGTCGGGCGAGTCAGGGTATTAGCAGCTGGTTAGCCTGGTATCAGCAGAAAC CAGAGAAAGCCCCTAAGTCCCTGATCTATGCTGCATCCAGTTTGCAAAGTGGGGTCCCA TCAAGGTTCAGCGGCAGTGGATCTGGGACAGATTTCACTCTCACCATCAGCAGCCTGCA GCCTGAAGATTTTGCAACTTATTACTGCCAACAGTATAATAGTTACCCTCCGACTTTTG GCCAGGGGACCAAGCTGGAGATCAAA |
| 149 | P1-047265 VH | CAGGTGCAGCTGGTGCAGTCTGGGGCTGAGGTGAAGAAGCCTGGGGCCTCAGTGAAGGT CTCCTGCAAGGCTTCTGGATACACCTTCCCCACTTATGATATCAACTGGGTGCGACAGG CCACTGGACAAGGGCTTGAGTGGATGGGATGGGTGAACCCTAACAGTGGTAACACAGGC TATGCACAGAAGTTCCAGGACAGAGTCACCATGACCAGGAACACCTCCATAAGCACAGC CTACATGGAGCTGAGCAGCCTGAGATCTGAGGACACGGCCGTGTATTACTGTGCGAGTG ACGGCCTTAATATGGTTCGGGGAGTTCACAACTACTACGGTATGGACGTCTGGGGCCAA GGGACCACGGTCACCGTCTCCTCA |
| 176 | P1-047265 VL | GACATCCAGATGACCCAGTCTCCAACCTCACTGTCTGCATCTGTAGGAGACAGAGTCAC CATCACTTGTCGGGCGAGTCAGGGTATTAGCAGCTGGTTAGCCTGGTATCAGCAGAAAC CAGAGAAAGCCCCTAAGTCCCTGATCTATGCTGCATCCAGTTTGCAAAGTGGGGTCCCA TCAAGGTTCAGCGGCAGTGGATCTGGGACAGATTTCACTCTCACCATCAGCAGCCTGCA GCCTGAAGATTTTGCAACTTATTACTGCCAACAGTATAATAGTTACCCGTACACTTTTG GCCAGGGGACCAAGCTGGAGATCAAA |
| 160 | P1-047317 VH | CAGGTGCAGCTGGTGCAGTCTGGGGCTGAGGTGAAGAGGCCTGGGTCCTCGGTGAAGGT CTCCTGCAAGGCTTCTGGAGGCACCTTCAGTATCTATGTTATCAGCTGGGTGCGACAGG CCCCTGGACAAGGGCTTGAGTGGATGGGAGGGATCATCCCTCTCTTTGGTACACCAAAC |

TABLE 4 -continued

| SEQ ID No. | Description | Sequences |
|---|---|---|
| Exemplary VH and VL Nucleotide Sequences for Non-Epitope-Steered Anti-TREM-1 Antibodies | | |
| | | TACGCACAGCAGTTCCAGGACAGAGTCACGATTACCGCGGACGAATCCACGAGGACAGC CTACATGGAGCTGAATAGCCTGAAATCTGAGGACACGGCCGTATATTACTGTGCGAGGG GACATGGTCCGGGGAGTTCCCACTACTCCTACTACGGTTTGGACGTCTGGGGCCAAGGG ACCACGGTCACCGGTCTCCTCA |
| 191 | P1-047317 VL | GAAATTGTGTTGACGCAGTCTCCAGGCACCCTGTCTTTGTCTCCAGGGGAAAGAGCCAC CCTCTCCTGCAGGGCCAGTCAGAGTGTTAGCAGCTACTTAGCCTGGTACCAACAGAAAC CTGGCCAGGCTCCCAGGCTCCTCATCTATGGTGCATCCAGCAGGGCCACTGGCATCCCA GACAGGTTCAGTGGCAGTGGGTCTGGGACAGACTTCACTCTCACCATCAGCAGACTGGA GCCTGAAGATTTTGCAGTGTATTACTGTCAGCAGTATGGTAGCTCACCGCTCACTTTCG GCGGAGGGACCAAGGTGGAGATCAAA |

TABLE 5

Exemplary Heavy Chain and Light Chain CDRs for Epitope-Steered Anti-TREM-1 Antibodies

| | Heavy Chain | | | Light Chain | | |
|---|---|---|---|---|---|---|
| Antibody | CDR1 | CDR2 | CDR3 | CDR1 | CDR2 | CDR3 |
| P1-047248 | SSYWS (SEQ ID NO: 26) | YTHYSGISN YNPSLKS (SEQ ID NO: 27) | EGYDILTGY EYYGMDV (SEQ ID NO: 28) | RASQSVSSS YLA (SEQ ID NO: 29) | GASSRAT (SEQ ID NO: 30) | QQYGSSPT (SEQ ID NO: 31) |
| P1-047246 | NYYWT (SEQ ID NO: 32) | YIYDSGTIN YNPSLKS (SEQ ID NO: 33) | GVLWFGEL LPLLDY (SEQ ID NO: 34) | RASQGISSA LA (SEQ ID NO: 35) | DASSLES (SEQ ID NO: 36) | QQFNSYPYT (SEQ ID NO: 37) |
| P1-047247 | NYYWT (SEQ ID NO: 32) | YIYDSGYTN YNPSLKS (SEQ ID NO: 33) | GVLWFGEL LIThILDY (SEQ ID NO: 34) | RASQSVSSS YLA (SEQ ID NO: 29) | GASSRAT (SEQ ID NO: 30) | QQYGSSPLT (SEQ ID NO: 38) |
| P1-047334 | SSAIS (SEQ ID NO: 45) | GIIPIFGTTN GAQKFQG (SEQ ID NO: 46) | MVRGNYFY FYGMDV (SEQ ID NO: 47) | RASQGISSA LA (SEQ ID NO: 35) | AASSLQS (SEQ ID NO: 48) | QQYNSYPL T (SEQ ID NO: 49) |
| P1-017139 | NYGMH (SEQ ID NO: 50) | VIWYDGSN KYYADSVK G (SEQ ID NO: 51) | DGRHYYGS TSYFGMDV (SEQ ID NO: 52) | RASQGISSA LA (SEQ ID NO: 35) | DASSLES (SEQ ID NO: 36) | QQFNSYPYT (SEQ ID NO: 37) |
| P1-047121 | NSEAIN (SEQ ID NO: 136) | GIIPIFDITN YAQKFQG (SEQ ID NO: 137) | TYYDILTYH YHYGMDV (SEQ ID NO: 138) | RASQGISSA LA (SEQ ID NO: 35) | DASSLES (SEQ ID NO: 36) | QQFNSYPIT (SEQ ID NO: 139) |
| P1-047328 | NSEAIN (SEQ ID NO: 136) | GIIPIFDITN YAQKFQGG (SEQ ID NO: 137) | TYYDILTYH YHYGMDV (SEQ ID NO: 138) | RASQGISSA LA (SEQ ID NO: 35) | DASSLES (SEQ ID NO: 36) | QQYNSYKT (SEQ ID NO: 103) |

TABLE 6

Exemplary Heavy Chain and Light CDRs for Non-Epitope-Steered Anti-TREM-1 Antibodies

| | Heavy Chain | | | Light Chain | | |
|---|---|---|---|---|---|---|
| Antibody | CDR1 | CDR2 | CDR3 | CDR1 | CDR2 | CDR3 |
| P1-047305 | SSAVS (SEQ ID NO: 84) | GITPIFGTAD YAQKFQG (SEQ ID NO: 85) | TPRYRGSSH HYYYALGV (SEQ ID NO: 86) | RASQGISSW LA (SEQ ID NO: 87) | AASSLQS (SEQ ID NO: 48) | QQYNSYPY T (SEQ ID NO: 88) |
| P1-047309 | TYAIS (SEQ ID NO; 89) | GINPIFGTA NYAQKFQG (SEQ ID NO: 90) | GGAVGFAY (SEQ ID NO: 91) | RASQGISSW LA (SEQ ID NO: 87) | AASSLQS (SEQ ID NO: 48) | QQANSFPFT (SEQ ID NO: 92) |
| P1-047313 | IYVIS (SEQ ID NO: 93) | GIIPLFGTPN YAQRFQD (SEQ ID NO: 94) | GHGPGSSH YSYYGLDV (SEQ ID NO: 95) | RASQGISSW LA (SEQ ID NO: 87) | AASSLQS (SEQ ID NO: 48) | QQYNSYPW T (SEQ ID NO: 96) |
| P1-047307 | IYVIS (SEQ ID NO: 93) | GIIPLFGTPN YAQQFQD (SEQ ID NO: 97) | GHGPGSSH YSYYGLDV (SEQ ID NO: 95) | RASQGISSW LA (SEQ ID NO: 87) | AASSLQS (SEQ ID NO: 48) | QQYNSYPL T (SEQ ID NO: 49) |
| P1-047312 | IYVIS (SEQ ID NO: 93) | GIIPLFGTPN YAQQFQD (SEQ ID NO: 97) | GHGPGSSII YSYYGLDV (SEQ ID NO: 95) | RASQGISSW LA (SEQ ID NO: 87) | AASSLQS (SEQ ID NO: 48) | QQYNSYPY T (SEQ ID NO: 88) |
| P1-047314 | IYVIS (SEQ ID NO: 93) | GIIPLFGTPN YAQQFQD (SEQ ID NO: 97) | GHGPGSSH YSYYGLDV (SEQ ID NO: 95) | RASQGISSW LA (SEQ ID NO: 87) | AASSLQS (SEQ ID NO: 48) | QQYNSYPY T (SEQ ID NO: 88) |
| P1-047118 | IYVIS (SEQ ID NO: 93) | GIIPLFGTPN YAQQFQD (SEQ ID NO: 97) | GHGPGSSH YSYYGLDV (SEQ ID NO: 95) | RASQGISSW LA (SEQ ID NO: 87) | AASSLQS (SEQ ID NO: 48) | QQYNSYPY T (SEQ ID NO: 88) |
| P1-047310 | IYVIS (SEQ ID NO: 93) | GIIPLFGTPN YAQQFQD (SEQ ID NO: 97) | GHGPGSSH YSYYGLDV (SEQ ID NO: 95) | RASQGISSW LA (SEQ ID NO: 87) | AASSLQS (SEQ ID NO: 48) | QQYNSYPY T (SEQ ID NO: 88) |
| P1-047311 | IYVIS (SEQ ID NO: 93) | GIIPLFGTAN YAQQFQD (SEQ ID NO: 98) | GHGPGSSH NSYYGLDV (SEQ ID NO: 95) | RASQGISSW LA (SEQ ID NO: 87) | AASSLQS (SEQ ID NO 48) | QQYNSYPL T (SEQ ID NO: 49) |
| P1-047294 | REIMS (SEQ ID NO: 99) | GIIPLFGTAN YAQEFQG (SEQ ID NO: 100) | SYFYGSGSS NYYYYGLD V (SEQ ID NO: 101) | RASQGISSW LA (SEQ ID NO: 87) | AASSLQS (SEQ ID NO: 48) | QQYNSYPL T (SEQ ID NO: 49) |
| P1-047290 | RHAIS (SEQ ID NO: 99) | GIIPLFGTAN YAQKFQG (SEQ ID NO: 102) | SYFYGSGSS NYYYYGLD V (SEQ IT) NO: 101) | RASQGISSW LA (SEQ ID NO: 87) | AASSLQS (SEQ ID NO: 48) | QQYNSYPY T (SEQ ID NO: 88) |
| P1-047291 | RHAIS (SEQ ID NO: 99) | GIIPLFGTAN YAQKFQG (SEQ ID NO: 102) | SYFYGSGSS NYYYYGLD V (SEQ ID NO: 101) | RASQGISSW LA (SEQ ID NO: 87) | AASSLQS (SEQ ID NO: 48) | QQYNSYPY T (SEQ ID NO: 88) |
| P1-047296 | RHAIS (SEQ ID NO: 99) | GIIPLFGTAN YAQKFQG (SEQ ID NO: 102) | SYFYGSGSS NYYYGLD V (SEQ ID NO: 101) | RASQGISSW LA (SEQ ID NO: 87) | AASSLQS (SEQ ID NO: 48) | QQYNSYPIT (SEQ ID NO 103) |
| P1-047297 | RHAIS (SEQ ID NO: 99) | GIIPLFGTAN YAQKFQG (SEQ ID NO: 102) | SYFYGSGSS NYYYYGLD V (SEQ ID NO: 101) | RASQGISSW LA. (SEQ ID NO: 87) | AASSLQS (SEQ ID NO: 48) | QQYNSYPL T (SEQ ID NO: 49) |

TABLE 6 -continued

Exemplary Heavy Chain and Light CDRs for Non-Epitope-Steered Anti-TREM-1 Antibodies

| | Heavy Chain | | | Light Chain | | |
|---|---|---|---|---|---|---|
| Antibody | CDR1 | CDR2 | CDR3 | CDR1 | CDR2 | CDR3 |
| P1-047300 | RHAIS (SEQ ID NO: 99) | GIIPLEGTAN YAQ.KFQG (SEQ ID NO: 102) | SYFYGSGSS NYYYYGLD V (SEQ ID NO: 101) | RASQGISSW LA (SEQ ID NO: 87) | AASSLQS (SEQ ID NO: 48) | QQYNSYPL T (SI- HQ ID NO: 49) |
| P1-047302 | RHAIS (SEQ ID NO: 99) | GIIPLFGTAN YAQKFQG (SEQ ID NO: 102) | SYFYGSGSS NYYYYGLD V (SEQ ID NO: 101) | RASQGISSW LA (SEQ ID NO: 87) | AASSLQS (SEQ ID NO: 48) | QQYNSYPL T (SEQ ID NO: 49) |
| P1-047308 | IYVIS (SEQ ID NO: 93) | GHPLEGTAN YAQKFQG (SEQ ID NO: 102) | GHGPGSSH YSYYGLDV (SEQ ID NO: 95) | RASQGISSW LA (SEQ ID NO: 87) | AASSLQS (SEQ ID NO: 48) | QQYNSYPY T (SEQ ID NO: 88) |
| P1-047319 | IYVIS (SEQ ID NO: 93) | GIIPLEGTAN YAQKFQG (SEQ ID NO: 102) | GHGPGSSH YSYYGLDV (SEQ ID NO: 95) | RASQGISSW LA (SEQ ID NO: 87) | AASSLQS (SEQ ID NO: 48) | QQYNSYPY T (SEQ ID NO: 881 |
| P1-047292 | SSAIS (SEQ ID NO: 45) | GIIPIESTGN YAQKFQG (SEQ ID NO: 104) | STRVRGVS HYYYYGLD V (SEQ ID NO: 105) | RASQGISSW LA (SEQ ID NO: 87) | AASSLQS (SEQ ID NO: 48) | QQYNSYPY T (SEQ ID NO: 88) |
| P1-047322 | SYAFT (SEQ ID NO: 106) | GHPIFRTAN YAQKFQG (SEQ ID NO: 107) | SHFSGSGSS HYYYYGM HV (SEQ ID NO: 108) | RASQGISSW LA (SEQ ID Na 871 | AASSLQS (SEQ ID NO: 48) | QQYNSYPY T (SEQ ID NO: 88) |
| P1-047310 | RYAIS (SEQ ID NO: 109) | GIIPIFGTSN YAQKFQG (SEQ ID NO: 110) | GGNSWTTS LYYYGMDV (SEQ ID NO: 111) | RASQGISSW LA (SEQ ID NO: 87) | AASSLQS (SEQ ID NO: 48) | QQYNSYPL T (SEQ ID NO: 49) |
| P1-047299 | RYAFS (SEQ ID NO: 112) | GHPIFGTPN YAQKFQG (SEQ ID NO: 113) | SHFYGSGSS HFYYYGMT1 V (SEQ ID NO: 114) | RASQGISSW LA (SEQ ID NO: 87) | AASSLQS (SEQ ID NO: 48) | QQYNSYPW T (SEQ ID NO: 96) |
| P1-047301 | RYAFS (SEQ ID NO: 112) | GIIPLFGTPN YAQKFQG (SEQ ID NO: 113) | SHFYGSGSS NYYYYGLD -V (SEQ ID NO: 115) | RASQGISSW LA (SEQ ID NO: 87) | AASSLQS (SEQ ID NO: 48) | QQYNSYPY T (SEQ ID NO: 88) |
| P1-047289 | SSAIS (SEQ ID 45) | GIIPIEGTAD SAQKTQG (SEQ ID NO: 116) | TPRYRGSSI-1 HYFYALGV (SEQ ID NO: 117) | RASQGISSW LA (SEQ ID NO: 87) | AASSLQS (SEQ ID NO: 48) | QQFNSYTLT (SEQ ID NO: 118) |
| P1-047306 | SSAIS (SEQ ID NO: 45) | GIIPITGTAN YAQKFQG (SEQ ID NO: 119) | ASQSRSSNY YYYGLDV (SEQ ID NO: 120) | RASQGISSW LA (SEQ ID NO: 87) | AASSLQS (SEQ ID NO: 48) | QQYNSYPL T (SEQ ID NO: 49) |
| P1-047763 | TYD IN (SEQ ID NO: 140) | WVNPINSGN TGYAQKFQ D (SEQ ID NO: 141) | DGLINMVRG VHNYYGM DV (SEQ ID NO: 142) | RASQGISSW LA (SEQ ID NO: 87) | AASSLQS (SEQ ID NO: 48) | QQYNSYPPT (SEQ ID NO: 143) |
| P1-047265 | TYDIN (SEQ ID NO: 140) | WVNPNSGN TGYAQKFQ D (SEQ ID NO: 141) | DGLNMVPG VHNYYGM DV (SEQ ID NO: 142) | RASQGISSW LA (SEQ ID NO: 87) | AASSLQS (SEQ ID NO: 48) | QQYNSYPY T (SEQ ID NO: 88) |
| P1-047317 | IYVIS (SEQ ID NO: 93) | GIIPLFGTPN YAQQFQD (SEQ ID NO: 97) | GHGPGSSH YSYYGLDV (SEQ ID NO: 95) | RASQSVSSY LA (SEQ ID NO: 42) | GASSRAT (SEQ ID NO: 30) | QQYGSSPLT (SEQ ID NO: 38) |

What is claimed:

1. An isolated antibody which specifically binds to a triggering receptor expressed on myeloid cells-1 (TREM-1) and comprises a heavy chain variable region (VH) and a light chain variable region (VL), further comprising a heavy chain CDR1, CDR2, and CDR3 in the VH and a light chain CDR1, CDR2, and CDR3 in the VL, wherein (a) the heavy chain CDR1, CDR2, and CDR3 comprises the amino acid sequence set forth as SEQ ID NOs: 26, 27, and 28, respectively, and the light chain CDR1, CDR2, and CDR3 comprises the amino acid sequence set forth as SEQ ID NOs: 29, 30, and 31, respectively;

(b) the heavy chain CDR1, CDR2, and CDR3 comprises the amino acid sequence set forth as SEQ ID NOs: 32, 33, and 34, respectively, and the light chain CDR1, CDR2, and CDR3 comprises the amino acid sequence set forth as SEQ ID NOs: 35, 36, and 37, respectively;

(c) the heavy chain CDR1, CDR2, and CDR3 comprises the amino acid sequence set forth as SEQ ID NOs: 32, 33, and 34, respectively, and the light chain CDR1, CDR2, and CDR3 comprises the amino acid sequence set forth as SEQ ID NOs: 29, 30, and 38, respectively;

(d) the heavy chain CDR1, CDR2, and CDR3 comprises the amino acid sequence set forth as SEQ ID NOs: 45, 46, and 47, respectively, and the light chain CDR1, CDR2, and CDR3 comprises the amino acid sequence set forth as SEQ ID NOs: 35, 48, and 49, respectively;

(e) the heavy chain CDR1, CDR2, and CDR3 comprises the amino acid sequence set forth as SEQ ID NOs: 50, 51, and 52, respectively, and the light chain CDR1, CDR2, and CDR3 comprises the amino acid sequence set forth as SEQ ID NOs: 35, 36, and 37, respectively;

(f) the heavy chain CDR1, CDR2, and CDR3 comprises the amino acid sequence set forth as SEQ ID NOs: 136, 137, and 138, respectively, and the light chain CDR1, CDR2, and CDR3 comprises the amino acid sequence set forth as SEQ ID NOs: 35, 36, and 139, respectively; or (g) the heavy chain CDR1, CDR2, and CDR3 comprises the amino acid sequence set forth as SEQ ID NOs: 136, 137, and 138, respectively, and the light chain CDR1, CDR2, and CDR3 comprises the amino acid sequence set forth as SEQ ID NOs: 35, 36, and 103, respectively.

2. The antibody of claim 1, wherein (a) the VH comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 13, 15, 23, 25, or 130, and/or (b) the VL comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 14, 16, 17, 24, 131, or 132.

3. The antibody of claim 1, wherein:

(a) the VH comprises SEQ ID NO: 13 and the VL comprises SEQ ID NO: 14;

(b) the VH comprises SEQ ID NO: 15 and the VL comprises SEQ ID NO: 16;

(c) the VH comprises SEQ ID NO: 15 and the VL comprises SEQ ID NO: 17;

(d) the VH comprises SEQ ID NO: 23 and the VL comprises SEQ ID NO: 24;

(e) the VH comprises SEQ ID NO: 25 and the VL comprises SEQ ID NO: 16;

(f) the VH comprises SEQ ID NO: 130 and the VL comprises SEQ ID NO: 131; or (g) the VH comprises SEQ ID NO: 130 and the VL comprises SEQ ID NO: 132.

4. The antibody of claim 1, further comprising a heavy chain (HC) constant region and a light chain (LC) constant region, wherein (a) the HC constant region comprises an amino acid sequence that is at least about 70%, at least about 80%, at least about 85%, at least about 90%, at least about 95%, at least about 96%, at least about 97%, at least about 98%, at least about 99%, or about 100% identical to SEQ ID NO: 123, SEQ ID NO: 122, SEQ ID NO: 124, or SEQ ID NO: 125, and/or (b) the LC constant region comprises an amino acid sequence that is at least about 70%, at least about 80%, at least about 85%, at least about 90%, at least about 95%, at least about 96%, at least about 97%, at least about 98%, at least about 99%, or about 100% identical to SEQ ID NO: 126.

5. A bispecific molecule comprising the antibody of claim 1, linked to a molecule having a second binding specificity.

6. A nucleic acid encoding the antibody of claim 1.

7. A vector comprising the nucleic acid of claim 6.

8. A cell comprising the vector of claim 7.

9. An immunoconjugate comprising the antibody of claim 1 linked to an agent.

10. A composition comprising the antibody of claim 1 and a carrier.

11. A kit comprising the antibody of claim 1 and an instruction for use.

12. A method of inhibiting TREM-1 activity in a subject in need thereof, comprising administering the antibody of claim 1 to the subject.

13. The method of claim 12, further comprising administering one or more additional therapeutics.

14. The method of claim 13, wherein the one or more additional therapeutics is an anti-IP-10 antibody or an anti-TNF-α antibody.

15. A method of treating an inflammatory disease or an autoimmune disease in a subject in need thereof, comprising administering the antibody of claim 1 to the subject, wherein the inflammatory disease or the autoimmune disease is selected from the group consisting of an inflammatory bowel disease (IBD), Crohn's disease (CD), ulcerative colitis (UC), irritable bowel syndrome, rheumatoid arthritis (RA), psoriasis, psoriatic arthritis, systemic lupus erythematosus (SLE), lupus nephritis, vasculitis, sepsis, systemic inflammatory response syndrome (SIRS), type I diabetes, Grave's disease, multiple sclerosis (MS), autoimmune myocarditis, Kawasaki disease, coronary artery disease, chronic obstructive pulmonary disease, interstitial lung disease, autoimmune thyroiditis, scleroderma, systemic sclerosis, osteoarthritis, atopic dermatitis, vitiligo, graft versus host disease, Sjogren's syndrome, autoimmune nephritis, Goodpasture syndrome, chronic inflammatory demyelinating polyneuropathy, allergy, asthma, other autoimmune diseases that are a result of either acute or chronic inflammation, and any combinations thereof.

* * * * *

SEQUENCE LISTING

<160> NUMBER OF SEQ ID NOS: 343

<210> SEQ ID NO 1
<211> LENGTH: 234
<212> TYPE: PRT
<213> ORGANISM: Homo Sapien

<400> SEQUENCE: 1

Met Arg Lys Thr Arg Leu Trp Gly Leu Leu Trp Met Leu Phe Val Ser
1 5 10 15

Glu Leu Arg Ala Ala Thr Lys Leu Thr Glu Glu Lys Tyr Glu Leu Lys
20 25 30

Glu Gly Gln Thr Leu Asp Val Lys Cys Asp Tyr Thr Leu Glu Lys Phe
35 40 45

Ala Ser Ser Gln Lys Ala Trp Gln Ile Ile Arg Asp Gly Glu Met Pro
50 55 60

Lys Thr Leu Ala Cys Thr Glu Arg Pro Ser Lys Asn Ser His Pro Val
65 70 75 80

Gln Val Gly Arg Ile Ile Leu Glu Asp Tyr His Asp His Gly Leu Leu
85 90 95

Arg Val Arg Met Val Asn Leu Gln Val Glu Asp Ser Gly Leu Tyr Gln
100 105 110

Cys Val Ile Tyr Gln Pro Pro Lys Glu Pro His Met Leu Phe Asp Arg
115 120 125

Ile Arg Leu Val Val Thr Lys Gly Phe Ser Gly Thr Pro Gly Ser Asn
130 135 140

Glu Asn Ser Thr Gln Asn Val Tyr Lys Ile Pro Pro Thr Thr Thr Lys
145 150 155 160

Ala Leu Cys Pro Leu Tyr Thr Ser Pro Arg Thr Val Thr Gln Ala Pro
165 170 175

Pro Lys Ser Thr Ala Asp Val Ser Thr Pro Asp Ser Glu Ile Asn Leu
180 185 190

Thr Asn Val Thr Asp Ile Ile Arg Val Pro Val Phe Asn Ile Val Ile
195 200 205

Leu Leu Ala Gly Gly Phe Leu Ser Lys Ser Leu Val Phe Ser Val Leu
210 215 220

Phe Ala Val Thr Leu Arg Ser Phe Val Pro
225 230

<210> SEQ ID NO 2
<211> LENGTH: 225
<212> TYPE: PRT
<213> ORGANISM: Homo Sapien

<400> SEQUENCE: 2

Met Arg Lys Thr Arg Leu Trp Gly Leu Leu Trp Met Leu Phe Val Ser
1 5 10 15

Glu Leu Arg Ala Ala Thr Lys Leu Thr Glu Glu Lys Tyr Glu Leu Lys
20 25 30

Glu Gly Gln Thr Leu Asp Val Lys Cys Asp Tyr Thr Leu Glu Lys Phe
35 40 45

Ala Ser Ser Gln Lys Ala Trp Gln Ile Ile Arg Asp Gly Glu Met Pro
50 55 60

Lys Thr Leu Ala Cys Thr Glu Arg Pro Ser Lys Asn Ser His Pro Val
65 70 75 80

Gln Val Gly Arg Ile Ile Leu Glu Asp Tyr His Asp His Gly Leu Leu

```
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
    130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Tyr Ser Phe Gln Val Pro Gly Pro
        195                 200                 205

Leu Val Trp Thr Leu Ser Pro Leu Phe Pro Ser Leu Cys Ala Glu Arg
    210                 215                 220

Met
225


<210> SEQ ID NO 3
<211> LENGTH: 150
<212> TYPE: PRT
<213> ORGANISM: Homo Sapien

<400> SEQUENCE: 3

Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Arg Cys Ser Thr Leu Ser Phe
    130                 135                 140

Ser Trp Leu Val Asp Ser
145                 150


<210> SEQ ID NO 4
<211> LENGTH: 3333
<212> TYPE: DNA
<213> ORGANISM: Homo Sapien

<400> SEQUENCE: 4

gtgcaacttt ccgaagcctc taggtcattg tggtgccttg tagctgtccc gggagccctc      60

agcagcagtt ggagctggtg cacaggaagg atgaggaaga ccaggctctg gggctgctg     120
```

-continued

```
tggatgctct ttgtctcaga actccgagct gcaactaaat taactgagga aaagtatgaa    180
ctgaaagagg ggcagaccct ggatgtgaaa tgtgactaca cgctagagaa gtttgccagc    240
agccagaaag cttggcagat aataagggac ggagagatgc ccaagaccct ggcatgcaca    300
gagaggcctt caaagaattc ccatccagtc caagtgggga ggatcatact agaagactac    360
catgatcatg gtttactgcg cgtccgaatg gtcaaccttc aagtggaaga ttctggactg    420
tatcagtgtg tgatctacca gcctcccaag gagcctcaca tgctgttcga tcgcatccgc    480
ttggtggtga ccaagggttt ttcagggacc cctggctcca atgagaattc tacccagaat    540
gtgtataaga ttcctcctac caccactaag gccttgtgcc cactctatac cagccccaga    600
actgtgaccc aagctccacc caagtcaact gccgatgtct ccactcctga ctctgaaatc    660
aaccttacaa atgtgacaga tatcatcagg gttccggtgt tcaacattgt cattctcctg    720
gctggtggat tcctgagtaa gagcctggtc ttctctgtcc tgtttgctgt cacgctgagg    780
tcatttgtac cctaggccca cgaacccacg agaatgtcct ctgacttcca gccacatcca    840
tctggcagtt gtgccaaggg aggagggagg aggtaaaagg cagggagtta ataacatgaa    900
ttaaatctgt aatcaccggc tatttctaaa gtcagcgtct caccttcctg cccactgccc    960
tcgttcctct aataatcttg ggtgggcatt tgtgcctcag aaaagaagtt acagccccaa   1020
acatgcttgg tccttcattc caccagccac ttggggttgg catgaaatac agacagctca   1080
atgcttttca ccgtaattct cttgtggggg ctgtgacatg cagaaggcac acctgatact   1140
tctcctgctc agttttgccc tggaccatac aattttggcc tgacctggac agagctccca   1200
ctacagaagc atcctgctcg ccccatgctg ggacttcctc tttctagcat cagacacttg   1260
ggtttcatgc ttatgtgtgg ttctttccaa cactcccaga aaagggtgtt gaagattgtg   1320
gaacctggag aaataagaca tcgtggtgag aaagtgcatc cttctcagag aaaagagtta   1380
aactgagtat cttcttctgg ggaaatactg gcaggccgag atgggatcca taggagagca   1440
acaacagacc atgtcagaca tcctgtgtgc atttatcgct ggatcctgaa aatagccccg   1500
tgaaggcaga aatgtatgtg actagaacga ggccacatga ataagccact gcccactggc   1560
aggagtgaaa actgaagcgc tccttacctg aaggacccca aaaccatata gaatagaata   1620
accaggagtt ccgcctgtgt ctaaatgcct cttttcctgt atcacacaag ggtcagggat   1680
ggtggagtaa aagctctccc cctgggaggc ttctggaggc tgtccccatg tgcttgccta   1740
gttccccact ctgccctcct cctcttctct cagtctgctc ctggaacacc tgcctcagtt   1800
tccatgctct ctccagtgcc ctccccggtg aagcaggtag gtgttcaggc caccacagag   1860
acaatctctg tgggagattg tcttgcaatc tcccacagat ttcaatcagg attttgttat   1920
ttcctacttt gagctttaaa gggaaatggg cctcatgggt ggggaaagga tggtgggtcc   1980
ttccagccca atttagtgat gcccagggca gatattatcc tcagttccca agagcaatca   2040
tacttttcca cacataccgt gtgtctcatg ttaggtaaat gtatttttac aatgagcacc   2100
acttctgtgg aaaaagttcc ctgcacgggg aggtccagct tccagactgc tccatcgcat   2160
aaggacttcc ccattcccct aaatgctgct ctgtcagaac ctgcccaggt aatggtaatg   2220
accctagaga gatgatttct gaaccgcaat tttgagccca ttagaaggtg tgtggtgggc   2280
atttatttca tcctgatgct ctggtgagaa tctttgcaga cgcactagat ccagaagctg   2340
ttaatcttgg tgcatttatt ttcctaccta aaagaaccaa gcagctcaga ggcagtgact   2400
gtacaggatg cagtgtttat aataatgctg agcttgctgg tctggaaccc cacactttag   2460
caatcccagc attgttcctg tttatgaagt tgacaaagtg accagggcaa gggggtatta   2520
```

```
tcattaaata cactctagga gaggcagaac acatgagggc aatgtttttc agaggtcttt   2580

aggccaccgc atcagattct cctggagcat aaagcaaatg ctttatgagt ccagggcccc   2640

tgcagaccta ctgtatacta gtatacagct ccctcttagt ggatctcaag cttgtttcca   2700

aaaagtcatt acactcctta ccaaagccca tgacacattc atacagattc atccagacat   2760

aacccactgc atggtccagt gcatgcttgt gtgcttaact tattatagat caagtgttat   2820

ttaagtccaa catattaaac gtgactgaaa tattatatgc actaaatcgg aagacaaatg   2880

gccgtgctgg atactctccc atttgcactt acaggccacg ccatgctcca tcctccccat   2940

cctgcctggg aacctgacca atgtggctaa accagcaggc tccctggctg ccagcttctg   3000

gctggttgag ccaatgggaa gcatgagagg agagccgagg gtggggagac agtcagatca   3060

gggtttctgt cctcagggct ccctccctgg caggtggtgg caggagtggc tgcattcccc   3120

tctgaaggct ccttcaagcc tctcagcaaa cagctcccat ctccaagtcc agccacctgt   3180

tccatcctct cctctgtagg cccagcagtg ggaatgaccc accactattg ccagcctcag   3240

catactgaag caccccttac tggattccct aaattctatg cacatgttta ttaaatgctc   3300

ctcaattacc cagttaaaaa aaaaaaaaaa aaa                                3333
```

<210> SEQ ID NO 5
<211> LENGTH: 2128
<212> TYPE: DNA
<213> ORGANISM: Homo Sapien

<400> SEQUENCE: 5

```
gtgcaacttt ccgaagcctc taggtcattg tggtgccttg tagctgtccc gggagccctc     60

agcagcagtt ggagctggtg cacaggaagg atgaggaaga ccaggctctg ggggctgctg    120

tggatgctct ttgtctcaga actccgagct gcaactaaat taactgagga aaagtatgaa    180

ctgaaagagg ggcagaccct ggatgtgaaa tgtgactaca cgctagagaa gtttgccagc    240

agccagaaag cttggcagat aataagggac ggagagatgc ccaagaccct ggcatgcaca    300

gagaggcctt caaagaattc ccatccagtc caagtgggga ggatcatact agaagactac    360

catgatcatg gtttactgcg cgtccgaatg gtcaaccttc aagtggaaga ttctggactg    420

tatcagtgtg tgatctacca gcctcccaag gagcctcaca tgctgttcga tcgcatccgc    480

ttggtggtga ccaagggttt ttcagggacc cctggctcca atgagaattc tacccagaat    540

gtgtataaga ttcctcctac caccactaag gccttgtgcc cactctatac cagccccaga    600

actgtgaccc aagctccacc caagtcaact gccgatgtct ccactcctga ctctgaaatc    660

aaccttacaa atgtgacaga tatcatcagg tatagtttcc aggtccctgg gcccctggtt    720

tggacactga gccctttgtt tcccagtctg tgtgctgaga ggatgtgaaa gtgagggaaa    780

ggggagggtg gggcaggaga agacttgagt cacattagtc tgggtagaaa tgtccagggg    840

aagaaggaag tggtgatgga gaatagggga ggctctcagc caggctgtcc ttctccccag    900

ttcaccttct ttgtttcctt gcaacctgag tattaaagag agggaaatgg catcttcccc    960

aagttccagt ggagctcatc caaccccagg ggcctgatgg gcagtgggaa agcactctga   1020

gtgaggggcc ctggatctag tgttggcctg actaactgaa tgtgactttg ggtgagtcag   1080

gaaccctctc tggctttagc ttctttgaca attcagtagg catggtagaa acccaaagct   1140

ggaagacatt gtccacctaa taactctcag caggagctgg agctggggct aaatgcagta   1200

ttggtttttg ccttattgtt ttttaaataa cattgttgca tgtgcccaat tatagataaa   1260
```

tagaatcaga atttttgcag atgaggtccc tctcagtatt tttaataaga tgtttaggag 1320
atttctaatg tgtaggcaaa cttaagaacc actaacttag caatttcaca cctctttaca 1380
gttattaaat gttgatttat attagaatgt gtttatcatt aaatactgaa ttatcaggat 1440
ggaaatactt ttccacatca ccactagtct aacatgtctt ttttctcata ttctcttcta 1500
gtctttattc atgtttatac atattttaat atggcagtaa gtctaattat acatgttttt 1560
attcttttcc ttgctgaaat tattctttga tgctgctacc taaatttcat aaatataatt 1620
tcaatgagtg catattttc tatcaattgg gaaagccata acttacataa ccattggcct 1680
gttcttagac attgatatag tgttgataac tctgagataa acatattctt gcagatatat 1740
ttttcttctt ttaaataatt aactcgaaat ttccatgaga taatttaaac actgatatca 1800
ttttgtatac aaatagcatc taccaatggt cttccaaaag attggaaaca atttgcagtg 1860
tgatccatta agcataaata aagcagtgtc atggcaggct tacagacacg gatttagtct 1920
tttaaatcat taaatagtgt gagttaaatc acattcctgc taaaacaaat gtgaactggt 1980
gcctgctcta atttctctat gagtgtagac tccacctcca tatgggtagt ggcagtgcct 2040
ttttccccat tatgttgttt ggggaacaaa gtgctcatta aacttctgtg gaataaatca 2100
aacgaatgat caaaaaaaaa aaaaaaaa 2128

<210> SEQ ID NO 6
<211> LENGTH: 3140
<212> TYPE: DNA
<213> ORGANISM: Homo Sapien

<400> SEQUENCE: 6
gtgcaacttt ccgaagcctc taggtcattg tggtgccttg tagctgtccc gggagccctc 60
agcagcagtt ggagctggtg cacaggaagg atgaggaaga ccaggctctg ggggctgctg 120
tggatgctct ttgtctcaga actccgagct gcaactaaat taactgagga aaagtatgaa 180
ctgaaagagg ggcagaccct ggatgtgaaa tgtgactaca cgctagagaa gtttgccagc 240
agccagaaag cttggcagat aataagggac ggagagatgc ccaagaccct ggcatgcaca 300
gagaggcctt caaagaattc ccatccagtc caagtgggga ggatcatact agaagactac 360
catgatcatg gtttactgcg cgtccgaatg gtcaaccttc aagtggaaga ttctggactg 420
tatcagtgtg tgatctacca gcctcccaag gagcctcaca tgctgttcga tcgcatccgc 480
ttggtggtga ccaaggggtt ccggtgttca acattgtcat tctcctggct ggtggattcc 540
tgagtaagag cctggtcttc tctgtcctgt ttgctgtcac gctgaggtca tttgtaccct 600
aggcccacga acccacgaga atgtcctctg acttccagcc acatccatct ggcagttgtg 660
ccaagggagg agggaggagg taaaaggcag ggagttaata acatgaatta aatctgtaat 720
caccggctat ttctaaagtc agcgtctcac cttcctgccc actgccctcg ttcctctaat 780
aatcttgggt gggcatttgt gcctcagaaa agaagttaca gccccaaaca tgcttggtcc 840
ttcattccac cagccacttg ggggttggcat gaaatacaga cagctcaatg cttttcaccg 900
taattctctt gtgggggctg tgacatgcag aaggcacacc tgatacttct cctgctcagt 960
tttgccctgg accatacaat tttggcctga cctggacaga gctcccacta cagaagcatc 1020
ctgctcgccc catgctggga cttcctcttt ctagcatcag acacttgggt ttcatgctta 1080
tgtgtggttc tttccaacac tcccagaaaa gggtgttgaa gattgtggaa cctggagaaa 1140
taagacatcg tggtgagaaa gtgcatcctt ctcagagaaa agagttaaac tgagtatctt 1200
cttctgggga aatactggca ggccgagatg ggatccatag gagagcaaca acagaccatg 1260

```
tcagacatcc tgtgtgcatt tatcgctgga tcctgaaaat agccccgtga aggcagaaat   1320

gtatgtgact agaacgaggc cacatgaata agccactgcc cactggcagg agtgaaaact   1380

gaagcgctcc ttacctgaag gaccccaaaa ccatatagaa tagaataacc aggagttccg   1440

cctgtgtcta aatgcctctt ttcctgtatc acacaagggt cagggatggt ggagtaaaag   1500

ctctcccct gggaggcttc tggaggctgt ccccatgtgc ttgcctagtt ccccactctg   1560

ccctcctcct cttctctcag tctgctcctg gaacacctgc ctcagtttcc atgctctctc   1620

cagtgccctc cccggtgaag caggtaggtg ttcaggccac cacagagaca atctctgtgg   1680

gagattgtct tgcaatctcc cacagatttc aatcaggatt ttgttatttc ctactttgag   1740

ctttaaaggg aaatgggcct catgggtggg gaaaggatgg tgggtccttc cagcccaatt   1800

tagtgatgcc cagggcagat attatcctca gttcccaaga gcaatcatac ttttccacac   1860

ataccgtgtg tctcatgtta ggtaaatgta tttttacaat gagcaccact tctgtggaaa   1920

aagttccctg cacggggagg tccagcttcc agactgctcc atcgcataag gacttcccca   1980

ttcccctaaa tgctgctctg tcagaacctg cccaggtaat ggtaatgacc ctagagagat   2040

gatttctgaa ccgcaatttt gagcccatta gaaggtgtgt ggtgggcatt tatttcatcc   2100

tgatgctctg gtgagaatct ttgcagacgc actagatcca gaagctgtta atcttggtgc   2160

atttattttc ctacctaaaa gaaccaagca gctcagaggc agtgactgta caggatgcag   2220

tgtttataat aatgctgagc ttgctggtct ggaaccccac actttagcaa tcccagcatt   2280

gttcctgttt atgaagttga caaagtgacc agggcaaggg ggtattatca ttaaatacac   2340

tctaggagag gcagaacaca tgagggcaat gtttttcaga ggtctttagg ccaccgcatc   2400

agattctcct ggagcataaa gcaaatgctt tatgagtcca gggcccctgc agacctactg   2460

tatactagta tacagctccc tcttagtgga tctcaagctt gtttccaaaa agtcattaca   2520

ctccttacca aagcccatga cacattcata cagattcatc cagacataac ccactgcatg   2580

gtccagtgca tgcttgtgtg cttaacttat tatagatcaa gtgttattta agtccaacat   2640

attaaacgtg actgaaatat tatatgcact aaatcggaag acaaatggcc gtgctggata   2700

ctctcccatt tgcacttaca ggccacgcca tgctccatcc tccccatcct gcctgggaac   2760

ctgaccaatg tggctaaacc agcaggctcc ctggctgcca gcttctggct ggttgagcca   2820

atgggaagca tgagaggaga gccgagggtg gggagacagt cagatcaggg tttctgtcct   2880

cagggctccc tccctggcag gtggtggcag gagtggctgc attcccctct gaaggctcct   2940

tcaagcctct cagcaaacag ctcccatctc caagtccagc cacctgttcc atcctctcct   3000

ctgtaggccc agcagtggga atgacccacc actattgcca gcctcagcat actgaagcac   3060

cccttactgg attccctaaa ttctatgcac atgtttatta aatgctcctc aattacccag   3120

ttaaaaaaaa aaaaaaaaaa                                               3140
```

<210> SEQ ID NO 7
<211> LENGTH: 233
<212> TYPE: PRT
<213> ORGANISM: Macaca fascicularis

<400> SEQUENCE: 7

```
Met Arg Lys Thr Arg Leu Trp Gly Leu Leu Trp Met Leu Phe Val Ser
1               5                   10                  15

Glu Leu Arg Ala Thr Thr Glu Leu Thr Glu Glu Lys Tyr Glu Tyr Lys
            20                  25                  30
```

```
Glu Gly Gln Thr Leu Glu Val Lys Cys Asp Tyr Ala Leu Glu Lys Tyr
        35                  40                  45

Ala Asn Ser Arg Lys Ala Trp Gln Lys Met Glu Gly Lys Met Pro Lys
    50                  55                  60

Ile Leu Ala Lys Thr Glu Arg Pro Ser Glu Asn Ser His Pro Val Gln
65                  70                  75                  80

Val Gly Arg Ile Thr Leu Glu Asp Tyr Pro Asp His Gly Leu Leu Gln
                85                  90                  95

Val Gln Met Thr Asn Leu Gln Val Glu Asp Ser Gly Leu Tyr Gln Cys
            100                 105                 110

Val Ile Tyr Gln His Pro Lys Glu Ser His Val Leu Phe Asn Pro Ile
        115                 120                 125

Cys Leu Val Val Thr Lys Gly Ser Ser Gly Thr Pro Gly Ser Ser Glu
    130                 135                 140

Asn Ser Thr Gln Asn Val Tyr Arg Thr Pro Ser Thr Thr Ala Lys Ala
145                 150                 155                 160

Leu Gly Pro Arg Tyr Thr Ser Pro Arg Thr Val Thr Gln Ala Pro Pro
                165                 170                 175

Glu Ser Thr Val Val Val Ser Thr Pro Gly Ser Glu Ile Asn Leu Thr
            180                 185                 190

Asn Val Thr Asp Ile Ile Arg Val Pro Val Phe Asn Ile Val Ile Ile
        195                 200                 205

Val Ala Gly Gly Phe Leu Ser Lys Ser Leu Val Phe Ser Val Leu Phe
    210                 215                 220

Ala Val Thr Leu Arg Ser Phe Gly Pro
225                 230


<210> SEQ ID NO 8
<211> LENGTH: 196
<212> TYPE: PRT
<213> ORGANISM: Homo Sapien

<400> SEQUENCE: 8

Met Ser Arg Arg Ser Met Leu Leu Ala Trp Ala Leu Pro Ser Leu Leu
1               5                   10                  15

Arg Leu Gly Ala Ala Gln Glu Thr Glu Asp Pro Ala Cys Cys Ser Pro
            20                  25                  30

Ile Val Pro Arg Asn Glu Trp Lys Ala Leu Ala Ser Glu Cys Ala Gln
        35                  40                  45

His Leu Ser Leu Pro Leu Arg Tyr Val Val Val Ser His Thr Ala Gly
    50                  55                  60

Ser Ser Cys Asn Thr Pro Ala Ser Cys Gln Gln Gln Ala Arg Asn Val
65                  70                  75                  80

Gln His Tyr His Met Lys Thr Leu Gly Trp Cys Asp Val Gly Tyr Asn
                85                  90                  95

Phe Leu Ile Gly Glu Asp Gly Leu Val Tyr Glu Gly Arg Gly Trp Asn
            100                 105                 110

Phe Thr Gly Ala His Ser Gly His Leu Trp Asn Pro Met Ser Ile Gly
        115                 120                 125

Ile Ser Phe Met Gly Asn Tyr Met Asp Arg Val Pro Thr Pro Gln Ala
    130                 135                 140

Ile Arg Ala Ala Gln Gly Leu Leu Ala Cys Gly Val Ala Gln Gly Ala
145                 150                 155                 160

Leu Arg Ser Asn Tyr Val Leu Lys Gly His Arg Asp Val Gln Arg Thr
                165                 170                 175
```

Leu Ser Pro Gly Asn Gln Leu Tyr His Leu Ile Gln Asn Trp Pro His
180 185 190

Tyr Arg Ser Pro
195

<210> SEQ ID NO 9
<211> LENGTH: 11
<212> TYPE: PRT
<213> ORGANISM: Artificial Sequence
<220> FEATURE:
<223> OTHER INFORMATION: Amino Acid Residues 27-37 of Human TREM-1, Isoform 1

<400> SEQUENCE: 9

Glu Lys Tyr Glu Leu Lys Glu Gly Gln Thr Leu
1 5 10

<210> SEQ ID NO 10
<211> LENGTH: 13
<212> TYPE: PRT
<213> ORGANISM: Artificial Sequence
<220> FEATURE:
<223> OTHER INFORMATION: Amino Acid Residues 88-100 of Human TREM-1, Isoform 1

<400> SEQUENCE: 10

Glu Asp Tyr His Asp His Gly Leu Leu Arg Val Arg Met
1 5 10

<210> SEQ ID NO 11
<211> LENGTH: 9
<212> TYPE: PRT
<213> ORGANISM: Artificial Sequence
<220> FEATURE:
<223> OTHER INFORMATION: Amino Acid Residues 120-128 of Human TREM-1, Isoform 1

<400> SEQUENCE: 11

Lys Glu Pro His Met Leu Phe Asp Arg
1 5

<210> SEQ ID NO 12
<211> LENGTH: 330
<212> TYPE: PRT
<213> ORGANISM: Homo sapiens

<400> SEQUENCE: 12

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro

```
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 13
<211> LENGTH: 124
<212> TYPE: PRT
<213> ORGANISM: Artificial Sequence
<220> FEATURE:
<223> OTHER INFORMATION: P1-047248 VH

<400> SEQUENCE: 13

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Tyr Trp Ser Trp Val Arg Gln Pro Pro Gly Lys Gly Leu Glu Trp Ile
        35                  40                  45

Gly Tyr Thr His Tyr Ser Gly Ile Ser Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Tyr Asp Ile Leu Thr Gly Tyr Glu Tyr Tyr Gly Met Asp
            100                 105                 110

Val Trp Gly Gln Gly Thr Thr Val Thr Val Ser Ser
        115                 120
```

<210> SEQ ID NO 14
<211> LENGTH: 107
<212> TYPE: PRT

```
<213> ORGANISM: Artificial Sequence
<220> FEATURE:
<223> OTHER INFORMATION: P1-047248 VL

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gly Gly Thr Lys Val Glu Ile Lys
            100                 105


<210> SEQ ID NO 15
<211> LENGTH: 122
<212> TYPE: PRT
<213> ORGANISM: Artificial Sequence
<220> FEATURE:
<223> OTHER INFORMATION: P1-047246, P1-047247 VH

<400> SEQUENCE: 15

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Asn Tyr
            20                  25                  30

Tyr Trp Thr Trp Ile Arg Gln Pro Pro Gly Lys Gly Leu Glu Trp Ile
        35                  40                  45

Gly Tyr Ile Tyr Asp Ser Gly Tyr Thr Asn Tyr Asn Pro Ser Leu Lys
    50                  55                  60

Ser Arg Val Thr Leu Ser Ile Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Val Leu Trp Phe Gly Glu Leu Leu Pro Leu Leu Asp Tyr Trp
            100                 105                 110

Gly Gln Gly Thr Leu Val Thr Val Ser Ser
        115                 120


<210> SEQ ID NO 16
<211> LENGTH: 107
<212> TYPE: PRT
<213> ORGANISM: Artificial Sequence
<220> FEATURE:
<223> OTHER INFORMATION: P1-047246; P1-047239 VL

<400> SEQUENCE: 16

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45
```

```
Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys
            100                 105


<210> SEQ ID NO 17
<211> LENGTH: 108
<212> TYPE: PRT
<213> ORGANISM: Artificial Sequence
<220> FEATURE:
<223> OTHER INFORMATION: P1-047247 VL

<400> SEQUENCE: 17

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Glu Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105


<210> SEQ ID NO 18

<400> SEQUENCE: 18

000


<210> SEQ ID NO 19

<400> SEQUENCE: 19

000


<210> SEQ ID NO 20

<400> SEQUENCE: 20

000


<210> SEQ ID NO 21

<400> SEQUENCE: 21

000


<210> SEQ ID NO 22

<400> SEQUENCE: 22

000
```

<210> SEQ ID NO 23
<211> LENGTH: 123
<212> TYPE: PRT
<213> ORGANISM: Artificial Sequence
<220> FEATURE:
<223> OTHER INFORMATION: P1-047334 VH

<400> SEQUENCE: 23

```
Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Ser Ser Ser
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Thr Asn Gly Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Met Val Arg Gly Asn Tyr Phe Tyr Phe Tyr Gly Met Asp Val
            100                 105                 110

Trp Gly Gln Gly Thr Thr Val Thr Val Ser Ser
        115                 120
```

<210> SEQ ID NO 24
<211> LENGTH: 107
<212> TYPE: PRT
<213> ORGANISM: Artificial Sequence
<220> FEATURE:
<223> OTHER INFORMATION: P1-047334 VL

<400> SEQUENCE: 24

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105
```

<210> SEQ ID NO 25
<211> LENGTH: 125
<212> TYPE: PRT
<213> ORGANISM: Artificial Sequence
<220> FEATURE:
<223> OTHER INFORMATION: P1-047239 VH

<400> SEQUENCE: 25

```
Gln Val Gln Leu Val Glu Ser Gly Gly Gly Val Val Gln Pro Gly Arg
1               5                   10                  15

Ser Leu Arg Leu Ser Cys Ala Ala Thr Glu Phe Thr Phe Ser Asn Tyr
```

```
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Ser Ala Glu Asp Ser Ala Val Tyr Tyr Cys
                85                  90                  95

Ala Arg Asp Gly Arg His Tyr Tyr Gly Ser Thr Ser Tyr Phe Gly Met
            100                 105                 110

Asp Val Trp Gly Gln Gly Thr Thr Val Thr Val Ser Ser
        115                 120                 125


<210> SEQ ID NO 26
<211> LENGTH: 5
<212> TYPE: PRT
<213> ORGANISM: Artificial Sequence
<220> FEATURE:
<223> OTHER INFORMATION: P1-047248 HCDR1

<400> SEQUENCE: 26

Ser Ser Tyr Trp Ser
1               5


<210> SEQ ID NO 27
<211> LENGTH: 16
<212> TYPE: PRT
<213> ORGANISM: Artificial Sequence
<220> FEATURE:
<223> OTHER INFORMATION: P1-047248 HCDR2

<400> SEQUENCE: 27

Tyr Thr His Tyr Ser Gly Ile Ser Asn Tyr Asn Pro Ser Leu Lys Ser
1               5                   10                  15


<210> SEQ ID NO 28
<211> LENGTH: 16
<212> TYPE: PRT
<213> ORGANISM: Artificial Sequence
<220> FEATURE:
<223> OTHER INFORMATION: P1-047248 HCDR3

<400> SEQUENCE: 28

Glu Gly Tyr Asp Ile Leu Thr Gly Tyr Glu Tyr Tyr Gly Met Asp Val
1               5                   10                  15


<210> SEQ ID NO 29
<211> LENGTH: 12
<212> TYPE: PRT
<213> ORGANISM: Artificial Sequence
<220> FEATURE:
<223> OTHER INFORMATION: P1-047248; P1-047247 LCDR1

<400> SEQUENCE: 29

Arg Ala Ser Gln Ser Val Ser Ser Ser Tyr Leu Ala
1               5                   10


<210> SEQ ID NO 30
<211> LENGTH: 7
<212> TYPE: PRT
<213> ORGANISM: Artificial Sequence
<220> FEATURE:
<223> OTHER INFORMATION: P1-047248; P1-047247; P1-047317 LCDR2
```

<400> SEQUENCE: 30

Gly Ala Ser Ser Arg Ala Thr
1 5

<210> SEQ ID NO 31
<211> LENGTH: 8
<212> TYPE: PRT
<213> ORGANISM: Artificial Sequence
<220> FEATURE:
<223> OTHER INFORMATION: P1-047248 LCDR3

<400> SEQUENCE: 31

Gln Gln Tyr Gly Ser Ser Pro Thr
1 5

<210> SEQ ID NO 32
<211> LENGTH: 5
<212> TYPE: PRT
<213> ORGANISM: Artificial Sequence
<220> FEATURE:
<223> OTHER INFORMATION: P1-047246; P1-047247 HCDR1

<400> SEQUENCE: 32

Asn Tyr Tyr Trp Thr
1 5

<210> SEQ ID NO 33
<211> LENGTH: 16
<212> TYPE: PRT
<213> ORGANISM: Artificial Sequence
<220> FEATURE:
<223> OTHER INFORMATION: P1-047246; P1-047247 HCDR2

<400> SEQUENCE: 33

Tyr Ile Tyr Asp Ser Gly Tyr Thr Asn Tyr Asn Pro Ser Leu Lys Ser
1 5 10 15

<210> SEQ ID NO 34
<211> LENGTH: 14
<212> TYPE: PRT
<213> ORGANISM: Artificial Sequence
<220> FEATURE:
<223> OTHER INFORMATION: P1-047246; P1-047247 HCDR3

<400> SEQUENCE: 34

Gly Val Leu Trp Phe Gly Glu Leu Leu Pro Leu Leu Asp Tyr
1 5 10

<210> SEQ ID NO 35
<211> LENGTH: 11
<212> TYPE: PRT
<213> ORGANISM: Artificial Sequence
<220> FEATURE:
<223> OTHER INFORMATION: P1-047246; P1-047334; P1-047239; P1-047323; P1-047328 LCDR1

<400> SEQUENCE: 35

Arg Ala Ser Gln Gly Ile Ser Ser Ala Leu Ala
1 5 10

<210> SEQ ID NO 36
<211> LENGTH: 7
<212> TYPE: PRT
<213> ORGANISM: Artificial Sequence
<220> FEATURE:
<223> OTHER INFORMATION: P1-047246; P1-047239; P1-047323; P1-047328

LCDR2

<400> SEQUENCE: 36

Asp Ala Ser Ser Leu Glu Ser
1 5

<210> SEQ ID NO 37
<211> LENGTH: 9
<212> TYPE: PRT
<213> ORGANISM: Artificial Sequence
<220> FEATURE:
<223> OTHER INFORMATION: P1-047246; P1-047239 LCDR3

<400> SEQUENCE: 37

Gln Gln Phe Asn Ser Tyr Pro Tyr Thr
1 5

<210> SEQ ID NO 38
<211> LENGTH: 9
<212> TYPE: PRT
<213> ORGANISM: Artificial Sequence
<220> FEATURE:
<223> OTHER INFORMATION: P1-047247; P1-047317 LCDR3

<400> SEQUENCE: 38

Gln Gln Tyr Gly Ser Ser Pro Leu Thr
1 5

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42
<211> LENGTH: 11
<212> TYPE: PRT
<213> ORGANISM: Artificial Sequence
<220> FEATURE:
<223> OTHER INFORMATION: P1-047317 LCDR1

<400> SEQUENCE: 42

Arg Ala Ser Gln Ser Val Ser Ser Tyr Leu Ala
1 5 10

<210> SEQ ID NO 43

<400> SEQUENCE: 43

000

<210> SEQ ID NO 44

<400> SEQUENCE: 44

000

<210> SEQ ID NO 45
<211> LENGTH: 5
<212> TYPE: PRT
<213> ORGANISM: Artificial Sequence
<220> FEATURE:
<223> OTHER INFORMATION: P1-047334; P1-047292; P1-047289; P1-047306
      HCDR1

<400> SEQUENCE: 45

Ser Ser Ala Ile Ser
1               5

<210> SEQ ID NO 46
<211> LENGTH: 17
<212> TYPE: PRT
<213> ORGANISM: Artificial Sequence
<220> FEATURE:
<223> OTHER INFORMATION: P1-047334 HCDR2

<400> SEQUENCE: 46

Gly Ile Ile Pro Ile Phe Gly Thr Thr Asn Gly Ala Gln Lys Phe Gln
1               5                   10                  15

Gly

<210> SEQ ID NO 47
<211> LENGTH: 14
<212> TYPE: PRT
<213> ORGANISM: Artificial Sequence
<220> FEATURE:
<223> OTHER INFORMATION: P1-047334 HCDR3

<400> SEQUENCE: 47

Met Val Arg Gly Asn Tyr Phe Tyr Phe Tyr Gly Met Asp Val
1               5                   10

<210> SEQ ID NO 48
<211> LENGTH: 7
<212> TYPE: PRT
<213> ORGANISM: Artificial Sequence
<220> FEATURE:
<223> OTHER INFORMATION: P1-047334; P1-047305; P1-047309; P1-047313;
      P1-047311; P1-047294; P1-047290; P1-047291; P1-047296; P1-047297;
      P1-047300; P1-047302; P1-047307; P1-047308; P1-047319; P1-047292;
      P1-047322; P1-047310; P1-047299; P1-047301; P1-047289; P1-047306;
      P1-047312; P1-0473

<400> SEQUENCE: 48

Ala Ala Ser Ser Leu Gln Ser
1               5

<210> SEQ ID NO 49
<211> LENGTH: 9
<212> TYPE: PRT
<213> ORGANISM: Artificial Sequence
<220> FEATURE:
<223> OTHER INFORMATION: P1-047334; P1-047307; P1-047311; P1-047294;
      P1-047297; P1-047300;
      P1-047302; P1-047310; P1-047306 LCDR3

<400> SEQUENCE: 49

Gln Gln Tyr Asn Ser Tyr Pro Leu Thr
1               5

<210> SEQ ID NO 50
<211> LENGTH: 5

```
<212> TYPE: PRT
<213> ORGANISM: Artificial Sequence
<220> FEATURE:
<223> OTHER INFORMATION: P1-047239 HCDR1

<400> SEQUENCE: 50

Asn Tyr Gly Met His
1               5


<210> SEQ ID NO 51
<211> LENGTH: 17
<212> TYPE: PRT
<213> ORGANISM: Artificial Sequence
<220> FEATURE:
<223> OTHER INFORMATION: P1-047239 HCDR2

<400> SEQUENCE: 51

Val Ile Trp Tyr Asp Gly Ser Asn Lys Tyr Tyr Ala Asp Ser Val Lys
1               5                   10                  15

Gly


<210> SEQ ID NO 52
<211> LENGTH: 16
<212> TYPE: PRT
<213> ORGANISM: Artificial Sequence
<220> FEATURE:
<223> OTHER INFORMATION: P1-047239 HCDR3

<400> SEQUENCE: 52

Asp Gly Arg His Tyr Tyr Gly Ser Thr Ser Tyr Phe Gly Met Asp Val
1               5                   10                  15


<210> SEQ ID NO 53
<211> LENGTH: 126
<212> TYPE: PRT
<213> ORGANISM: Artificial Sequence
<220> FEATURE:
<223> OTHER INFORMATION: P1-047305 VH

<400> SEQUENCE: 53

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Ser
            20                  25                  30

Ala Val Ser Trp Val Arg Gln Ala Pro Gly Gln Gly Leu Glu Trp Met
        35                  40                  45

Gly Gly Ile Thr Pro Ile Phe Gly Thr Ala Asp Tyr Ala Gln Lys Phe
    50                  55                  60

Gln Gly Arg Val Thr Ile Thr Ala Asp Ala Ser Thr Ser Thr Gly Tyr
65                  70                  75                  80

Met Glu Leu Ser Ser Leu Arg Ser Glu Asp Thr Ala Val Tyr Tyr Cys
                85                  90                  95

Ala Phe Thr Pro Arg Tyr Arg Gly Ser Ser His His Tyr Tyr Tyr Ala
            100                 105                 110

Leu Gly Val Trp Gly Gln Gly Thr Thr Val Thr Val Ser Ser
        115                 120                 125


<210> SEQ ID NO 54
<211> LENGTH: 107
<212> TYPE: PRT
<213> ORGANISM: Artificial Sequence
<220> FEATURE:
<223> OTHER INFORMATION: P1-047305; P1-047314; P1-047290; P1-047308;
```

P1-047292; P1-047322; P1-047301; P1-047265 VL

<400> SEQUENCE: 54

Asp Ile Gln Met Thr Gln Ser Pro Thr Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Tyr
85 90 95

Thr Phe Gly Gln Gly Thr Lys Leu Glu Ile Lys
100 105

<210> SEQ ID NO 55
<211> LENGTH: 117
<212> TYPE: PRT
<213> ORGANISM: Artificial Sequence
<220> FEATURE:
<223> OTHER INFORMATION: P1-047309 VH

<400> SEQUENCE: 55

Gln Val Gln Leu Val Gln Ser Gly Ala Glu Val Lys Lys Pro Gly Ser
1 5 10 15

Ser Val Lys Val Ser Cys Asn Pro Ser Gly Gly Thr Phe Ser Thr Tyr
20 25 30

Ala Ile Ser Trp Val Arg Gln Ala Pro Gly Gln Gly Leu Glu Trp Met
35 40 45

Gly Gly Ile Asn Pro Ile Phe Gly Thr Ala Asn Tyr Ala Gln Lys Phe
50 55 60

Gln Gly Arg Val Thr Ile Thr Ala Asp Glu Ser Thr Ser Pro Gly Tyr
65 70 75 80

Leu Glu Leu Ser Ser Leu Arg Ser Glu Asp Thr Ala Val Tyr Tyr Cys
85 90 95

Ala Arg Gly Gly Ala Val Gly Phe Ala Tyr Trp Gly Gln Gly Thr Leu
100 105 110

Val Thr Val Ser Ser
115

<210> SEQ ID NO 56
<211> LENGTH: 107
<212> TYPE: PRT
<213> ORGANISM: Artificial Sequence
<220> FEATURE:
<223> OTHER INFORMATION: P1-047309 VL

<400> SEQUENCE: 56

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln His Lys Pro Gly Lys Ala Pro Lys Leu Leu Ile
35 40 45

Tyr Ala Ala Ser Ser Leu Gln Ser Gly Val Pro Ser Arg Phe Ser Gly

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Gly Gly Thr Lys Val Glu Ile Lys
            100                 105


<210> SEQ ID NO 57
<211> LENGTH: 125
<212> TYPE: PRT
<213> ORGANISM: Artificial Sequence
<220> FEATURE:
<223> OTHER INFORMATION: P1-047313 VH

<400> SEQUENCE: 57

Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Ser Ile Tyr
            20                  25                  30

Val Ile Ser Trp Val Arg Gln Ala Pro Gly Gln Gly Leu Glu Trp Met
        35                  40                  45

Gly Gly Ile Ile Pro Leu Phe Gly Thr Pro Asn Tyr Ala Gln Arg Phe
    50                  55                  60

Gln Asp Arg Val Thr Ile Thr Ala Asp Glu Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Gly Pro Gly Ser Ser His Tyr Ser Tyr Tyr Gly Leu
            100                 105                 110

Asp Val Trp Gly Gln Gly Thr Thr Val Thr Val Ser Ser
        115                 120                 125


<210> SEQ ID NO 58
<211> LENGTH: 107
<212> TYPE: PRT
<213> ORGANISM: Artificial Sequence
<220> FEATURE:
<223> OTHER INFORMATION: P1-047313 VL

<400> SEQUENCE: 58

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys
            100                 105


<210> SEQ ID NO 59
<211> LENGTH: 125
```

<212> TYPE: PRT
<213> ORGANISM: Artificial Sequence
<220> FEATURE:
<223> OTHER INFORMATION: P1-047307; P1-047312; P1-047314; P1-047320; P1-047317 VH

<400> SEQUENCE: 59

```
Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Ser Ile Tyr
            20                  25                  30

Val Ile Ser Trp Val Arg Gln Ala Pro Gly Gln Gly Leu Glu Trp Met
        35                  40                  45

Gly Gly Ile Ile Pro Leu Phe Gly Thr Pro Asn Tyr Ala Gln Gln Phe
    50                  55                  60

Gln Asp Arg Val Thr Ile Thr Ala Asp Glu Ser Thr Arg Thr Ala Tyr
65                  70                  75                  80

Met Glu Leu Asn Ser Leu Lys Ser Glu Asp Thr Ala Val Tyr Tyr Cys
                85                  90                  95

Ala Arg Gly His Gly Pro Gly Ser Ser His Tyr Ser Tyr Tyr Gly Leu
            100                 105                 110

Asp Val Trp Gly Gln Gly Thr Thr Val Thr Val Ser Ser
        115                 120                 125
```

<210> SEQ ID NO 60
<211> LENGTH: 107
<212> TYPE: PRT
<213> ORGANISM: Artificial Sequence
<220> FEATURE:
<223> OTHER INFORMATION: P1-047307; P1-047302; P1-047306 VL

<400> SEQUENCE: 60

```
Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105
```

<210> SEQ ID NO 61
<211> LENGTH: 107
<212> TYPE: PRT
<213> ORGANISM: Artificial Sequence
<220> FEATURE:
<223> OTHER INFORMATION: P1-047312; P1-047318 VL

<400> SEQUENCE: 61

```
Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30
```

```
Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105


<210> SEQ ID NO 62
<211> LENGTH: 125
<212> TYPE: PRT
<213> ORGANISM: Artificial Sequence
<220> FEATURE:
<223> OTHER INFORMATION: P1-047318 VH

<400> SEQUENCE: 62

Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Ser Ile Tyr
            20                  25                  30

Val Ile Ser Trp Val Arg Gln Ala Pro Gly Gln Gly Leu Glu Trp Met
        35                  40                  45

Gly Gly Ile Ile Pro Leu Phe Gly Thr Pro Asn Tyr Ala Gln Gln Phe
    50                  55                  60

Gln Asp Arg Val Thr Ile Thr Ala Asp Glu Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Gly Pro Gly Ser Ser His Tyr Ser Tyr Tyr Gly Leu
            100                 105                 110

Asp Val Trp Gly Gln Gly Thr Thr Val Thr Val Ser Ser
        115                 120                 125


<210> SEQ ID NO 63
<211> LENGTH: 107
<212> TYPE: PRT
<213> ORGANISM: Artificial Sequence
<220> FEATURE:
<223> OTHER INFORMATION: P1-047320; P1-047319 VL

<400> SEQUENCE: 63

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105
```

<210> SEQ ID NO 64
<211> LENGTH: 125
<212> TYPE: PRT
<213> ORGANISM: Artificial Sequence
<220> FEATURE:
<223> OTHER INFORMATION: P1-047311 VH

<400> SEQUENCE: 64

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ile Tyr
            20                  25                  30

Val Ile Ser Trp Val Arg Gln Ala Pro Gly Gln Gly Leu Glu Trp Met
        35                  40                  45

Gly Gly Ile Ile Pro Leu Phe Gly Thr Ala Asn Tyr Ala Gln Gln Phe
    50                  55                  60

Gln Asp Arg Val Thr Ile Thr Ala Asp Glu Ser Thr Arg Thr Ala Tyr
65                  70                  75                  80

Met Glu Leu Asn Ser Leu Lys Ser Glu Asp Thr Ala Val Tyr Tyr Cys
                85                  90                  95

Ala Arg Gly His Gly Pro Gly Ser Ser His Tyr Ser Tyr Tyr Gly Leu
            100                 105                 110

Asp Val Trp Gly Gln Gly Thr Thr Val Thr Val Ser Ser
        115                 120                 125
```

<210> SEQ ID NO 65
<211> LENGTH: 107
<212> TYPE: PRT
<213> ORGANISM: Artificial Sequence
<220> FEATURE:
<223> OTHER INFORMATION: P1-047311 VL

<400> SEQUENCE: 65

```
Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105
```

<210> SEQ ID NO 66
<211> LENGTH: 127
<212> TYPE: PRT
<213> ORGANISM: Artificial Sequence
<220> FEATURE:
<223> OTHER INFORMATION: P1-047294 VH

<400> SEQUENCE: 66

```
Gln Val Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Asn Arg His
            20                  25                  30

Ala Ile Ser Trp Val Arg Gln Ala Pro Gly Gln Gly Leu Glu Trp Met
        35                  40                  45

Gly Gly Ile Ile Pro Leu Phe Gly Thr Ala Asn Tyr Ala Gln Glu Phe
    50                  55                  60

Gln Gly Arg Val Thr Ile Ala Ala Asp Glu Pro Thr Ser Thr Thr Tyr
65                  70                  75                  80

Met Glu Leu Arg Ser Leu Arg Ser Glu Asp Thr Ala Val Tyr Tyr Cys
                85                  90                  95

Ala Ser Ser Tyr Phe Tyr Gly Ser Gly Ser Ser Asn Tyr Tyr Tyr Tyr
            100                 105                 110

Gly Leu Asp Val Trp Gly Gln Gly Thr Thr Val Thr Val Ser Ser
        115                 120                 125


<210> SEQ ID NO 67
<211> LENGTH: 107
<212> TYPE: PRT
<213> ORGANISM: Artificial Sequence
<220> FEATURE:
<223> OTHER INFORMATION: P1-047294 VL

<400> SEQUENCE: 67

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105


<210> SEQ ID NO 68
<211> LENGTH: 127
<212> TYPE: PRT
<213> ORGANISM: Artificial Sequence
<220> FEATURE:
<223> OTHER INFORMATION: P1-047290; P1-047291; P1-047296; P1-047297;
      P1-047300; P1-047302 VH

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg His
            20                  25                  30

Ala Ile Ser Trp Val Arg Gln Ala Pro Gly Gln Gly Leu Glu Trp Met
        35                  40                  45

Gly Gly Ile Ile Pro Leu Phe Gly Thr Ala Asn Tyr Ala Gln Lys Phe
    50                  55                  60

Gln Gly Arg Val Thr Ile Ala Ala Asp Glu Pro Thr Ser Thr Thr Tyr
65                  70                  75                  80

Met Glu Leu Arg Ser Leu Arg Ser Glu Asp Thr Ala Val Tyr Tyr Cys
```

```
                85                  90                  95

Ala Ser Ser Tyr Phe Tyr Gly Ser Gly Ser Ser Asn Tyr Tyr Tyr Tyr
            100                 105                 110

Gly Leu Asp Val Trp Gly Gln Gly Thr Thr Val Thr Val Ser Ser
        115                 120                 125


<210> SEQ ID NO 69
<211> LENGTH: 107
<212> TYPE: PRT
<213> ORGANISM: Artificial Sequence
<220> FEATURE:
<223> OTHER INFORMATION: P1-047291 VL

<400> SEQUENCE: 69

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105


<210> SEQ ID NO 70
<211> LENGTH: 107
<212> TYPE: PRT
<213> ORGANISM: Artificial Sequence
<220> FEATURE:
<223> OTHER INFORMATION: P1-047296 VL

<400> SEQUENCE: 70

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105


<210> SEQ ID NO 71
<211> LENGTH: 107
<212> TYPE: PRT
<213> ORGANISM: Artificial Sequence
<220> FEATURE:
<223> OTHER INFORMATION: P1-047297 VL

<400> SEQUENCE: 71
```

Asp Ile Gln Met Thr Gln Ser Pro Thr Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln His Lys Pro Gly Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Leu
85 90 95

Thr Phe Gly Gly Gly Thr Lys Val Glu Ile Lys
100 105

<210> SEQ ID NO 72
<211> LENGTH: 107
<212> TYPE: PRT
<213> ORGANISM: Artificial Sequence
<220> FEATURE:
<223> OTHER INFORMATION: P1-047300 VL

<400> SEQUENCE: 72

Asp Ile Gln Met Thr Gln Ser Pro Thr Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

His Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Leu
85 90 95

Thr Phe Gly Gly Gly Thr Lys Val Glu Ile Lys
100 105

<210> SEQ ID NO 73
<211> LENGTH: 125
<212> TYPE: PRT
<213> ORGANISM: Artificial Sequence
<220> FEATURE:
<223> OTHER INFORMATION: P1-047308; P1-047319 VH

<400> SEQUENCE: 73

Gln Val Gln Leu Val Gln Ser Gly Ala Glu Val Lys Arg Pro Gly Ser
1 5 10 15

Ser Val Lys Val Ser Cys Lys Ala Ser Gly Gly Thr Phe Ser Ile Tyr
20 25 30

Val Ile Ser Trp Val Arg Gln Ala Pro Gly Gln Gly Leu Glu Trp Met
35 40 45

Gly Gly Ile Ile Pro Leu Phe Gly Thr Ala Asn Tyr Ala Gln Lys Phe
50 55 60

Gln Gly Arg Val Thr Ile Thr Ala Asp Glu Ser Thr Asn Thr Ala Tyr
65 70 75 80

Met Glu Leu Ser Ser Leu Arg Ser Glu Asp Thr Ala Val Tyr Tyr Cys

```
                85                  90                  95

Ala Arg Gly His Gly Pro Gly Ser Ser His Tyr Ser Tyr Tyr Gly Leu
            100                 105                 110

Asp Val Trp Gly Gln Gly Thr Thr Val Thr Val Ser Ser
        115                 120                 125


<210> SEQ ID NO 74
<211> LENGTH: 126
<212> TYPE: PRT
<213> ORGANISM: Artificial Sequence
<220> FEATURE:
<223> OTHER INFORMATION: P1-047292 VH

<400> SEQUENCE: 74

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Ser
            20                  25                  30

Ala Ile Ser Trp Val Arg Gln Ala Pro Gly Gln Gly Leu Glu Trp Met
        35                  40                  45

Gly Gly Ile Ile Pro Ile Phe Ser Thr Gly Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Asp Leu Ser Ser Leu Arg Ser Glu Asp Thr Ala Val Tyr Tyr Cys
                85                  90                  95

Ala Arg Ser Thr Arg Val Arg Gly Val Ser His Tyr Tyr Tyr Tyr Gly
            100                 105                 110

Leu Asp Val Trp Gly Gln Gly Thr Thr Val Thr Val Ser Ser
        115                 120                 125


<210> SEQ ID NO 75
<211> LENGTH: 127
<212> TYPE: PRT
<213> ORGANISM: Artificial Sequence
<220> FEATURE:
<223> OTHER INFORMATION: P1-047322 VH

<400> SEQUENCE: 75

Gln Val Gln Leu Val Gln Ser Gly Ala Glu Val Lys Lys Pro Gly Ser
1               5                   10                  15

Ser Val Lys Val Ser Cys Lys Ser Ser Gly Gly Thr Phe Ser Ser Tyr
            20                  25                  30

Ala Phe Thr Trp Val Arg Gln Ala Pro Gly Gln Gly Leu Glu Trp Met
        35                  40                  45

Gly Gly Ile Ile Pro Ile Phe Arg Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser His Phe Ser Gly Ser Gly Ser Ser His Tyr Tyr Tyr Tyr
            100                 105                 110

Gly Met His Val Trp Gly Gln Gly Thr Thr Val Thr Val Ser Ser
        115                 120                 125


<210> SEQ ID NO 76
<211> LENGTH: 125
```

<212> TYPE: PRT
<213> ORGANISM: Artificial Sequence
<220> FEATURE:
<223> OTHER INFORMATION: P1-047310 VH

<400> SEQUENCE: 76

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ser Asn Tyr Ala Gln Lys Phe
    50                  55                  60

Gln Gly Arg Val Thr Ile Lys Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Ser Trp Thr Thr Ser Leu Tyr Tyr Tyr Gly Met
            100                 105                 110

Asp Val Trp Gly Gln Gly Thr Thr Val Thr Val Ser Ser
        115                 120                 125
```

<210> SEQ ID NO 77
<211> LENGTH: 107
<212> TYPE: PRT
<213> ORGANISM: Artificial Sequence
<220> FEATURE:
<223> OTHER INFORMATION: P1-047310 VL

<400> SEQUENCE: 77

```
Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105
```

<210> SEQ ID NO 78
<211> LENGTH: 127
<212> TYPE: PRT
<213> ORGANISM: Artificial Sequence
<220> FEATURE:
<223> OTHER INFORMATION: P1-047299 VH

<400> SEQUENCE: 78

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg Tyr
            20                  25                  30

Ala Phe Ser Trp Val Arg Gln Ala Pro Gly Gln Gly Leu Glu Trp Met
```

```
        35                  40                  45

Gly Gly Ile Ile Pro Ile Phe Gly Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Ile Ser Glu Asp Thr Ala Val Tyr Tyr Cys
                85                  90                  95

Ala Ser Ser His Phe Tyr Gly Ser Gly Ser Ser His Phe Tyr Tyr Tyr
            100                 105                 110

Gly Met His Val Trp Gly Gln Gly Thr Thr Val Thr Val Ser Ser
        115                 120                 125


<210> SEQ ID NO 79
<211> LENGTH: 107
<212> TYPE: PRT
<213> ORGANISM: Artificial Sequence
<220> FEATURE:
<223> OTHER INFORMATION: P1-047299 VL

<400> SEQUENCE: 79

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys
            100                 105


<210> SEQ ID NO 80
<211> LENGTH: 127
<212> TYPE: PRT
<213> ORGANISM: Artificial Sequence
<220> FEATURE:
<223> OTHER INFORMATION: P1-047301 VH

<400> SEQUENCE: 80

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg Tyr
            20                  25                  30

Ala Phe Ser Trp Val Arg Gln Ala Pro Gly Gln Gly Leu Glu Trp Met
        35                  40                  45

Gly Gly Ile Ile Pro Ile Phe Gly Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Ile Ser Glu Asp Thr Ala Val Tyr Tyr Cys
                85                  90                  95

Ala Ser Ser His Phe Tyr Gly Ser Gly Ser Ser Asn Tyr Tyr Tyr Tyr
            100                 105                 110
```

```
Gly Leu Asp Val Trp Gly Gln Gly Thr Thr Val Thr Val Ser Ser
        115                 120                 125


<210> SEQ ID NO 81
<211> LENGTH: 126
<212> TYPE: PRT
<213> ORGANISM: Artificial Sequence
<220> FEATURE:
<223> OTHER INFORMATION: P1-047289 VH

<400> SEQUENCE: 81

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Ser
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asp Ser Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Asn Ser Leu Arg Ser Glu Asp Thr Ala Val Tyr Tyr Cys
                85                  90                  95

Ala Phe Thr Pro Arg Tyr Arg Gly Ser Ser His His Tyr Phe Tyr Ala
            100                 105                 110

Leu Gly Val Trp Gly Gln Gly Thr Thr Val Thr Val Ser Ser
        115                 120                 125


<210> SEQ ID NO 82
<211> LENGTH: 107
<212> TYPE: PRT
<213> ORGANISM: Artificial Sequence
<220> FEATURE:
<223> OTHER INFORMATION: P1-047289 VL

<400> SEQUENCE: 82

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105


<210> SEQ ID NO 83
<211> LENGTH: 125
<212> TYPE: PRT
<213> ORGANISM: Artificial Sequence
<220> FEATURE:
<223> OTHER INFORMATION: P1-047306 VH

<400> SEQUENCE: 83

Gln Val Gln Leu Val Gln Ser Gly Ala Glu Val Lys Lys Pro Gly Ser
```

```
1               5                   10                  15

Ser Val Lys Val Ser Cys Lys Ala Ser Gly Gly Thr Phe Ser Ser Ser
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Gln Ser Arg Ser Ser Asn Tyr Tyr Tyr Tyr Gly Leu
            100                 105                 110

Asp Val Trp Gly Gln Gly Thr Thr Val Thr Val Ser Ser
        115                 120                 125


<210> SEQ ID NO 84
<211> LENGTH: 5
<212> TYPE: PRT
<213> ORGANISM: Artificial Sequence
<220> FEATURE:
<223> OTHER INFORMATION: P1-047305 HCDR1

<400> SEQUENCE: 84

Ser Ser Ala Val Ser
1               5


<210> SEQ ID NO 85
<211> LENGTH: 17
<212> TYPE: PRT
<213> ORGANISM: Artificial Sequence
<220> FEATURE:
<223> OTHER INFORMATION: P1-047305 HCDR2

<400> SEQUENCE: 85

Gly Ile Thr Pro Ile Phe Gly Thr Ala Asp Tyr Ala Gln Lys Phe Gln
1               5                   10                  15

Gly


<210> SEQ ID NO 86
<211> LENGTH: 17
<212> TYPE: PRT
<213> ORGANISM: Artificial Sequence
<220> FEATURE:
<223> OTHER INFORMATION: P1-047305 HCDR3

<400> SEQUENCE: 86

Thr Pro Arg Tyr Arg Gly Ser Ser His His Tyr Tyr Tyr Ala Leu Gly
1               5                   10                  15

Val


<210> SEQ ID NO 87
<211> LENGTH: 11
<212> TYPE: PRT
<213> ORGANISM: Artificial Sequence
<220> FEATURE:
<223> OTHER INFORMATION: P1-047305; P1-047309; P1-047313; P1-047307;
      P1-047312; P1-047314; P1-047318; P1-047320; P1-047311; P1-047294;
      P1-047290; P1-047291; P1-047296; P1-047297; P1-047300; P1-047302;
      P1-047308; P1-047319; P1-047292; P1-047322; P1-047310; P1-047299;
      P1-047301; P1-0472

<400> SEQUENCE: 87
```

Arg Ala Ser Gln Gly Ile Ser Ser Trp Leu Ala
1               5                   10

<210> SEQ ID NO 88
<211> LENGTH: 9
<212> TYPE: PRT
<213> ORGANISM: Artificial Sequence
<220> FEATURE:
<223> OTHER INFORMATION: P1-047305; P1-047312; P1-047314; P1-047318;
      P1-047320; P1-047290; P1-047291; P1-047308; P1-047319; P1-047292;
      P1-047322; P1-047301; P1-047265 LCDR3

<400> SEQUENCE: 88

Gln Gln Tyr Asn Ser Tyr Pro Tyr Thr
1               5

<210> SEQ ID NO 89
<211> LENGTH: 5
<212> TYPE: PRT
<213> ORGANISM: Artificial Sequence
<220> FEATURE:
<223> OTHER INFORMATION: P1-047309 HCDR1

<400> SEQUENCE: 89

Thr Tyr Ala Ile Ser
1               5

<210> SEQ ID NO 90
<211> LENGTH: 17
<212> TYPE: PRT
<213> ORGANISM: Artificial Sequence
<220> FEATURE:
<223> OTHER INFORMATION: P1-047309 HCDR2

<400> SEQUENCE: 90

Gly Ile Asn Pro Ile Phe Gly Thr Ala Asn Tyr Ala Gln Lys Phe Gln
1               5                   10                  15

Gly

<210> SEQ ID NO 91
<211> LENGTH: 8
<212> TYPE: PRT
<213> ORGANISM: Artificial Sequence
<220> FEATURE:
<223> OTHER INFORMATION: P1-047309 HCDR3

<400> SEQUENCE: 91

Gly Gly Ala Val Gly Phe Ala Tyr
1               5

<210> SEQ ID NO 92
<211> LENGTH: 9
<212> TYPE: PRT
<213> ORGANISM: Artificial Sequence
<220> FEATURE:
<223> OTHER INFORMATION: P1-047309 LCDR3

<400> SEQUENCE: 92

Gln Gln Ala Asn Ser Phe Pro Phe Thr
1               5

<210> SEQ ID NO 93
<211> LENGTH: 5
<212> TYPE: PRT
<213> ORGANISM: Artificial Sequence
<220> FEATURE:

<223> OTHER INFORMATION: P1-047313; P1-047307; P1-047312; P1-047314;
P1-047318; P1-047320; P1-047311; P1-047308; P1-047319; P1-047317
HCDR1

<400> SEQUENCE: 93

Ile Tyr Val Ile Ser
1 5

<210> SEQ ID NO 94
<211> LENGTH: 17
<212> TYPE: PRT
<213> ORGANISM: Artificial Sequence
<220> FEATURE:
<223> OTHER INFORMATION: P1-047313 HCDR2

<400> SEQUENCE: 94

Gly Ile Ile Pro Leu Phe Gly Thr Pro Asn Tyr Ala Gln Arg Phe Gln
1 5 10 15

Asp

<210> SEQ ID NO 95
<211> LENGTH: 16
<212> TYPE: PRT
<213> ORGANISM: Artificial Sequence
<220> FEATURE:
<223> OTHER INFORMATION: P1-047313; P1-047307; P1-047312; P1-047314;
P1-047318; P1-047320; P1-047311; P1-047308; P1-047319; P1-047317
HCDR3

<400> SEQUENCE: 95

Gly His Gly Pro Gly Ser Ser His Tyr Ser Tyr Tyr Gly Leu Asp Val
1 5 10 15

<210> SEQ ID NO 96
<211> LENGTH: 9
<212> TYPE: PRT
<213> ORGANISM: Artificial Sequence
<220> FEATURE:
<223> OTHER INFORMATION: P1-047313; P1-047299 LCDR3

<400> SEQUENCE: 96

Gln Gln Tyr Asn Ser Tyr Pro Trp Thr
1 5

<210> SEQ ID NO 97
<211> LENGTH: 17
<212> TYPE: PRT
<213> ORGANISM: Artificial Sequence
<220> FEATURE:
<223> OTHER INFORMATION: P1-047307; P1-047312; P1-047314; P1-047318;
P1-047320; P1-047317 HCDR2

<400> SEQUENCE: 97

Gly Ile Ile Pro Leu Phe Gly Thr Pro Asn Tyr Ala Gln Gln Phe Gln
1 5 10 15

Asp

<210> SEQ ID NO 98
<211> LENGTH: 17
<212> TYPE: PRT
<213> ORGANISM: Artificial Sequence
<220> FEATURE:
<223> OTHER INFORMATION: P1-047311 HCDR2

<400> SEQUENCE: 98

Gly Ile Ile Pro Leu Phe Gly Thr Ala Asn Tyr Ala Gln Gln Phe Gln 1 5 10 15

Asp

<210> SEQ ID NO 99
<211> LENGTH: 5
<212> TYPE: PRT
<213> ORGANISM: Artificial Sequence
<220> FEATURE:
<223> OTHER INFORMATION: P1-047294; P1-047290; P1-047291; P1-047296; P1-047297; P1-047300; P1-047302 HCDR1

<400> SEQUENCE: 99

Arg His Ala Ile Ser
1 5

<210> SEQ ID NO 100
<211> LENGTH: 17
<212> TYPE: PRT
<213> ORGANISM: Artificial Sequence
<220> FEATURE:
<223> OTHER INFORMATION: P1-047294 HCDR2

<400> SEQUENCE: 100

Gly Ile Ile Pro Leu Phe Gly Thr Ala Asn Tyr Ala Gln Glu Phe Gln
1 5 10 15

Gly

<210> SEQ ID NO 101
<211> LENGTH: 18
<212> TYPE: PRT
<213> ORGANISM: Artificial Sequence
<220> FEATURE:
<223> OTHER INFORMATION: P1-047294; P1-047291; P1-047296; P1-047297; P1-047300; P1-047302 HCDR3

<400> SEQUENCE: 101

Ser Tyr Phe Tyr Gly Ser Gly Ser Ser Asn Tyr Tyr Tyr Tyr Gly Leu
1 5 10 15

Asp Val

<210> SEQ ID NO 102
<211> LENGTH: 17
<212> TYPE: PRT
<213> ORGANISM: Artificial Sequence
<220> FEATURE:
<223> OTHER INFORMATION: P1-047290; P1-047291; P1-047296; P1-047297; P1-047300; P1-047302; P1-047308; P1-047319 HCDR2

<400> SEQUENCE: 102

Gly Ile Ile Pro Leu Phe Gly Thr Ala Asn Tyr Ala Gln Lys Phe Gln
1 5 10 15

Gly

<210> SEQ ID NO 103
<211> LENGTH: 9
<212> TYPE: PRT
<213> ORGANISM: Artificial Sequence
<220> FEATURE:
<223> OTHER INFORMATION: P1-047296; P1-047328 LCDR3

<400> SEQUENCE: 103

Gln Gln Tyr Asn Ser Tyr Pro Ile Thr
1 5

<210> SEQ ID NO 104
<211> LENGTH: 17
<212> TYPE: PRT
<213> ORGANISM: Artificial Sequence
<220> FEATURE:
<223> OTHER INFORMATION: P1-047292 HCDR2

<400> SEQUENCE: 104

Gly Ile Ile Pro Ile Phe Ser Thr Gly Asn Tyr Ala Gln Lys Phe Gln
1 5 10 15

Gly

<210> SEQ ID NO 105
<211> LENGTH: 17
<212> TYPE: PRT
<213> ORGANISM: Artificial Sequence
<220> FEATURE:
<223> OTHER INFORMATION: P1-047292 HCDR3

<400> SEQUENCE: 105

Ser Thr Arg Val Arg Gly Val Ser His Tyr Tyr Tyr Tyr Gly Leu Asp
1 5 10 15

Val

<210> SEQ ID NO 106
<211> LENGTH: 5
<212> TYPE: PRT
<213> ORGANISM: Artificial Sequence
<220> FEATURE:
<223> OTHER INFORMATION: P1-047322 HCDR1

<400> SEQUENCE: 106

Ser Tyr Ala Phe Thr
1 5

<210> SEQ ID NO 107
<211> LENGTH: 17
<212> TYPE: PRT
<213> ORGANISM: Artificial Sequence
<220> FEATURE:
<223> OTHER INFORMATION: P1-047322 HCDR2

<400> SEQUENCE: 107

Gly Ile Ile Pro Ile Phe Arg Thr Ala Asn Tyr Ala Gln Lys Phe Gln
1 5 10 15

Gly

<210> SEQ ID NO 108
<211> LENGTH: 18
<212> TYPE: PRT
<213> ORGANISM: Artificial Sequence
<220> FEATURE:
<223> OTHER INFORMATION: P1-047322 HCDR3

<400> SEQUENCE: 108

Ser His Phe Ser Gly Ser Gly Ser Ser His Tyr Tyr Tyr Tyr Gly Met
1 5 10 15

His Val

<210> SEQ ID NO 109
<211> LENGTH: 5
<212> TYPE: PRT
<213> ORGANISM: Artificial Sequence
<220> FEATURE:
<223> OTHER INFORMATION: P1-047310 HCDR1

<400> SEQUENCE: 109

Arg Tyr Ala Ile Ser
1 5

<210> SEQ ID NO 110
<211> LENGTH: 17
<212> TYPE: PRT
<213> ORGANISM: Artificial Sequence
<220> FEATURE:
<223> OTHER INFORMATION: P1-047310 HCDR2

<400> SEQUENCE: 110

Gly Ile Ile Pro Ile Phe Gly Thr Ser Asn Tyr Ala Gln Lys Phe Gln
1 5 10 15

Gly

<210> SEQ ID NO 111
<211> LENGTH: 16
<212> TYPE: PRT
<213> ORGANISM: Artificial Sequence
<220> FEATURE:
<223> OTHER INFORMATION: P1-047310 HCDR3

<400> SEQUENCE: 111

Gly Gly Asn Ser Trp Thr Thr Ser Leu Tyr Tyr Tyr Gly Met Asp Val
1 5 10 15

<210> SEQ ID NO 112
<211> LENGTH: 5
<212> TYPE: PRT
<213> ORGANISM: Artificial Sequence
<220> FEATURE:
<223> OTHER INFORMATION: P1-047299; P1-047301 HCDR1

<400> SEQUENCE: 112

Arg Tyr Ala Phe Ser
1 5

<210> SEQ ID NO 113
<211> LENGTH: 17
<212> TYPE: PRT
<213> ORGANISM: Artificial Sequence
<220> FEATURE:
<223> OTHER INFORMATION: P1-047299; P1-047301 HCDR2

<400> SEQUENCE: 113

Gly Ile Ile Pro Ile Phe Gly Thr Pro Asn Tyr Ala Gln Lys Phe Gln
1 5 10 15

Gly

<210> SEQ ID NO 114
<211> LENGTH: 18
<212> TYPE: PRT
<213> ORGANISM: Artificial Sequence
<220> FEATURE:
<223> OTHER INFORMATION: P1-047299 HCDR3

<400> SEQUENCE: 114

Ser His Phe Tyr Gly Ser Gly Ser Ser His Phe Tyr Tyr Tyr Gly Met
1 5 10 15

His Val

<210> SEQ ID NO 115

<211> LENGTH: 18
<212> TYPE: PRT
<213> ORGANISM: Artificial Sequence
<220> FEATURE:
<223> OTHER INFORMATION: P1-047301 HCDR3

<400> SEQUENCE: 115

Ser His Phe Tyr Gly Ser Gly Ser Ser Asn Tyr Tyr Tyr Tyr Gly Leu
1 5 10 15

Asp Val

<210> SEQ ID NO 116
<211> LENGTH: 17
<212> TYPE: PRT
<213> ORGANISM: Artificial Sequence
<220> FEATURE:
<223> OTHER INFORMATION: P1-047289 HCDR2

<400> SEQUENCE: 116

Gly Ile Ile Pro Ile Phe Gly Thr Ala Asp Ser Ala Gln Lys Phe Gln
1 5 10 15

Gly

<210> SEQ ID NO 117
<211> LENGTH: 17
<212> TYPE: PRT
<213> ORGANISM: Artificial Sequence
<220> FEATURE:
<223> OTHER INFORMATION: P1-047289 HCDR3

<400> SEQUENCE: 117

Thr Pro Arg Tyr Arg Gly Ser Ser His His Tyr Phe Tyr Ala Leu Gly
1 5 10 15

Val

<210> SEQ ID NO 118
<211> LENGTH: 9
<212> TYPE: PRT
<213> ORGANISM: Artificial Sequence
<220> FEATURE:
<223> OTHER INFORMATION: P1-047289 LCDR3

<400> SEQUENCE: 118

Gln Gln Phe Asn Ser Tyr Pro Leu Thr
1 5

<210> SEQ ID NO 119
<211> LENGTH: 17
<212> TYPE: PRT
<213> ORGANISM: Artificial Sequence
<220> FEATURE:
<223> OTHER INFORMATION: P1-047306 HCDR2

<400> SEQUENCE: 119

Gly Ile Ile Pro Ile Phe Gly Thr Ala Asn Tyr Ala Gln Lys Phe Gln
1 5 10 15

Gly

<210> SEQ ID NO 120
<211> LENGTH: 16
<212> TYPE: PRT
<213> ORGANISM: Artificial Sequence
<220> FEATURE:
<223> OTHER INFORMATION: P1-047306 HCDR3

```
<400> SEQUENCE: 120

Ala Ser Gln Ser Arg Ser Ser Asn Tyr Tyr Tyr Tyr Gly Leu Asp Val
1               5                   10                  15


<210> SEQ ID NO 121
<211> LENGTH: 330
<212> TYPE: PRT
<213> ORGANISM: Homo Sapien

<400> SEQUENCE: 121

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 122
<211> LENGTH: 330
```

<212> TYPE: PRT
<213> ORGANISM: Artificial Sequence
<220> FEATURE:
<223> OTHER INFORMATION: IgG1.1f HC Constant Region

<400> SEQUENCE: 122

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 123
<211> LENGTH: 330
<212> TYPE: PRT
<213> ORGANISM: Artificial Sequence
<220> FEATURE:
<223> OTHER INFORMATION: IgG1.3f HC Constant Region

<400> SEQUENCE: 123

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 124
<211> LENGTH: 330
<212> TYPE: PRT
<213> ORGANISM: Artificial Sequence
<220> FEATURE:
<223> OTHER INFORMATION: IgG1-Aba HC Constant Region

<400> SEQUENCE: 124

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Ser Pro Pro Ser
            100                 105                 110

Pro Ala Pro Glu Leu Leu Gly Gly Ser Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 125
<211> LENGTH: 330
<212> TYPE: PRT
<213> ORGANISM: Artificial Sequence
<220> FEATURE:
<223> OTHER INFORMATION: IgG4-Aba HC Constant Region

<400> SEQUENCE: 125

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Pro Lys Ser Cys Asp Lys Thr His Thr Ser Pro Pro Ser
            100                 105                 110

Pro Ala Pro Glu Leu Leu Gly Gly Ser Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 126
<211> LENGTH: 107
<212> TYPE: PRT
<213> ORGANISM: Homo Sapien

<400> SEQUENCE: 126

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
```

```
            100                 105


<210> SEQ ID NO 127
<211> LENGTH: 5
<212> TYPE: PRT
<213> ORGANISM: Artificial Sequence
<220> FEATURE:
<223> OTHER INFORMATION: LSPGK (C-terminal end of heavy chain)

<400> SEQUENCE: 127

Leu Ser Pro Gly Lys
1               5


<210> SEQ ID NO 128
<211> LENGTH: 4
<212> TYPE: PRT
<213> ORGANISM: Artificial Sequence
<220> FEATURE:
<223> OTHER INFORMATION: LSPG (C-terminal end of heavy chain)

<400> SEQUENCE: 128

Leu Ser Pro Gly
1


<210> SEQ ID NO 129
<211> LENGTH: 5
<212> TYPE: PRT
<213> ORGANISM: Artificial Sequence
<220> FEATURE:
<223> OTHER INFORMATION: Linker

<400> SEQUENCE: 129

Pro Val Gly Val Val
1               5


<210> SEQ ID NO 130
<211> LENGTH: 126
<212> TYPE: PRT
<213> ORGANISM: Artificial Sequence
<220> FEATURE:
<223> OTHER INFORMATION: P1-047323; P1-047328 VH

<400> SEQUENCE: 130

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ile Asn Ser
            20                  25                  30

Glu Ala Ile Asn Trp Val Arg Gln Ala Pro Gly Gln Gly Leu Glu Trp
        35                  40                  45

Met Gly Gly Ile Ile Pro Ile Phe Asp Ile Thr Asn Tyr Ala Gln Lys
    50                  55                  60

Phe Gln Gly Arg Val Thr Ile Thr Ala Asp Glu Ser Met Ser Thr Ala
65                  70                  75                  80

Tyr Met Glu Leu Ser Ser Leu Arg Ser Glu Asp Thr Ala Val Tyr Tyr
                85                  90                  95

Cys Ala Lys Thr Tyr Tyr Asp Ile Leu Thr Tyr His Tyr His Tyr Gly
            100                 105                 110

Met Asp Val Trp Gly Gln Gly Thr Thr Val Thr Val Ser Ser
        115                 120                 125


<210> SEQ ID NO 131
<211> LENGTH: 107
<212> TYPE: PRT
```

<213> ORGANISM: Artificial Sequence
<220> FEATURE:
<223> OTHER INFORMATION: P1-047323 VL

<400> SEQUENCE: 131

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys
            100                 105

<210> SEQ ID NO 132
<211> LENGTH: 107
<212> TYPE: PRT
<213> ORGANISM: Artificial Sequence
<220> FEATURE:
<223> OTHER INFORMATION: P1-047328 VL

<400> SEQUENCE: 132

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105

<210> SEQ ID NO 133
<211> LENGTH: 126
<212> TYPE: PRT
<213> ORGANISM: Artificial Sequence
<220> FEATURE:
<223> OTHER INFORMATION: P1-047263; P1-047265 VH

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Thr Tyr
            20                  25                  30

Asp Ile Asn Trp Val Arg Gln Ala Thr Gly Gln Gly Leu Glu Trp Met
        35                  40                  45

Gly Trp Val Asn Pro Asn Ser Gly Asn Thr Gly Tyr Ala Gln Lys Phe
    50                  55                  60

```
Gln Asp Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Asp Gly Leu Asn Met Val Arg Gly Val His Asn Tyr Tyr Gly
            100                 105                 110

Met Asp Val Trp Gly Gln Gly Thr Thr Val Thr Val Ser Ser
        115                 120                 125


<210> SEQ ID NO 134
<211> LENGTH: 107
<212> TYPE: PRT
<213> ORGANISM: Artificial Sequence
<220> FEATURE:
<223> OTHER INFORMATION: P1-047263 VL

<400> SEQUENCE: 134

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Lys Leu Glu Ile Lys
            100                 105


<210> SEQ ID NO 135
<211> LENGTH: 107
<212> TYPE: PRT
<213> ORGANISM: Artificial Sequence
<220> FEATURE:
<223> OTHER INFORMATION: P1-047317 VL

<400> SEQUENCE: 135

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Leu
                85                  90                  95

Thr Phe Gly Gly Gly Thr Lys Val Glu Ile Lys
            100                 105


<210> SEQ ID NO 136
<211> LENGTH: 6
<212> TYPE: PRT
```

<213> ORGANISM: Artificial Sequence
<220> FEATURE:
<223> OTHER INFORMATION: P1-047323; P1-047328 HCDR1

<400> SEQUENCE: 136

Asn Ser Glu Ala Ile Asn
1               5

<210> SEQ ID NO 137
<211> LENGTH: 17
<212> TYPE: PRT
<213> ORGANISM: Artificial Sequence
<220> FEATURE:
<223> OTHER INFORMATION: P1-047323; P1-047328 HCDR2

<400> SEQUENCE: 137

Gly Ile Ile Pro Ile Phe Asp Ile Thr Asn Tyr Ala Gln Lys Phe Gln
1               5                   10                  15

Gly

<210> SEQ ID NO 138
<211> LENGTH: 16
<212> TYPE: PRT
<213> ORGANISM: Artificial Sequence
<220> FEATURE:
<223> OTHER INFORMATION: P1-047323; P1-047328 HCDR3

<400> SEQUENCE: 138

Thr Tyr Tyr Asp Ile Leu Thr Tyr His Tyr His Tyr Gly Met Asp Val
1               5                   10                  15

<210> SEQ ID NO 139
<211> LENGTH: 9
<212> TYPE: PRT
<213> ORGANISM: Artificial Sequence
<220> FEATURE:
<223> OTHER INFORMATION: P1-047323 LCDR3

<400> SEQUENCE: 139

Gln Gln Phe Asn Ser Tyr Pro Ile Thr
1               5

<210> SEQ ID NO 140
<211> LENGTH: 5
<212> TYPE: PRT
<213> ORGANISM: Artificial Sequence
<220> FEATURE:
<223> OTHER INFORMATION: P1-047263; P1-047265 HCDR1

<400> SEQUENCE: 140

Thr Tyr Asp Ile Asn
1               5

<210> SEQ ID NO 141
<211> LENGTH: 17
<212> TYPE: PRT
<213> ORGANISM: Artificial Sequence
<220> FEATURE:
<223> OTHER INFORMATION: P1-047263; P1-047265 HCDR2

<400> SEQUENCE: 141

Trp Val Asn Pro Asn Ser Gly Asn Thr Gly Tyr Ala Gln Lys Phe Gln
1               5                   10                  15

Asp

<210> SEQ ID NO 142
<211> LENGTH: 17
<212> TYPE: PRT
<213> ORGANISM: Artificial Sequence
<220> FEATURE:
<223> OTHER INFORMATION: P1-047263; P1-047265 HCDR3

<400> SEQUENCE: 142

Asp Gly Leu Asn Met Val Arg Gly Val His Asn Tyr Tyr Gly Met Asp
1               5                   10                  15

Val

<210> SEQ ID NO 143
<211> LENGTH: 9
<212> TYPE: PRT
<213> ORGANISM: Artificial Sequence
<220> FEATURE:
<223> OTHER INFORMATION: P1-047263 LCDR3

<400> SEQUENCE: 143

Gln Gln Tyr Asn Ser Tyr Pro Pro Thr
1               5

<210> SEQ ID NO 144
<211> LENGTH: 375
<212> TYPE: DNA
<213> ORGANISM: Artificial Sequence
<220> FEATURE:
<223> OTHER INFORMATION: P1-047239 VH

<400> SEQUENCE: 144
caggtgcagc tggtggagtc tgggggaggc gtggtccagc ctgggaggtc cctgagactc     60
tcctgtgcag ctactgaatt caccttcagt aactatggca tgcactgggt ccgccaggct    120
ccaggcaagg ggctggagtg ggtggcagtt atatggtatg atggaagtaa taaatactat    180
gcagactccg tgaagggccg cttcaccatc tccagagaca attccaagaa cacgctgtat    240
ctgcaattga acagcctgag cgccgaggac tcggctgtgt attactgtgc gagagatggg    300
aggcattact atggttcgac ctcctacttc ggcatggacg tctggggcca agggaccacg    360
gtcaccgtct cctca                                                      375

<210> SEQ ID NO 145
<211> LENGTH: 366
<212> TYPE: DNA
<213> ORGANISM: Artificial Sequence
<220> FEATURE:
<223> OTHER INFORMATION: P1-047246; P1-047247 VH

<400> SEQUENCE: 145
caggtgcagc tgcaggagtc gggcccagga ctggtgaagc cttcggagac cctgtccctc     60
acctgcactg tctctggtgg ctccatcact aattactact ggacctggat ccggcagccc    120
ccagggaagg gactggagtg gattgggtat atctatgaca gtgggtacac caactacaac    180
ccctccctca agagtcgagt caccttatca atagacacgt ccaagaacca gttctccctg    240
aagctgagct ctgtgaccgc tgcggacacg gccgtttatt actgtgcgag aggggttcta    300
tggttcgggg agttattacc tctccttgac tactggggcc agggaaccct ggtcaccgtc    360
tcctca                                                               366

<210> SEQ ID NO 146
<211> LENGTH: 372
<212> TYPE: DNA

<213> ORGANISM: Artificial Sequence
<220> FEATURE:
<223> OTHER INFORMATION: P1-047248 VH

<400> SEQUENCE: 146
caggtgcagc tgcaggagtc gggcccagga ctggtgaagc cttcggagac cctgtccctc 60
acctgcactg tgtctggtgg ctccatcagt agttcctact ggagctgggt ccggcagccc 120
ccagggaagg gactggagtg gattggatat acccattaca gtgggatcag caactacaac 180
ccctccctca agagtcgagt caccatatca gtagacacgt ccaagaacca gttctccctg 240
aagctgagct ctgtgaccgc tgcggacacg gccgtgtatt actgtgcgag agaagggtac 300
gatattttga ctggttatga gtactacggt atggacgtct ggggccaagg gaccacggtc 360
accgtctcct ca 372

<210> SEQ ID NO 147
<211> LENGTH: 378
<212> TYPE: DNA
<213> ORGANISM: Artificial Sequence
<220> FEATURE:
<223> OTHER INFORMATION: P1-047323; P1-047328 VH

<400> SEQUENCE: 147
caggtgcagc tggtgcagtc tggggctgag gtgaagaagc ctgggtcctc ggtgaaggtc 60
tcctgcaagg cttctggagg caccttcatc aatagcgaag ctatcaactg ggtgcgacag 120
gcccctggac aagggcttga gtggatggga gggatcatcc ctatctttga cattacaaac 180
tacgcacaga agttccaggg cagagtcacg attaccgcgg acgaatccat gagcacagcc 240
tacatggagc tgagcagcct gagatctgag gacacggccg tgtattactg tgcgaagacg 300
tattacgata ttttgactta tcactatcac tacggtatgg acgtctgggg ccaagggacc 360
acggtcaccg tctcctca 378

<210> SEQ ID NO 148
<211> LENGTH: 369
<212> TYPE: DNA
<213> ORGANISM: Artificial Sequence
<220> FEATURE:
<223> OTHER INFORMATION: P1-047334 VH

<400> SEQUENCE: 148
caggtgcagc tggtgcagtc tggggctgag gtgaagaggc ctgggtcctc tgtgaaggtc 60
tcctgcaagg cttctggagg caccttcagt agttccgcta tcagctgggt gcgacaggcc 120
cctggacaag ggcttgagtg gatgggaggg atcatcccta tctttggtac aacaaacggc 180
gcacagaagt tccagggcag agtcacgatt accgcggacg aatccacgag cacagcctac 240
atggagctga gcagcctgag atctgaggac acggccgtgt attactgtgc ggctatggtt 300
cggggaaatt acttctactt ctacggtatg gacgtctggg gccaagggac cacggtcacc 360
gtctcctca 369

<210> SEQ ID NO 149
<211> LENGTH: 378
<212> TYPE: DNA
<213> ORGANISM: Artificial Sequence
<220> FEATURE:
<223> OTHER INFORMATION: P1-047263; P1-047265 VH

<400> SEQUENCE: 149
caggtgcagc tggtgcagtc tggggctgag gtgaagaagc ctggggcctc agtgaaggtc 60

```
tcctgcaagg cttctggata caccttcccc acttatgata tcaactgggt gcgacaggcc    120

actggacaag ggcttgagtg gatgggatgg gtgaacccta acagtggtaa cacaggctat    180

gcacagaagt tccaggacag agtcaccatg accaggaaca cctccataag cacagcctac    240

atggagctga gcagcctgag atctgaggac acggccgtgt attactgtgc gagtgacggc    300

cttaatatgg ttcggggagt tcacaactac tacggtatgg acgtctgggg ccaagggacc    360

acggtcaccg tctcctca                                                  378
```

<210> SEQ ID NO 150
<211> LENGTH: 378
<212> TYPE: DNA
<213> ORGANISM: Artificial Sequence
<220> FEATURE:
<223> OTHER INFORMATION: P1-047289 VH

<400> SEQUENCE: 150

```
caggtgcagc tggtgcagtc tggggctgag gtgaagaagc ctgggtcctc ggtgaaggtc     60

tcctgcaagg cttctggagg caccttcagc agctctgcta tcagctgggt gcgacaggcc    120

cctggacaag ggcttgagtg gatgggagga atcatcccta tcttcggtac agcagactcc    180

gcacagaagt tccagggcag agtcacgatt accgcggacg agtccacgag cacagcctac    240

atggaattga acagcctgag atctgaggac acggccgttt actactgtgc gttcacaccc    300

cggtatcgtg ggagctccca ccactacttc tacgctttgg gcgtctgggg ccaagggacc    360

acggtcaccg tctcctca                                                  378
```

<210> SEQ ID NO 151
<211> LENGTH: 381
<212> TYPE: DNA
<213> ORGANISM: Artificial Sequence
<220> FEATURE:
<223> OTHER INFORMATION: P1-047290; P1-047291; P1-047296; P1-047297 VH

<400> SEQUENCE: 151

```
caggtgcagc tggtgcagtc tggggctgag gtgaagaagc ctgggtcctc ggtgaaggtc     60

tcctgcaagg cttctggagg caccttcaac agacatgcta tcagctgggt gcgacaggcc    120

cctggacaag ggcttgagtg gatgggaggg atcatccctc tctttggtac agcaaactac    180

gcgcagaagt tccagggcag agtcacgatt gccgcggacg aacccacgag cacaacctac    240

atggagctgc gcagcctgag atctgaggac acggccgtgt attactgtgc gagttcgtat    300

ttctatggtt cggggagttc caactactac tactacggtt tggacgtctg gggccaaggg    360

accacggtca ccgtctcctc a                                              381
```

<210> SEQ ID NO 152
<211> LENGTH: 378
<212> TYPE: DNA
<213> ORGANISM: Artificial Sequence
<220> FEATURE:
<223> OTHER INFORMATION: P1-047292 VH

<400> SEQUENCE: 152

```
caggtgcagc tggtgcagtc tggggctgag gtgaagaagc ctgggtcctc ggtgaaggtc     60

tcctgcaagg cttctggagg caccttcagc agctctgcta tcagctgggt gcgacaggcc    120

cctggacaag ggcttgagtg gatgggaggg atcatcccta tctttagtac aggaaactac    180

gcacagaagt tccagggcag agtcacgatt accgcggacg aatccacgaa cacagcctac    240
```

atggatctga gcagcctgag atctgaggac acggccgtgt attactgtgc gagatccact 300
agggttcggg gagtttccca ctactactac tacggtttgg acgtctgggg ccaagggacc 360
acggtcaccg tctcctca 378

<210> SEQ ID NO 153
<211> LENGTH: 381
<212> TYPE: DNA
<213> ORGANISM: Artificial Sequence
<220> FEATURE:
<223> OTHER INFORMATION: P1-047294 VH

<400> SEQUENCE: 153
caggtgcagc tggtgcagtc tggggctgag gtgaagaagc ctgggtcctc ggtgaaggtc 60
tcctgcaagg cttctggagg caccttcaac agacatgcta tcagctgggt gcgacaggcc 120
cctggacaag ggcttgagtg gatgggaggg atcatccctc tctttggtac agcaaactac 180
gcgcaggagt tccagggcag agtcacgatt gccgcggacg aacccacgag cacaacctac 240
atggagctgc gcagcctgag atctgaggac acggccgtgt attactgtgc gagttcgtat 300
ttctatggtt cggggagttc caactactac tactacggtt tggacgtctg gggccaaggg 360
accacggtca ccgtctcctc a 381

<210> SEQ ID NO 154
<211> LENGTH: 381
<212> TYPE: DNA
<213> ORGANISM: Artificial Sequence
<220> FEATURE:
<223> OTHER INFORMATION: P1-047299 VH

<400> SEQUENCE: 154
caggtgcagc tggtgcagtc tggggctgag gtgaagaagc ctgggtcctc ggtgaaggtc 60
tcctgcaagg cttctggagg caccttcaac agatatgctt tcagctgggt gcgacaggcc 120
cctggacaag ggcttgagtg gatgggaggg atcatcccta tctttggtac acccaactac 180
gcacagaagt tccagggcag agtcacgatt accgcggacg aatccacgag cacggcctac 240
atggagctga gcagcctgat atctgaggac acggccgtgt attactgtgc gagcagccat 300
ttctatggtt cggggagttc ccacttttac tactacggta tgcacgtctg gggccaaggg 360
accacggtca ccgtctcctc a 381

<210> SEQ ID NO 155
<211> LENGTH: 381
<212> TYPE: DNA
<213> ORGANISM: Artificial Sequence
<220> FEATURE:
<223> OTHER INFORMATION: P1-047300 VH

<400> SEQUENCE: 155
caggtgcagc tggtgcagtc tggggctgag gtgaagaagc ctgggtcctc ggtgaaggtc 60
tcctgcaagg cttctggagg caccttcaac agacatgcta tcagctgggt gcgacaggcc 120
cctggacaag ggcttgagtg gatgggaggg atcatccctc tctttggtac agcaaactac 180
gcgcagaagt tccagggcag agtcacgatt gccgcggacg aacccacgag cacaacctac 240
atggagctgc gcagcctgag atctgaggac acggccgtgt attactgtgc aagttcgtat 300
ttctatggtt cggggagttc caactactac tactacggtt tggacgtctg gggccaaggg 360
accacggtca ccgtctcctc a 381

<210> SEQ ID NO 156
<211> LENGTH: 381
<212> TYPE: DNA
<213> ORGANISM: Artificial Sequence
<220> FEATURE:
<223> OTHER INFORMATION: P1-047301 VH

<400> SEQUENCE: 156
caggtgcagc tggtgcagtc tggggctgag gtgaagaagc ctgggtcctc ggtgaaggtc 60
tcctgcaagg cttctggagg caccttcaac agatatgctt tcagctgggt gcgacaggcc 120
cctggacaag ggcttgagtg gatgggaggg atcatcccta tctttggtac acccaactac 180
gcacagaagt tccagggcag agtcacgatt accgcggacg aatccacgag cacggcctac 240
atggagctga gcagcctgat atctgaggac acggccgtgt attactgtgc gagcagccat 300
ttctatggtt cggggagttc caactactac tactacggtt tggacgtctg gggccaaggg 360
accacggtca ccgtctcctc a 381

<210> SEQ ID NO 157
<211> LENGTH: 381
<212> TYPE: DNA
<213> ORGANISM: Artificial Sequence
<220> FEATURE:
<223> OTHER INFORMATION: P1-047302 VH

<400> SEQUENCE: 157
caggtgcagc tggtgcagtc tggggctgag gtgaagaagc ctgggtcctc ggtgaaggtc 60
tcctgcaagg cttctggagg caccttcaac agacatgcta tcagctgggt gcgacaggcc 120
cctggacaag ggcttgagtg gatgggaggg atcatccctc tctttggtac agcaaactac 180
gcgcagaagt tccagggcag agtcacgatt gccgcggacg aacccacgag cacaacctac 240
atggagctgc gcagcctgag atctgaggac acggccgtgt attactgtgc gagttcgtat 300
ttctatggtt cggggagttc caactattac tactacggtt tggacgtctg gggccaaggg 360
accacggtca ccgtctcctc a 381

<210> SEQ ID NO 158
<211> LENGTH: 378
<212> TYPE: DNA
<213> ORGANISM: Artificial Sequence
<220> FEATURE:
<223> OTHER INFORMATION: P1-047305 VH

<400> SEQUENCE: 158
caggtgcagc tggtgcagtc tggggctgag gtgaagaagc ctgggtcctc ggtgaaggtc 60
tcctgcaaga cttctggagg caccttcagc agctctgctg tcagctgggt gcgacaggcc 120
cctggacaag ggcttgaatg gatgggagga atcacccccta tttttggtac agcagactac 180
gcacagaagt tccagggcag agtcacgatt accgcggacg catccacgag cacaggttat 240
atggaactga gcagcctgag atctgaggac acggccgttt actactgtgc gttcacaccc 300
cgatatcgtg ggagctccca ccactactac tacgctttgg gcgtctgggg ccaagggacc 360
acggtcaccg tctcctca 378

<210> SEQ ID NO 159
<211> LENGTH: 375
<212> TYPE: DNA
<213> ORGANISM: Artificial Sequence
<220> FEATURE:
<223> OTHER INFORMATION: P1-047306 VH

<400> SEQUENCE: 159
caggtgcagc tggtgcagtc tggggctgag gtgaagaagc ctgggtcctc ggtgaaggtc 60
tcctgcaagg cttctggagg caccttcagc agctctgcta tcagctgggt acgacaggcc 120
cctggacaag ggcttgagtg gatgggaggg atcatcccta tctttggtac agcgaactac 180
gcacagaagt tccagggcag agtcacgatt accgcggacg aatccacgag cacagcctac 240
atggagctga gcagcctgag atctgaggac acggccgtgt attactgtgc gagagcctcc 300
caaagcagga gctcgaacta ctactactac ggtctggacg tctggggcca agggaccacg 360
gtcaccgtct cctca 375

<210> SEQ ID NO 160
<211> LENGTH: 375
<212> TYPE: DNA
<213> ORGANISM: Artificial Sequence
<220> FEATURE:
<223> OTHER INFORMATION: P1-047307; P1-047312; P1-047314; P1-047317;
P1-047320 VH

<400> SEQUENCE: 160
caggtgcagc tggtgcagtc tggggctgag gtgaagaggc ctgggtcctc ggtgaaggtc 60
tcctgcaagg cttctggagg caccttcagt atctatgtta tcagctgggt gcgacaggcc 120
cctggacaag ggcttgagtg gatgggaggg atcatccctc tctttggtac accaaactac 180
gcacagcagt tccaggacag agtcacgatt accgcggacg aatccacgag gacagcctac 240
atggagctga atagcctgaa atctgaggac acggccgtat attactgtgc gaggggacat 300
ggtccgggga gttcccacta ctcctactac ggtttggacg tctggggcca agggaccacg 360
gtcaccgtct cctca 375

<210> SEQ ID NO 161
<211> LENGTH: 375
<212> TYPE: DNA
<213> ORGANISM: Artificial Sequence
<220> FEATURE:
<223> OTHER INFORMATION: P1-047308; P1-047319 VH

<400> SEQUENCE: 161
caggtgcagc tggtgcagtc tggggctgag gtgaagaggc ctgggtcctc ggtgaaggtc 60
tcctgcaagg cttctggagg caccttcagt atctatgtta tcagctgggt gcgacaggcc 120
cctggacaag ggcttgagtg gatgggaggg atcatccctc tctttggtac agcaaactac 180
gcacagaagt tccagggcag agtcacgatt accgcggacg aatccacgaa tacagcctac 240
atggagctga gtagcctgag atctgaggac acggccgtgt attactgtgc gaggggacat 300
ggtccgggga gttcccacta ctcctactac ggtttggacg tctggggcca agggaccacg 360
gtcaccgtct cctca 375

<210> SEQ ID NO 162
<211> LENGTH: 351
<212> TYPE: DNA
<213> ORGANISM: Artificial Sequence
<220> FEATURE:
<223> OTHER INFORMATION: P1-047309 VH

<400> SEQUENCE: 162
caggtgcagc tggtgcagtc tggggctgag gtgaagaagc ctgggtcctc ggtgaaggtc 60
tcctgcaacc cttctggagg caccttcagc acctacgcta tcagctgggt gcgacaggcc 120
cctggacaag ggcttgagtg gatgggaggg atcaacccta tctttggaac agcaaactac 180
gcacagaagt tccagggcag agtcacaatt accgcggacg aatccacgag tccaggctac 240
ctggagctga gcagcctgag atctgaggac acggccgttt attactgtgc gagaggggga 300
gcagtgggtt ttgcctattg gggccaggga accctggtca ccgtctcctc a 351

<210> SEQ ID NO 163
<211> LENGTH: 375
<212> TYPE: DNA
<213> ORGANISM: Artificial Sequence
<220> FEATURE:
<223> OTHER INFORMATION: P1-047310 VH

<400> SEQUENCE: 163
caggtgcagc tggtgcagtc tggggctgag gtgaagaagc ctgggtcctc ggtgaaggtc 60
tcctgcaagg cttctggagg caccttcagc agatatgcta tcagctgggt gcgacaggcc 120
cctggacaag ggcttgagtg gatgggaggg atcatcccta tctttggtac atcaaactac 180
gcacagaagt tccagggcag agtcacgatt aaagcggacg aatccacgag cacagcctac 240
atggagctga gcagcctgag atctgaggac acggccgtgt attactgtgc gagagggggc 300
aacagctgga ccactagttt gtactactac ggtatggacg tctggggcca agggaccacg 360
gtcaccgtct cctca 375

<210> SEQ ID NO 164
<211> LENGTH: 375
<212> TYPE: DNA
<213> ORGANISM: Artificial Sequence
<220> FEATURE:
<223> OTHER INFORMATION: P1-047311 VH

<400> SEQUENCE: 164
caggtgcagc tggtgcagtc tggggctgag gtgaagaagc ctgggtcctc ggtgaaggtc 60
tcctgcaagg cttctggagg caccttcagt atctatgtta tcagctgggt gcgacaggcc 120
cctggacaag ggcttgagtg gatgggaggg atcatccctc tctttggtac agcaaactac 180
gcacagcagt tccaggacag agtcacgatt accgcggacg aatccacgag gacagcctac 240
atggagctga atagcctgaa atctgaggac acggctgtat attactgtgc gaggggacat 300
ggtccgggga gttcccacta ctcctactac ggtttggacg tctggggcca agggaccacg 360
gtcaccgtct cctca 375

<210> SEQ ID NO 165
<211> LENGTH: 375
<212> TYPE: DNA
<213> ORGANISM: Artificial Sequence
<220> FEATURE:
<223> OTHER INFORMATION: P1-047313 VH

<400> SEQUENCE: 165
caggtgcagc tggtgcagtc tggggctgag gtgaagaggc ctgggtcctc ggtgaaggtc 60
tcctgcaagg cttctggagg caccttcagt atctatgtta tcagctgggt gcgacaggcc 120
cctggacaag ggcttgagtg gatgggaggg atcatccctc tctttggtac accaaactac 180
gcacagcggt tccaggacag agtcacgatt accgcggacg aatccacgag gacagcctac 240
atggagctga gtagcctgag atctgaggac acggccgtgt attactgtgc gaggggacat 300
ggtccgggga gttcccacta ctcctactac ggtttggacg tctggggcca agggaccacg 360
gtcaccgtct cctca 375

<210> SEQ ID NO 166
<211> LENGTH: 375
<212> TYPE: DNA
<213> ORGANISM: Artificial Sequence
<220> FEATURE:
<223> OTHER INFORMATION: P1-047318 VH

<400> SEQUENCE: 166
caggtgcagc tggtgcagtc tggggctgag gtgaagaggc ctgggtcctc ggtgaaggtc 60
tcctgcaagg cttctggagg caccttcagt atctatgtta tcagctgggt ccgacaggcc 120
cctggacaag ggcttgagtg gatgggaggg atcatccctc tctttggtac accaaactac 180
gcacagcagt tccaggacag agtcacgatt accgcggacg aatccacgag gacagcctac 240
atggagctga gtagcctgag atctgaggac acggccgtgt attactgtgc gaggggacat 300
ggtccgggga gttcccacta ctcctactac ggtttggacg tctggggcca agggaccacg 360
gtcaccgtct cctca 375

<210> SEQ ID NO 167

<400> SEQUENCE: 167

000

<210> SEQ ID NO 168
<211> LENGTH: 381
<212> TYPE: DNA
<213> ORGANISM: Artificial Sequence
<220> FEATURE:
<223> OTHER INFORMATION: P1-047322 VH

<400> SEQUENCE: 168
caggtgcagc tggtgcagtc tggggctgag gtgaagaagc ctgggtcctc ggtgaaggtc 60
tcctgcaagt cttctggagg caccttcagc agctatgctt tcacctgggt gcgacaggcc 120
cctggacaag ggcttgagtg gatgggaggg atcatcccta tctttcgtac agcaaactac 180
gcacagaagt tccagggcag agtcacgatt accgcggacg aatccacgag cacagcctac 240
atggagctga gcagcctgag atctgaggac acggccgtgt attactgtgc gagcagccat 300
ttctctggtt cgggaagttc ccactactac tactacggta tgcacgtctg gggccaaggg 360
accacggtca ccgtctcctc a 381

<210> SEQ ID NO 169
<211> LENGTH: 321
<212> TYPE: DNA
<213> ORGANISM: Artificial Sequence
<220> FEATURE:
<223> OTHER INFORMATION: P1-047239; P1-047246 VL

<400> SEQUENCE: 169
gccatccagt tgacccagtc tccatcctcc ctgtctgcat ctgtaggaga cagagtcacc 60
atcacttgcc gggcaagtca gggcattagc agtgctttag cctggtatca gcagaaacca 120
gggaaagctc ctaagctcct gatctatgat gcctccagtt tggaaagtgg ggtcccatca 180
aggttcagcg gcagtggatc tgggacagat ttcactctca ccatcagcag cctgcagcct 240
gaagattttg caacttatta ctgtcaacag tttaatagtt acccgtacac ttttggccag 300
gggaccaagc tggagatcaa a 321

<210> SEQ ID NO 170
<211> LENGTH: 324
<212> TYPE: DNA
<213> ORGANISM: Artificial Sequence
<220> FEATURE:
<223> OTHER INFORMATION: P1-047247 VL

<400> SEQUENCE: 170
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gagaggttca gtggcagtgg gtctgggaca gacttcactc tcaccatcag cagactggag 240
cctgaagatt ttgcagtgta ttactgtcag cagtatggta gctcaccgct cactttcggc 300
ggagggacca aggtggagat caaa 324

<210> SEQ ID NO 171
<211> LENGTH: 321
<212> TYPE: DNA
<213> ORGANISM: Artificial Sequence
<220> FEATURE:
<223> OTHER INFORMATION: P1-047248 VL

<400> SEQUENCE: 171
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcacctac tttcggcgga 300
gggaccaagg tggagatcaa a 321

<210> SEQ ID NO 172
<211> LENGTH: 321
<212> TYPE: DNA
<213> ORGANISM: Artificial Sequence
<220> FEATURE:
<223> OTHER INFORMATION: P1-047323 VL

<400> SEQUENCE: 172
gccatccagt tgacccagtc tccatcctcc ctgtctgcat ctgtaggaga cagagtcacc 60
atcacttgcc gggcaagtca gggcattagc agtgctttag cctggtatca gcagaaacca 120
gggaaagctc ctaagctcct gatctatgat gcctccagtt tggaaagtgg ggtcccatca 180
aggttcagcg gcagtggatc tgggacagat ttcactctca ccatcagcag cctgcagcct 240
gaagattttg caacttatta ctgtcaacag tttaatagtt acccgatcac cttcggccaa 300
gggacacgac tggagattaa a 321

<210> SEQ ID NO 173

<400> SEQUENCE: 173

000

<210> SEQ ID NO 174
<211> LENGTH: 321
<212> TYPE: DNA
<213> ORGANISM: Artificial Sequence
<220> FEATURE:
<223> OTHER INFORMATION: P1-047328 VL

<400> SEQUENCE: 174
gccatccagt tgacccagtc tccatcctcc ctgtctgcat ctgtaggaga cagagtcacc 60
atcacttgcc gggcaagtca gggcattagc agtgctttag cctggtatca gcagaaacca 120
gggaaagctc ctaagctcct gatctatgat gcctccagtt tggaaagtgg ggtcccatca 180
aggttcagcg gcagtggatc tgggacagat ttcactctca ccatcagcag cctgcagcct 240
gaagattttg caacttatta ctgccaacag tataatagtt acccgatcac cttcggccaa 300
gggacacgac tggagattaa a 321

<210> SEQ ID NO 175
<211> LENGTH: 321
<212> TYPE: DNA
<213> ORGANISM: Artificial Sequence
<220> FEATURE:
<223> OTHER INFORMATION: P1-047334 VL

<400> SEQUENCE: 175
gccatccagt tgacccagtc tccatcctcc ctgtctgcat ctgtaggaga cagagtcacc 60
atcacttgcc gggcaagtca gggcattagc agtgctttag cctggtatca gcagaaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgctcac tttcggcgga 300
gggaccaagg tggagatcaa a 321

<210> SEQ ID NO 176
<211> LENGTH: 321
<212> TYPE: DNA
<213> ORGANISM: Artificial Sequence
<220> FEATURE:
<223> OTHER INFORMATION: P1-047265; P1-047290; P1-047292; P1-047301;
P1-047305; P1-047308; P1-047314 VL

<400> SEQUENCE: 176
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgtacac ttttggccag 300
gggaccaagc tggagatcaa a 321

<210> SEQ ID NO 177
<211> LENGTH: 321
<212> TYPE: DNA
<213> ORGANISM: Artificial Sequence
<220> FEATURE:
<223> OTHER INFORMATION: P1-047263 VL

<400> SEQUENCE: 177
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt accctccgac ttttggccag 300
gggaccaagc tggagatcaa a 321

<210> SEQ ID NO 178

<400> SEQUENCE: 178

000

<210> SEQ ID NO 179
<211> LENGTH: 321
<212> TYPE: DNA
<213> ORGANISM: Artificial Sequence
<220> FEATURE:
<223> OTHER INFORMATION: P1-047291 VL

<400> SEQUENCE: 179
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gatgattttg caacttatta ctgccaacag tataatagtt acccgtacac ttttggccag 300
gggaccaagc tggagatcaa a 321

<210> SEQ ID NO 180
<211> LENGTH: 321
<212> TYPE: DNA
<213> ORGANISM: Artificial Sequence
<220> FEATURE:
<223> OTHER INFORMATION: P1-047294 VL

<400> SEQUENCE: 180
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcggtggatc tgggacagat ttcactctca ccatcagcag cctgcagcct 240
gaagattttg caacttatta ctgccaacag tataatagtt acccgctcac tttcggcgga 300
gggaccaagg tggagatcaa a 321

<210> SEQ ID NO 181
<211> LENGTH: 321
<212> TYPE: DNA
<213> ORGANISM: Artificial Sequence
<220> FEATURE:
<223> OTHER INFORMATION: P1-047297 VL

<400> SEQUENCE: 181
gacatccaga tgacccagtc tccaacctca ctgtctgcat ctgtaggaga cagagtcacc 60
atcacttgtc gggcgagtca gggtattagc agctggttag cctggtatca gcataaacca 120
gggaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgctcac tttcggcgga 300
gggaccaagg tggagatcaa a 321

<210> SEQ ID NO 182
<211> LENGTH: 321

<212> TYPE: DNA
<213> ORGANISM: Artificial Sequence
<220> FEATURE:
<223> OTHER INFORMATION: P1-047296 VL

<400> SEQUENCE: 182
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgatcac cttcggccaa 300
gggacacgac tggagattaa a 321

<210> SEQ ID NO 183
<211> LENGTH: 321
<212> TYPE: DNA
<213> ORGANISM: Artificial Sequence
<220> FEATURE:
<223> OTHER INFORMATION: P1-047319; P1-047320 VL

<400> SEQUENCE: 183
gacatccaga tgacccagtc tccaacctca ctgtctgcat ctgtaggaga cagagtcacc 60
atcacttgtc gggcgagtca gggtattagc agctggttag cctggtatca gcataaacca 120
gggaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgtacac ttttggccag 300
gggaccaagc tggagatcaa a 321

<210> SEQ ID NO 184
<211> LENGTH: 321
<212> TYPE: DNA
<213> ORGANISM: Artificial Sequence
<220> FEATURE:
<223> OTHER INFORMATION: P1-047302; P1-047306; P1-047307 VL

<400> SEQUENCE: 184
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt accctctcac tttcggcgga 300
gggaccaagg tggagatcaa a 321

<210> SEQ ID NO 185
<211> LENGTH: 321
<212> TYPE: DNA
<213> ORGANISM: Artificial Sequence
<220> FEATURE:
<223> OTHER INFORMATION: P1-047300 VL

<400> SEQUENCE: 185
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatccatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgctcac tttcggcgga 300
gggaccaagg tggagatcaa a 321

<210> SEQ ID NO 186
<211> LENGTH: 321
<212> TYPE: DNA
<213> ORGANISM: Artificial Sequence
<220> FEATURE:
<223> OTHER INFORMATION: P1-047309 VL

<400> SEQUENCE: 186
gacatccaga tgacccagtc tccatcttcc gtgtctgcat ctgtaggaga cagagtcacc 60
atcacttgtc gggcgagtca gggtattagc agctggttag cctggtatca gcataaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttacta ttgtcaacag gctaatagtt tcccgttcac tttcggcgga 300
gggaccaagg tggagatcaa a 321

<210> SEQ ID NO 187
<211> LENGTH: 321
<212> TYPE: DNA
<213> ORGANISM: Artificial Sequence
<220> FEATURE:
<223> OTHER INFORMATION: P1-047310 VL

<400> SEQUENCE: 187
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacggat tacactctca ccatcagcag cctgcagcct 240
gaagattttg caacttatta ctgccaacag tataatagtt acccgctcac tttcggcgga 300
gggaccaagg tggagatcaa a 321

<210> SEQ ID NO 188
<211> LENGTH: 321
<212> TYPE: DNA
<213> ORGANISM: Artificial Sequence
<220> FEATURE:
<223> OTHER INFORMATION: P1-047311 VL

<400> SEQUENCE: 188
gacatccaga tgacccagtc tccaacctca ctgtctgcat ctgtaggaga cagagtcacc 60
atcacttgtc gggcgagtca gggtattagc agctggttag cctggtatca gcagaaacca 120
gggaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgctcac tttcggcgga 300
gggaccaagg tggagatcaa a 321

<210> SEQ ID NO 189
<211> LENGTH: 321
<212> TYPE: DNA
<213> ORGANISM: Artificial Sequence
<220> FEATURE:
<223> OTHER INFORMATION: P1-047312; P1-047318 VL

<400> SEQUENCE: 189
gacatccaga tgacccagtc tccaacctca ctgtctgcat ctgtaggaga cagagtcacc 60
atcacttgtc gggcgagtca gggtattagc agctggttag cctggtatca gcataaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgtacac ttttggccag 300
gggaccaagc tggagatcaa a 321

<210> SEQ ID NO 190
<211> LENGTH: 321
<212> TYPE: DNA
<213> ORGANISM: Artificial Sequence
<220> FEATURE:
<223> OTHER INFORMATION: P1-047313 VL

<400> SEQUENCE: 190
gacatccaga tgacccagtc tccaacctca ctgtctgcat ctgtaggaga cagagtcacc 60
atcacttgtc gggcgagtca gggtattagc agctggttag cctggtatca gcataaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccctggac gttcggccaa 300
gggaccaagg tggaaatcaa a 321

<210> SEQ ID NO 191
<211> LENGTH: 321
<212> TYPE: DNA
<213> ORGANISM: Artificial Sequence
<220> FEATURE:
<223> OTHER INFORMATION: P1-047317 VL

<400> SEQUENCE: 191
gaaattgtgt tgacgcagtc tccaggcacc ctgtctttgt ctccagggga aagagccacc 60
ctctcctgca gggccagtca gagtgttagc agctacttag cctggtacca acagaaacct 120
ggccaggctc ccaggctcct catctatggt gcatccagca gggccactgg catcccagac 180
aggttcagtg gcagtgggtc tgggacagac ttcactctca ccatcagcag actggagcct 240
gaagattttg cagtgtatta ctgtcagcag tatggtagct caccgctcac tttcggcgga 300
gggaccaagg tggagatcaa a 321

<210> SEQ ID NO 192
<211> LENGTH: 321
<212> TYPE: DNA
<213> ORGANISM: Artificial Sequence
<220> FEATURE:
<223> OTHER INFORMATION: P1-047322 VL

<400> SEQUENCE: 192
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggtttagcg gcagtggatc tgggacagat ttcactctca ccatcagcag cctgcagcct 240
gaagattttg caacttatta ctgccaacag tataatagtt acccgtacac ttttggccag 300
gggaccaagc tggagatcaa a 321

<210> SEQ ID NO 193
<211> LENGTH: 448
<212> TYPE: PRT
<213> ORGANISM: Artificial Sequence
<220> FEATURE:
<223> OTHER INFORMATION: mAb 0170 VH

<400> SEQUENCE: 193

Glu Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Ser Thr Tyr
20 25 30

Ala Met His Trp Val Arg Gln Ala Ser Gly Lys Gly Leu Glu Trp Val
35 40 45

Gly Arg Ile Arg Thr Lys Ser Ser Asn Tyr Ala Thr Tyr Tyr Ala Ala
50 55 60

Ser Val Lys Gly Arg Phe Thr Ile Ser Arg Asp Asp Ser Lys Asn Thr
65 70 75 80

Ala Tyr Leu Gln Met Asn Ser Leu Lys Thr Glu Asp Thr Ala Val Tyr
85 90 95

Tyr Cys Thr Arg Asp Met Gly Ile Arg Arg Gln Phe Ala Tyr Trp Gly
100 105 110

Gln Gly Thr Leu Val Thr Val Ser Ser Ala Ser Thr Lys Gly Pro Ser
115 120 125

Val Phe Pro Leu Ala Pro Cys Ser Arg Ser Thr Ser Glu Ser Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Lys Thr Tyr Thr Cys Asn Val Asp His
195 200 205

Lys Pro Ser Asn Thr Lys Val Asp Lys Arg Val Glu Ser Lys Tyr Gly
210 215 220

Pro Pro Cys Pro Pro Cys Pro Ala Pro Glu Phe Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser Gln Glu Asp Pro
260 265 270

Glu Val Gln Phe Asn Trp Tyr Val Asp Gly Val Glu Val His Asn Ala
275 280 285

Lys Thr Lys Pro Arg Glu Glu Gln Phe Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Gly Leu Pro Ser Ser Ile Glu Lys Thr
325 330 335

Ile Ser Lys Ala Lys Gly Gln Pro Arg Glu Pro Gln Val Tyr Thr Leu
340 345 350

Pro Pro Ser Gln Glu Glu Met Thr Lys Asn Gln Val Ser Leu Thr Cys

```
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 194
<211> LENGTH: 218
<212> TYPE: PRT
<213> ORGANISM: Artificial Sequence
<220> FEATURE:
<223> OTHER INFORMATION: mAb 0170 VL

<400> SEQUENCE: 194

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Phe
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 195
<211> LENGTH: 321
<212> TYPE: DNA
<213> ORGANISM: Artificial Sequence
<220> FEATURE:
<223> OTHER INFORMATION: P1-047289 VL

<400> SEQUENCE: 195
```

gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgtcaacag tttaatagtt accctctcac tttcggcgga 300
gggaccaagg tggagatcaa a 321

<210> SEQ ID NO 196
<211> LENGTH: 321
<212> TYPE: DNA
<213> ORGANISM: Artificial Sequence
<220> FEATURE:
<223> OTHER INFORMATION: P1-047299 VL

<400> SEQUENCE: 196
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgtggac gttcggccaa 300
gggaccaagg tggaaatcaa a 321

<210> SEQ ID NO 197
<211> LENGTH: 454
<212> TYPE: PRT
<213> ORGANISM: Artificial Sequence
<220> FEATURE:
<223> OTHER INFORMATION: P1-047239 Heavy Chain

<400> SEQUENCE: 197

Gln Val Gln Leu Val Glu Ser Gly Gly Gly Val Val Gln Pro Gly Arg
1 5 10 15

Ser Leu Arg Leu Ser Cys Ala Ala Thr Glu Phe Thr Phe Ser Asn Tyr
20 25 30

Gly Met His Trp Val Arg Gln Ala Pro Gly Lys Gly Leu Glu Trp Val
35 40 45

Ala Val Ile Trp Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Leu Asn Ser Leu Ser Ala Glu Asp Ser Ala Val Tyr Tyr Cys
85 90 95

Ala Arg Asp Gly Arg His Tyr Tyr Gly Ser Thr Ser Tyr Phe Gly Met
100 105 110

Asp Val Trp Gly Gln Gly Thr Thr Val Thr Val Ser Ser Ala Ser Thr
115 120 125

Lys Gly Pro Ser Val Phe Pro Leu Ala Pro Ser Ser Lys Ser Thr Ser
130 135 140

Gly Gly Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Gln Thr Tyr Ile Cys
195 200 205

Asn Val Asn His Lys Pro Ser Asn Thr Lys Val Asp Lys Arg Val Glu
210 215 220

Pro Lys Ser Cys Asp Lys Thr His Thr Cys Pro Pro Cys Pro Ala Pro
225 230 235 240

Glu Ala Glu Gly Ala Pro Ser Val Phe Leu Phe Pro Pro Lys Pro Lys
245 250 255

Asp Thr Leu Met Ile Ser Arg Thr Pro Glu Val Thr Cys Val Val Val
260 265 270

Asp Val Ser His Glu Asp Pro Glu Val Lys Phe Asn Trp Tyr Val Asp
275 280 285

Gly Val Glu Val His Asn Ala Lys Thr Lys Pro Arg Glu Glu Gln Tyr
290 295 300

Asn Ser Thr Tyr Arg Val Val Ser Val Leu Thr Val Leu His Gln Asp
305 310 315 320

Trp Leu Asn Gly Lys Glu Tyr Lys Cys Lys Val Ser Asn Lys Ala Leu
325 330 335

Pro Ser Ser Ile Glu Lys Thr Ile Ser Lys Ala Lys Gly Gln Pro Arg
340 345 350

Glu Pro Gln Val Tyr Thr Leu Pro Pro Ser Arg Glu Glu Met Thr Lys
355 360 365

Asn Gln Val Ser Leu Thr Cys Leu Val Lys Gly Phe Tyr Pro Ser Asp
370 375 380

Ile Ala Val Glu Trp Glu Ser Asn Gly Gln Pro Glu Asn Asn Tyr Lys
385 390 395 400

Thr Thr Pro Pro Val Leu Asp Ser Asp Gly Ser Phe Phe Leu Tyr Ser
405 410 415

Lys Leu Thr Val Asp Lys Ser Arg Trp Gln Gln Gly Asn Val Phe Ser
420 425 430

Cys Ser Val Met His Glu Ala Leu His Asn His Tyr Thr Gln Lys Ser
435 440 445

Leu Ser Leu Ser Pro Gly
450

<210> SEQ ID NO 198
<211> LENGTH: 451
<212> TYPE: PRT
<213> ORGANISM: Artificial Sequence
<220> FEATURE:
<223> OTHER INFORMATION: P1-047246 Heavy Chain

<400> SEQUENCE: 198

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Thr Asn Tyr
20 25 30

Tyr Trp Thr Trp Ile Arg Gln Pro Pro Gly Lys Gly Leu Glu Trp Ile
35 40 45

Gly Tyr Ile Tyr Asp Ser Gly Tyr Thr Asn Tyr Asn Pro Ser Leu Lys
50 55 60

Ser Arg Val Thr Leu Ser Ile Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Gly Val Leu Trp Phe Gly Glu Leu Leu Pro Leu Leu Asp Tyr Trp
100 105 110

Gly Gln Gly Thr Leu Val Thr Val Ser Ser Ala Ser Thr Lys Gly Pro
115 120 125

Ser Val Phe Pro Leu Ala Pro Ser Ser Lys Ser Thr Ser Gly Gly Thr
130 135 140

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Gln Thr Tyr Ile Cys Asn Val Asn
195 200 205

His Lys Pro Ser Asn Thr Lys Val Asp Lys Arg Val Glu Pro Lys Ser
210 215 220

Cys Asp Lys Thr His Thr Cys Pro Pro Cys Pro Ala Pro Glu Ala Glu
225 230 235 240

Gly Ala Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

His Glu Asp Pro Glu Val Lys Phe Asn Trp Tyr Val Asp Gly Val Glu
275 280 285

Val His Asn Ala Lys Thr Lys Pro Arg Glu Glu Gln Tyr Asn Ser Thr
290 295 300

Tyr Arg Val Val Ser Val Leu Thr Val Leu His Gln Asp Trp Leu Asn
305 310 315 320

Gly Lys Glu Tyr Lys Cys Lys Val Ser Asn Lys Ala Leu Pro Ser Ser
325 330 335

Ile Glu Lys Thr Ile Ser Lys Ala Lys Gly Gln Pro Arg Glu Pro Gln
340 345 350

Val Tyr Thr Leu Pro Pro Ser Arg Glu Glu Met Thr Lys Asn Gln Val
355 360 365

Ser Leu Thr Cys Leu Val Lys Gly Phe Tyr Pro Ser Asp Ile Ala Val
370 375 380

Glu Trp Glu Ser Asn Gly Gln Pro Glu Asn Asn Tyr Lys Thr Thr Pro
385 390 395 400

Pro Val Leu Asp Ser Asp Gly Ser Phe Phe Leu Tyr Ser Lys Leu Thr
405 410 415

Val Asp Lys Ser Arg Trp Gln Gln Gly Asn Val Phe Ser Cys Ser Val
420 425 430

Met His Glu Ala Leu His Asn His Tyr Thr Gln Lys Ser Leu Ser Leu
435 440 445

Ser Pro Gly
450

<210> SEQ ID NO 199
<211> LENGTH: 451
<212> TYPE: PRT
<213> ORGANISM: Artificial Sequence
<220> FEATURE:
<223> OTHER INFORMATION: P1-047247 Heavy Chain

<400> SEQUENCE: 199

-continued

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Asn Tyr
            20                  25                  30

Tyr Trp Thr Trp Ile Arg Gln Pro Pro Gly Lys Gly Leu Glu Trp Ile
        35                  40                  45

Gly Tyr Ile Tyr Asp Ser Gly Tyr Thr Asn Tyr Asn Pro Ser Leu Lys
    50                  55                  60

Ser Arg Val Thr Leu Ser Ile Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Val Leu Trp Phe Gly Glu Leu Leu Pro Leu Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Glu
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415
```

```
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450


<210> SEQ ID NO 200
<211> LENGTH: 453
<212> TYPE: PRT
<213> ORGANISM: Artificial Sequence
<220> FEATURE:
<223> OTHER INFORMATION: P1-047248 Heavy Chain

<400> SEQUENCE: 200

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Tyr Trp Ser Trp Val Arg Gln Pro Pro Gly Lys Gly Leu Glu Trp Ile
        35                  40                  45

Gly Tyr Thr His Tyr Ser Gly Ile Ser Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Tyr Asp Ile Leu Thr Gly Tyr Glu Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Ala Glu Gly Ala Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320
```

```
Leu Asn Gly Lys Glu Tyr Lys Cys Lys Val Ser Asn Lys Ala Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450
```

<210> SEQ ID NO 201
<211> LENGTH: 455
<212> TYPE: PRT
<213> ORGANISM: Artificial Sequence
<220> FEATURE:
<223> OTHER INFORMATION: P1-047323 Heavy Chain

<400> SEQUENCE: 201

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ile Asn Ser
            20                  25                  30

Glu Ala Ile Asn Trp Val Arg Gln Ala Pro Gly Gln Gly Leu Glu Trp
        35                  40                  45

Met Gly Gly Ile Ile Pro Ile Phe Asp Ile Thr Asn Tyr Ala Gln Lys
    50                  55                  60

Phe Gln Gly Arg Val Thr Ile Thr Ala Asp Glu Ser Met Ser Thr Ala
65                  70                  75                  80

Tyr Met Glu Leu Ser Ser Leu Arg Ser Glu Asp Thr Ala Val Tyr Tyr
                85                  90                  95

Cys Ala Lys Thr Tyr Tyr Asp Ile Leu Thr Tyr His Tyr His Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220
```

Glu Pro Lys Ser Cys Asp Lys Thr His Thr Cys Pro Pro Cys Pro Ala
225 230 235 240

Pro Glu Ala Glu Gly Ala Pro Ser Val Phe Leu Phe Pro Pro Lys Pro
245 250 255

Lys Asp Thr Leu Met Ile Ser Arg Thr Pro Glu Val Thr Cys Val Val
260 265 270

Val Asp Val Ser His Glu Asp Pro Glu Val Lys Phe Asn Trp Tyr Val
275 280 285

Asp Gly Val Glu Val His Asn Ala Lys Thr Lys Pro Arg Glu Glu Gln
290 295 300

Tyr Asn Ser Thr Tyr Arg Val Val Ser Val Leu Thr Val Leu His Gln
305 310 315 320

Asp Trp Leu Asn Gly Lys Glu Tyr Lys Cys Lys Val Ser Asn Lys Ala
325 330 335

Leu Pro Ser Ser Ile Glu Lys Thr Ile Ser Lys Ala Lys Gly Gln Pro
340 345 350

Arg Glu Pro Gln Val Tyr Thr Leu Pro Pro Ser Arg Glu Glu Met Thr
355 360 365

Lys Asn Gln Val Ser Leu Thr Cys Leu Val Lys Gly Phe Tyr Pro Ser
370 375 380

Asp Ile Ala Val Glu Trp Glu Ser Asn Gly Gln Pro Glu Asn Asn Tyr
385 390 395 400

Lys Thr Thr Pro Pro Val Leu Asp Ser Asp Gly Ser Phe Phe Leu Tyr
405 410 415

Ser Lys Leu Thr Val Asp Lys Ser Arg Trp Gln Gln Gly Asn Val Phe
420 425 430

Ser Cys Ser Val Met His Glu Ala Leu His Asn His Tyr Thr Gln Lys
435 440 445

Ser Leu Ser Leu Ser Pro Gly
450 455

<210> SEQ ID NO 202
<211> LENGTH: 455
<212> TYPE: PRT
<213> ORGANISM: Artificial Sequence
<220> FEATURE:
<223> OTHER INFORMATION: P1-047328 Heavy Chain

<400> SEQUENCE: 202

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ile Asn Ser
20 25 30

Glu Ala Ile Asn Trp Val Arg Gln Ala Pro Gly Gln Gly Leu Glu Trp
35 40 45

Met Gly Gly Ile Ile Pro Ile Phe Asp Ile Thr Asn Tyr Ala Gln Lys
50 55 60

Phe Gln Gly Arg Val Thr Ile Thr Ala Asp Glu Ser Met Ser Thr Ala
65 70 75 80

Tyr Met Glu Leu Ser Ser Leu Arg Ser Glu Asp Thr Ala Val Tyr Tyr
85 90 95

Cys Ala Lys Thr Tyr Tyr Asp Ile Leu Thr Tyr His Tyr His Tyr Gly
100 105 110

Met Asp Val Trp Gly Gln Gly Thr Thr Val Thr Val Ser Ser Ala Ser
115 120 125

```
Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Ala Glu Gly Ala Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ser Ser Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly
    450                 455
```

<210> SEQ ID NO 203
<211> LENGTH: 452
<212> TYPE: PRT
<213> ORGANISM: Artificial Sequence
<220> FEATURE:
<223> OTHER INFORMATION: P1-047334 Heavy Chain

<400> SEQUENCE: 203

```
Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Ser Ser Ser
            20                  25                  30
```

```
Ala Ile Ser Trp Val Arg Gln Ala Pro Gly Gln Gly Leu Glu Trp Met
        35                  40                  45

Gly Gly Ile Ile Pro Ile Phe Gly Thr Thr Asn Gly Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Met Val Arg Gly Asn Tyr Phe Tyr Phe Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Ala
225                 230                 235                 240

Glu Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
```

450

<210> SEQ ID NO 204
<211> LENGTH: 455
<212> TYPE: PRT
<213> ORGANISM: Artificial Sequence
<220> FEATURE:
<223> OTHER INFORMATION: P1-047263 Heavy Chain

<400> SEQUENCE: 204

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Thr Tyr
            20                  25                  30

Asp Ile Asn Trp Val Arg Gln Ala Thr Gly Gln Gly Leu Glu Trp Met
        35                  40                  45

Gly Trp Val Asn Pro Asn Ser Gly Asn Thr Gly Tyr Ala Gln Lys Phe
    50                  55                  60

Gln Asp Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Asp Gly Leu Asn Met Val Arg Gly Val His Asn Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Ala Glu Gly Ala Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ser Ser Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr

```
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly
    450                 455


<210> SEQ ID NO 205
<211> LENGTH: 455
<212> TYPE: PRT
<213> ORGANISM: Artificial Sequence
<220> FEATURE:
<223> OTHER INFORMATION: P1-047265 Heavy Chain

<400> SEQUENCE: 205

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Thr Tyr
            20                  25                  30

Asp Ile Asn Trp Val Arg Gln Ala Thr Gly Gln Gly Leu Glu Trp Met
        35                  40                  45

Gly Trp Val Asn Pro Asn Ser Gly Asn Thr Gly Tyr Ala Gln Lys Phe
    50                  55                  60

Gln Asp Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Asp Gly Leu Asn Met Val Arg Gly Val His Asn Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Ala Glu Gly Ala Pro Ser Val Phe Leu Phe Pro Pro Lys Pro
                245                 250                 255

Lys Asp Thr Leu Met Ile Ser Arg Thr Pro Glu Val Thr Cys Val Val
```

```
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ser Ser Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly
    450                 455


<210> SEQ ID NO 206
<211> LENGTH: 455
<212> TYPE: PRT
<213> ORGANISM: Artificial Sequence
<220> FEATURE:
<223> OTHER INFORMATION: P1-047289 Heavy Chain

<400> SEQUENCE: 206

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Ser
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asp Ser Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Asn Ser Leu Arg Ser Glu Asp Thr Ala Val Tyr Tyr Cys
                85                  90                  95

Ala Phe Thr Pro Arg Tyr Arg Gly Ser Ser His His Tyr Phe Tyr Ala
            100                 105                 110

Leu Gly Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
```

```
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Ala Glu Gly Ala Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ser Ser Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly
    450                 455


<210> SEQ ID NO 207
<211> LENGTH: 456
<212> TYPE: PRT
<213> ORGANISM: Artificial Sequence
<220> FEATURE:
<223> OTHER INFORMATION: P1-047290 Heavy Chain

<400> SEQUENCE: 207

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg His
            20                  25                  30

Ala Ile Ser Trp Val Arg Gln Ala Pro Gly Gln Gly Leu Glu Trp Met
        35                  40                  45

Gly Gly Ile Ile Pro Leu Phe Gly Thr Ala Asn Tyr Ala Gln Lys Phe
    50                  55                  60

Gln Gly Arg Val Thr Ile Ala Ala Asp Glu Pro Thr Ser Thr Thr Tyr
```

```
65                  70                  75                  80

Met Glu Leu Arg Ser Leu Arg Ser Glu Asp Thr Ala Val Tyr Tyr Cys
                85                  90                  95

Ala Ser Ser Tyr Phe Tyr Gly Ser Gly Ser Ser Asn Tyr Tyr Tyr Tyr
            100                 105                 110

Gly Leu Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Ala Glu Gly Ala Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly
    450                 455
```

<210> SEQ ID NO 208

<400> SEQUENCE: 208

000

<210> SEQ ID NO 209
<211> LENGTH: 456
<212> TYPE: PRT
<213> ORGANISM: Artificial Sequence
<220> FEATURE:
<223> OTHER INFORMATION: P1-047291 Heavy Chain

<400> SEQUENCE: 209

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg His
            20                  25                  30

Ala Ile Ser Trp Val Arg Gln Ala Pro Gly Gln Gly Leu Glu Trp Met
        35                  40                  45

Gly Gly Ile Ile Pro Leu Phe Gly Thr Ala Asn Tyr Ala Gln Lys Phe
    50                  55                  60

Gln Gly Arg Val Thr Ile Ala Ala Asp Glu Pro Thr Ser Thr Thr Tyr
65                  70                  75                  80

Met Glu Leu Arg Ser Leu Arg Ser Glu Asp Thr Ala Val Tyr Tyr Cys
                85                  90                  95

Ala Ser Ser Tyr Phe Tyr Gly Ser Gly Ser Ser Asn Tyr Tyr Tyr Tyr
            100                 105                 110

Gly Leu Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Ala Glu Gly Ala Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met

```
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly
    450                 455


<210> SEQ ID NO 210
<211> LENGTH: 455
<212> TYPE: PRT
<213> ORGANISM: Artificial Sequence
<220> FEATURE:
<223> OTHER INFORMATION: P1-047292 Heavy Chain

<400> SEQUENCE: 210

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Ser
            20                  25                  30

Ala Ile Ser Trp Val Arg Gln Ala Pro Gly Gln Gly Leu Glu Trp Met
        35                  40                  45

Gly Gly Ile Ile Pro Ile Phe Ser Thr Gly Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Asp Leu Ser Ser Leu Arg Ser Glu Asp Thr Ala Val Tyr Tyr Cys
                85                  90                  95

Ala Arg Ser Thr Arg Val Arg Gly Val Ser His Tyr Tyr Tyr Tyr Gly
            100                 105                 110

Leu Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Ala Glu Gly Ala Pro Ser Val Phe Leu Phe Pro Pro Lys Pro
                245                 250                 255

Lys Asp Thr Leu Met Ile Ser Arg Thr Pro Glu Val Thr Cys Val Val
```

```
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ser Ser Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly
    450                 455


<210> SEQ ID NO 211
<211> LENGTH: 456
<212> TYPE: PRT
<213> ORGANISM: Artificial Sequence
<220> FEATURE:
<223> OTHER INFORMATION: P1-047294 Heavy Chain

<400> SEQUENCE: 211

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg His
            20                  25                  30

Ala Ile Ser Trp Val Arg Gln Ala Pro Gly Gln Gly Leu Glu Trp Met
        35                  40                  45

Gly Gly Ile Ile Pro Leu Phe Gly Thr Ala Asn Tyr Ala Gln Glu Phe
    50                  55                  60

Gln Gly Arg Val Thr Ile Ala Ala Asp Glu Pro Thr Ser Thr Thr Tyr
65                  70                  75                  80

Met Glu Leu Arg Ser Leu Arg Ser Glu Asp Thr Ala Val Tyr Tyr Cys
                85                  90                  95

Ala Ser Ser Tyr Phe Tyr Gly Ser Gly Ser Ser Asn Tyr Tyr Tyr Tyr
            100                 105                 110

Gly Leu Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
```

```
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Ala Glu Gly Ala Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly
    450                 455


<210> SEQ ID NO 212
<211> LENGTH: 456
<212> TYPE: PRT
<213> ORGANISM: Artificial Sequence
<220> FEATURE:
<223> OTHER INFORMATION: P1-047296 Heavy Chain

<400> SEQUENCE: 212

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg His
            20                  25                  30

Ala Ile Ser Trp Val Arg Gln Ala Pro Gly Gln Gly Leu Glu Trp Met
        35                  40                  45

Gly Gly Ile Ile Pro Leu Phe Gly Thr Ala Asn Tyr Ala Gln Lys Phe
    50                  55                  60

Gln Gly Arg Val Thr Ile Ala Ala Asp Glu Pro Thr Ser Thr Thr Tyr
```

65 70 75 80

Met Glu Leu Arg Ser Leu Arg Ser Glu Asp Thr Ala Val Tyr Tyr Cys
85 90 95

Ala Ser Ser Tyr Phe Tyr Gly Ser Gly Ser Ser Asn Tyr Tyr Tyr Tyr
100 105 110

Gly Leu Asp Val Trp Gly Gln Gly Thr Thr Val Thr Val Ser Ser Ala
115 120 125

Ser Thr Lys Gly Pro Ser Val Phe Pro Leu Ala Pro Ser Ser Lys Ser
130 135 140

Thr Ser Gly Gly Thr Ala Ala Leu Gly Cys Leu Val Lys Asp Tyr Phe
145 150 155 160

Pro Glu Pro Val Thr Val Ser Trp Asn Ser Gly Ala Leu Thr Ser Gly
165 170 175

Val His Thr Phe Pro Ala Val Leu Gln Ser Ser Gly Leu Tyr Ser Leu
180 185 190

Ser Ser Val Val Thr Val Pro Ser Ser Ser Leu Gly Thr Gln Thr Tyr
195 200 205

Ile Cys Asn Val Asn His Lys Pro Ser Asn Thr Lys Val Asp Lys Arg
210 215 220

Val Glu Pro Lys Ser Cys Asp Lys Thr His Thr Cys Pro Pro Cys Pro
225 230 235 240

Ala Pro Glu Ala Glu Gly Ala Pro Ser Val Phe Leu Phe Pro Pro Lys
245 250 255

Pro Lys Asp Thr Leu Met Ile Ser Arg Thr Pro Glu Val Thr Cys Val
260 265 270

Val Val Asp Val Ser His Glu Asp Pro Glu Val Lys Phe Asn Trp Tyr
275 280 285

Val Asp Gly Val Glu Val His Asn Ala Lys Thr Lys Pro Arg Glu Glu
290 295 300

Gln Tyr Asn Ser Thr Tyr Arg Val Val Ser Val Leu Thr Val Leu His
305 310 315 320

Gln Asp Trp Leu Asn Gly Lys Glu Tyr Lys Cys Lys Val Ser Asn Lys
325 330 335

Ala Leu Pro Ser Ser Ile Glu Lys Thr Ile Ser Lys Ala Lys Gly Gln
340 345 350

Pro Arg Glu Pro Gln Val Tyr Thr Leu Pro Pro Ser Arg Glu Glu Met
355 360 365

Thr Lys Asn Gln Val Ser Leu Thr Cys Leu Val Lys Gly Phe Tyr Pro
370 375 380

Ser Asp Ile Ala Val Glu Trp Glu Ser Asn Gly Gln Pro Glu Asn Asn
385 390 395 400

Tyr Lys Thr Thr Pro Pro Val Leu Asp Ser Asp Gly Ser Phe Phe Leu
405 410 415

Tyr Ser Lys Leu Thr Val Asp Lys Ser Arg Trp Gln Gln Gly Asn Val
420 425 430

Phe Ser Cys Ser Val Met His Glu Ala Leu His Asn His Tyr Thr Gln
435 440 445

Lys Ser Leu Ser Leu Ser Pro Gly
450 455

<210> SEQ ID NO 213
<211> LENGTH: 456
<212> TYPE: PRT
<213> ORGANISM: Artificial Sequence
<220> FEATURE:
<223> OTHER INFORMATION: P1-047297 Heavy Chain

<400> SEQUENCE: 213

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg His
            20                  25                  30

Ala Ile Ser Trp Val Arg Gln Ala Pro Gly Gln Gly Leu Glu Trp Met
        35                  40                  45

Gly Gly Ile Ile Pro Leu Phe Gly Thr Ala Asn Tyr Ala Gln Lys Phe
    50                  55                  60

Gln Gly Arg Val Thr Ile Ala Ala Asp Glu Pro Thr Ser Thr Thr Tyr
65                  70                  75                  80

Met Glu Leu Arg Ser Leu Arg Ser Glu Asp Thr Ala Val Tyr Tyr Cys
                85                  90                  95

Ala Ser Ser Tyr Phe Tyr Gly Ser Gly Ser Ser Asn Tyr Tyr Tyr Tyr
            100                 105                 110

Gly Leu Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Ala Glu Gly Ala Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400
```

```
Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly
    450                 455


<210> SEQ ID NO 214
<211> LENGTH: 456
<212> TYPE: PRT
<213> ORGANISM: Artificial Sequence
<220> FEATURE:
<223> OTHER INFORMATION: P1-047299 Heavy Chain

<400> SEQUENCE: 214

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg Tyr
            20                  25                  30

Ala Phe Ser Trp Val Arg Gln Ala Pro Gly Gln Gly Leu Glu Trp Met
        35                  40                  45

Gly Gly Ile Ile Pro Ile Phe Gly Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Ile Ser Glu Asp Thr Ala Val Tyr Tyr Cys
                85                  90                  95

Ala Ser Ser His Phe Tyr Gly Ser Gly Ser Ser His Phe Tyr Tyr Tyr
            100                 105                 110

Gly Met His Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Ala Glu Gly Ala Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300
```

Gln Tyr Asn Ser Thr Tyr Arg Val Val Ser Val Leu Thr Val Leu His
305 310 315 320

Gln Asp Trp Leu Asn Gly Lys Glu Tyr Lys Cys Lys Val Ser Asn Lys
325 330 335

Ala Leu Pro Ser Ser Ile Glu Lys Thr Ile Ser Lys Ala Lys Gly Gln
340 345 350

Pro Arg Glu Pro Gln Val Tyr Thr Leu Pro Pro Ser Arg Glu Glu Met
355 360 365

Thr Lys Asn Gln Val Ser Leu Thr Cys Leu Val Lys Gly Phe Tyr Pro
370 375 380

Ser Asp Ile Ala Val Glu Trp Glu Ser Asn Gly Gln Pro Glu Asn Asn
385 390 395 400

Tyr Lys Thr Thr Pro Pro Val Leu Asp Ser Asp Gly Ser Phe Phe Leu
405 410 415

Tyr Ser Lys Leu Thr Val Asp Lys Ser Arg Trp Gln Gln Gly Asn Val
420 425 430

Phe Ser Cys Ser Val Met His Glu Ala Leu His Asn His Tyr Thr Gln
435 440 445

Lys Ser Leu Ser Leu Ser Pro Gly
450 455

<210> SEQ ID NO 215
<211> LENGTH: 456
<212> TYPE: PRT
<213> ORGANISM: Artificial Sequence
<220> FEATURE:
<223> OTHER INFORMATION: P1-047300 Heavy Chain

<400> SEQUENCE: 215

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Asn Arg His
20 25 30

Ala Ile Ser Trp Val Arg Gln Ala Pro Gly Gln Gly Leu Glu Trp Met
35 40 45

Gly Gly Ile Ile Pro Leu Phe Gly Thr Ala Asn Tyr Ala Gln Lys Phe
50 55 60

Gln Gly Arg Val Thr Ile Ala Ala Asp Glu Pro Thr Ser Thr Thr Tyr
65 70 75 80

Met Glu Leu Arg Ser Leu Arg Ser Glu Asp Thr Ala Val Tyr Tyr Cys
85 90 95

Ala Ser Ser Tyr Phe Tyr Gly Ser Gly Ser Ser Asn Tyr Tyr Tyr Tyr
100 105 110

Gly Leu Asp Val Trp Gly Gln Gly Thr Thr Val Thr Val Ser Ser Ala
115 120 125

Ser Thr Lys Gly Pro Ser Val Phe Pro Leu Ala Pro Ser Ser Lys Ser
130 135 140

Thr Ser Gly Gly Thr Ala Ala Leu Gly Cys Leu Val Lys Asp Tyr Phe
145 150 155 160

Pro Glu Pro Val Thr Val Ser Trp Asn Ser Gly Ala Leu Thr Ser Gly
165 170 175

Val His Thr Phe Pro Ala Val Leu Gln Ser Ser Gly Leu Tyr Ser Leu
180 185 190

Ser Ser Val Val Thr Val Pro Ser Ser Ser Leu Gly Thr Gln Thr Tyr
195 200 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Ala Glu Gly Ala Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly
    450                 455

<210> SEQ ID NO 216
<211> LENGTH: 456
<212> TYPE: PRT
<213> ORGANISM: Artificial Sequence
<220> FEATURE:
<223> OTHER INFORMATION: P1-047301 Heavy Chain

<400> SEQUENCE: 216

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg Tyr
            20                  25                  30

Ala Phe Ser Trp Val Arg Gln Ala Pro Gly Gln Gly Leu Glu Trp Met
        35                  40                  45

Gly Gly Ile Ile Pro Ile Phe Gly Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Ile Ser Glu Asp Thr Ala Val Tyr Tyr Cys
                85                  90                  95

Ala Ser Ser His Phe Tyr Gly Ser Gly Ser Ser Asn Tyr Tyr Tyr Tyr
            100                 105                 110

```
Gly Leu Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Ala Glu Gly Ala Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly
    450                 455


<210> SEQ ID NO 217
<211> LENGTH: 456
<212> TYPE: PRT
<213> ORGANISM: Artificial Sequence
<220> FEATURE:
<223> OTHER INFORMATION: P1-047302 Heavy Chain

<400> SEQUENCE: 217

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Asn Arg His
            20                  25                  30

Ala Ile Ser Trp Val Arg Gln Ala Pro Gly Gln Gly Leu Glu Trp Met
        35                  40                  45

Gly Gly Ile Ile Pro Leu Phe Gly Thr Ala Asn Tyr Ala Gln Lys Phe
    50                  55                  60

Gln Gly Arg Val Thr Ile Ala Ala Asp Glu Pro Thr Ser Thr Thr Tyr
65                  70                  75                  80

Met Glu Leu Arg Ser Leu Arg Ser Glu Asp Thr Ala Val Tyr Tyr Cys
                85                  90                  95

Ala Ser Ser Tyr Phe Tyr Gly Ser Gly Ser Ser Asn Tyr Tyr Tyr Tyr
            100                 105                 110

Gly Leu Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Ala Glu Gly Ala Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430
```

```
Phe Ser Cys Ser Val Met His Glu Ala Leu His Asn His Tyr Thr Gln
        435                 440                 445

Lys Ser Leu Ser Leu Ser Pro Gly
    450                 455


<210> SEQ ID NO 218
<211> LENGTH: 455
<212> TYPE: PRT
<213> ORGANISM: Artificial Sequence
<220> FEATURE:
<223> OTHER INFORMATION: P1-047305 Heavy Chain

<400> SEQUENCE: 218

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Ser
            20                  25                  30

Ala Val Ser Trp Val Arg Gln Ala Pro Gly Gln Gly Leu Glu Trp Met
        35                  40                  45

Gly Gly Ile Thr Pro Ile Phe Gly Thr Ala Asp Tyr Ala Gln Lys Phe
    50                  55                  60

Gln Gly Arg Val Thr Ile Thr Ala Asp Ala Ser Thr Ser Thr Gly Tyr
65                  70                  75                  80

Met Glu Leu Ser Ser Leu Arg Ser Glu Asp Thr Ala Val Tyr Tyr Cys
                85                  90                  95

Ala Phe Thr Pro Arg Tyr Arg Gly Ser Ser His His Tyr Tyr Tyr Ala
            100                 105                 110

Leu Gly Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Ala Glu Gly Ala Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335
```

```
Leu Pro Ser Ser Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly
    450                 455


<210> SEQ ID NO 219
<211> LENGTH: 454
<212> TYPE: PRT
<213> ORGANISM: Artificial Sequence
<220> FEATURE:
<223> OTHER INFORMATION: P1-047306 Heavy Chain

<400> SEQUENCE: 219

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Ser
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Gln Ser Arg Ser Ser Asn Tyr Tyr Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240
```

Glu Ala Glu Gly Ala Pro Ser Val Phe Leu Phe Pro Pro Lys Pro Lys
245 250 255

Asp Thr Leu Met Ile Ser Arg Thr Pro Glu Val Thr Cys Val Val Val
260 265 270

Asp Val Ser His Glu Asp Pro Glu Val Lys Phe Asn Trp Tyr Val Asp
275 280 285

Gly Val Glu Val His Asn Ala Lys Thr Lys Pro Arg Glu Glu Gln Tyr
290 295 300

Asn Ser Thr Tyr Arg Val Val Ser Val Leu Thr Val Leu His Gln Asp
305 310 315 320

Trp Leu Asn Gly Lys Glu Tyr Lys Cys Lys Val Ser Asn Lys Ala Leu
325 330 335

Pro Ser Ser Ile Glu Lys Thr Ile Ser Lys Ala Lys Gly Gln Pro Arg
340 345 350

Glu Pro Gln Val Tyr Thr Leu Pro Pro Ser Arg Glu Glu Met Thr Lys
355 360 365

Asn Gln Val Ser Leu Thr Cys Leu Val Lys Gly Phe Tyr Pro Ser Asp
370 375 380

Ile Ala Val Glu Trp Glu Ser Asn Gly Gln Pro Glu Asn Asn Tyr Lys
385 390 395 400

Thr Thr Pro Pro Val Leu Asp Ser Asp Gly Ser Phe Phe Leu Tyr Ser
405 410 415

Lys Leu Thr Val Asp Lys Ser Arg Trp Gln Gln Gly Asn Val Phe Ser
420 425 430

Cys Ser Val Met His Glu Ala Leu His Asn His Tyr Thr Gln Lys Ser
435 440 445

Leu Ser Leu Ser Pro Gly
450

<210> SEQ ID NO 220
<211> LENGTH: 454
<212> TYPE: PRT
<213> ORGANISM: Artificial Sequence
<220> FEATURE:
<223> OTHER INFORMATION: P1-047307 Heavy Chain

<400> SEQUENCE: 220

Gln Val Gln Leu Val Gln Ser Gly Ala Glu Val Lys Arg Pro Gly Ser
1 5 10 15

Ser Val Lys Val Ser Cys Lys Ala Ser Gly Gly Thr Phe Ser Ile Tyr
20 25 30

Val Ile Ser Trp Val Arg Gln Ala Pro Gly Gln Gly Leu Glu Trp Met
35 40 45

Gly Gly Ile Ile Pro Leu Phe Gly Thr Pro Asn Tyr Ala Gln Gln Phe
50 55 60

Gln Asp Arg Val Thr Ile Thr Ala Asp Glu Ser Thr Arg Thr Ala Tyr
65 70 75 80

Met Glu Leu Asn Ser Leu Lys Ser Glu Asp Thr Ala Val Tyr Tyr Cys
85 90 95

Ala Arg Gly His Gly Pro Gly Ser Ser His Tyr Ser Tyr Tyr Gly Leu
100 105 110

Asp Val Trp Gly Gln Gly Thr Thr Val Thr Val Ser Ser Ala Ser Thr
115 120 125

Lys Gly Pro Ser Val Phe Pro Leu Ala Pro Ser Ser Lys Ser Thr Ser
130 135 140

```
Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450


<210> SEQ ID NO 221
<211> LENGTH: 454
<212> TYPE: PRT
<213> ORGANISM: Artificial Sequence
<220> FEATURE:
<223> OTHER INFORMATION: P1-047308 Heavy Chain

<400> SEQUENCE: 221

Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Ser Ile Tyr
            20                  25                  30

Val Ile Ser Trp Val Arg Gln Ala Pro Gly Gln Gly Leu Glu Trp Met
        35                  40                  45
```

```
Gly Gly Ile Ile Pro Leu Phe Gly Thr Ala Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Gly Pro Gly Ser Ser His Tyr Ser Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450
```

<210> SEQ ID NO 222
<211> LENGTH: 446
<212> TYPE: PRT
<213> ORGANISM: Artificial Sequence
<220> FEATURE:
<223> OTHER INFORMATION: P1-047309 Heavy Chain

<400> SEQUENCE: 222

```
Gln Val Gln Leu Val Gln Ser Gly Ala Glu Val Lys Lys Pro Gly Ser
1               5                   10                  15

Ser Val Lys Val Ser Cys Asn Pro Ser Gly Gly Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Asn Pro Ile Phe Gly Thr Ala Asn Tyr Ala Gln Lys Phe
    50                  55                  60

Gln Gly Arg Val Thr Ile Thr Ala Asp Glu Ser Thr Ser Pro Gly Tyr
65                  70                  75                  80

Leu Glu Leu Ser Ser Leu Arg Ser Glu Asp Thr Ala Val Tyr Tyr Cys
                85                  90                  95

Ala Arg Gly Gly Ala Val Gly Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Glu Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
```

```
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445


<210> SEQ ID NO 223
<211> LENGTH: 454
<212> TYPE: PRT
<213> ORGANISM: Artificial Sequence
<220> FEATURE:
<223> OTHER INFORMATION: P1-047310 Heavy Chain

<400> SEQUENCE: 223

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ser Asn Tyr Ala Gln Lys Phe
    50                  55                  60

Gln Gly Arg Val Thr Ile Lys Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Ser Trp Thr Thr Ser Leu Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
```

290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450

<210> SEQ ID NO 224
<211> LENGTH: 454
<212> TYPE: PRT
<213> ORGANISM: Artificial Sequence
<220> FEATURE:
<223> OTHER INFORMATION: P1-047311 Heavy Chain

<400> SEQUENCE: 224

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ile Tyr
            20                  25                  30

Val Ile Ser Trp Val Arg Gln Ala Pro Gly Gln Gly Leu Glu Trp Met
        35                  40                  45

Gly Gly Ile Ile Pro Leu Phe Gly Thr Ala Asn Tyr Ala Gln Gln Phe
    50                  55                  60

Gln Asp Arg Val Thr Ile Thr Ala Asp Glu Ser Thr Arg Thr Ala Tyr
65                  70                  75                  80

Met Glu Leu Asn Ser Leu Lys Ser Glu Asp Thr Ala Val Tyr Tyr Cys
                85                  90                  95

Ala Arg Gly His Gly Pro Gly Ser Ser His Tyr Ser Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys

```
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450
```

<210> SEQ ID NO 225
<211> LENGTH: 454
<212> TYPE: PRT
<213> ORGANISM: Artificial Sequence
<220> FEATURE:
<223> OTHER INFORMATION: P1-047312 Heavy Chain

<400> SEQUENCE: 225

```
Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Ser Ile Tyr
            20                  25                  30

Val Ile Ser Trp Val Arg Gln Ala Pro Gly Gln Gly Leu Glu Trp Met
        35                  40                  45

Gly Gly Ile Ile Pro Leu Phe Gly Thr Pro Asn Tyr Ala Gln Gln Phe
    50                  55                  60

Gln Asp Arg Val Thr Ile Thr Ala Asp Glu Ser Thr Arg Thr Ala Tyr
65                  70                  75                  80

Met Glu Leu Asn Ser Leu Lys Ser Glu Asp Thr Ala Val Tyr Tyr Cys
                85                  90                  95

Ala Arg Gly His Gly Pro Gly Ser Ser His Tyr Ser Tyr Tyr Gly Leu
```

```
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450
```

<210> SEQ ID NO 226
<211> LENGTH: 454
<212> TYPE: PRT
<213> ORGANISM: Artificial Sequence
<220> FEATURE:
<223> OTHER INFORMATION: P1-047313 Heavy Chain

<400> SEQUENCE: 226

```
Gln Val Gln Leu Val Gln Ser Gly Ala Glu Val Lys Arg Pro Gly Ser
```

-continued

```
1               5                   10                  15

Ser Val Lys Val Ser Cys Lys Ala Ser Gly Gly Thr Phe Ser Ile Tyr
            20                  25                  30

Val Ile Ser Trp Val Arg Gln Ala Pro Gly Gln Gly Leu Glu Trp Met
        35                  40                  45

Gly Gly Ile Ile Pro Leu Phe Gly Thr Pro Asn Tyr Ala Gln Arg Phe
    50                  55                  60

Gln Asp Arg Val Thr Ile Thr Ala Asp Glu Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Gly Pro Gly Ser Ser His Tyr Ser Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430
```

```
Cys Ser Val Met His Glu Ala Leu His Asn His Tyr Thr Gln Lys Ser
        435                 440                 445

Leu Ser Leu Ser Pro Gly
    450


<210> SEQ ID NO 227
<211> LENGTH: 454
<212> TYPE: PRT
<213> ORGANISM: Artificial Sequence
<220> FEATURE:
<223> OTHER INFORMATION: P1-047314 Heavy Chain

<400> SEQUENCE: 227

Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Ser Ile Tyr
            20                  25                  30

Val Ile Ser Trp Val Arg Gln Ala Pro Gly Gln Gly Leu Glu Trp Met
        35                  40                  45

Gly Gly Ile Ile Pro Leu Phe Gly Thr Pro Asn Tyr Ala Gln Gln Phe
    50                  55                  60

Gln Asp Arg Val Thr Ile Thr Ala Asp Glu Ser Thr Arg Thr Ala Tyr
65                  70                  75                  80

Met Glu Leu Asn Ser Leu Lys Ser Glu Asp Thr Ala Val Tyr Tyr Cys
                85                  90                  95

Ala Arg Gly His Gly Pro Gly Ser Ser His Tyr Ser Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335
```

Pro Ser Ser Ile Glu Lys Thr Ile Ser Lys Ala Lys Gly Gln Pro Arg
340 345 350

Glu Pro Gln Val Tyr Thr Leu Pro Pro Ser Arg Glu Glu Met Thr Lys
355 360 365

Asn Gln Val Ser Leu Thr Cys Leu Val Lys Gly Phe Tyr Pro Ser Asp
370 375 380

Ile Ala Val Glu Trp Glu Ser Asn Gly Gln Pro Glu Asn Asn Tyr Lys
385 390 395 400

Thr Thr Pro Pro Val Leu Asp Ser Asp Gly Ser Phe Phe Leu Tyr Ser
405 410 415

Lys Leu Thr Val Asp Lys Ser Arg Trp Gln Gln Gly Asn Val Phe Ser
420 425 430

Cys Ser Val Met His Glu Ala Leu His Asn His Tyr Thr Gln Lys Ser
435 440 445

Leu Ser Leu Ser Pro Gly
450

<210> SEQ ID NO 228
<211> LENGTH: 454
<212> TYPE: PRT
<213> ORGANISM: Artificial Sequence
<220> FEATURE:
<223> OTHER INFORMATION: P1-047317 Heavy Chain

<400> SEQUENCE: 228

Gln Val Gln Leu Val Gln Ser Gly Ala Glu Val Lys Arg Pro Gly Ser
1 5 10 15

Ser Val Lys Val Ser Cys Lys Ala Ser Gly Gly Thr Phe Ser Ile Tyr
20 25 30

Val Ile Ser Trp Val Arg Gln Ala Pro Gly Gln Gly Leu Glu Trp Met
35 40 45

Gly Gly Ile Ile Pro Leu Phe Gly Thr Pro Asn Tyr Ala Gln Gln Phe
50 55 60

Gln Asp Arg Val Thr Ile Thr Ala Asp Glu Ser Thr Arg Thr Ala Tyr
65 70 75 80

Met Glu Leu Asn Ser Leu Lys Ser Glu Asp Thr Ala Val Tyr Tyr Cys
85 90 95

Ala Arg Gly His Gly Pro Gly Ser Ser His Tyr Ser Tyr Tyr Gly Leu
100 105 110

Asp Val Trp Gly Gln Gly Thr Thr Val Thr Val Ser Ser Ala Ser Thr
115 120 125

Lys Gly Pro Ser Val Phe Pro Leu Ala Pro Ser Ser Lys Ser Thr Ser
130 135 140

Gly Gly Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Gln Thr Tyr Ile Cys
195 200 205

Asn Val Asn His Lys Pro Ser Asn Thr Lys Val Asp Lys Arg Val Glu
210 215 220

Pro Lys Ser Cys Asp Lys Thr His Thr Cys Pro Pro Cys Pro Ala Pro
225 230 235 240

```
Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450


<210> SEQ ID NO 229
<211> LENGTH: 454
<212> TYPE: PRT
<213> ORGANISM: Artificial Sequence
<220> FEATURE:
<223> OTHER INFORMATION: P1-047318 Heavy Chain

<400> SEQUENCE: 229

Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Ser Ile Tyr
            20                  25                  30

Val Ile Ser Trp Val Arg Gln Ala Pro Gly Gln Gly Leu Glu Trp Met
        35                  40                  45

Gly Gly Ile Ile Pro Leu Phe Gly Thr Pro Asn Tyr Ala Gln Gln Phe
    50                  55                  60

Gln Asp Arg Val Thr Ile Thr Ala Asp Glu Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Gly Pro Gly Ser Ser His Tyr Ser Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140
```

Gly Gly Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Gln Thr Tyr Ile Cys
195 200 205

Asn Val Asn His Lys Pro Ser Asn Thr Lys Val Asp Lys Arg Val Glu
210 215 220

Pro Lys Ser Cys Asp Lys Thr His Thr Cys Pro Pro Cys Pro Ala Pro
225 230 235 240

Glu Ala Glu Gly Ala Pro Ser Val Phe Leu Phe Pro Pro Lys Pro Lys
245 250 255

Asp Thr Leu Met Ile Ser Arg Thr Pro Glu Val Thr Cys Val Val Val
260 265 270

Asp Val Ser His Glu Asp Pro Glu Val Lys Phe Asn Trp Tyr Val Asp
275 280 285

Gly Val Glu Val His Asn Ala Lys Thr Lys Pro Arg Glu Glu Gln Tyr
290 295 300

Asn Ser Thr Tyr Arg Val Val Ser Val Leu Thr Val Leu His Gln Asp
305 310 315 320

Trp Leu Asn Gly Lys Glu Tyr Lys Cys Lys Val Ser Asn Lys Ala Leu
325 330 335

Pro Ser Ser Ile Glu Lys Thr Ile Ser Lys Ala Lys Gly Gln Pro Arg
340 345 350

Glu Pro Gln Val Tyr Thr Leu Pro Pro Ser Arg Glu Glu Met Thr Lys
355 360 365

Asn Gln Val Ser Leu Thr Cys Leu Val Lys Gly Phe Tyr Pro Ser Asp
370 375 380

Ile Ala Val Glu Trp Glu Ser Asn Gly Gln Pro Glu Asn Asn Tyr Lys
385 390 395 400

Thr Thr Pro Pro Val Leu Asp Ser Asp Gly Ser Phe Phe Leu Tyr Ser
405 410 415

Lys Leu Thr Val Asp Lys Ser Arg Trp Gln Gln Gly Asn Val Phe Ser
420 425 430

Cys Ser Val Met His Glu Ala Leu His Asn His Tyr Thr Gln Lys Ser
435 440 445

Leu Ser Leu Ser Pro Gly
450

<210> SEQ ID NO 230
<211> LENGTH: 454
<212> TYPE: PRT
<213> ORGANISM: Artificial Sequence
<220> FEATURE:
<223> OTHER INFORMATION: P1-047319 Heavy Chain

<400> SEQUENCE: 230

Gln Val Gln Leu Val Gln Ser Gly Ala Glu Val Lys Arg Pro Gly Ser
1 5 10 15

Ser Val Lys Val Ser Cys Lys Ala Ser Gly Gly Thr Phe Ser Ile Tyr
20 25 30

Val Ile Ser Trp Val Arg Gln Ala Pro Gly Gln Gly Leu Glu Trp Met
35 40 45

-continued

```
Gly Gly Ile Ile Pro Leu Phe Gly Thr Ala Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Gly Pro Gly Ser Ser His Tyr Ser Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450
```

<210> SEQ ID NO 231
<211> LENGTH: 454
<212> TYPE: PRT
<213> ORGANISM: Artificial Sequence
<220> FEATURE:
<223> OTHER INFORMATION: P1-047320 Heavy Chain

<400> SEQUENCE: 231

```
Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Ser Ile Tyr
            20                  25                  30

Val Ile Ser Trp Val Arg Gln Ala Pro Gly Gln Gly Leu Glu Trp Met
        35                  40                  45

Gly Gly Ile Ile Pro Leu Phe Gly Thr Pro Asn Tyr Ala Gln Gln Phe
    50                  55                  60

Gln Asp Arg Val Thr Ile Thr Ala Asp Glu Ser Thr Arg Thr Ala Tyr
65                  70                  75                  80

Met Glu Leu Asn Ser Leu Lys Ser Glu Asp Thr Ala Val Tyr Tyr Cys
                85                  90                  95

Ala Arg Gly His Gly Pro Gly Ser Ser His Tyr Ser Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365
```

```
Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450


<210> SEQ ID NO 232
<211> LENGTH: 456
<212> TYPE: PRT
<213> ORGANISM: Artificial Sequence
<220> FEATURE:
<223> OTHER INFORMATION: P1-047322 Heavy Chain

<400> SEQUENCE: 232

Gln Val Gln Leu Val Gln Ser Gly Ala Glu Val Lys Lys Pro Gly Ser
1               5                   10                  15

Ser Val Lys Val Ser Cys Lys Ser Ser Gly Gly Thr Phe Ser Ser Tyr
            20                  25                  30

Ala Phe Thr Trp Val Arg Gln Ala Pro Gly Gln Gly Leu Glu Trp Met
        35                  40                  45

Gly Gly Ile Ile Pro Ile Phe Arg Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser His Phe Ser Gly Ser Gly Ser Ser His Tyr Tyr Tyr Tyr
            100                 105                 110

Gly Met His Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Ala Glu Gly Ala Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270
```

```
Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly
    450                 455
```

<210> SEQ ID NO 233
<211> LENGTH: 214
<212> TYPE: PRT
<213> ORGANISM: Artificial Sequence
<220> FEATURE:
<223> OTHER INFORMATION: P1-047239 Light Chain

<400> SEQUENCE: 233

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 234
<211> LENGTH: 214
<212> TYPE: PRT
<213> ORGANISM: Artificial Sequence
<220> FEATURE:
<223> OTHER INFORMATION: P1-047246 Light Chain

<400> SEQUENCE: 234

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 235
<211> LENGTH: 215
<212> TYPE: PRT
<213> ORGANISM: Artificial Sequence
<220> FEATURE:
<223> OTHER INFORMATION: P1-047247 Light Chain

<400> SEQUENCE: 235

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

```
Ile Tyr Gly Ala Ser Ser Arg Ala Thr Gly Ile Pro Glu Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 236
<211> LENGTH: 214
<212> TYPE: PRT
<213> ORGANISM: Artificial Sequence
<220> FEATURE:
<223> OTHER INFORMATION: P1-047248 Light Chain

<400> SEQUENCE: 236

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
        195                 200                 205

Phe Asn Arg Gly Glu Cys
    210

<210> SEQ ID NO 237
<211> LENGTH: 214
<212> TYPE: PRT
<213> ORGANISM: Artificial Sequence
<220> FEATURE:
<223> OTHER INFORMATION: P1-047323 Light Chain

<400> SEQUENCE: 237

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 238
<211> LENGTH: 214
<212> TYPE: PRT
<213> ORGANISM: Artificial Sequence
<220> FEATURE:
<223> OTHER INFORMATION: P1-047328 Light Chain

<400> SEQUENCE: 238

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 239
<211> LENGTH: 214
<212> TYPE: PRT
<213> ORGANISM: Artificial Sequence
<220> FEATURE:
<223> OTHER INFORMATION: P1-047334 Light Chain

<400> SEQUENCE: 239

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

```
        195                 200                 205

Phe Asn Arg Gly Glu Cys
    210


<210> SEQ ID NO 240
<211> LENGTH: 214
<212> TYPE: PRT
<213> ORGANISM: Artificial Sequence
<220> FEATURE:
<223> OTHER INFORMATION: P1-047263 Light Chain

<400> SEQUENCE: 240

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 241
<211> LENGTH: 214
<212> TYPE: PRT
<213> ORGANISM: Artificial Sequence
<220> FEATURE:
<223> OTHER INFORMATION: P1-047265 Light Chain

<400> SEQUENCE: 241

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 242
<211> LENGTH: 214
<212> TYPE: PRT
<213> ORGANISM: Artificial Sequence
<220> FEATURE:
<223> OTHER INFORMATION: P1-047289 Light Chain

<400> SEQUENCE: 242

Asp Ile Gln Met Thr Gln Ser Pro Thr Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Asn Ser Tyr Pro Leu
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 243
<211> LENGTH: 214
<212> TYPE: PRT
<213> ORGANISM: Artificial Sequence
<220> FEATURE:
<223> OTHER INFORMATION: P1-047290 Light Chain

<400> SEQUENCE: 243

Asp Ile Gln Met Thr Gln Ser Pro Thr Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 244

<400> SEQUENCE: 244

000

<210> SEQ ID NO 245
<211> LENGTH: 214
<212> TYPE: PRT
<213> ORGANISM: Artificial Sequence
<220> FEATURE:
<223> OTHER INFORMATION: P1-047291 Light Chain

<400> SEQUENCE: 245

Asp Ile Gln Met Thr Gln Ser Pro Thr Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile 35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Asp Asp Phe Ala Thr Tyr Tyr Cys Gln Gln Tyr Asn Ser Tyr Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 246
<211> LENGTH: 214
<212> TYPE: PRT
<213> ORGANISM: Artificial Sequence
<220> FEATURE:
<223> OTHER INFORMATION: P1-047292 Light Chain

<400> SEQUENCE: 246

Asp Ile Gln Met Thr Gln Ser Pro Thr Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr 180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 247
<211> LENGTH: 214
<212> TYPE: PRT
<213> ORGANISM: Artificial Sequence
<220> FEATURE:
<223> OTHER INFORMATION: P1-047294 Light Chain

<400> SEQUENCE: 247

Asp Ile Gln Met Thr Gln Ser Pro Thr Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Gly Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Leu
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 248
<211> LENGTH: 214
<212> TYPE: PRT
<213> ORGANISM: Artificial Sequence
<220> FEATURE:
<223> OTHER INFORMATION: P1-047296 Light Chain

<400> SEQUENCE: 248

Asp Ile Gln Met Thr Gln Ser Pro Thr Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 249
<211> LENGTH: 214
<212> TYPE: PRT
<213> ORGANISM: Artificial Sequence
<220> FEATURE:
<223> OTHER INFORMATION: P1-047297 Light Chain

<400> SEQUENCE: 249

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210


<210> SEQ ID NO 250
<211> LENGTH: 214
<212> TYPE: PRT
<213> ORGANISM: Artificial Sequence
<220> FEATURE:
<223> OTHER INFORMATION: P1-047299 Light Chain

<400> SEQUENCE: 250

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 251
<211> LENGTH: 214
<212> TYPE: PRT
<213> ORGANISM: Artificial Sequence
<220> FEATURE:
<223> OTHER INFORMATION: P1-047300 Light Chain

<400> SEQUENCE: 251

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

His Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 252
<211> LENGTH: 214
<212> TYPE: PRT
<213> ORGANISM: Artificial Sequence
<220> FEATURE:
<223> OTHER INFORMATION: P1-047301 Light Chain

<400> SEQUENCE: 252

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210


<210> SEQ ID NO 253
<211> LENGTH: 214
<212> TYPE: PRT
<213> ORGANISM: Artificial Sequence
<220> FEATURE:
<223> OTHER INFORMATION: P1-047302 Light Chain

<400> SEQUENCE: 253

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 254
<211> LENGTH: 214
<212> TYPE: PRT
<213> ORGANISM: Artificial Sequence
<220> FEATURE:
<223> OTHER INFORMATION: P1-047305 Light Chain

<400> SEQUENCE: 254

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

```
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 255
<211> LENGTH: 214
<212> TYPE: PRT
<213> ORGANISM: Artificial Sequence
<220> FEATURE:
<223> OTHER INFORMATION: P1-047306 Light Chain

<400> SEQUENCE: 255

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

210

<210> SEQ ID NO 256
<211> LENGTH: 214
<212> TYPE: PRT
<213> ORGANISM: Artificial Sequence
<220> FEATURE:
<223> OTHER INFORMATION: P1-047307 Light Chain

<400> SEQUENCE: 256

```
Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 257
<211> LENGTH: 214
<212> TYPE: PRT
<213> ORGANISM: Artificial Sequence
<220> FEATURE:
<223> OTHER INFORMATION: P1-047308 Light Chain

<400> SEQUENCE: 257

```
Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 258
<211> LENGTH: 214
<212> TYPE: PRT
<213> ORGANISM: Artificial Sequence
<220> FEATURE:
<223> OTHER INFORMATION: P1-047309 Light Chain

<400> SEQUENCE: 258

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 259
<211> LENGTH: 214
<212> TYPE: PRT
<213> ORGANISM: Artificial Sequence
<220> FEATURE:
<223> OTHER INFORMATION: P1-047310 Light Chain

<400> SEQUENCE: 259

```
Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 260
<211> LENGTH: 214
<212> TYPE: PRT
<213> ORGANISM: Artificial Sequence
<220> FEATURE:
<223> OTHER INFORMATION: P1-047311 Light Chain

<400> SEQUENCE: 260

```
Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95
```

```
Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 261
<211> LENGTH: 214
<212> TYPE: PRT
<213> ORGANISM: Artificial Sequence
<220> FEATURE:
<223> OTHER INFORMATION: P1-047312 Light Chain

<400> SEQUENCE: 261

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 262
```

<211> LENGTH: 214
<212> TYPE: PRT
<213> ORGANISM: Artificial Sequence
<220> FEATURE:
<223> OTHER INFORMATION: P1-047313 Light Chain

<400> SEQUENCE: 262

Asp Ile Gln Met Thr Gln Ser Pro Thr Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln His Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Trp
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 263
<211> LENGTH: 214
<212> TYPE: PRT
<213> ORGANISM: Artificial Sequence
<220> FEATURE:
<223> OTHER INFORMATION: P1-047314 Light Chain

<400> SEQUENCE: 263

Asp Ile Gln Met Thr Gln Ser Pro Thr Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Tyr
85 90 95

Thr Phe Gly Gln Gly Thr Lys Leu Glu Ile Lys Arg Thr Val Ala Ala

```
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 264
<211> LENGTH: 214
<212> TYPE: PRT
<213> ORGANISM: Artificial Sequence
<220> FEATURE:
<223> OTHER INFORMATION: P1-047317 Light Chain

<400> SEQUENCE: 264

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 265
<211> LENGTH: 214
<212> TYPE: PRT
```

<213> ORGANISM: Artificial Sequence
<220> FEATURE:
<223> OTHER INFORMATION: P1-047318 Light Chain

<400> SEQUENCE: 265

Asp Ile Gln Met Thr Gln Ser Pro Thr Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln His Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 266
<211> LENGTH: 214
<212> TYPE: PRT
<213> ORGANISM: Artificial Sequence
<220> FEATURE:
<223> OTHER INFORMATION: P1-047319 Light Chain

<400> SEQUENCE: 266

Asp Ile Gln Met Thr Gln Ser Pro Thr Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln His Lys Pro Gly Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Tyr
85 90 95

Thr Phe Gly Gln Gly Thr Lys Leu Glu Ile Lys Arg Thr Val Ala Ala
100 105 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 267
<211> LENGTH: 214
<212> TYPE: PRT
<213> ORGANISM: Artificial Sequence
<220> FEATURE:
<223> OTHER INFORMATION: P1-047320 Light Chain

<400> SEQUENCE: 267

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 268
<211> LENGTH: 214
<212> TYPE: PRT
<213> ORGANISM: Artificial Sequence
<220> FEATURE:
```

<223> OTHER INFORMATION: P1-047322 Light Chain

<400> SEQUENCE: 268

Asp Ile Gln Met Thr Gln Ser Pro Thr Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 269
<211> LENGTH: 1362
<212> TYPE: DNA
<213> ORGANISM: Artificial Sequence
<220> FEATURE:
<223> OTHER INFORMATION: P1-047239 Heavy Chain

<400> SEQUENCE: 269
caggtgcagc tggtggagtc tgggggaggc gtggtccagc ctgggaggtc cctgagactc 60
tcctgtgcag ctactgaatt caccttcagt aactatggca tgcactgggt ccgccaggct 120
ccaggcaagg ggctggagtg ggtggcagtt atatggtatg atggaagtaa taaatactat 180
gcagactccg tgaagggccg cttcaccatc tccagagaca attccaagaa cacgctgtat 240
ctgcaattga acagcctgag cgccgaggac tcggctgtgt attactgtgc gagagatggg 300
aggcattact atggttcgac ctcctacttc ggcatggacg tctggggcca agggaccacg 360
gtcaccgtct cctcagcgtc gaccaagggc ccatcggtct tccccctggc accctcctcc 420
aagagcacct ctgggggcac agcggccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcaccc agacctacat ctgcaacgtg aatcacaagc ccagcaacac caaggtggac 660
aagagagttg agcccaaatc ttgtgacaaa actcacacat gcccaccgtg cccagcacct 720
gaagccgaag gggccccgtc agtcttcctc ttccccccaa aacccaagga caccctcatg 780
atctcccgga cccctgaggt cacatgcgtg gtggtggacg tgagccacga agaccctgag 840
gtcaagttca actggtacgt ggacggcgtg gaggtgcata atgccaagac aaagccgcgg 900
gaggagcagt acaacagcac gtaccgtgtg gtcagcgtcc tcaccgtcct gcaccaggac 960
tggctgaatg gcaaggagta caagtgcaag gtctccaaca aagccctccc aagcagcatc 1020
gagaaaacca tctccaaagc caaagggcag ccccgagaac cacaggtgta caccctgccc 1080
ccatcccggg aggagatgac caagaaccag gtcagcctga cctgcctggt caaaggcttc 1140
tatcccagcg acatcgccgt ggagtgggag agcaatgggc agccggagaa caactacaag 1200
accacgcctc ccgtgctgga ctccgacggc tccttcttcc tctatagcaa gctcaccgtg 1260
gacaagagca ggtggcagca ggggaacgtc ttctcatgct ccgtgatgca tgaggctctg 1320
cacaaccact acacgcagaa gagcctctcc ctgtccccgg gt 1362

<210> SEQ ID NO 270
<211> LENGTH: 1353
<212> TYPE: DNA
<213> ORGANISM: Artificial Sequence
<220> FEATURE:
<223> OTHER INFORMATION: P1-047246 Heavy Chain

<400> SEQUENCE: 270
caggtgcagc tgcaggagtc gggcccagga ctggtgaagc cttcggagac cctgtccctc 60
acctgcactg tctctggtgg ctccatcact aattactact ggacctggat ccggcagccc 120
ccagggaagg gactggagtg gattgggtat atctatgaca gtgggtacac caactacaac 180
ccctccctca agagtcgagt caccttatca atagacacgt ccaagaacca gttctccctg 240
aagctgagct ctgtgaccgc tgcggacacg gccgtttatt actgtgcgag aggggttcta 300
tggttcgggg agttattacc tctccttgac tactggggcc agggaaccct ggtcaccgtc 360
tcctcagcgt cgaccaaggg cccatcggtc ttcccccctgg caccctcctc caagagcacc 420
tctgggggca cagcggccct gggctgcctg gtcaaggact acttccccga accggtgacg 480
gtgtcgtgga actcaggcgc cctgaccagc ggcgtgcaca ccttcccggc tgtcctacag 540
tcctcaggac tctactccct cagcagcgtg gtgaccgtgc cctccagcag cttgggcacc 600
cagacctaca tctgcaacgt gaatcacaag cccagcaaca ccaaggtgga caagagagtt 660
gagcccaaat cttgtgacaa aactcacaca tgcccaccgt gcccagcacc tgaagccgaa 720
ggggccccgt cagtcttcct cttcccccca aaacccaagg acaccctcat gatctcccgg 780
acccctgagg tcacatgcgt ggtggtggac gtgagccacg aagaccctga ggtcaagttc 840
aactggtacg tggacggcgt ggaggtgcat aatgccaaga caaagccgcg ggaggagcag 900
tacaacagca cgtaccgtgt ggtcagcgtc ctcaccgtcc tgcaccagga ctggctgaat 960
ggcaaggagt acaagtgcaa ggtctccaac aaagccctcc caagcagcat cgagaaaacc 1020
atctccaaag ccaaagggca gccccgagaa ccacaggtgt acaccctgcc cccatcccgg 1080
gaggagatga ccaagaacca ggtcagcctg acctgcctgg tcaaaggctt ctatcccagc 1140
gacatcgccg tggagtggga gagcaatggg cagccggaga acaactacaa gaccacgcct 1200
cccgtgctgg actccgacgg ctccttcttc ctctatagca agctcaccgt ggacaagagc 1260
aggtggcagc aggggaacgt cttctcatgc tccgtgatgc atgaggctct gcacaaccac 1320
tacacgcaga agagcctctc cctgtccccg ggt 1353

<210> SEQ ID NO 271
<211> LENGTH: 1353
<212> TYPE: DNA
<213> ORGANISM: Artificial Sequence
<220> FEATURE:
<223> OTHER INFORMATION: P1-047247 Heavy Chain

<400> SEQUENCE: 271
caggtgcagc tgcaggagtc gggcccagga ctggtgaagc cttcggagac cctgtccctc 60
acctgcactg tctctggtgg ctccatcact aattactact ggacctggat ccggcagccc 120
ccagggaagg gactggagtg gattgggtat atctatgaca gtgggtacac caactacaac 180
ccctccctca agagtcgagt caccttatca atagacacgt ccaagaacca gttctccctg 240
aagctgagct ctgtgaccgc tgcggacacg gccgtttatt actgtgcgag aggggttcta 300
tggttcgggg agttattacc tctccttgac tactggggcc agggaaccct ggtcaccgtc 360
tcctcagcgt cgaccaaggg cccatcggtc ttcccccctgg caccctcctc caagagcacc 420
tctgggggca cagcggccct gggctgcctg gtcaaggact acttccccga accggtgacg 480
gtgtcgtgga actcaggcgc cctgaccagc ggcgtgcaca ccttcccggc tgtcctacag 540
tcctcaggac tctactccct cagcagcgtg gtgaccgtgc cctccagcag cttgggcacc 600
cagacctaca tctgcaacgt gaatcacaag cccagcaaca ccaaggtgga caagagagtt 660
gagcccaaat cttgtgacaa aactcacaca tgcccaccgt gcccagcacc tgaagccgaa 720
ggggccccgt cagtcttcct cttcccccca aaacccaagg acaccctcat gatctcccgg 780
acccctgagg tcacatgcgt ggtggtggac gtgagccacg aagaccctga ggtcaagttc 840
aactggtacg tggacggcgt ggaggtgcat aatgccaaga caaagccgcg ggaggagcag 900
tacaacagca cgtaccgtgt ggtcagcgtc ctcaccgtcc tgcaccagga ctggctgaat 960
ggcaaggagt acaagtgcaa ggtctccaac aaagccctcc caagcagcat cgagaaaacc 1020
atctccaaag ccaaagggca gccccgagaa ccacaggtgt acaccctgcc cccatcccgg 1080
gaggagatga ccaagaacca ggtcagcctg acctgcctgg tcaaaggctt ctatcccagc 1140
gacatcgccg tggagtggga gagcaatggg cagccggaga acaactacaa gaccacgcct 1200
cccgtgctgg actccgacgg ctccttcttc ctctatagca agctcaccgt ggacaagagc 1260
aggtggcagc aggggaacgt cttctcatgc tccgtgatgc atgaggctct gcacaaccac 1320
tacacgcaga agagcctctc cctgtccccg ggt 1353

<210> SEQ ID NO 272
<211> LENGTH: 1359
<212> TYPE: DNA
<213> ORGANISM: Artificial Sequence
<220> FEATURE:
<223> OTHER INFORMATION: P1-047248 Heavy Chain

<400> SEQUENCE: 272
caggtgcagc tgcaggagtc gggcccagga ctggtgaagc cttcggagac cctgtccctc 60
acctgcactg tgtctggtgg ctccatcagt agttcctact ggagctgggt ccggcagccc 120
ccagggaagg gactggagtg gattggatat acccattaca gtgggatcag caactacaac 180
ccctccctca agagtcgagt caccatatca gtagacacgt ccaagaacca gttctccctg 240
aagctgagct ctgtgaccgc tgcggacacg gccgtgtatt actgtgcgag agaagggtac 300
gatattttga ctggttatga gtactacggt atggacgtct ggggccaagg gaccacggtc 360
accgtctcct cagcgtcgac caagggccca tcggtcttcc ccctggcacc ctcctccaag 420
agcacctctg ggggcacagc ggccctgggc tgcctggtca aggactactt ccccgaaccg 480
gtgacggtgt cgtggaactc aggcgccctg accagcggcg tgcacacctt cccggctgtc 540
ctacagtcct caggactcta ctccctcagc agcgtggtga ccgtgccctc cagcagcttg 600
ggcacccaga cctacatctg caacgtgaat cacaagccca gcaacaccaa ggtggacaag 660
agagttgagc ccaaatcttg tgacaaaact cacacatgcc caccgtgccc agcacctgaa 720
gccgaagggg ccccgtcagt cttcctcttc cccccaaaac ccaaggacac cctcatgatc 780
tcccggaccc ctgaggtcac atgcgtggtg gtggacgtga gccacgaaga ccctgaggtc 840
aagttcaact ggtacgtgga cggcgtggag gtgcataatg ccaagacaaa gccgcgggag 900
gagcagtaca acagcacgta ccgtgtggtc agcgtcctca ccgtcctgca ccaggactgg 960
ctgaatggca aggagtacaa gtgcaaggtc tccaacaaag ccctcccaag cagcatcgag 1020
aaaaccatct ccaaagccaa agggcagccc cgagaaccac aggtgtacac cctgccccca 1080
tcccgggagg agatgaccaa gaaccaggtc agcctgacct gcctggtcaa aggcttctat 1140
cccagcgaca tcgccgtgga gtgggagagc aatgggcagc cggagaacaa ctacaagacc 1200
acgcctcccg tgctggactc cgacggctcc ttcttcctct atagcaagct caccgtggac 1260
aagagcaggt ggcagcaggg gaacgtcttc tcatgctccg tgatgcatga ggctctgcac 1320
aaccactaca cgcagaagag cctctccctg tccccgggt 1359

<210> SEQ ID NO 273
<211> LENGTH: 1365
<212> TYPE: DNA
<213> ORGANISM: Artificial Sequence
<220> FEATURE:
<223> OTHER INFORMATION: P1-047323 Heavy Chain

<400> SEQUENCE: 273
caggtgcagc tggtgcagtc tggggctgag gtgaagaagc ctgggtcctc ggtgaaggtc 60
tcctgcaagg cttctggagg caccttcatc aatagcgaag ctatcaactg ggtgcgacag 120
gcccctggac aagggcttga gtggatggga gggatcatcc ctatctttga cattacaaac 180
tacgcacaga agttccaggg cagagtcacg attaccgcgg acgaatccat gagcacagcc 240
tacatggagc tgagcagcct gagatctgag gacacggccg tgtattactg tgcgaagacg 300
tattacgata ttttgactta tcactatcac tacggtatgg acgtctgggg ccaagggacc 360
acggtcaccg tctcctcagc gtcgaccaag ggcccatcgg tcttccccct ggcaccctcc 420
tccaagagca cctctggggg cacagcggcc ctgggctgcc tggtcaagga ctacttcccc 480
gaaccggtga cggtgtcgtg gaactcaggc gccctgacca gcggcgtgca caccttcccg 540
gctgtcctac agtcctcagg actctactcc ctcagcagcg tggtgaccgt gccctccagc 600
agcttgggca cccagaccta catctgcaac gtgaatcaca agcccagcaa caccaaggtg 660
gacaagagag ttgagcccaa atcttgtgac aaaactcaca catgcccacc gtgcccagca 720
cctgaagccg aaggggcccc gtcagtcttc ctcttccccc caaaacccaa ggacaccctc 780
atgatctccc ggacccctga ggtcacatgc gtggtggtgg acgtgagcca cgaagaccct 840
gaggtcaagt tcaactggta cgtggacggc gtggaggtgc ataatgccaa gacaaagccg 900
cgggaggagc agtacaacag cacgtaccgt gtggtcagcg tcctcaccgt cctgcaccag 960
gactggctga atggcaagga gtacaagtgc aaggtctcca acaaagccct cccaagcagc 1020
atcgagaaaa ccatctccaa agccaaaggg cagccccgag aaccacaggt gtacaccctg 1080

```
cccccatccc gggaggagat gaccaagaac caggtcagcc tgacctgcct ggtcaaaggc   1140

ttctatccca gcgacatcgc cgtggagtgg gagagcaatg ggcagccgga gaacaactac   1200

aagaccacgc ctcccgtgct ggactccgac ggctccttct tcctctatag caagctcacc   1260

gtggacaaga gcaggtggca gcaggggaac gtcttctcat gctccgtgat gcatgaggct   1320

ctgcacaacc actacacgca gaagagcctc tccctgtccc cgggt                   1365
```

<210> SEQ ID NO 274
<211> LENGTH: 1365
<212> TYPE: DNA
<213> ORGANISM: Artificial Sequence
<220> FEATURE:
<223> OTHER INFORMATION: P1-047328 Heavy Chain

<400> SEQUENCE: 274

```
caggtgcagc tggtgcagtc tggggctgag gtgaagaagc ctgggtcctc ggtgaaggtc     60

tcctgcaagg cttctggagg caccttcatc aatagcgaag ctatcaactg ggtgcgacag    120

gcccctggac aagggcttga gtggatggga gggatcatcc ctatctttga cattacaaac    180

tacgcacaga agttccaggg cagagtcacg attaccgcgg acgaatccat gagcacagcc    240

tacatggagc tgagcagcct gagatctgag gacacggccg tgtattactg tgcgaagacg    300

tattacgata ttttgactta tcactatcac tacggtatgg acgtctgggg ccaagggacc    360

acggtcaccg tctcctcagc gtcgaccaag ggcccatcgg tcttcccct ggcaccctcc    420

tccaagagca cctctggggg cacagcggcc ctgggctgcc tggtcaagga ctacttcccc    480

gaaccggtga cggtgtcgtg gaactcaggc gccctgacca gcggcgtgca caccttcccg    540

gctgtcctac agtcctcagg actctactcc ctcagcagcg tggtgaccgt gccctccagc    600

agcttgggca cccagaccta catctgcaac gtgaatcaca agcccagcaa caccaaggtg    660

gacaagagag ttgagcccaa atcttgtgac aaaactcaca catgcccacc gtgcccagca    720

cctgaagccg aaggggcccc gtcagtcttc ctcttccccc caaaacccaa ggacaccctc    780

atgatctccc ggacccctga ggtcacatgc gtggtggtgg acgtgagcca cgaagaccct    840

gaggtcaagt tcaactggta cgtggacggc gtggaggtgc ataatgccaa gacaaagccg    900

cgggaggagc agtacaacag cacgtaccgt gtggtcagcg tcctcaccgt cctgcaccag    960

gactggctga atggcaagga gtacaagtgc aaggtctcca acaaagccct cccaagcagc   1020

atcgagaaaa ccatctccaa agccaaaggg cagccccgag aaccacaggt gtacaccctg   1080

cccccatccc gggaggagat gaccaagaac caggtcagcc tgacctgcct ggtcaaaggc   1140

ttctatccca gcgacatcgc cgtggagtgg gagagcaatg ggcagccgga gaacaactac   1200

aagaccacgc ctcccgtgct ggactccgac ggctccttct tcctctatag caagctcacc   1260

gtggacaaga gcaggtggca gcaggggaac gtcttctcat gctccgtgat gcatgaggct   1320

ctgcacaacc actacacgca gaagagcctc tccctgtccc cgggt                   1365
```

<210> SEQ ID NO 275
<211> LENGTH: 1356
<212> TYPE: DNA
<213> ORGANISM: Artificial Sequence
<220> FEATURE:
<223> OTHER INFORMATION: P1-047334 Heavy Chain

<400> SEQUENCE: 275

```
caggtgcagc tggtgcagtc tggggctgag gtgaagaggc ctgggtcctc tgtgaaggtc     60

tcctgcaagg cttctggagg caccttcagt agttccgcta tcagctgggt gcgacaggcc    120
```

```
cctggacaag ggcttgagtg gatgggaggg atcatcccta tctttggtac aacaaacggc    180
gcacagaagt tccagggcag agtcacgatt accgcggacg aatccacgag cacagcctac    240
atggagctga gcagcctgag atctgaggac acggccgtgt attactgtgc ggctatggtt    300
cggggaaatt acttctactt ctacggtatg gacgtctggg gccaagggac cacggtcacc    360
gtctcctcag cgtcgaccaa gggcccatcg gtcttccccc tggcaccctc ctccaagagc    420
acctctgggg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt ggacaagaga    660
gttgagccca aatcttgtga caaaactcac acatgcccac cgtgcccagc acctgaagcc    720
gaaggggccc cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccaagcag catcgagaaa   1020
accatctcca aagccaaagg gcagccccga gaaccacagg tgtacaccct gcccccatcc   1080
cgggaggaga tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctata gcaagctcac cgtggacaag   1260
agcaggtggc agcaggggaa cgtcttctca tgctccgtga tgcatgaggc tctgcacaac   1320
cactacacgc agaagagcct ctccctgtcc ccgggt                             1356
```

<210> SEQ ID NO 276
<211> LENGTH: 1365
<212> TYPE: DNA
<213> ORGANISM: Artificial Sequence
<220> FEATURE:
<223> OTHER INFORMATION: P1-047263 Heavy Chain

<400> SEQUENCE: 276

```
caggtgcagc tggtgcagtc tggggctgag gtgaagaagc ctggggcctc agtgaaggtc     60
tcctgcaagg cttctggata caccttcccc acttatgata tcaactgggt gcgacaggcc    120
actggacaag ggcttgagtg gatgggatgg gtgaacccta acagtggtaa cacaggctat    180
gcacagaagt tccaggacag agtcaccatg accaggaaca cctccataag cacagcctac    240
atggagctga gcagcctgag atctgaggac acggccgtgt attactgtgc gagtgacggc    300
cttaatatgg ttcggggagt tcacaactac tacggtatgg acgtctgggg ccaagggacc    360
acggtcaccg tctcctcagc gtcgaccaag ggcccatcgg tcttccccct ggcaccctcc    420
tccaagagca cctctggggg cacagcggcc ctgggctgcc tggtcaagga ctacttcccc    480
gaaccggtga cggtgtcgtg gaactcaggc gccctgacca gcggcgtgca caccttcccg    540
gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagagag ttgagcccaa atcttgtgac aaaactcaca catgcccacc gtgcccagca    720
cctgaagccg aaggggcccc gtcagtcttc ctcttccccc caaaacccaa ggacaccctc    780
```

atgatctccc ggacccctga ggtcacatgc gtggtggtgg acgtgagcca cgaagaccct 840
gaggtcaagt tcaactggta cgtggacggc gtggaggtgc ataatgccaa gacaaagccg 900
cgggaggagc agtacaacag cacgtaccgt gtggtcagcg tcctcaccgt cctgcaccag 960
gactggctga atggcaagga gtacaagtgc aaggtctcca acaaagccct cccaagcagc 1020
atcgagaaaa ccatctccaa agccaaaggg cagccccgag aaccacaggt gtacaccctg 1080
cccccatccc gggaggagat gaccaagaac caggtcagcc tgacctgcct ggtcaaaggc 1140
ttctatccca gcgacatcgc cgtggagtgg gagagcaatg ggcagccgga gaacaactac 1200
aagaccacgc ctcccgtgct ggactccgac ggctccttct tcctctatag caagctcacc 1260
gtggacaaga gcaggtggca gcaggggaac gtcttctcat gctccgtgat gcatgaggct 1320
ctgcacaacc actacacgca gaagagcctc tccctgtccc cgggt 1365

<210> SEQ ID NO 277
<211> LENGTH: 1365
<212> TYPE: DNA
<213> ORGANISM: Artificial Sequence
<220> FEATURE:
<223> OTHER INFORMATION: P1-047265 Heavy Chain

<400> SEQUENCE: 277
caggtgcagc tggtgcagtc tggggctgag gtgaagaagc ctggggcctc agtgaaggtc 60
tcctgcaagg cttctggata caccttcccc acttatgata tcaactgggt gcgacaggcc 120
actggacaag ggcttgagtg gatgggatgg gtgaacccta acagtggtaa cacaggctat 180
gcacagaagt tccaggacag agtcaccatg accaggaaca cctccataag cacagcctac 240
atggagctga gcagcctgag atctgaggac acggccgtgt attactgtgc gagtgacggc 300
cttaatatgg ttcggggagt tcacaactac tacggtatgg acgtctgggg ccaagggacc 360
acggtcaccg tctcctcagc gtcgaccaag ggcccatcgg tcttccccct ggcaccctcc 420
tccaagagca cctctggggg cacagcggcc ctgggctgcc tggtcaagga ctacttcccc 480
gaaccggtga cggtgtcgtg gaactcaggc gccctgacca gcggcgtgca caccttcccg 540
gctgtcctac agtcctcagg actctactcc ctcagcagcg tggtgaccgt gccctccagc 600
agcttgggca cccagaccta catctgcaac gtgaatcaca agcccagcaa caccaaggtg 660
gacaagagag ttgagcccaa atcttgtgac aaaactcaca catgcccacc gtgcccagca 720
cctgaagccg aaggggcccc gtcagtcttc ctcttccccc caaaacccaa ggacaccctc 780
atgatctccc ggacccctga ggtcacatgc gtggtggtgg acgtgagcca cgaagaccct 840
gaggtcaagt tcaactggta cgtggacggc gtggaggtgc ataatgccaa gacaaagccg 900
cgggaggagc agtacaacag cacgtaccgt gtggtcagcg tcctcaccgt cctgcaccag 960
gactggctga atggcaagga gtacaagtgc aaggtctcca acaaagccct cccaagcagc 1020
atcgagaaaa ccatctccaa agccaaaggg cagccccgag aaccacaggt gtacaccctg 1080
cccccatccc gggaggagat gaccaagaac caggtcagcc tgacctgcct ggtcaaaggc 1140
ttctatccca gcgacatcgc cgtggagtgg gagagcaatg ggcagccgga gaacaactac 1200
aagaccacgc ctcccgtgct ggactccgac ggctccttct tcctctatag caagctcacc 1260
gtggacaaga gcaggtggca gcaggggaac gtcttctcat gctccgtgat gcatgaggct 1320
ctgcacaacc actacacgca gaagagcctc tccctgtccc cgggt 1365

<210> SEQ ID NO 278
<211> LENGTH: 1365

<212> TYPE: DNA
<213> ORGANISM: Artificial Sequence
<220> FEATURE:
<223> OTHER INFORMATION: P1-047289 Heavy Chain

<400> SEQUENCE: 278
caggtgcagc tggtgcagtc tggggctgag gtgaagaagc ctgggtcctc ggtgaaggtc 60
tcctgcaagg cttctggagg caccttcagc agctctgcta tcagctgggt gcgacaggcc 120
cctggacaag ggcttgagtg gatgggagga atcatcccta tcttcggtac agcagactcc 180
gcacagaagt tccagggcag agtcacgatt accgcggacg agtccacgag cacagcctac 240
atggaattga acagcctgag atctgaggac acggccgttt actactgtgc gttcacaccc 300
cggtatcgtg ggagctccca ccactacttc tacgctttgg gcgtctgggg ccaagggacc 360
acggtcaccg tctcctcagc gtcgaccaag ggcccatcgg tcttccccct ggcaccctcc 420
tccaagagca cctctggggg cacagcggcc ctgggctgcc tggtcaagga ctacttcccc 480
gaaccggtga cggtgtcgtg gaactcaggc gccctgacca gcggcgtgca caccttcccg 540
gctgtcctac agtcctcagg actctactcc ctcagcagcg tggtgaccgt gccctccagc 600
agcttgggca cccagaccta catctgcaac gtgaatcaca agcccagcaa caccaaggtg 660
gacaagagag ttgagcccaa atcttgtgac aaaactcaca catgcccacc gtgcccagca 720
cctgaagccg aaggggcccc gtcagtcttc ctcttccccc caaaacccaa ggacaccctc 780
atgatctccc ggacccctga ggtcacatgc gtggtggtgg acgtgagcca cgaagaccct 840
gaggtcaagt tcaactggta cgtggacggc gtggaggtgc ataatgccaa gacaaagccg 900
cgggaggagc agtacaacag cacgtaccgt gtggtcagcg tcctcaccgt cctgcaccag 960
gactggctga atggcaagga gtacaagtgc aaggtctcca acaaagccct cccaagcagc 1020
atcgagaaaa ccatctccaa agccaaaggg cagccccgag aaccacaggt gtacaccctg 1080
cccccatccc gggaggagat gaccaagaac caggtcagcc tgacctgcct ggtcaaaggc 1140
ttctatccca gcgacatcgc cgtggagtgg gagagcaatg ggcagccgga gaacaactac 1200
aagaccacgc ctcccgtgct ggactccgac ggctccttct tcctctatag caagctcacc 1260
gtggacaaga gcaggtggca gcaggggaac gtcttctcat gctccgtgat gcatgaggct 1320
ctgcacaacc actacacgca gaagagcctc tccctgtccc cgggt 1365

<210> SEQ ID NO 279
<211> LENGTH: 1368
<212> TYPE: DNA
<213> ORGANISM: Artificial Sequence
<220> FEATURE:
<223> OTHER INFORMATION: P1-047290 Heavy Chain

<400> SEQUENCE: 279
caggtgcagc tggtgcagtc tggggctgag gtgaagaagc ctgggtcctc ggtgaaggtc 60
tcctgcaagg cttctggagg caccttcaac agacatgcta tcagctgggt gcgacaggcc 120
cctggacaag ggcttgagtg gatgggaggg atcatccctc tctttggtac agcaaactac 180
gcgcagaagt tccagggcag agtcacgatt gccgcggacg aacccacgag cacaacctac 240
atggagctgc gcagcctgag atctgaggac acggccgtgt attactgtgc gagttcgtat 300
ttctatggtt cggggagttc caactactac tactacggtt tggacgtctg gggccaaggg 360
accacggtca ccgtctcctc agcgtcgacc aagggcccat cggtcttccc cctggcaccc 420
tcctccaaga gcacctctgg gggcacagcg gccctgggct gcctggtcaa ggactacttc 480

```
cccgaaccgg tgacggtgtc gtggaactca ggcgccctga ccagcggcgt gcacaccttc    540

ccggctgtcc tacagtcctc aggactctac tccctcagca gcgtggtgac cgtgccctcc    600

agcagcttgg gcacccagac ctacatctgc aacgtgaatc acaagcccag caacaccaag    660

gtggacaaga gagttgagcc caaatcttgt gacaaaactc acacatgccc accgtgccca    720

gcacctgaag ccgaaggggc cccgtcagtc ttcctcttcc ccccaaaacc caaggacacc    780

ctcatgatct cccggacccc tgaggtcaca tgcgtggtgg tggacgtgag ccacgaagac    840

cctgaggtca agttcaactg gtacgtggac ggcgtggagg tgcataatgc caagacaaag    900

ccgcgggagg agcagtacaa cagcacgtac cgtgtggtca gcgtcctcac cgtcctgcac    960

caggactggc tgaatggcaa ggagtacaag tgcaaggtct ccaacaaagc cctcccaagc   1020

agcatcgaga aaaccatctc caaagccaaa gggcagcccc gagaaccaca ggtgtacacc   1080

ctgcccccat cccgggagga gatgaccaag aaccaggtca gcctgacctg cctggtcaaa   1140

ggcttctatc ccagcgacat cgccgtggag tgggagagca atgggcagcc ggagaacaac   1200

tacaagacca cgcctcccgt gctggactcc gacggctcct tcttcctcta tagcaagctc   1260

accgtggaca agagcaggtg gcagcagggg aacgtcttct catgctccgt gatgcatgag   1320

gctctgcaca accactacac gcagaagagc ctctccctgt ccccgggt                1368
```

<210> SEQ ID NO 280

<400> SEQUENCE: 280

000

<210> SEQ ID NO 281
<211> LENGTH: 1368
<212> TYPE: DNA
<213> ORGANISM: Artificial Sequence
<220> FEATURE:
<223> OTHER INFORMATION: P1-047291 Heavy Chain

<400> SEQUENCE: 281

```
caggtgcagc tggtgcagtc tggggctgag gtgaagaagc ctgggtcctc ggtgaaggtc     60

tcctgcaagg cttctggagg caccttcaac agacatgcta tcagctgggt gcgacaggcc    120

cctggacaag ggcttgagtg gatgggaggg atcatccctc tctttggtac agcaaactac    180

gcgcagaagt tccagggcag agtcacgatt gccgcggacg aacccacgag cacaacctac    240

atggagctgc gcagcctgag atctgaggac acggccgtgt attactgtgc gagttcgtat    300

ttctatggtt cggggagttc caactactac tactacggtt tggacgtctg gggccaaggg    360

accacggtca ccgtctcctc agcgtcgacc aagggcccat cggtcttccc cctggcaccc    420

tcctccaaga gcacctctgg gggcacagcg gccctgggct gcctggtcaa ggactacttc    480

cccgaaccgg tgacggtgtc gtggaactca ggcgccctga ccagcggcgt gcacaccttc    540

ccggctgtcc tacagtcctc aggactctac tccctcagca gcgtggtgac cgtgccctcc    600

agcagcttgg gcacccagac ctacatctgc aacgtgaatc acaagcccag caacaccaag    660

gtggacaaga gagttgagcc caaatcttgt gacaaaactc acacatgccc accgtgccca    720

gcacctgaag ccgaaggggc cccgtcagtc ttcctcttcc ccccaaaacc caaggacacc    780

ctcatgatct cccggacccc tgaggtcaca tgcgtggtgg tggacgtgag ccacgaagac    840

cctgaggtca agttcaactg gtacgtggac ggcgtggagg tgcataatgc caagacaaag    900

ccgcgggagg agcagtacaa cagcacgtac cgtgtggtca gcgtcctcac cgtcctgcac    960
```

caggactggc tgaatggcaa ggagtacaag tgcaaggtct ccaacaaagc cctcccaagc 1020
agcatcgaga aaaccatctc caaagccaaa gggcagcccc gagaaccaca ggtgtacacc 1080
ctgcccccat cccgggagga gatgaccaag aaccaggtca gcctgacctg cctggtcaaa 1140
ggcttctatc ccagcgacat cgccgtggag tgggagagca atgggcagcc ggagaacaac 1200
tacaagacca cgcctcccgt gctggactcc gacggctcct tcttcctcta tagcaagctc 1260
accgtggaca agagcaggtg gcagcagggg aacgtcttct catgctccgt gatgcatgag 1320
gctctgcaca accactacac gcagaagagc ctctccctgt ccccgggt 1368

<210> SEQ ID NO 282
<211> LENGTH: 1365
<212> TYPE: DNA
<213> ORGANISM: Artificial Sequence
<220> FEATURE:
<223> OTHER INFORMATION: P1-047292 Heavy Chain

<400> SEQUENCE: 282
caggtgcagc tggtgcagtc tggggctgag gtgaagaagc ctgggtcctc ggtgaaggtc 60
tcctgcaagg cttctggagg caccttcagc agctctgcta tcagctgggt gcgacaggcc 120
cctggacaag ggcttgagtg gatgggaggg atcatcccta tctttagtac aggaaactac 180
gcacagaagt tccagggcag agtcacgatt accgcggacg aatccacgaa cacagcctac 240
atggatctga gcagcctgag atctgaggac acggccgtgt attactgtgc gagatccact 300
agggttcggg gagtttccca ctactactac tacggtttgg acgtctgggg ccaagggacc 360
acggtcaccg tctcctcagc gtcgaccaag ggcccatcgg tcttccccct ggcaccctcc 420
tccaagagca cctctggggg cacagcggcc ctgggctgcc tggtcaagga ctacttcccc 480
gaaccggtga cggtgtcgtg gaactcaggc gccctgacca gcggcgtgca caccttcccg 540
gctgtcctac agtcctcagg actctactcc ctcagcagcg tggtgaccgt gccctccagc 600
agcttgggca cccagaccta catctgcaac gtgaatcaca agcccagcaa caccaaggtg 660
gacaagagag ttgagcccaa atcttgtgac aaaactcaca catgcccacc gtgcccagca 720
cctgaagccg aaggggcccc gtcagtcttc ctcttccccc caaaacccaa ggacaccctc 780
atgatctccc ggacccctga ggtcacatgc gtggtggtgg acgtgagcca cgaagaccct 840
gaggtcaagt tcaactggta cgtggacggc gtggaggtgc ataatgccaa gacaaagccg 900
cgggaggagc agtacaacag cacgtaccgt gtggtcagcg tcctcaccgt cctgcaccag 960
gactggctga atggcaagga gtacaagtgc aaggtctcca acaaagccct cccaagcagc 1020
atcgagaaaa ccatctccaa agccaaaggg cagccccgag aaccacaggt gtacaccctg 1080
cccccatccc gggaggagat gaccaagaac caggtcagcc tgacctgcct ggtcaaaggc 1140
ttctatccca gcgacatcgc cgtggagtgg gagagcaatg ggcagccgga gaacaactac 1200
aagaccacgc ctcccgtgct ggactccgac ggctccttct tcctctatag caagctcacc 1260
gtggacaaga gcaggtggca gcaggggaac gtcttctcat gctccgtgat gcatgaggct 1320
ctgcacaacc actacacgca gaagagcctc tccctgtccc cgggt 1365

<210> SEQ ID NO 283
<211> LENGTH: 1368
<212> TYPE: DNA
<213> ORGANISM: Artificial Sequence
<220> FEATURE:
<223> OTHER INFORMATION: P1-047294 Heavy Chain

<400> SEQUENCE: 283

```
caggtgcagc tggtgcagtc tggggctgag gtgaagaagc ctgggtcctc ggtgaaggtc     60
tcctgcaagg cttctggagg caccttcaac agacatgcta tcagctgggt gcgacaggcc    120
cctggacaag ggcttgagtg gatgggaggg atcatccctc tctttggtac agcaaactac    180
gcgcaggagt tccagggcag agtcacgatt gccgcggacg aacccacgag cacaacctac    240
atggagctgc gcagcctgag atctgaggac acggccgtgt attactgtgc gagttcgtat    300
ttctatggtt cggggagttc caactactac tactacggtt tggacgtctg ggccaaggg     360
accacggtca ccgtctcctc agcgtcgacc aagggcccat cggtcttccc cctggcaccc    420
tcctccaaga gcacctctgg gggcacagcg gccctgggct gcctggtcaa ggactacttc    480
cccgaaccgg tgacggtgtc gtggaactca ggcgccctga ccagcggcgt gcacaccttc    540
ccggctgtcc tacagtcctc aggactctac tccctcagca gcgtggtgac cgtgccctcc    600
agcagcttgg gcacccagac ctacatctgc aacgtgaatc acaagcccag caacaccaag    660
gtggacaaga gagttgagcc caaatcttgt gacaaaactc acacatgccc accgtgccca    720
gcacctgaag ccgaaggggc cccgtcagtc ttcctcttcc ccccaaaacc caaggacacc    780
ctcatgatct cccggacccc tgaggtcaca tgcgtggtgg tggacgtgag ccacgaagac    840
cctgaggtca agttcaactg gtacgtggac ggcgtggagg tgcataatgc caagacaaag    900
ccgcgggagg agcagtacaa cagcacgtac cgtgtggtca gcgtcctcac cgtcctgcac    960
caggactggc tgaatggcaa ggagtacaag tgcaaggtct ccaacaaagc cctcccaagc   1020
agcatcgaga aaaccatctc caaagccaaa gggcagcccc gagaaccaca ggtgtacacc   1080
ctgcccccat cccgggagga gatgaccaag aaccaggtca gcctgacctg cctggtcaaa   1140
ggcttctatc ccagcgacat cgccgtggag tgggagagca atgggcagcc ggagaacaac   1200
tacaagacca cgcctcccgt gctggactcc gacggctcct tcttcctcta tagcaagctc   1260
accgtggaca agagcaggtg gcagcagggg aacgtcttct catgctccgt gatgcatgag   1320
gctctgcaca accactacac gcagaagagc ctctccctgt ccccgggt                1368
```

```
<210> SEQ ID NO 284
<211> LENGTH: 1368
<212> TYPE: DNA
<213> ORGANISM: Artificial Sequence
<220> FEATURE:
<223> OTHER INFORMATION: P1-047296 Heavy Chain

<400> SEQUENCE: 284
```

```
caggtgcagc tggtgcagtc tggggctgag gtgaagaagc ctgggtcctc ggtgaaggtc     60
tcctgcaagg cttctggagg caccttcaac agacatgcta tcagctgggt gcgacaggcc    120
cctggacaag ggcttgagtg gatgggaggg atcatccctc tctttggtac agcaaactac    180
gcgcagaagt tccagggcag agtcacgatt gccgcggacg aacccacgag cacaacctac    240
atggagctgc gcagcctgag atctgaggac acggccgtgt attactgtgc gagttcgtat    300
ttctatggtt cggggagttc caactactac tactacggtt tggacgtctg ggccaaggg     360
accacggtca ccgtctcctc agcgtcgacc aagggcccat cggtcttccc cctggcaccc    420
tcctccaaga gcacctctgg gggcacagcg gccctgggct gcctggtcaa ggactacttc    480
cccgaaccgg tgacggtgtc gtggaactca ggcgccctga ccagcggcgt gcacaccttc    540
ccggctgtcc tacagtcctc aggactctac tccctcagca gcgtggtgac cgtgccctcc    600
agcagcttgg gcacccagac ctacatctgc aacgtgaatc acaagcccag caacaccaag    660
```

```
gtggacaaga gagttgagcc caaatcttgt gacaaaactc acacatgccc accgtgccca    720

gcacctgaag ccgaaggggc cccgtcagtc ttcctcttcc ccccaaaacc caaggacacc    780

ctcatgatct cccggacccc tgaggtcaca tgcgtggtgg tggacgtgag ccacgaagac    840

cctgaggtca agttcaactg gtacgtggac ggcgtggagg tgcataatgc caagacaaag    900

ccgcgggagg agcagtacaa cagcacgtac cgtgtggtca gcgtcctcac cgtcctgcac    960

caggactggc tgaatggcaa ggagtacaag tgcaaggtct ccaacaaagc cctcccaagc   1020

agcatcgaga aaaccatctc caaagccaaa gggcagcccc gagaaccaca ggtgtacacc   1080

ctgcccccat cccgggagga gatgaccaag aaccaggtca gcctgacctg cctggtcaaa   1140

ggcttctatc ccagcgacat cgccgtggag tgggagagca atgggcagcc ggagaacaac   1200

tacaagacca cgcctcccgt gctggactcc gacggctcct tcttcctcta tagcaagctc   1260

accgtggaca agagcaggtg gcagcagggg aacgtcttct catgctccgt gatgcatgag   1320

gctctgcaca accactacac gcagaagagc ctctccctgt ccccgggt                1368


<210> SEQ ID NO 285
<211> LENGTH: 1368
<212> TYPE: DNA
<213> ORGANISM: Artificial Sequence
<220> FEATURE:
<223> OTHER INFORMATION: P1-047297 Heavy Chain

<400> SEQUENCE: 285

caggtgcagc tggtgcagtc tggggctgag gtgaagaagc ctgggtcctc ggtgaaggtc     60

tcctgcaagg cttctggagg caccttcaac agacatgcta tcagctgggt gcgacaggcc    120

cctggacaag ggcttgagtg gatgggaggg atcatccctc tctttggtac agcaaactac    180

gcgcagaagt tccagggcag agtcacgatt gccgcggacg aacccacgag cacaacctac    240

atggagctgc gcagcctgag atctgaggac acggccgtgt attactgtgc gagttcgtat    300

ttctatggtt cggggagttc caactactac tactacggtt tggacgtctg gggccaaggg    360

accacggtca ccgtctcctc agcgtcgacc aagggcccat cggtcttccc cctggcaccc    420

tcctccaaga gcacctctgg gggcacagcg gccctgggct gcctggtcaa ggactacttc    480

cccgaaccgg tgacggtgtc gtggaactca ggcgccctga ccagcggcgt gcacaccttc    540

ccggctgtcc tacagtcctc aggactctac tccctcagca gcgtggtgac cgtgccctcc    600

agcagcttgg gcacccagac ctacatctgc aacgtgaatc acaagcccag caacaccaag    660

gtggacaaga gagttgagcc caaatcttgt gacaaaactc acacatgccc accgtgccca    720

gcacctgaag ccgaaggggc cccgtcagtc ttcctcttcc ccccaaaacc caaggacacc    780

ctcatgatct cccggacccc tgaggtcaca tgcgtggtgg tggacgtgag ccacgaagac    840

cctgaggtca agttcaactg gtacgtggac ggcgtggagg tgcataatgc caagacaaag    900

ccgcgggagg agcagtacaa cagcacgtac cgtgtggtca gcgtcctcac cgtcctgcac    960

caggactggc tgaatggcaa ggagtacaag tgcaaggtct ccaacaaagc cctcccaagc   1020

agcatcgaga aaaccatctc caaagccaaa gggcagcccc gagaaccaca ggtgtacacc   1080

ctgcccccat cccgggagga gatgaccaag aaccaggtca gcctgacctg cctggtcaaa   1140

ggcttctatc ccagcgacat cgccgtggag tgggagagca atgggcagcc ggagaacaac   1200

tacaagacca cgcctcccgt gctggactcc gacggctcct tcttcctcta tagcaagctc   1260

accgtggaca agagcaggtg gcagcagggg aacgtcttct catgctccgt gatgcatgag   1320

gctctgcaca accactacac gcagaagagc ctctccctgt ccccgggt                1368
```

<210> SEQ ID NO 286
<211> LENGTH: 1368
<212> TYPE: DNA
<213> ORGANISM: Artificial Sequence
<220> FEATURE:
<223> OTHER INFORMATION: P1-047299 Heavy Chain

<400> SEQUENCE: 286
caggtgcagc tggtgcagtc tggggctgag gtgaagaagc ctgggtcctc ggtgaaggtc 60
tcctgcaagg cttctggagg caccttcaac agatatgctt tcagctgggt gcgacaggcc 120
cctggacaag ggcttgagtg gatgggaggg atcatcccta tctttggtac acccaactac 180
gcacagaagt tccagggcag agtcacgatt accgcggacg aatccacgag cacggcctac 240
atggagctga gcagcctgat atctgaggac acggccgtgt attactgtgc gagcagccat 300
ttctatggtt cggggagttc ccacttttac tactacggta tgcacgtctg gggccaaggg 360
accacggtca ccgtctcctc agcgtcgacc aagggcccat cggtcttccc cctggcaccc 420
tcctccaaga gcacctctgg gggcacagcg gccctgggct gcctggtcaa ggactacttc 480
cccgaaccgg tgacggtgtc gtggaactca ggcgccctga ccagcggcgt gcacaccttc 540
ccggctgtcc tacagtcctc aggactctac tccctcagca gcgtggtgac cgtgccctcc 600
agcagcttgg gcacccagac ctacatctgc aacgtgaatc acaagcccag caacaccaag 660
gtggacaaga gagttgagcc caaatcttgt gacaaaactc acacatgccc accgtgccca 720
gcacctgaag ccgaaggggc cccgtcagtc ttcctcttcc ccccaaaacc caaggacacc 780
ctcatgatct cccggacccc tgaggtcaca tgcgtggtgg tggacgtgag ccacgaagac 840
cctgaggtca agttcaactg gtacgtggac ggcgtggagg tgcataatgc caagacaaag 900
ccgcgggagg agcagtacaa cagcacgtac cgtgtggtca gcgtcctcac cgtcctgcac 960
caggactggc tgaatggcaa ggagtacaag tgcaaggtct ccaacaaagc cctcccaagc 1020
agcatcgaga aaaccatctc caaagccaaa gggcagcccc gagaaccaca ggtgtacacc 1080
ctgcccccat cccgggagga gatgaccaag aaccaggtca gcctgacctg cctggtcaaa 1140
ggcttctatc ccagcgacat cgccgtggag tgggagagca atgggcagcc ggagaacaac 1200
tacaagacca cgcctcccgt gctggactcc gacggctcct tcttcctcta tagcaagctc 1260
accgtggaca agagcaggtg gcagcagggg aacgtcttct catgctccgt gatgcatgag 1320
gctctgcaca accactacac gcagaagagc ctctccctgt ccccgggt 1368

<210> SEQ ID NO 287
<211> LENGTH: 1368
<212> TYPE: DNA
<213> ORGANISM: Artificial Sequence
<220> FEATURE:
<223> OTHER INFORMATION: P1-047300 Heavy Chain

<400> SEQUENCE: 287
caggtgcagc tggtgcagtc tggggctgag gtgaagaagc ctgggtcctc ggtgaaggtc 60
tcctgcaagg cttctggagg caccttcaac agacatgcta tcagctgggt gcgacaggcc 120
cctggacaag ggcttgagtg gatgggaggg atcatccctc tctttggtac agcaaactac 180
gcgcagaagt tccagggcag agtcacgatt gccgcggacg aacccacgag cacaacctac 240
atggagctgc gcagcctgag atctgaggac acggccgtgt attactgtgc aagttcgtat 300
ttctatggtt cggggagttc caactactac tactacggtt tggacgtctg gggccaaggg 360
accacggtca ccgtctcctc agcgtcgacc aagggcccat cggtcttccc cctggcaccc 420
tcctccaaga gcacctctgg gggcacagcg gccctgggct gcctggtcaa ggactacttc 480
cccgaaccgg tgacggtgtc gtggaactca ggcgccctga ccagcggcgt gcacaccttc 540
ccggctgtcc tacagtcctc aggactctac tccctcagca gcgtggtgac cgtgccctcc 600
agcagcttgg gcacccagac ctacatctgc aacgtgaatc acaagcccag caacaccaag 660
gtggacaaga gagttgagcc caaatcttgt gacaaaactc acacatgccc accgtgccca 720
gcacctgaag ccgaaggggc cccgtcagtc ttcctcttcc ccccaaaacc caaggacacc 780
ctcatgatct cccggacccc tgaggtcaca tgcgtggtgg tggacgtgag ccacgaagac 840
cctgaggtca agttcaactg gtacgtggac ggcgtggagg tgcataatgc caagacaaag 900
ccgcgggagg agcagtacaa cagcacgtac cgtgtggtca gcgtcctcac cgtcctgcac 960
caggactggc tgaatggcaa ggagtacaag tgcaaggtct ccaacaaagc cctcccaagc 1020
agcatcgaga aaaccatctc caaagccaaa gggcagcccc gagaaccaca ggtgtacacc 1080
ctgcccccat cccgggagga gatgaccaag aaccaggtca gcctgacctg cctggtcaaa 1140
ggcttctatc ccagcgacat cgccgtggag tgggagagca atgggcagcc ggagaacaac 1200
tacaagacca cgcctcccgt gctggactcc gacggctcct tcttcctcta tagcaagctc 1260
accgtggaca agagcaggtg gcagcagggg aacgtcttct catgctccgt gatgcatgag 1320
gctctgcaca accactacac gcagaagagc ctctccctgt ccccgggt 1368

<210> SEQ ID NO 288
<211> LENGTH: 1368
<212> TYPE: DNA
<213> ORGANISM: Artificial Sequence
<220> FEATURE:
<223> OTHER INFORMATION: P1-047301 Heavy Chain

<400> SEQUENCE: 288
caggtgcagc tggtgcagtc tggggctgag gtgaagaagc ctgggtcctc ggtgaaggtc 60
tcctgcaagg cttctggagg caccttcaac agatatgctt tcagctgggt gcgacaggcc 120
cctggacaag ggcttgagtg gatgggaggg atcatcccta tctttggtac acccaactac 180
gcacagaagt tccagggcag agtcacgatt accgcggacg aatccacgag cacggcctac 240
atggagctga gcagcctgat atctgaggac acggccgtgt attactgtgc gagcagccat 300
ttctatggtt cggggagttc caactactac tactacggtt tggacgtctg gggccaaggg 360
accacggtca ccgtctcctc agcgtcgacc aagggcccat cggtcttccc cctggcaccc 420
tcctccaaga gcacctctgg gggcacagcg gccctgggct gcctggtcaa ggactacttc 480
cccgaaccgg tgacggtgtc gtggaactca ggcgccctga ccagcggcgt gcacaccttc 540
ccggctgtcc tacagtcctc aggactctac tccctcagca gcgtggtgac cgtgccctcc 600
agcagcttgg gcacccagac ctacatctgc aacgtgaatc acaagcccag caacaccaag 660
gtggacaaga gagttgagcc caaatcttgt gacaaaactc acacatgccc accgtgccca 720
gcacctgaag ccgaaggggc cccgtcagtc ttcctcttcc ccccaaaacc caaggacacc 780
ctcatgatct cccggacccc tgaggtcaca tgcgtggtgg tggacgtgag ccacgaagac 840
cctgaggtca agttcaactg gtacgtggac ggcgtggagg tgcataatgc caagacaaag 900
ccgcgggagg agcagtacaa cagcacgtac cgtgtggtca gcgtcctcac cgtcctgcac 960
caggactggc tgaatggcaa ggagtacaag tgcaaggtct ccaacaaagc cctcccaagc 1020
agcatcgaga aaaccatctc caaagccaaa gggcagcccc gagaaccaca ggtgtacacc 1080

```
ctgcccccat cccgggagga gatgaccaag aaccaggtca gcctgacctg cctggtcaaa   1140

ggcttctatc ccagcgacat cgccgtggag tgggagagca atgggcagcc ggagaacaac   1200

tacaagacca cgcctcccgt gctggactcc gacggctcct tcttcctcta tagcaagctc   1260

accgtggaca agagcaggtg gcagcagggg aacgtcttct catgctccgt gatgcatgag   1320

gctctgcaca accactacac gcagaagagc ctctccctgt ccccgggt               1368
```

<210> SEQ ID NO 289
<211> LENGTH: 1368
<212> TYPE: DNA
<213> ORGANISM: Artificial Sequence
<220> FEATURE:
<223> OTHER INFORMATION: P1-047302 Heavy Chain

<400> SEQUENCE: 289

```
caggtgcagc tggtgcagtc tggggctgag gtgaagaagc ctgggtcctc ggtgaaggtc     60

tcctgcaagg cttctggagg caccttcaac agacatgcta tcagctgggt gcgacaggcc    120

cctggacaag ggcttgagtg gatgggaggg atcatccctc tctttggtac agcaaactac    180

gcgcagaagt tccagggcag agtcacgatt gccgcggacg aacccacgag cacaacctac    240

atggagctgc gcagcctgag atctgaggac acggccgtgt attactgtgc gagttcgtat    300

ttctatggtt cggggagttc caactattac tactacggtt tggacgtctg gggccaaggg    360

accacggtca ccgtctcctc agcgtcgacc aagggcccat cggtcttccc cctggcaccc    420

tcctccaaga gcacctctgg gggcacagcg gccctgggct gcctggtcaa ggactacttc    480

cccgaaccgg tgacggtgtc gtggaactca ggcgccctga ccagcggcgt gcacaccttc    540

ccggctgtcc tacagtcctc aggactctac tccctcagca gcgtggtgac cgtgccctcc    600

agcagcttgg gcacccagac ctacatctgc aacgtgaatc acaagcccag caacaccaag    660

gtggacaaga gagttgagcc caaatcttgt gacaaaactc acacatgccc accgtgccca    720

gcacctgaag ccgaaggggc cccgtcagtc ttcctcttcc ccccaaaacc caaggacacc    780

ctcatgatct cccggacccc tgaggtcaca tgcgtggtgg tggacgtgag ccacgaagac    840

cctgaggtca agttcaactg gtacgtggac ggcgtggagg tgcataatgc caagacaaag    900

ccgcgggagg agcagtacaa cagcacgtac cgtgtggtca gcgtcctcac cgtcctgcac    960

caggactggc tgaatggcaa ggagtacaag tgcaaggtct ccaacaaagc cctcccaagc   1020

agcatcgaga aaaccatctc caaagccaaa gggcagcccc gagaaccaca ggtgtacacc   1080

ctgcccccat cccgggagga gatgaccaag aaccaggtca gcctgacctg cctggtcaaa   1140

ggcttctatc ccagcgacat cgccgtggag tgggagagca atgggcagcc ggagaacaac   1200

tacaagacca cgcctcccgt gctggactcc gacggctcct tcttcctcta tagcaagctc   1260

accgtggaca agagcaggtg gcagcagggg aacgtcttct catgctccgt gatgcatgag   1320

gctctgcaca accactacac gcagaagagc ctctccctgt ccccgggt               1368
```

<210> SEQ ID NO 290
<211> LENGTH: 1365
<212> TYPE: DNA
<213> ORGANISM: Artificial Sequence
<220> FEATURE:
<223> OTHER INFORMATION: P1-047305 Heavy Chain

<400> SEQUENCE: 290

```
caggtgcagc tggtgcagtc tggggctgag gtgaagaagc ctgggtcctc ggtgaaggtc     60
```

tcctgcaaga cttctggagg caccttcagc agctctgctg tcagctgggt gcgacaggcc 120
cctggacaag ggcttgaatg gatgggagga atcaccccta tttttggtac agcagactac 180
gcacagaagt tccagggcag agtcacgatt accgcggacg catccacgag cacaggttat 240
atggaactga gcagcctgag atctgaggac acggccgttt actactgtgc gttcacaccc 300
cgatatcgtg ggagctccca ccactactac tacgctttgg gcgtctgggg ccaagggacc 360
acggtcaccg tctcctcagc gtcgaccaag ggcccatcgg tcttccccct ggcaccctcc 420
tccaagagca cctctggggg cacagcggcc ctgggctgcc tggtcaagga ctacttcccc 480
gaaccggtga cggtgtcgtg gaactcaggc gccctgacca gcggcgtgca caccttcccg 540
gctgtcctac agtcctcagg actctactcc ctcagcagcg tggtgaccgt gccctccagc 600
agcttgggca cccagaccta catctgcaac gtgaatcaca agcccagcaa caccaaggtg 660
gacaagagag ttgagcccaa atcttgtgac aaaactcaca catgcccacc gtgcccagca 720
cctgaagccg aaggggcccc gtcagtcttc ctcttccccc caaaacccaa ggacaccctc 780
atgatctccc ggacccctga ggtcacatgc gtggtggtgg acgtgagcca cgaagaccct 840
gaggtcaagt tcaactggta cgtggacggc gtggaggtgc ataatgccaa gacaaagccg 900
cgggaggagc agtacaacag cacgtaccgt gtggtcagcg tcctcaccgt cctgcaccag 960
gactggctga atggcaagga gtacaagtgc aaggtctcca acaaagccct cccaagcagc 1020
atcgagaaaa ccatctccaa agccaaaggg cagccccgag aaccacaggt gtacaccctg 1080
cccccatccc gggaggagat gaccaagaac caggtcagcc tgacctgcct ggtcaaaggc 1140
ttctatccca gcgacatcgc cgtggagtgg gagagcaatg ggcagccgga gaacaactac 1200
aagaccacgc ctcccgtgct ggactccgac ggctccttct tcctctatag caagctcacc 1260
gtggacaaga gcaggtggca gcaggggaac gtcttctcat gctccgtgat gcatgaggct 1320
ctgcacaacc actacacgca gaagagcctc tccctgtccc cgggt 1365

<210> SEQ ID NO 291
<211> LENGTH: 1362
<212> TYPE: DNA
<213> ORGANISM: Artificial Sequence
<220> FEATURE:
<223> OTHER INFORMATION: P1-047306 Heavy Chain

<400> SEQUENCE: 291
caggtgcagc tggtgcagtc tggggctgag gtgaagaagc ctgggtcctc ggtgaaggtc 60
tcctgcaagg cttctggagg caccttcagc agctctgcta tcagctgggt acgacaggcc 120
cctggacaag ggcttgagtg gatgggaggg atcatcccta tctttggtac agcgaactac 180
gcacagaagt tccagggcag agtcacgatt accgcggacg aatccacgag cacagcctac 240
atggagctga gcagcctgag atctgaggac acggccgtgt attactgtgc gagagcctcc 300
caaagcagga gctcgaacta ctactactac ggtctggacg tctggggcca agggaccacg 360
gtcaccgtct cctcagcgtc gaccaagggc ccatcggtct tccccctggc accctcctcc 420
aagagcacct ctgggggcac agcggccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcaccc agacctacat ctgcaacgtg aatcacaagc ccagcaacac caaggtggac 660
aagagagttg agcccaaatc ttgtgacaaa actcacacat gcccaccgtg cccagcacct 720
gaagccgaag ggccccgtc agtcttcctc ttccccccaa aacccaagga caccctcatg 780
atctcccgga cccctgaggt cacatgcgtg gtggtggacg tgagccacga agaccctgag 840
gtcaagttca actggtacgt ggacggcgtg gaggtgcata atgccaagac aaagccgcgg 900
gaggagcagt acaacagcac gtaccgtgtg gtcagcgtcc tcaccgtcct gcaccaggac 960
tggctgaatg gcaaggagta caagtgcaag gtctccaaca aagccctccc aagcagcatc 1020
gagaaaacca tctccaaagc caaagggcag ccccgagaac cacaggtgta caccctgccc 1080
ccatcccggg aggagatgac caagaaccag gtcagcctga cctgcctggt caaaggcttc 1140
tatcccagcg acatcgccgt ggagtgggag agcaatgggc agccggagaa caactacaag 1200
accacgcctc ccgtgctgga ctccgacggc tccttcttcc tctatagcaa gctcaccgtg 1260
gacaagagca ggtggcagca ggggaacgtc ttctcatgct ccgtgatgca tgaggctctg 1320
cacaaccact acacgcagaa gagcctctcc ctgtccccgg gt 1362

<210> SEQ ID NO 292
<211> LENGTH: 1362
<212> TYPE: DNA
<213> ORGANISM: Artificial Sequence
<220> FEATURE:
<223> OTHER INFORMATION: P1-047307 Heavy Chain

<400> SEQUENCE: 292
caggtgcagc tggtgcagtc tggggctgag gtgaagaggc ctgggtcctc ggtgaaggtc 60
tcctgcaagg cttctggagg caccttcagt atctatgtta tcagctgggt gcgacaggcc 120
cctggacaag ggcttgagtg gatgggaggg atcatccctc tctttggtac accaaactac 180
gcacagcagt tccaggacag agtcacgatt accgcggacg aatccacgag gacagcctac 240
atggagctga atagcctgaa atctgaggac acggccgtat attactgtgc gaggggacat 300
ggtccgggga gttcccacta ctcctactac ggtttggacg tctggggcca agggaccacg 360
gtcaccgtct cctcagcgtc gaccaagggc ccatcggtct tccccctggc accctcctcc 420
aagagcacct ctgggggcac agcggccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcaccc agacctacat ctgcaacgtg aatcacaagc ccagcaacac caaggtggac 660
aagagagttg agcccaaatc ttgtgacaaa actcacacat gcccaccgtg cccagcacct 720
gaagccgaag ggccccgtc agtcttcctc ttccccccaa aacccaagga caccctcatg 780
atctcccgga cccctgaggt cacatgcgtg gtggtggacg tgagccacga agaccctgag 840
gtcaagttca actggtacgt ggacggcgtg gaggtgcata atgccaagac aaagccgcgg 900
gaggagcagt acaacagcac gtaccgtgtg gtcagcgtcc tcaccgtcct gcaccaggac 960
tggctgaatg gcaaggagta caagtgcaag gtctccaaca aagccctccc aagcagcatc 1020
gagaaaacca tctccaaagc caaagggcag ccccgagaac cacaggtgta caccctgccc 1080
ccatcccggg aggagatgac caagaaccag gtcagcctga cctgcctggt caaaggcttc 1140
tatcccagcg acatcgccgt ggagtgggag agcaatgggc agccggagaa caactacaag 1200
accacgcctc ccgtgctgga ctccgacggc tccttcttcc tctatagcaa gctcaccgtg 1260
gacaagagca ggtggcagca ggggaacgtc ttctcatgct ccgtgatgca tgaggctctg 1320
cacaaccact acacgcagaa gagcctctcc ctgtccccgg gt 1362

<210> SEQ ID NO 293

<211> LENGTH: 1362
<212> TYPE: DNA
<213> ORGANISM: Artificial Sequence
<220> FEATURE:
<223> OTHER INFORMATION: P1-047308 Heavy Chain

<400> SEQUENCE: 293
caggtgcagc tggtgcagtc tggggctgag gtgaagaggc ctgggtcctc ggtgaaggtc 60
tcctgcaagg cttctggagg caccttcagt atctatgtta tcagctgggt gcgacaggcc 120
cctggacaag ggcttgagtg gatgggaggg atcatccctc tctttggtac agcaaactac 180
gcacagaagt tccagggcag agtcacgatt accgcggacg aatccacgaa tacagcctac 240
atggagctga gtagcctgag atctgaggac acggccgtgt attactgtgc gaggggacat 300
ggtccgggga gttcccacta ctcctactac ggtttggacg tctggggcca agggaccacg 360
gtcaccgtct cctcagcgtc gaccaagggc ccatcggtct tccccctggc accctcctcc 420
aagagcacct ctgggggcac agcggccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcaccc agacctacat ctgcaacgtg aatcacaagc ccagcaacac caaggtggac 660
aagagagttg agcccaaatc ttgtgacaaa actcacacat gcccaccgtg cccagcacct 720
gaagccgaag ggggccccgtc agtcttcctc ttccccccaa aacccaagga caccctcatg 780
atctcccgga cccctgaggt cacatgcgtg gtggtggacg tgagccacga agaccctgag 840
gtcaagttca actggtacgt ggacggcgtg gaggtgcata atgccaagac aaagccgcgg 900
gaggagcagt acaacagcac gtaccgtgtg gtcagcgtcc tcaccgtcct gcaccaggac 960
tggctgaatg gcaaggagta caagtgcaag gtctccaaca aagccctccc aagcagcatc 1020
gagaaaacca tctccaaagc caaagggcag ccccgagaac cacaggtgta caccctgccc 1080
ccatcccggg aggagatgac caagaaccag gtcagcctga cctgcctggt caaaggcttc 1140
tatcccagcg acatcgccgt ggagtgggag agcaatgggc agccggagaa caactacaag 1200
accacgcctc ccgtgctgga ctccgacggc tccttcttcc tctatagcaa gctcaccgtg 1260
gacaagagca ggtggcagca ggggaacgtc ttctcatgct ccgtgatgca tgaggctctg 1320
cacaaccact acacgcagaa gagcctctcc ctgtccccgg gt 1362

<210> SEQ ID NO 294
<211> LENGTH: 1338
<212> TYPE: DNA
<213> ORGANISM: Artificial Sequence
<220> FEATURE:
<223> OTHER INFORMATION: P1-047309 Heavy Chain

<400> SEQUENCE: 294
caggtgcagc tggtgcagtc tggggctgag gtgaagaagc ctgggtcctc ggtgaaggtc 60
tcctgcaacc cttctggagg caccttcagc acctacgcta tcagctgggt gcgacaggcc 120
cctggacaag ggcttgagtg gatgggaggg atcaacccta tctttggaac agcaaactac 180
gcacagaagt tccagggcag agtcacaatt accgcggacg aatccacgag tccaggctac 240
ctggagctga gcagcctgag atctgaggac acggccgttt attactgtgc gagaggggga 300
gcagtgggtt ttgcctattg gggccaggga accctggtca ccgtctcctc agcgtcgacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480

```
ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga gagttgagcc caaatcttgt    660

gacaaaactc acacatgccc accgtgccca gcacctgaag ccgaaggggc cccgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacaa cagcacgtac    900

cgtgtggtca gcgtcctcac cgtcctgcac caggactggc tgaatggcaa ggagtacaag    960

tgcaaggtct ccaacaaagc cctcccaagc agcatcgaga aaaccatctc caaagccaaa   1020

gggcagcccc gagaaccaca ggtgtacacc ctgcccccat cccgggagga gatgaccaag   1080

aaccaggtca gcctgacctg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta tagcaagctc accgtggaca agagcaggtg gcagcagggg   1260

aacgtcttct catgctccgt gatgcatgag gctctgcaca accactacac gcagaagagc   1320

ctctccctgt ccccgggt                                                 1338
```

<210> SEQ ID NO 295
<211> LENGTH: 1362
<212> TYPE: DNA
<213> ORGANISM: Artificial Sequence
<220> FEATURE:
<223> OTHER INFORMATION: P1-047310 Heavy Chain

<400> SEQUENCE: 295

```
caggtgcagc tggtgcagtc tggggctgag gtgaagaagc ctgggtcctc ggtgaaggtc     60

tcctgcaagg cttctggagg caccttcagc agatatgcta tcagctgggt gcgacaggcc    120

cctggacaag ggcttgagtg gatgggaggg atcatcccta tctttggtac atcaaactac    180

gcacagaagt tccagggcag agtcacgatt aaagcggacg aatccacgag cacagcctac    240

atggagctga gcagcctgag atctgaggac acggccgtgt attactgtgc gagagggggc    300

aacagctgga ccactagttt gtactactac ggtatggacg tctggggcca agggaccacg    360

gtcaccgtct cctcagcgtc gaccaagggc ccatcggtct tccccctggc accctcctcc    420

aagagcacct ctgggggcac agcggccctg ggctgcctgg tcaaggacta cttccccgaa    480

ccggtgacgg tgtcgtggaa ctcaggcgcc ctgaccagcg gcgtgcacac cttcccggct    540

gtcctacagt cctcaggact ctactccctc agcagcgtgg tgaccgtgcc ctccagcagc    600

ttgggcaccc agacctacat ctgcaacgtg aatcacaagc ccagcaacac caaggtggac    660

aagagagttg agcccaaatc ttgtgacaaa actcacacat gcccaccgtg cccagcacct    720

gaagccgaag gggccccgtc agtcttcctc ttccccccaa aacccaagga caccctcatg    780

atctcccgga cccctgaggt cacatgcgtg gtggtggacg tgagccacga agaccctgag    840

gtcaagttca actggtacgt ggacggcgtg gaggtgcata atgccaagac aaagccgcgg    900

gaggagcagt acaacagcac gtaccgtgtg gtcagcgtcc tcaccgtcct gcaccaggac    960

tggctgaatg gcaaggagta caagtgcaag gtctccaaca aagccctccc aagcagcatc   1020

gagaaaacca tctccaaagc caaagggcag ccccgagaac cacaggtgta caccctgccc   1080

ccatcccggg aggagatgac caagaaccag gtcagcctga cctgcctggt caaaggcttc   1140
```

tatcccagcg acatcgccgt ggagtgggag agcaatgggc agccggagaa caactacaag 1200
accacgcctc ccgtgctgga ctccgacggc tccttcttcc tctatagcaa gctcaccgtg 1260
gacaagagca ggtggcagca ggggaacgtc ttctcatgct ccgtgatgca tgaggctctg 1320
cacaaccact acacgcagaa gagcctctcc ctgtccccgg gt 1362

<210> SEQ ID NO 296
<211> LENGTH: 1362
<212> TYPE: DNA
<213> ORGANISM: Artificial Sequence
<220> FEATURE:
<223> OTHER INFORMATION: P1-047311 Heavy Chain

<400> SEQUENCE: 296
caggtgcagc tggtgcagtc tggggctgag gtgaagaagc ctgggtcctc ggtgaaggtc 60
tcctgcaagg cttctggagg caccttcagt atctatgtta tcagctgggt gcgacaggcc 120
cctggacaag ggcttgagtg gatgggaggg atcatccctc tctttggtac agcaaactac 180
gcacagcagt tccaggacag agtcacgatt accgcggacg aatccacgag gacagcctac 240
atggagctga atagcctgaa atctgaggac acggctgtat attactgtgc gaggggacat 300
ggtccgggga gttcccacta ctcctactac ggtttggacg tctggggcca agggaccacg 360
gtcaccgtct cctcagcgtc gaccaagggc ccatcggtct tccccctggc accctcctcc 420
aagagcacct ctgggggcac agcggccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcaccc agacctacat ctgcaacgtg aatcacaagc ccagcaacac caaggtggac 660
aagagagttg agcccaaatc ttgtgacaaa actcacacat gcccaccgtg cccagcacct 720
gaagccgaag ggcccccgtc agtcttcctc ttccccccaa aacccaagga caccctcatg 780
atctcccgga cccctgaggt cacatgcgtg gtggtggacg tgagccacga agaccctgag 840
gtcaagttca actggtacgt ggacggcgtg gaggtgcata atgccaagac aaagccgcgg 900
gaggagcagt acaacagcac gtaccgtgtg gtcagcgtcc tcaccgtcct gcaccaggac 960
tggctgaatg gcaaggagta caagtgcaag gtctccaaca aagccctccc aagcagcatc 1020
gagaaaacca tctccaaagc caaagggcag ccccgagaac cacaggtgta caccctgccc 1080
ccatcccggg aggagatgac caagaaccag gtcagcctga cctgcctggt caaaggcttc 1140
tatcccagcg acatcgccgt ggagtgggag agcaatgggc agccggagaa caactacaag 1200
accacgcctc ccgtgctgga ctccgacggc tccttcttcc tctatagcaa gctcaccgtg 1260
gacaagagca ggtggcagca ggggaacgtc ttctcatgct ccgtgatgca tgaggctctg 1320
cacaaccact acacgcagaa gagcctctcc ctgtccccgg gt 1362

<210> SEQ ID NO 297
<211> LENGTH: 1362
<212> TYPE: DNA
<213> ORGANISM: Artificial Sequence
<220> FEATURE:
<223> OTHER INFORMATION: P1-047312 Heavy Chain

<400> SEQUENCE: 297
caggtgcagc tggtgcagtc tggggctgag gtgaagaggc ctgggtcctc ggtgaaggtc 60
tcctgcaagg cttctggagg caccttcagt atctatgtta tcagctgggt gcgacaggcc 120
cctggacaag ggcttgagtg gatgggaggg atcatccctc tctttggtac accaaactac 180

```
gcacagcagt tccaggacag agtcacgatt accgcggacg aatccacgag gacagcctac    240

atggagctga atagcctgaa atctgaggac acggccgtat attactgtgc gaggggacat    300

ggtccgggga gttcccacta ctcctactac ggtttggacg tctggggcca agggaccacg    360

gtcaccgtct cctcagcgtc gaccaagggc ccatcggtct tccccctggc accctcctcc    420

aagagcacct ctgggggcac agcggccctg ggctgcctgg tcaaggacta cttccccgaa    480

ccggtgacgg tgtcgtggaa ctcaggcgcc ctgaccagcg gcgtgcacac cttcccggct    540

gtcctacagt cctcaggact ctactccctc agcagcgtgg tgaccgtgcc ctccagcagc    600

ttgggcaccc agacctacat ctgcaacgtg aatcacaagc ccagcaacac caaggtggac    660

aagagagttg agcccaaatc ttgtgacaaa actcacacat gcccaccgtg cccagcacct    720

gaagccgaag ggggccccgtc agtcttcctc ttccccccaa aacccaagga caccctcatg    780

atctcccgga cccctgaggt cacatgcgtg gtggtggacg tgagccacga agaccctgag    840

gtcaagttca actggtacgt ggacggcgtg gaggtgcata atgccaagac aaagccgcgg    900

gaggagcagt acaacagcac gtaccgtgtg gtcagcgtcc tcaccgtcct gcaccaggac    960

tggctgaatg gcaaggagta caagtgcaag gtctccaaca aagccctccc aagcagcatc   1020

gagaaaacca tctccaaagc caaagggcag ccccgagaac cacaggtgta caccctgccc   1080

ccatcccggg aggagatgac caagaaccag gtcagcctga cctgcctggt caaaggcttc   1140

tatcccagcg acatcgccgt ggagtgggag agcaatgggc agccggagaa caactacaag   1200

accacgcctc ccgtgctgga ctccgacggc tccttcttcc tctatagcaa gctcaccgtg   1260

gacaagagca ggtggcagca ggggaacgtc ttctcatgct ccgtgatgca tgaggctctg   1320

cacaaccact acacgcagaa gagcctctcc ctgtccccgg gt                      1362
```

<210> SEQ ID NO 298
<211> LENGTH: 1362
<212> TYPE: DNA
<213> ORGANISM: Artificial Sequence
<220> FEATURE:
<223> OTHER INFORMATION: P1-047313 Heavy Chain

<400> SEQUENCE: 298

```
caggtgcagc tggtgcagtc tggggctgag gtgaagaggc ctgggtcctc ggtgaaggtc     60

tcctgcaagg cttctggagg caccttcagt atctatgtta tcagctgggt gcgacaggcc    120

cctggacaag ggcttgagtg gatgggaggg atcatccctc tctttggtac accaaactac    180

gcacagcggt tccaggacag agtcacgatt accgcggacg aatccacgag gacagcctac    240

atggagctga gtagcctgag atctgaggac acggccgtgt attactgtgc gaggggacat    300

ggtccgggga gttcccacta ctcctactac ggtttggacg tctggggcca agggaccacg    360

gtcaccgtct cctcagcgtc gaccaagggc ccatcggtct tccccctggc accctcctcc    420

aagagcacct ctgggggcac agcggccctg ggctgcctgg tcaaggacta cttccccgaa    480

ccggtgacgg tgtcgtggaa ctcaggcgcc ctgaccagcg gcgtgcacac cttcccggct    540

gtcctacagt cctcaggact ctactccctc agcagcgtgg tgaccgtgcc ctccagcagc    600

ttgggcaccc agacctacat ctgcaacgtg aatcacaagc ccagcaacac caaggtggac    660

aagagagttg agcccaaatc ttgtgacaaa actcacacat gcccaccgtg cccagcacct    720

gaagccgaag ggggccccgtc agtcttcctc ttccccccaa aacccaagga caccctcatg    780

atctcccgga cccctgaggt cacatgcgtg gtggtggacg tgagccacga agaccctgag    840
```

gtcaagttca actggtacgt ggacggcgtg gaggtgcata atgccaagac aaagccgcgg 900
gaggagcagt acaacagcac gtaccgtgtg gtcagcgtcc tcaccgtcct gcaccaggac 960
tggctgaatg gcaaggagta caagtgcaag gtctccaaca aagccctccc aagcagcatc 1020
gagaaaacca tctccaaagc caaagggcag ccccgagaac cacaggtgta caccctgccc 1080
ccatcccggg aggagatgac caagaaccag gtcagcctga cctgcctggt caaaggcttc 1140
tatcccagcg acatcgccgt ggagtgggag agcaatgggc agccggagaa caactacaag 1200
accacgcctc ccgtgctgga ctccgacggc tccttcttcc tctatagcaa gctcaccgtg 1260
gacaagagca ggtggcagca ggggaacgtc ttctcatgct ccgtgatgca tgaggctctg 1320
cacaaccact acacgcagaa gagcctctcc ctgtccccgg gt 1362

<210> SEQ ID NO 299
<211> LENGTH: 1362
<212> TYPE: DNA
<213> ORGANISM: Artificial Sequence
<220> FEATURE:
<223> OTHER INFORMATION: P1-047314 Heavy Chain

<400> SEQUENCE: 299
caggtgcagc tggtgcagtc tggggctgag gtgaagaggc ctgggtcctc ggtgaaggtc 60
tcctgcaagg cttctggagg caccttcagt atctatgtta tcagctgggt gcgacaggcc 120
cctggacaag ggcttgagtg gatgggaggg atcatccctc tctttggtac accaaactac 180
gcacagcagt tccaggacag agtcacgatt accgcggacg aatccacgag gacagcctac 240
atggagctga atagcctgaa atctgaggac acggccgtat attactgtgc gaggggacat 300
ggtccgggga gttcccacta ctcctactac ggtttggacg tctggggcca agggaccacg 360
gtcaccgtct cctcagcgtc gaccaagggc ccatcggtct tccccctggc accctcctcc 420
aagagcacct ctgggggcac agcggccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcaccc agacctacat ctgcaacgtg aatcacaagc ccagcaacac caaggtggac 660
aagagagttg agcccaaatc ttgtgacaaa actcacacat gcccaccgtg cccagcacct 720
gaagccgaag ggggccccgtc agtcttcctc ttccccccaa aacccaagga caccctcatg 780
atctcccgga cccctgaggt cacatgcgtg gtggtggacg tgagccacga agaccctgag 840
gtcaagttca actggtacgt ggacggcgtg gaggtgcata atgccaagac aaagccgcgg 900
gaggagcagt acaacagcac gtaccgtgtg gtcagcgtcc tcaccgtcct gcaccaggac 960
tggctgaatg gcaaggagta caagtgcaag gtctccaaca aagccctccc aagcagcatc 1020
gagaaaacca tctccaaagc caaagggcag ccccgagaac cacaggtgta caccctgccc 1080
ccatcccggg aggagatgac caagaaccag gtcagcctga cctgcctggt caaaggcttc 1140
tatcccagcg acatcgccgt ggagtgggag agcaatgggc agccggagaa caactacaag 1200
accacgcctc ccgtgctgga ctccgacggc tccttcttcc tctatagcaa gctcaccgtg 1260
gacaagagca ggtggcagca ggggaacgtc ttctcatgct ccgtgatgca tgaggctctg 1320
cacaaccact acacgcagaa gagcctctcc ctgtccccgg gt 1362

<210> SEQ ID NO 300
<211> LENGTH: 1362
<212> TYPE: DNA
<213> ORGANISM: Artificial Sequence
<220> FEATURE:
<223> OTHER INFORMATION: P1-047317 Heavy Chain

<400> SEQUENCE: 300
caggtgcagc tggtgcagtc tggggctgag gtgaagaggc ctgggtcctc ggtgaaggtc 60
tcctgcaagg cttctggagg caccttcagt atctatgtta tcagctgggt gcgacaggcc 120
cctggacaag ggcttgagtg gatgggaggg atcatccctc tctttggtac accaaactac 180
gcacagcagt tccaggacag agtcacgatt accgcggacg aatccacgag gacagcctac 240
atggagctga atagcctgaa atctgaggac acggccgtat attactgtgc gaggggacat 300
ggtccgggga gttcccacta ctcctactac ggtttggacg tctggggcca agggaccacg 360
gtcaccgtct cctcagcgtc gaccaagggc ccatcggtct tccccctggc accctcctcc 420
aagagcacct ctgggggcac agcggccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcaccc agacctacat ctgcaacgtg aatcacaagc ccagcaacac caaggtggac 660
aagagagttg agcccaaatc ttgtgacaaa actcacacat gcccaccgtg cccagcacct 720
gaagccgaag ggggccccgtc agtcttcctc ttccccccaa aacccaagga caccctcatg 780
atctcccgga cccctgaggt cacatgcgtg gtggtggacg tgagccacga agaccctgag 840
gtcaagttca actggtacgt ggacggcgtg gaggtgcata atgccaagac aaagccgcgg 900
gaggagcagt acaacagcac gtaccgtgtg gtcagcgtcc tcaccgtcct gcaccaggac 960
tggctgaatg gcaaggagta caagtgcaag gtctccaaca aagccctccc aagcagcatc 1020
gagaaaacca tctccaaagc caaagggcag ccccgagaac cacaggtgta caccctgccc 1080
ccatcccggg aggagatgac caagaaccag gtcagcctga cctgcctggt caaaggcttc 1140
tatcccagcg acatcgccgt ggagtgggag agcaatgggc agccggagaa caactacaag 1200
accacgcctc ccgtgctgga ctccgacggc tccttcttcc tctatagcaa gctcaccgtg 1260
gacaagagca ggtggcagca ggggaacgtc ttctcatgct ccgtgatgca tgaggctctg 1320
cacaaccact acacgcagaa gagcctctcc ctgtccccgg gt 1362

<210> SEQ ID NO 301
<211> LENGTH: 1362
<212> TYPE: DNA
<213> ORGANISM: Artificial Sequence
<220> FEATURE:
<223> OTHER INFORMATION: P1-047318 Heavy Chain

<400> SEQUENCE: 301
caggtgcagc tggtgcagtc tggggctgag gtgaagaggc ctgggtcctc ggtgaaggtc 60
tcctgcaagg cttctggagg caccttcagt atctatgtta tcagctgggt ccgacaggcc 120
cctggacaag ggcttgagtg gatgggaggg atcatccctc tctttggtac accaaactac 180
gcacagcagt tccaggacag agtcacgatt accgcggacg aatccacgag gacagcctac 240
atggagctga gtagcctgag atctgaggac acggccgtgt attactgtgc gaggggacat 300
ggtccgggga gttcccacta ctcctactac ggtttggacg tctggggcca agggaccacg 360
gtcaccgtct cctcagcgtc gaccaagggc ccatcggtct tccccctggc accctcctcc 420
aagagcacct ctgggggcac agcggccctg ggctgcctgg tcaaggacta cttccccgaa 480
ccggtgacgg tgtcgtggaa ctcaggcgcc ctgaccagcg gcgtgcacac cttcccggct 540

```
gtcctacagt cctcaggact ctactccctc agcagcgtgg tgaccgtgcc ctccagcagc    600
ttgggcaccc agacctacat ctgcaacgtg aatcacaagc ccagcaacac caaggtggac    660
aagagagttg agcccaaatc ttgtgacaaa actcacacat gcccaccgtg cccagcacct    720
gaagccgaag ggggccccgtc agtcttcctc ttccccccaa aacccaagga caccctcatg    780
atctcccgga cccctgaggt cacatgcgtg gtggtggacg tgagccacga agaccctgag    840
gtcaagttca actggtacgt ggacggcgtg gaggtgcata atgccaagac aaagccgcgg    900
gaggagcagt acaacagcac gtaccgtgtg gtcagcgtcc tcaccgtcct gcaccaggac    960
tggctgaatg gcaaggagta caagtgcaag gtctccaaca aagccctccc aagcagcatc   1020
gagaaaacca tctccaaagc caaagggcag ccccgagaac cacaggtgta caccctgccc   1080
ccatcccggg aggagatgac caagaaccag gtcagcctga cctgcctggt caaaggcttc   1140
tatcccagcg acatcgccgt ggagtgggag agcaatgggc agccggagaa caactacaag   1200
accacgcctc ccgtgctgga ctccgacggc tccttcttcc tctatagcaa gctcaccgtg   1260
gacaagagca ggtggcagca ggggaacgtc ttctcatgct ccgtgatgca tgaggctctg   1320
cacaaccact acacgcagaa gagcctctcc ctgtccccgg gt                       1362
```

<210> SEQ ID NO 302
<211> LENGTH: 1362
<212> TYPE: DNA
<213> ORGANISM: Artificial Sequence
<220> FEATURE:
<223> OTHER INFORMATION: P1-047319 Heavy Chain

<400> SEQUENCE: 302

```
caggtgcagc tggtgcagtc tggggctgag gtgaagaggc ctgggtcctc ggtgaaggtc     60
tcctgcaagg cttctggagg caccttcagt atctatgtta tcagctgggt gcgacaggcc    120
cctggacaag ggcttgagtg gatgggaggg atcatccctc tctttggtac agcaaactac    180
gcacagaagt tccagggcag agtcacgatt accgcggacg aatccacgaa tacagcctac    240
atggagctga gtagcctgag atctgaggac acggccgtgt attactgtgc gaggggacat    300
ggtccgggga gttcccacta ctcctactac ggtttggacg tctggggcca agggaccacg    360
gtcaccgtct cctcagcgtc gaccaagggc ccatcggtct tccccctggc accctcctcc    420
aagagcacct ctgggggcac agcggccctg ggctgcctgg tcaaggacta cttccccgaa    480
ccggtgacgg tgtcgtggaa ctcaggcgcc ctgaccagcg gcgtgcacac cttcccggct    540
gtcctacagt cctcaggact ctactccctc agcagcgtgg tgaccgtgcc ctccagcagc    600
ttgggcaccc agacctacat ctgcaacgtg aatcacaagc ccagcaacac caaggtggac    660
aagagagttg agcccaaatc ttgtgacaaa actcacacat gcccaccgtg cccagcacct    720
gaagccgaag ggggccccgtc agtcttcctc ttccccccaa aacccaagga caccctcatg    780
atctcccgga cccctgaggt cacatgcgtg gtggtggacg tgagccacga agaccctgag    840
gtcaagttca actggtacgt ggacggcgtg gaggtgcata atgccaagac aaagccgcgg    900
gaggagcagt acaacagcac gtaccgtgtg gtcagcgtcc tcaccgtcct gcaccaggac    960
tggctgaatg gcaaggagta caagtgcaag gtctccaaca aagccctccc aagcagcatc   1020
gagaaaacca tctccaaagc caaagggcag ccccgagaac cacaggtgta caccctgccc   1080
ccatcccggg aggagatgac caagaaccag gtcagcctga cctgcctggt caaaggcttc   1140
tatcccagcg acatcgccgt ggagtgggag agcaatgggc agccggagaa caactacaag   1200
accacgcctc ccgtgctgga ctccgacggc tccttcttcc tctatagcaa gctcaccgtg   1260
```

```
gacaagagca ggtggcagca ggggaacgtc ttctcatgct ccgtgatgca tgaggctctg   1320

cacaaccact acacgcagaa gagcctctcc ctgtccccgg gt                      1362
```

```
<210> SEQ ID NO 303
<211> LENGTH: 1362
<212> TYPE: DNA
<213> ORGANISM: Artificial Sequence
<220> FEATURE:
<223> OTHER INFORMATION: P1-047320 Heavy Chain

<400> SEQUENCE: 303

caggtgcagc tggtgcagtc tggggctgag gtgaagaggc ctgggtcctc ggtgaaggtc     60

tcctgcaagg cttctggagg caccttcagt atctatgtta tcagctgggt gcgacaggcc    120

cctggacaag ggcttgagtg gatgggaggg atcatccctc tctttggtac accaaactac    180

gcacagcagt tccaggacag agtcacgatt accgcggacg aatccacgag gacagcctac    240

atggagctga atagcctgaa atctgaggac acggccgtat attactgtgc gaggggacat    300

ggtccgggga gttcccacta ctcctactac ggtttggacg tctggggcca agggaccacg    360

gtcaccgtct cctcagcgtc gaccaagggc ccatcggtct tccccctggc accctcctcc    420

aagagcacct ctgggggcac agcggccctg ggctgcctgg tcaaggacta cttccccgaa    480

ccggtgacgg tgtcgtggaa ctcaggcgcc ctgaccagcg gcgtgcacac cttcccggct    540

gtcctacagt cctcaggact ctactccctc agcagcgtgg tgaccgtgcc ctccagcagc    600

ttgggcaccc agacctacat ctgcaacgtg aatcacaagc ccagcaacac caaggtggac    660

aagagagttg agcccaaatc ttgtgacaaa actcacacat gcccaccgtg cccagcacct    720

gaagccgaag ggggccccgtc agtcttcctc ttccccccaa aacccaagga caccctcatg    780

atctcccgga cccctgaggt cacatgcgtg gtggtggacg tgagccacga agaccctgag    840

gtcaagttca actggtacgt ggacggcgtg gaggtgcata atgccaagac aaagccgcgg    900

gaggagcagt acaacagcac gtaccgtgtg gtcagcgtcc tcaccgtcct gcaccaggac    960

tggctgaatg gcaaggagta caagtgcaag gtctccaaca aagccctccc aagcagcatc   1020

gagaaaacca tctccaaagc caaagggcag ccccgagaac cacaggtgta caccctgccc   1080

ccatcccggg aggagatgac caagaaccag gtcagcctga cctgcctggt caaaggcttc   1140

tatcccagcg acatcgccgt ggagtgggag agcaatgggc agccggagaa caactacaag   1200

accacgcctc ccgtgctgga ctccgacggc tccttcttcc tctatagcaa gctcaccgtg   1260

gacaagagca ggtggcagca ggggaacgtc ttctcatgct ccgtgatgca tgaggctctg   1320

cacaaccact acacgcagaa gagcctctcc ctgtccccgg gt                      1362
```

```
<210> SEQ ID NO 304
<211> LENGTH: 1368
<212> TYPE: DNA
<213> ORGANISM: Artificial Sequence
<220> FEATURE:
<223> OTHER INFORMATION: P1-047322 Heavy Chain

<400> SEQUENCE: 304

caggtgcagc tggtgcagtc tggggctgag gtgaagaagc ctgggtcctc ggtgaaggtc     60

tcctgcaagt cttctggagg caccttcagc agctatgctt tcacctgggt gcgacaggcc    120

cctggacaag ggcttgagtg gatgggaggg atcatcccta tctttcgtac agcaaactac    180

gcacagaagt tccagggcag agtcacgatt accgcggacg aatccacgag cacagcctac    240
```

atggagctga gcagcctgag atctgaggac acggccgtgt attactgtgc gagcagccat 300
ttctctggtt cgggaagttc ccactactac tactacggta tgcacgtctg gggccaaggg 360
accacggtca ccgtctcctc agcgtcgacc aagggcccat cggtcttccc cctggcaccc 420
tcctccaaga gcacctctgg gggcacagcg gccctgggct gcctggtcaa ggactacttc 480
cccgaaccgg tgacggtgtc gtggaactca ggcgccctga ccagcggcgt gcacaccttc 540
ccggctgtcc tacagtcctc aggactctac tccctcagca gcgtggtgac cgtgccctcc 600
agcagcttgg gcacccagac ctacatctgc aacgtgaatc acaagcccag caacaccaag 660
gtggacaaga gagttgagcc caaatcttgt gacaaaactc acacatgccc accgtgccca 720
gcacctgaag ccgaaggggc cccgtcagtc ttcctcttcc ccccaaaacc caaggacacc 780
ctcatgatct cccggacccc tgaggtcaca tgcgtggtgg tggacgtgag ccacgaagac 840
cctgaggtca agttcaactg gtacgtggac ggcgtggagg tgcataatgc caagacaaag 900
ccgcgggagg agcagtacaa cagcacgtac cgtgtggtca gcgtcctcac cgtcctgcac 960
caggactggc tgaatggcaa ggagtacaag tgcaaggtct ccaacaaagc cctcccaagc 1020
agcatcgaga aaaccatctc caaagccaaa gggcagcccc gagaaccaca ggtgtacacc 1080
ctgcccccat cccgggagga gatgaccaag aaccaggtca gcctgacctg cctggtcaaa 1140
ggcttctatc ccagcgacat cgccgtggag tgggagagca atgggcagcc ggagaacaac 1200
tacaagacca cgcctcccgt gctggactcc gacggctcct tcttcctcta tagcaagctc 1260
accgtggaca agagcaggtg gcagcagggg aacgtcttct catgctccgt gatgcatgag 1320
gctctgcaca accactacac gcagaagagc ctctccctgt ccccgggt 1368

<210> SEQ ID NO 305
<211> LENGTH: 642
<212> TYPE: DNA
<213> ORGANISM: Artificial Sequence
<220> FEATURE:
<223> OTHER INFORMATION: P1-047239 Light Chain

<400> SEQUENCE: 305
gccatccagt tgacccagtc tccatcctcc ctgtctgcat ctgtaggaga cagagtcacc 60
atcacttgcc gggcaagtca gggcattagc agtgctttag cctggtatca gcagaaacca 120
gggaaagctc ctaagctcct gatctatgat gcctccagtt tggaaagtgg ggtcccatca 180
aggttcagcg gcagtggatc tgggacagat ttcactctca ccatcagcag cctgcagcct 240
gaagattttg caacttatta ctgtcaacag tttaatagtt acccgtacac ttttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 306
<211> LENGTH: 642
<212> TYPE: DNA
<213> ORGANISM: Artificial Sequence
<220> FEATURE:
<223> OTHER INFORMATION: P1-047246 Light Chain

<400> SEQUENCE: 306
gccatccagt tgacccagtc tccatcctcc ctgtctgcat ctgtaggaga cagagtcacc 60
atcacttgcc gggcaagtca gggcattagc agtgctttag cctggtatca gcagaaacca 120
gggaaagctc ctaagctcct gatctatgat gcctccagtt tggaaagtgg ggtcccatca 180
aggttcagcg gcagtggatc tgggacagat ttcactctca ccatcagcag cctgcagcct 240
gaagattttg caacttatta ctgtcaacag tttaatagtt acccgtacac ttttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 307
<211> LENGTH: 645
<212> TYPE: DNA
<213> ORGANISM: Artificial Sequence
<220> FEATURE:
<223> OTHER INFORMATION: P1-047247 Light Chain

<400> SEQUENCE: 307
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gagaggttca gtggcagtgg gtctgggaca gacttcactc tcaccatcag cagactggag 240
cctgaagatt ttgcagtgta ttactgtcag cagtatggta gctcaccgct cactttcggc 300
ggagggacca aggtggagat caaacgtacg gtggctgcac catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgt 645

<210> SEQ ID NO 308
<211> LENGTH: 642
<212> TYPE: DNA
<213> ORGANISM: Artificial Sequence
<220> FEATURE:
<223> OTHER INFORMATION: P1-047248 Light Chain

<400> SEQUENCE: 308
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcacctac tttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 309
<211> LENGTH: 642
<212> TYPE: DNA
<213> ORGANISM: Artificial Sequence
<220> FEATURE:
<223> OTHER INFORMATION: P1-047323 Light Chain

<400> SEQUENCE: 309
gccatccagt tgacccagtc tccatcctcc ctgtctgcat ctgtaggaga cagagtcacc 60
atcacttgcc gggcaagtca gggcattagc agtgctttag cctggtatca gcagaaacca 120
gggaaagctc ctaagctcct gatctatgat gcctccagtt tggaaagtgg ggtcccatca 180
aggttcagcg gcagtggatc tgggacagat ttcactctca ccatcagcag cctgcagcct 240
gaagattttg caacttatta ctgtcaacag tttaatagtt acccgatcac cttcggccaa 300
gggacacgac tggagattaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 310
<211> LENGTH: 642
<212> TYPE: DNA
<213> ORGANISM: Artificial Sequence
<220> FEATURE:
<223> OTHER INFORMATION: P1-047334 Light Chain

<400> SEQUENCE: 310
gccatccagt tgacccagtc tccatcctcc ctgtctgcat ctgtaggaga cagagtcacc 60
atcacttgcc gggcaagtca gggcattagc agtgctttag cctggtatca gcagaaacca 120
gggaaagctc ctaagctcct gatctatgat gcctccagtt tggaaagtgg ggtcccatca 180
aggttcagcg gcagtggatc tgggacagat ttcactctca ccatcagcag cctgcagcct 240
gaagattttg caacttatta ctgccaacag tataatagtt acccgatcac cttcggccaa 300
gggacacgac tggagattaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 311
<211> LENGTH: 642
<212> TYPE: DNA
<213> ORGANISM: Artificial Sequence
<220> FEATURE:
<223> OTHER INFORMATION: P1-047334 Light Chain

<400> SEQUENCE: 311
gccatccagt tgacccagtc tccatcctcc ctgtctgcat ctgtaggaga cagagtcacc 60
atcacttgcc gggcaagtca gggcattagc agtgctttag cctggtatca gcagaaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgctcac tttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 312
<211> LENGTH: 642
<212> TYPE: DNA
<213> ORGANISM: Artificial Sequence
<220> FEATURE:
<223> OTHER INFORMATION: P1-047263 Light Chain

<400> SEQUENCE: 312
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt accctccgac ttttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 313
<211> LENGTH: 642
<212> TYPE: DNA
<213> ORGANISM: Artificial Sequence
<220> FEATURE:
<223> OTHER INFORMATION: P1-047265 Light Chain

<400> SEQUENCE: 313
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgtacac ttttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 314
<211> LENGTH: 642
<212> TYPE: DNA
<213> ORGANISM: Artificial Sequence
<220> FEATURE:
<223> OTHER INFORMATION: P1-047290 Light Chain

<400> SEQUENCE: 314
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgtcaacag tttaatagtt accctctcac tttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 315
<211> LENGTH: 642
<212> TYPE: DNA
<213> ORGANISM: Artificial Sequence
<220> FEATURE:
<223> OTHER INFORMATION: P1-047291 Light Chain

<400> SEQUENCE: 315
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgtacac ttttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 316

<400> SEQUENCE: 316

000

<210> SEQ ID NO 317
<211> LENGTH: 642
<212> TYPE: DNA
<213> ORGANISM: Artificial Sequence
<220> FEATURE:
<223> OTHER INFORMATION: P1-047291 Light Chain

<400> SEQUENCE: 317
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gatgattttg caacttatta ctgccaacag tataatagtt acccgtacac ttttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 318
<211> LENGTH: 642
<212> TYPE: DNA
<213> ORGANISM: Artificial Sequence
<220> FEATURE:
<223> OTHER INFORMATION: P1-047292 Light Chain

<400> SEQUENCE: 318
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgtacac ttttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 319
<211> LENGTH: 642
<212> TYPE: DNA
<213> ORGANISM: Artificial Sequence
<220> FEATURE:
<223> OTHER INFORMATION: P1-047294 Light Chain

<400> SEQUENCE: 319
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcggtggatc tgggacagat ttcactctca ccatcagcag cctgcagcct 240
gaagattttg caacttatta ctgccaacag tataatagtt acccgctcac tttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 320
<211> LENGTH: 642
<212> TYPE: DNA
<213> ORGANISM: Artificial Sequence
<220> FEATURE:
<223> OTHER INFORMATION: P1-047296 Light Chain

<400> SEQUENCE: 320
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgatcac cttcggccaa 300
gggacacgac tggagattaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 321
<211> LENGTH: 642
<212> TYPE: DNA
<213> ORGANISM: Artificial Sequence
<220> FEATURE:
<223> OTHER INFORMATION: P1-047297 Light Chain

<400> SEQUENCE: 321
gacatccaga tgacccagtc tccaacctca ctgtctgcat ctgtaggaga cagagtcacc 60
atcacttgtc gggcgagtca gggtattagc agctggttag cctggtatca gcataaacca 120
gggaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgctcac tttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 322
<211> LENGTH: 642
<212> TYPE: DNA
<213> ORGANISM: Artificial Sequence
<220> FEATURE:
<223> OTHER INFORMATION: P1-047299 Light Chain

<400> SEQUENCE: 322
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgtggac gttcggccaa 300
gggaccaagg tggaaatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 323
<211> LENGTH: 642
<212> TYPE: DNA
<213> ORGANISM: Artificial Sequence
<220> FEATURE:
<223> OTHER INFORMATION: P1-047300 Light Chain

<400> SEQUENCE: 323
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatccatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgctcac tttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 324
<211> LENGTH: 642
<212> TYPE: DNA
<213> ORGANISM: Artificial Sequence
<220> FEATURE:
<223> OTHER INFORMATION: P1-047301 Light Chain

<400> SEQUENCE: 324
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgtacac ttttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 325
<211> LENGTH: 642
<212> TYPE: DNA
<213> ORGANISM: Artificial Sequence
<220> FEATURE:
<223> OTHER INFORMATION: P1-047302 Light Chain

<400> SEQUENCE: 325
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt accctctcac tttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 326
<211> LENGTH: 642
<212> TYPE: DNA
<213> ORGANISM: Artificial Sequence
<220> FEATURE:
<223> OTHER INFORMATION: P1-047305 Light Chain

<400> SEQUENCE: 326
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgtacac ttttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480

```
gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 327
<211> LENGTH: 642
<212> TYPE: DNA
<213> ORGANISM: Artificial Sequence
<220> FEATURE:
<223> OTHER INFORMATION: P1-047306 Light Chain

<400> SEQUENCE: 327

```
gacatccaga tgacccagtc tccaacctca ctgtctgcat ctgtaggaga cagagtcacc     60

atcacttgtc gggcgagtca gggtattagc agctggttag cctggtatca gcagaaacca    120

gagaaagccc ctaagtccct gatctatgct gcatccagtt tgcaaagtgg ggtcccatca    180

aggttcagcg gcagtggatc tgggacagat ttcactctca ccatcagcag cctgcagcct    240

gaagattttg caacttatta ctgccaacag tataatagtt accctctcac tttcggcgga    300

gggaccaagg tggagatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 328
<211> LENGTH: 642
<212> TYPE: DNA
<213> ORGANISM: Artificial Sequence
<220> FEATURE:
<223> OTHER INFORMATION: P1-047307 Light Chain

<400> SEQUENCE: 328

```
gacatccaga tgacccagtc tccaacctca ctgtctgcat ctgtaggaga cagagtcacc     60

atcacttgtc gggcgagtca gggtattagc agctggttag cctggtatca gcagaaacca    120

gagaaagccc ctaagtccct gatctatgct gcatccagtt tgcaaagtgg ggtcccatca    180

aggttcagcg gcagtggatc tgggacagat ttcactctca ccatcagcag cctgcagcct    240

gaagattttg caacttatta ctgccaacag tataatagtt accctctcac tttcggcgga    300

gggaccaagg tggagatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 329
<211> LENGTH: 642
<212> TYPE: DNA
<213> ORGANISM: Artificial Sequence
<220> FEATURE:
<223> OTHER INFORMATION: P1-047308 Light Chain

<400> SEQUENCE: 329
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgtacac ttttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 330
<211> LENGTH: 642
<212> TYPE: DNA
<213> ORGANISM: Artificial Sequence
<220> FEATURE:
<223> OTHER INFORMATION: P1-047309 Light Chain

<400> SEQUENCE: 330
gacatccaga tgacccagtc tccatcttcc gtgtctgcat ctgtaggaga cagagtcacc 60
atcacttgtc gggcgagtca gggtattagc agctggttag cctggtatca gcataaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttacta ttgtcaacag gctaatagtt tcccgttcac tttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 331
<211> LENGTH: 642
<212> TYPE: DNA
<213> ORGANISM: Artificial Sequence
<220> FEATURE:
<223> OTHER INFORMATION: P1-047310 Light Chain

<400> SEQUENCE: 331
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacggat tacactctca ccatcagcag cctgcagcct 240
gaagattttg caacttatta ctgccaacag tataatagtt acccgctcac tttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 332
<211> LENGTH: 642
<212> TYPE: DNA
<213> ORGANISM: Artificial Sequence
<220> FEATURE:
<223> OTHER INFORMATION: P1-047311 Light Chain

<400> SEQUENCE: 332
gacatccaga tgacccagtc tccaacctca ctgtctgcat ctgtaggaga cagagtcacc 60
atcacttgtc gggcgagtca gggtattagc agctggttag cctggtatca gcagaaacca 120
gggaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgctcac tttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 333
<211> LENGTH: 642
<212> TYPE: DNA
<213> ORGANISM: Artificial Sequence
<220> FEATURE:
<223> OTHER INFORMATION: P1-047312 Light Chain

<400> SEQUENCE: 333
gacatccaga tgacccagtc tccaacctca ctgtctgcat ctgtaggaga cagagtcacc 60
atcacttgtc gggcgagtca gggtattagc agctggttag cctggtatca gcataaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgtacac ttttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 334
<211> LENGTH: 642
<212> TYPE: DNA
<213> ORGANISM: Artificial Sequence
<220> FEATURE:
<223> OTHER INFORMATION: P1-047313 Light Chain

<400> SEQUENCE: 334
gacatccaga tgacccagtc tccaacctca ctgtctgcat ctgtaggaga cagagtcacc 60
atcacttgtc gggcgagtca gggtattagc agctggttag cctggtatca gcataaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccctggac gttcggccaa 300
gggaccaagg tggaaatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 335
<211> LENGTH: 642
<212> TYPE: DNA
<213> ORGANISM: Artificial Sequence
<220> FEATURE:
<223> OTHER INFORMATION: P1-047314 Light Chain

<400> SEQUENCE: 335
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgtacac ttttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 336
<211> LENGTH: 642
<212> TYPE: DNA
<213> ORGANISM: Artificial Sequence
<220> FEATURE:
<223> OTHER INFORMATION: P1-047317 Light Chain

<400> SEQUENCE: 336
gaaattgtgt tgacgcagtc tccaggcacc ctgtctttgt ctccagggga aagagccacc 60
ctctcctgca gggccagtca gagtgttagc agctacttag cctggtacca acagaaacct 120
ggccaggctc ccaggctcct catctatggt gcatccagca gggccactgg catcccagac 180
aggttcagtg gcagtgggtc tgggacagac ttcactctca ccatcagcag actggagcct 240
gaagattttg cagtgtatta ctgtcagcag tatggtagct caccgctcac tttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 337
<211> LENGTH: 642
<212> TYPE: DNA
<213> ORGANISM: Artificial Sequence
<220> FEATURE:
<223> OTHER INFORMATION: P1-047318 Light Chain

<400> SEQUENCE: 337
gacatccaga tgacccagtc tccaacctca ctgtctgcat ctgtaggaga cagagtcacc 60
atcacttgtc gggcgagtca gggtattagc agctggttag cctggtatca gcataaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgtacac ttttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 338
<211> LENGTH: 642
<212> TYPE: DNA
<213> ORGANISM: Artificial Sequence
<220> FEATURE:
<223> OTHER INFORMATION: P1-047319 Light Chain

<400> SEQUENCE: 338
gacatccaga tgacccagtc tccaacctca ctgtctgcat ctgtaggaga cagagtcacc 60
atcacttgtc gggcgagtca gggtattagc agctggttag cctggtatca gcataaacca 120
gggaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgtacac ttttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 339
<211> LENGTH: 642
<212> TYPE: DNA
<213> ORGANISM: Artificial Sequence
<220> FEATURE:
<223> OTHER INFORMATION: P1-047320 Light Chain

<400> SEQUENCE: 339
gacatccaga tgacccagtc tccaacctca ctgtctgcat ctgtaggaga cagagtcacc 60
atcacttgtc gggcgagtca gggtattagc agctggttag cctggtatca gcataaacca 120
gggaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt acccgtacac ttttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 340
<211> LENGTH: 642
<212> TYPE: DNA
<213> ORGANISM: Artificial Sequence
<220> FEATURE:
<223> OTHER INFORMATION: P1-047322 Light Chain

<400> SEQUENCE: 340
gacatccaga tgacccagtc tccaacctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggtttagcg gcagtggatc tgggacagat ttcactctca ccatcagcag cctgcagcct 240
gaagattttg caacttatta ctgccaacag tataatagtt acccgtacac ttttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 341
<211> LENGTH: 12
<212> TYPE: PRT
<213> ORGANISM: Artificial Sequence
<220> FEATURE:
<223> OTHER INFORMATION: LCDR1
<220> FEATURE:
<221> NAME/KEY: SITE
<222> LOCATION: (5)..(5)
<223> OTHER INFORMATION: X may be S or G
<220> FEATURE:
<221> NAME/KEY: SITE
<222> LOCATION: (6)..(6)
<223> OTHER INFORMATION: X may be V or I
<220> FEATURE:
<221> NAME/KEY: SITE
<222> LOCATION: (7)..(7)
<223> OTHER INFORMATION: X may be S or none
<220> FEATURE:

-continued

```
<221> NAME/KEY: SITE
<222> LOCATION: (10)..(10)
<223> OTHER INFORMATION: X may be Y or A

<400> SEQUENCE: 341

Arg Ala Ser Gln Xaa Xaa Xaa Ser Ser Xaa Leu Ala
1               5                   10


<210> SEQ ID NO 342
<211> LENGTH: 9
<212> TYPE: PRT
<213> ORGANISM: Artificial Sequence
<220> FEATURE:
<223> OTHER INFORMATION: LCDR3
<220> FEATURE:
<221> NAME/KEY: SITE
<222> LOCATION: (3)..(3)
<223> OTHER INFORMATION: X may be Y or F
<220> FEATURE:
<221> NAME/KEY: SITE
<222> LOCATION: (4)..(4)
<223> OTHER INFORMATION: X may be G or N
<220> FEATURE:
<221> NAME/KEY: SITE
<222> LOCATION: (6)..(6)
<223> OTHER INFORMATION: X may be S or Y
<220> FEATURE:
<221> NAME/KEY: SITE
<222> LOCATION: (8)..(8)
<223> OTHER INFORMATION: X may be L, Y, or none

<400> SEQUENCE: 342

Gln Gln Xaa Xaa Ser Xaa Pro Xaa Thr
1               5


<210> SEQ ID NO 343
<211> LENGTH: 9
<212> TYPE: PRT
<213> ORGANISM: Artificial Sequence
<220> FEATURE:
<223> OTHER INFORMATION: LCDR3
<220> FEATURE:
<221> NAME/KEY: SITE
<222> LOCATION: (3)..(3)
<223> OTHER INFORMATION: X may be Y or F
<220> FEATURE:
<221> NAME/KEY: SITE
<222> LOCATION: (4)..(4)
<223> OTHER INFORMATION: X may be G or N
<220> FEATURE:
<221> NAME/KEY: SITE
<222> LOCATION: (6)..(6)
<223> OTHER INFORMATION: X may be S or Y
<220> FEATURE:
<221> NAME/KEY: SITE
<222> LOCATION: (8)..(8)
<223> OTHER INFORMATION: X may be L, Y, I, or none

<400> SEQUENCE: 343

Gln Gln Xaa Xaa Ser Xaa Pro Xaa Thr
1               5
```